(12) United States Patent
del Carmen Cuevas Marchante et al.

(10) Patent No.: US 10,538,535 B2
(45) Date of Patent: Jan. 21, 2020

(54) ANTITUMORAL COMPOUNDS

(71) Applicant: Pharma Mar, S.A., Madrid (ES)

(72) Inventors: María del Carmen Cuevas Marchante, Madrid (ES); Andrés Francesch Solloso, Madrid (ES); Valentín Martínez Barrasa, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 0 days.

(21) Appl. No.: 15/964,381

(22) Filed: Apr. 27, 2018

(65) Prior Publication Data

US 2018/0312529 A1 Nov. 1, 2018

(30) Foreign Application Priority Data

Apr. 27, 2017 (EP) .................................... 17382228
Jul. 26, 2017 (EP) .................................... 17382497

(51) Int. Cl.
*C07D 515/22* (2006.01)
*A61P 35/00* (2006.01)

(52) U.S. Cl.
CPC ............ *C07D 515/22* (2013.01); *A61P 35/00* (2018.01)

(58) Field of Classification Search
CPC .................................................. C07D 515/22
See application file for complete search history.

(56) References Cited

U.S. PATENT DOCUMENTS

| | | |
|---|---|---|
| 4,393,225 A | 7/1983 | Hayashi et al. |
| 4,400,752 A | 8/1983 | Charolle |
| 4,493,796 A | 1/1985 | Rinehart |
| 4,537,883 A | 8/1985 | Alexander et al. |
| 4,548,814 A | 10/1985 | Rinehart |
| 4,567,253 A | 1/1986 | Durst et al. |
| 4,631,149 A | 12/1986 | Rinehart et al. |
| 4,670,262 A | 6/1987 | Battelli et al. |
| 4,737,510 A | 4/1988 | Rinehart |
| 4,762,949 A | 8/1988 | Rinehart et al. |
| 4,782,135 A | 11/1988 | Rinehart |
| 4,816,450 A | 3/1989 | Bell et al. |
| 4,847,246 A | 7/1989 | Wilson et al. |
| 4,948,791 A | 8/1990 | Rinehart et al. |
| 4,950,649 A | 8/1990 | Rinehart |
| 4,952,399 A | 8/1990 | Lewenstein |
| 5,053,559 A | 10/1991 | Jefford |
| 5,089,273 A | 2/1992 | Rinehart |
| 5,093,330 A | 3/1992 | Caravatti et al. |
| 5,137,870 A | 8/1992 | Rinehart |
| 5,149,804 A | 9/1992 | Rinehart |
| 5,190,876 A | 3/1993 | Merrill et al. |
| 5,256,663 A | 10/1993 | Rinehart et al. |
| 5,294,603 A | 3/1994 | Rinehart |
| 5,336,669 A | 8/1994 | Palepu et al. |
| 5,449,684 A | 9/1995 | Tanaka et al. |
| 5,462,726 A | 10/1995 | Lodge |
| 5,478,932 A | 12/1995 | Rinehart et al. |
| 5,514,705 A | 5/1996 | Ichiba et al. |
| 5,514,708 A | 5/1996 | Rinehart et al. |
| 5,523,456 A | 6/1996 | Stokker et al. |
| 5,556,777 A | 9/1996 | Faircloth et al. |
| 5,559,145 A | 9/1996 | Jefford |
| 5,569,757 A | 10/1996 | Rinehart et al. |
| 5,571,927 A | 11/1996 | Alexander et al. |
| 5,580,871 A | 12/1996 | Earl |
| 5,605,905 A | 2/1997 | Avendano et al. |
| 5,654,426 A | 8/1997 | Rinehart et al. |
| 5,661,175 A | 8/1997 | Kashman et al. |
| 5,681,813 A | 10/1997 | Baz et al. |

(Continued)

FOREIGN PATENT DOCUMENTS

| | | |
|---|---|---|
| CN | 1360503 | 7/2002 |
| DE | 3612278 | 10/1986 |

(Continued)

OTHER PUBLICATIONS

Kohomoto, S.; McConnell, O.J.; Wright, A.; Koehn, F.; Thompson, W.; Lui, M.; Snader, K.M. J. Nat. Prod 1987, 50,336.
Kozawa Y et al. Tetrahedron Lett., 2002, vol. 43,111.
Kraft, A.S.; Smith, J.B.; Berkow, R. L. Proc. Natl. Acad Sci. USA 1986, 83, 1334-1338.
Kubo A et al Journal of Organic Chemistry vol. 53, No. 18, pp. 4295-4310, 1987.

(Continued)

*Primary Examiner* — Bruck Kifle

(74) *Attorney, Agent, or Firm* — Kenneth H. Sonnenfeld; Kristine Waddell; King & Spalding LLP

(57) ABSTRACT

A compound of general formula I, wherein X, $R_1$-$R_4$ take various meanings, for use in the treatment of cancer.

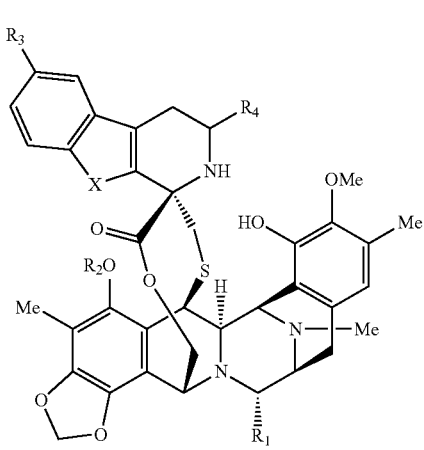

51 Claims, 34 Drawing Sheets

(56) References Cited

U.S. PATENT DOCUMENTS

| | | | |
|---|---|---|---|
| 5,681,847 A | 10/1997 | Longley et al. |
| 5,683,895 A | 11/1997 | Rinehart et al. |
| 5,721,352 A | 2/1998 | Moyer et al. |
| 5,721,362 A | 2/1998 | Corey et al. |
| 5,739,114 A | 4/1998 | Gordaliza et al. |
| 5,744,623 A | 4/1998 | Gravalos et al. |
| 5,747,529 A | 5/1998 | Gordaliza et al. |
| 5,756,734 A | 5/1998 | Rinehart et al. |
| 5,786,492 A | 7/1998 | Gravalos et al. |
| 5,834,505 A | 11/1998 | Peters et al. |
| 5,834,507 A | 11/1998 | Gordaliza et al. |
| 5,834,586 A | 11/1998 | Rinehart et al. |
| 5,849,540 A | 12/1998 | Rinehart et al. |
| 5,852,033 A | 12/1998 | Fernandez et al. |
| 5,925,671 A | 7/1999 | Hernandez et al. |
| 5,952,332 A | 9/1999 | Rinehart et al. |
| 5,985,876 A | 11/1999 | Rinehart et al. |
| 6,011,010 A | 1/2000 | Scheuer et al. |
| 6,025,466 A | 2/2000 | Bowden et al. |
| 6,028,077 A | 2/2000 | Rinehart et al. |
| 6,030,943 A | 2/2000 | Crumb et al. |
| 6,034,058 A | 3/2000 | Rinehart et al. |
| 6,087,370 A | 7/2000 | Puentes et al. |
| 6,107,520 A | 8/2000 | Rinehart et al. |
| 6,124,292 A | 9/2000 | Corey et al. |
| 6,124,293 A | 9/2000 | Rinehart et al. |
| 6,153,731 A | 11/2000 | Rinehart et al. |
| 6,156,724 A | 12/2000 | Rinehart et al. |
| 6,214,793 B1 | 4/2001 | Baz et al. |
| 6,245,759 B1 | 6/2001 | Bilodeau et al. |
| 6,274,551 B1 | 8/2001 | Scheuer et al. |
| 6,316,214 B1 | 11/2001 | Rinehart et al. |
| 6,348,467 B1 | 2/2002 | Corey et al. |
| 6,350,743 B1 | 2/2002 | Kashman et al. |
| 6,391,900 B1 | 5/2002 | Higa et al. |
| 6,420,357 B1 | 7/2002 | Kashman et al. |
| 6,509,315 B1 | 1/2003 | Joullie et al. |
| 6,521,757 B1 | 2/2003 | Banwell et al. |
| 6,525,063 B2 | 2/2003 | Avenndano et al. |
| 6,544,560 B1 | 4/2003 | Bullent et al. |
| 6,635,656 B1 | 10/2003 | Kashman et al. |
| 6,656,948 B2 | 12/2003 | Puentes et al. |
| 6,686,470 B2 | 2/2004 | Danishefsky et al. |
| 6,710,029 B1 | 3/2004 | Rinehart et al. |
| 6,712,023 B2 | 3/2004 | Targotay et al. |
| 6,800,661 B1 | 10/2004 | Rinehart et al. |
| 6,812,245 B2 | 11/2004 | Canedo et al. |
| 6,841,530 B2 | 1/2005 | Rinehart et al. |
| 6,852,715 B1 | 2/2005 | Gravalos et al. |
| 6,864,283 B2 | 3/2005 | Higa et al. |
| 6,867,334 B2 | 3/2005 | Rinehart et al. |
| RE38,793 E | 9/2005 | Rinehart et al. |
| 7,064,105 B2 | 6/2006 | Joullie et al. |
| 7,109,244 B2 | 9/2006 | Rinehart et al. |
| 7,115,743 B2 | 10/2006 | Rinehart et al. |
| 7,122,519 B2 | 10/2006 | Joullie et al. |
| 7,135,494 B2 | 11/2006 | Munro et al. |
| 7,138,547 B2 | 11/2006 | Acena et al. |
| 7,153,885 B2 | 12/2006 | Duran et al. |
| RE39,496 E | 2/2007 | Scheuer |
| 7,202,361 B2 | 4/2007 | Flores et al. |
| 7,241,892 B1 | 7/2007 | Cuevas et al. |
| 7,247,629 B2 | 7/2007 | Manzanares et al. |
| RE39,887 E | 10/2007 | Rinehart |
| 7,309,601 B2 | 12/2007 | Esteban et al. |
| 7,320,981 B2 | 1/2008 | Morris et al. |
| 7,323,444 B2 | 1/2008 | Delso |
| 7,329,666 B2 | 2/2008 | Alvarez et al. |
| 7,348,310 B2 | 3/2008 | Rodriguez et al. |
| 7,348,311 B2 | 3/2008 | Rinehart et al. |
| 7,381,703 B2 | 6/2008 | Bertino et al. |
| 7,396,837 B2 | 7/2008 | Bailly et al. |
| 7,410,969 B2 | 8/2008 | Manzanares |
| 7,420,051 B2 | 9/2008 | Francesch et al. |
| 7,446,094 B2 | 11/2008 | Romero et al. |
| 7,473,681 B2 | 1/2009 | Faircloth et al. |
| 7,482,429 B2 | 1/2009 | Albericio et al. |
| 7,495,000 B2 | 2/2009 | Remuiñan et al. |
| 7,507,708 B2 | 3/2009 | Faircloth et al. |
| 7,507,766 B2 | 3/2009 | Lazaro et al. |
| 7,521,478 B2 | 4/2009 | del Pozo Losada et al. |
| 7,524,956 B2 | 4/2009 | Cuevas et al. |
| 7,531,506 B2 | 5/2009 | Palomera et al. |
| 7,548,060 B2 | 6/2009 | Herrmann et al. |
| 7,576,188 B2 | 8/2009 | Bertino et al. |
| 7,622,458 B2 | 11/2009 | Rybak |
| 7,651,997 B2 | 1/2010 | Joullie et al. |
| 7,662,387 B2 | 2/2010 | Law et al. |
| 7,678,765 B2 | 3/2010 | Rodriguez et al. |
| 7,683,028 B2 | 3/2010 | Faircloth et al. |
| 7,723,068 B2 | 5/2010 | Iglesias et al. |
| 7,737,114 B2 | 6/2010 | Joullie et al. |
| 7,759,345 B2 | 7/2010 | Martinez et al. |
| 7,763,615 B2 | 7/2010 | Gallego et al. |
| 7,767,659 B2 | 8/2010 | Barrasa et al. |
| 7,772,241 B2 | 8/2010 | Remuinan et al. |
| 7,795,260 B2 | 9/2010 | Barrasa et al. |
| 7,919,493 B2 | 4/2011 | Flores et al. |
| 7,947,671 B2 | 5/2011 | Barrasa et al. |
| 8,012,975 B2 | 9/2011 | Manzanares et al. |
| 8,076,337 B2 | 12/2011 | Martinez et al. |
| 8,119,638 B2 | 2/2012 | Cvitkovich et al. |
| 8,188,312 B2 | 5/2012 | de Fonseca et al. |
| 8,258,098 B2 | 9/2012 | Faircloth et al. |
| 8,324,406 B2 | 12/2012 | Lopez et al. |
| 8,420,130 B1 | 4/2013 | Nuijen et al. |
| 8,435,992 B2 | 5/2013 | Ocio et al. |
| 8,501,968 B2 | 8/2013 | Lopez et al. |
| 8,710,264 B2 | 4/2014 | Vincente et al. |
| 8,748,388 B2 | 6/2014 | Tulla-Puche et al. |
| 8,895,557 B2 | 11/2014 | Beijnen et al. |
| 8,962,602 B2 | 2/2015 | Fernéndez Rodríguez et al. |
| 9,187,445 B2 | 11/2015 | Vicente et al. |
| 9,192,568 B2 | 11/2015 | Calvo Salve et al. |
| 9,428,524 B2 * | 8/2016 | Martin Lopez ...... C07D 515/22 |
| 9,827,257 B2 | 11/2017 | Vicente et al. |
| 2001/0039041 A1 | 11/2001 | Faircloth et al. |
| 2002/0143038 A1 | 10/2002 | Bandyopadhyay et al. |
| 2002/0198379 A1 | 12/2002 | Kinnel et al. |
| 2003/0187075 A1 | 10/2003 | Junichi et al. |
| 2003/0216397 A1 | 11/2003 | Flores et al. |
| 2004/0002602 A1 | 1/2004 | Francesch et al. |
| 2004/0010043 A1 | 1/2004 | Lazaro et al. |
| 2004/0019027 A1 | 1/2004 | Forman et al. |
| 2004/0019056 A1 | 1/2004 | Manzanares et al. |
| 2004/0033940 A1 | 2/2004 | Bowden et al. |
| 2004/0067895 A1 | 4/2004 | Faircloth et al. |
| 2004/0108086 A1 | 6/2004 | Takahashi et al. |
| 2004/0115685 A1 | 6/2004 | Tercero et al. |
| 2005/0004012 A1 | 1/2005 | Mangues et al. |
| 2005/0004018 A1 | 1/2005 | Jimeno et al. |
| 2005/0054555 A1 | 3/2005 | Jimeno et al. |
| 2005/0272727 A1 | 12/2005 | Dong et al. |
| 2006/0019256 A1 | 1/2006 | Clarke et al. |
| 2006/0030571 A1 | 2/2006 | Rinehart et al. |
| 2006/0178298 A1 | 10/2006 | Bertino et al. |
| 2006/0287529 A1 | 12/2006 | Alvarez et al. |
| 2007/0004691 A1 | 1/2007 | Donald et al. |
| 2007/0082856 A1 | 4/2007 | Gianni et al. |
| 2007/0117743 A1 | 5/2007 | Palomera et al. |
| 2007/0128201 A1 | 6/2007 | D'Incalci et al. |
| 2007/0149446 A1 | 6/2007 | Joullie et al. |
| 2007/0207948 A1 | 9/2007 | Solloso et al. |
| 2007/0275942 A1 | 11/2007 | Cvitkovich et al. |
| 2008/0076772 A1 | 3/2008 | Allavena et al. |
| 2008/0090757 A1 | 4/2008 | Delso et al. |
| 2008/0234279 A1 | 9/2008 | Rinehart et al. |
| 2008/0234363 A1 | 9/2008 | Reyes Benitez et al. |
| 2008/0242670 A2 | 10/2008 | Allavena et al. |
| 2008/0255132 A1 | 10/2008 | Rowinsky et al. |
| 2008/0269511 A2 | 10/2008 | Losada et al. |
| 2008/0293725 A1 | 11/2008 | Rosell Costa et al. |
| 2008/0318849 A1 | 12/2008 | Albericio et al. |
| 2009/0030068 A1 | 1/2009 | Martin Lopez et al. |

(56) References Cited

U.S. PATENT DOCUMENTS

| | | | |
|---|---|---|---|
| 2009/0117176 A1 | 5/2009 | Gilles et al. | |
| 2009/0124647 A1 | 5/2009 | Benitez et al. | |
| 2009/0130675 A1 | 5/2009 | Castro et al. | |
| 2009/0170860 A1 | 7/2009 | Scotto et al. | |
| 2009/0186938 A1 | 7/2009 | Martin Lopez et al. | |
| 2009/0227490 A1 | 9/2009 | Bertino et al. | |
| 2009/0246168 A1 | 10/2009 | Faircloth et al. | |
| 2009/0247533 A1 | 10/2009 | Rinehart et al. | |
| 2009/0298752 A1 | 12/2009 | Faircloth et al. | |
| 2009/0324744 A1 | 12/2009 | Takahashi et al. | |
| 2010/0009906 A1 | 1/2010 | Elsayed | |
| 2010/0041594 A1 | 2/2010 | Mangues et al. | |
| 2010/0216817 A1 | 8/2010 | Benitez et al. | |
| 2010/0226919 A1 | 9/2010 | Pérez-Soler et al. | |
| 2010/0240595 A1 | 9/2010 | Sorbello et al. | |
| 2010/0267732 A1 | 10/2010 | Rosell Costa et al. | |
| 2010/0280108 A1 | 11/2010 | Rodriguez Vicente et al. | |
| 2010/0323021 A1 | 12/2010 | Hosta et al. | |
| 2011/0009335 A1 | 1/2011 | LePage et al. | |
| 2011/0015135 A1 | 1/2011 | Cajal Agüeras et al. | |
| 2011/0070232 A1 | 3/2011 | LePage et al. | |
| 2011/0105409 A1 | 5/2011 | Acebes et al. | |
| 2011/0118343 A1 | 5/2011 | Reyes Benítez et al. | |
| 2011/0237520 A1 | 9/2011 | Coello Molinero et al. | |
| 2012/0107417 A1 | 5/2012 | Takahashi et al. | |
| 2013/0266666 A1 | 10/2013 | Moneo Ocaña et al. | |
| 2015/0094313 A1 | 4/2015 | Beijnen et al. | |
| 2016/0129128 A1 | 5/2016 | Cuevas Marchante et al. | |

FOREIGN PATENT DOCUMENTS

| | | |
|---|---|---|
| EP | 0048149 | 3/1982 |
| EP | 0111105 | 6/1984 |
| EP | 0309477 | 4/1989 |
| EP | 0358418 | 3/1990 |
| EP | 0381514 | 8/1990 |
| EP | 0393883 | 10/1990 |
| EP | 0399685 | 11/1990 |
| EP | 0559838 | 9/1993 |
| EP | 0572109 | 12/1993 |
| EP | 0610076 | 8/1994 |
| EP | 0610078 | 8/1994 |
| EP | 0626383 | 11/1994 |
| EP | 0711765 | 5/1996 |
| EP | 0813531 | 12/1997 |
| EP | 0821068 | 1/1998 |
| EP | 0894092 | 2/1999 |
| EP | 1054686 | 11/2000 |
| EP | 1069894 | 1/2001 |
| EP | 1070067 | 1/2001 |
| EP | 1176964 | 2/2002 |
| EP | 1185536 | 3/2002 |
| EP | 1189908 | 3/2002 |
| EP | 1280809 | 2/2003 |
| EP | 1286990 | 3/2003 |
| EP | 1287004 | 3/2003 |
| EP | 1289999 | 3/2003 |
| EP | 1294747 | 3/2003 |
| EP | 1330254 | 7/2003 |
| EP | 1406907 | 4/2004 |
| EP | 1496060 | 1/2005 |
| EP | 1532139 | 5/2005 |
| EP | 1572726 | 9/2005 |
| EP | 1702618 | 9/2006 |
| EP | 1716853 | 11/2006 |
| EP | 1827500 | 9/2007 |
| EP | 1864682 | 12/2007 |
| EP | 2029155 | 3/2009 |
| EP | 2032551 | 3/2009 |
| EP | 2231590 | 9/2010 |
| EP | 2231633 | 9/2010 |
| EP | 2270018 | 1/2011 |
| EP | 2305689 | 4/2011 |
| EP | 2597091 | 5/2013 |
| EP | 3395821 | 10/2018 |
| ES | 2102322 | 7/1997 |
| JP | S59225189 | 12/1984 |
| JP | S61109717 | 5/1986 |
| JP | H05-039283 | 2/1993 |
| JP | H05247055 | 9/1993 |
| JP | 5922518 | 5/2016 |
| JP | 6084288 | 2/2017 |
| WO | WO 8604062 | 7/1986 |
| WO | WO 8704709 | 8/1987 |
| WO | WO 8707610 | 12/1987 |
| WO | WO 9005731 | 5/1990 |
| WO | WO 9104985 | 4/1991 |
| WO | WO 9209607 | 6/1992 |
| WO | WO 9300362 | 1/1993 |
| WO | WO 9404541 | 3/1994 |
| WO | WO 9618404 | 6/1996 |
| WO | WO 9812198 | 3/1998 |
| WO | WO 9817275 | 4/1998 |
| WO | WO 9817302 | 4/1998 |
| WO | WO 9846080 | 10/1998 |
| WO | WO 9942125 | 8/1999 |
| WO | WO 9958125 | 11/1999 |
| WO | WO 2000/018233 | 4/2000 |
| WO | WO 2000/020411 | 4/2000 |
| WO | WO 2000/069441 | 11/2000 |
| WO | WO 2000/069862 | 11/2000 |
| WO | WO 2001/035974 | 5/2001 |
| WO | WO 2001/058934 | 6/2001 |
| WO | WO 2001/076616 | 10/2001 |
| WO | WO 2001/077115 | 10/2001 |
| WO | WO 2001/087894 | 11/2001 |
| WO | WO 2001/087895 | 11/2001 |
| WO | WO 2002/002596 | 1/2002 |
| WO | WO 2002/005868 | 1/2002 |
| WO | WO 2002/030441 | 4/2002 |
| WO | WO 2002/036135 | 5/2002 |
| WO | WO 2002/058688 | 8/2002 |
| WO | WO 2002/064843 | 8/2002 |
| WO | WO 2003/008423 | 1/2003 |
| WO | WO 2003/014127 | 2/2003 |
| WO | WO 2003/033012 | 4/2003 |
| WO | WO 2003033013 | 4/2003 |
| WO | WO 2003/039571 | 5/2003 |
| WO | WO 2003/070234 | 8/2003 |
| WO | WO 2004010957 | 2/2004 |
| WO | WO 2004073598 | 9/2004 |
| WO | WO 2004080421 | 9/2004 |
| WO | WO 2004080477 | 9/2004 |
| WO | WO 2005014574 | 2/2005 |
| WO | WO 2005037992 | 4/2005 |
| WO | WO 2005049029 | 6/2005 |
| WO | WO 2005117894 | 12/2005 |
| WO | WO 2005118584 | 12/2005 |
| WO | WO 2006046079 | 5/2006 |
| WO | WO 2006060533 | 6/2006 |
| WO | WO 2006066183 | 6/2006 |
| WO | WO 2007052076 | 5/2007 |
| WO | WO 2007101235 | 9/2007 |
| WO | WO 2007144423 | 12/2007 |
| WO | WO 2009080761 | 7/2009 |
| WO | WO 2009143313 | 11/2009 |
| WO | WO 2010009124 | 1/2010 |
| WO | WO 2010149688 | 12/2010 |
| WO | WO 2011147828 | 12/2011 |
| WO | WO 2012062920 | 5/2012 |
| WO | WO 2014191578 | 12/2014 |
| WO | WO 2018197663 | 11/2018 |

OTHER PUBLICATIONS

Kubo, A.; Saito, N.; Kitahara, Y.; Takahashi, K.; Tazawa, K.; Arai, T. Chem Pharm. Bull. 1987, 35, 440-442.

Kuhnt M et al, Microbial Conversion Products of Leptomycin B, Applied and Environmental Microbiology, 1998, pp. 714-720.

Kunze B et al. J. Antibiot., 1994, vol. 47, 881-886.

Kupchan, S.M.; Britton, R. W.; Ziegler, M.F.; Sigel, C.W. J. Org. Chem. 1973, 38, 178-179.

L.S. Thurston et al., Antitumor Agents. 100. Inhibition of Human DNA Topoisomerase II by Cytotoxic Ether and Ester Derivatives of

(56) References Cited

OTHER PUBLICATIONS

Podophyllotoxin and alpha-Peltatin, Journal of Medicinal Chemistry, Washington US, vol. 32, No. 3, 1989.
Labadie J W et al. J. Org. Chem., 1983, vol. 48,4634-4642.
Lacerda J.F. et al., Blood, (1995), vol. 85, No. 10, pp. 2675-2679.
Laverdiere Caroline et al, Phase II study of ecteinascidin 743 in heavily pretreated patients with recurrent osterosarcoma American Cancer Society, vol. 98, No. 4, 832-840, 2003.
Leal JFM et. al. British J. Pharmacol. 2010, 161, 1099-1110.
Louis Rey et al Freeze Drying Lyphilization of Pharmaceutical and Biological Products Chapter 5 p. 150 2004 Edition.
Lown et al. Biochemistry, 1982, vol. 21, 419-428.
Lown, J. W.; Hanstock, C. C.; Joshua, A. V.; Arai, T; Takahashi, K. J. Antibiot. 1983, 36, 1184-1194.
Luber-Narod J et al, Evaluation of the use of in vitro methodologies as tools for screening new compounds for potential in vivo toxicity., Toxicology In Vitro, vol. 15, No. 4-5, ISSN 0887-2333, pp. 571-577, 2001.
M. Albericci et al., Chemical Studies of Marine Invertebrates-XLV, Tetrahedron, (Incl. Tetrahedron Reports), Oxford GB, (1982), vol. 38, No. 13, pp. 1881-1890.
Mackay and Hall, J. Biol. Chem., 273, 20685-20688, 1998).
Manzanares I. et al. Org. Lett., 2000, vol. 2 (16),2545-2548.
Marayama, W.; Kobayashi, T.; Kosuge, Y.; Yano, H.; Nunogaki, Y.; Nunogake, K. J. Chromatogr. 1982, 239,643-649.
Martinez E J et al., Phtalascidin, A synthetic antitumor agent with potency and Mode Ofaction Compatable to exteinmascidin 743 Proceedings of the national acadmemy of science, Washington, US, vol. 96, No. 7, Mar. 1999 p. 3496-3501.
Merrill, A.H., Jr. J. Bioenerg. Biomem. 1991, 23, 83-104.
Merrill, A.H., Jr.; Nimkar, S.; Menaldino, D.; Hannun, Y.A.; Loomis, C.; Bell, R.M., Tyagi, S.R.; Lambeth, J.D.;Stevens, V.L.; Hunter, R.; Liotta, D.C. Biochemistry 1989, 28, 3138-3145.
Mikami, Y.; Takahashi, K; Yazawa, K.; Hour-Young, C.; Arai, T.; Saito, N.; Kubo, A. J. Antibiot. 1988, 41,734-740.
Mitsiades C.S. et al, Blood, 2001, vol. 98, 795-804.
Mitsiades C.S. et al,Oncogene, 2002, vol. 21, 5673-5683.
Mitsiades N et.al. Blood., 2003, vol. 101,2377-2380.
Mitsiades N et.al. Proc Natl Acad Sci USA, 2002, vol. 99, 14374-14379.
Mitsiades N. et al, Blood, 2003, vol. 101, 4055-4062.
Modeling Oppurtunities in Comparative Oncology for Drug Devlopment, I.Gordon et al., ILAR Journal, p. 214-221. 2010.
Montgomery, D.W., Zukoski, C.F., Transplantation, vol. 40 p. 49-56, 1985.
Mosmann et al. Journal of Immunological. Methods, 1983, vol. 65 (1-2), 55-63.
Murata, M.; Legrand, A.M.; Ishibashi, Y.; Fukani, M.; Yasumoto, T. J. Am. Chem. Soc. 1990, 112, 4380-4386.
Nakagawa et al. J. Amer. Chem. Soc., 1989, vol. 111, 2721-2722.
Nakamura, H. et al. Tetrahedron Lett. 1984, 25, 2989-2992.
Nishizuka, Y., Nature 308 693-698, 1984.
Nishizuka, Y., Nature 334 661-665, 1988.
Nuijen B et al, Development of a lyophilized parenteral pharmaceutical formulation of the investigational polypeptide marine anticancer agent kahalalide F, Medline, 27:8 p. 767-780, 2001.
Nuijen et al Drug Development and Industrial Pharmacy vol. 27 767-780 (2001).
O. Buchardt et al., Journal of Pharmaceutical Sciences vol. 75, No. 11, 1986.
Oku, N., et al., Journal Natural Products, 2003, vol. 66, 1136-9.
Org. Chem., 1989, 54,4256).
Org.Lett., 2002, vol. 4, 2853.
Organic Syntheses, vol. 48, 32, 1868.
Osby, J.O.; Martin, M.G.; Ganem, B. Tetrahedron Lett. 1984, 25, 2093-2096.
P.Cironi et al, Organic Letters, vol. 5, No. 16, 2003, p. 2959-2962.
Pansare, S.V. ; Gnana R.R. J. Org. Chem., 1998, vol. 63, 4120-4124.
Pera et. al,ACS Chemical Biology 2013, 8, 2084-2094.
Perry, N.B. J. Nat. Prod. 1987, 50, 290-292.
Zips et.al. In vivo, 2005, 19 1-7.
Zmijewski et al., Chem. Biol. Interactions, (1985), vol. 52, pp. 361-375.
Blunt, J.W. et al., "Reverse Phase Flash Chromatography: A Method for the Rapid Partitioning of Natural Product Extracts," vol. 50, No. 2, pp. 290-292, Apr. 1987.
Perry, N.B.; Blunt, J.W.; Munro, M.H.G.; Higa, T.; Sakai, R. J. Org. Chem. 1988, 53, 4127-4128.
Pettit, G.R. et al Can. J. Chem. 1990, 68,1621-1624.
Pettit, G.R.; Gao, F.; Herald, D.L.; Blumberg, P.M.; Lewin, N.E.; Neiman, R.A. J. Am Chem. Soc. 1991, 113,6693-6695.
Pettit, G.R.; Gao, F.; Sengupta, D.; Coll, J.C.; Herald, C.L.; Doubek, D.L.; Schmidt, J.M.; Van Camp, J.R.; Rudloe,J.J.; Nieman, R.A. Tetrahedron 1991, 47, 3601-3610.
Pettit, G.R.; Herald, C. L.; Doubek, D. L.; Herald, D. L., Arnold, E.; Clardy, J. J. Am. Chem. Soc. 1982, 104.
Pharmaceutical Chemistry Journal, 2006, vol. 40 (7), 367-372.
Pharmacokinetics of Pegylated Liposomal Doxorubicin, Alberto Gabisozn et al, Clin.Pharmacokinetics, 2003 42 (5).
Pla D et al. J. Org. Chem., 2005, vol. 70, 8231.
Pommier et al. Biochemistry, 1996, vol. 35, 13303-13309.
Potent Antitumor Agents From the Caribbean Tunicate Ecteinascidia Turbinata, vol. 55, pp. 4512-4515,1990.
Pozdnev, V. F. Tetrahedron Letters, 1995, vol. 36,7115-7118.
Proc. Natl. Acad. Sci. USA. vol. 96, pp. 3496-3501, 1999.
Proc. Natl.Acad. Sci. USA, vol. 89, No. 23, pp. 11456-11460, 1999.
Puchalski T.A. et al, Cancer chemotherapy Pharmacol, 2002, vol. 50, 309.
Pure and Applied Chemistry vol. 58, No. 5, 1986, Oxford GB pp. 701-710 Yoshimasa Hirata et al Halichodrins-antitumor polyether macrolides from a marine sponge.
Pure Appl. Chem., 1990, 62, 1277-1280.
R Sakai et al., Structure-activity relationship of didemnins, Journal of Medicinal Chemistry., (1996), vol. 39, No. 14, pp. 2819-2834.
R. Cooper, S. Unger. The Journal of Antibiotics. vol. XXXVIII, N°1, 1985.
R.B. Kinnel et al., Palau'amine A Cytotoxic and Immunosuppressive Hexacyclic Bisguanidien Antibiotic from the Sponge Stylotella agminata, J. Am. Chem. Soc., (1993), vol. 115, No. 8, pp. 3376-3377.
Raub, M.F., Cardellina, J.H., II; Choudhary, M.I.; Ni, C.-Z.; Clardy, J.; Alley, M. C. J. Am. Chem. Soc. 1991, 113,3178-3180.
Raymond J. Bergeron et al. Biochem.Bioph. Res. Comm. 1984, 121 (3), 848-854.
Rimassa et al, Breast Cancer Research and Treatment, 77, 185-188, 2003.
Rinehart et al. Bioactive Compounds from Aquatic and Terrestrial Sources. Journal of National Products,1990, vol. 53, 771-792.
Rinehart et al. Biologically active natural products. Pure and Appl. Chem., 1990, vol. 62, 1277-1280.
Rinehart et al. J. Med. Chem., 1996, vol. 39, 2819-2834.
Rinehart et al., Biochemistry, 23, 3290-3297, (1984)).
Rinehart et.al. Total Synthesis of Didemnins A, B, C J.Am.Chem. Soc. vol. 109, p. 6846-6848, 1987.
Rinehart, Jr. et al. J. Am. Chem. Soc, 1981, vol. 103, 1857-59.
Rinehart, Jr. et.al., Pure and Appl. Chem., vol. 54, pp. 2409-2424, 1982.
Rinehart, K.L.; Kishore, V. Bible, K.C.; Sakai, R.; Sullins, D.W.; Li, K.-M. J. Nat. Prod 1988, 51, 1-21.
Ryan D.P. et al, Clinical Cancer Research, 2001, vol. 7, 231.
Ryan et al A Phase II and Pharmacokinetic Study of Ecteinascidin 743 in Patients with Gastrointestinal Stromal Tumors the Oncologist Dec. 2002 vol. 7 No. 6 531-538.
Ryuichi et al J Amm Chem Soc, vol. 118, p. 9017-9023, 1996.
S.D.Rychnovsky et al., J.Org.Chem., 1993, vol. 58, 3511-3515.
S.P. Forsey et al., Comprehensive Synthetic Route to Eight Diastereomeric Podophyllum Lignans, Journal of Organic Chemistry vol. 54, No. 18, p. 4280-4290, 1989.
Saito et al., Synthesis of Saframycins. Preparation of a Key tricyclic Lactam Intermediate to Saframycin A, J. Org. Chem., (1989), vol. 54, p. 5391.

(56) References Cited

OTHER PUBLICATIONS

Sakai et al. Additional antitumor ecteinascidins from a Caribbean tunicate Crystal structures and activities in vivo. Proc. Natl. Acad. Sci. USA, 1992, vol. 89,11456-11460.
Sakai, R.; Kohmoto, S.; Higa, T.; Jefford, C.W.; Bernardinelli, G. Tetrahedron Lett. 1987, 28, 5493-5496.
Sakemi, S.; Higa, T.; Anthoni, U.; Christophersen, C. Tetrahedron 1987, 43, 263-268.
Sakemi, S.; Ichiba, T.; Kohomoto, S.; Saucy, G.; Higa, T. J. Am Chem. Soc. 1988, 110, 4851-4853.
Sakemi, S.; Sun, H.H. J. Org. Chem. 1991, 56, 4304-4307.
Sakemi, S.; Sun, H.H.; Jefford, C.W.; Bernardinelli, G. Tetrahedron Lett. 1989, 30, 2517-2520.
Sakemi, S.; Totton, L.E.; Sun, H.H. J. Nat. Prod. 1990, 53, 995-999.
San Miguel JF et al., Curr. Treat. Options Oncol., (2003), vol. 4, pp. 247-258.
Schaufelberger, B.W.; Muschik, G.M. J. Org. Chem. 1991,56,2895-2900.
Scheuer P.J. et al., A new depsipeptide from the sacoglossan mollusk *Elysisa ornata* and the green alga Bryopsis species J.Nat.Prod., 2000, vol. 63(1),152-4.
Scheuer P.J. et al., Two acyclic kahalidades from the sacoglossan mollusk *elysis rufescens*, J.Nat.Prod., 1997, vol. 60, 562-567.
Schiff PB et al. Nature, 1979, vol. 277, 665-667.
Schmidt et.al. Total Synthesis of Didemnins-2 . . . Tetrahedron Letters, vol. 29, p. 4407-4408, 1988.
Schmitz, F. J.; Vanderah, D.J.; Hollenbeak, K.H.; Enwall, C.E.L.; Gopichand, Y.;SenGupta, P.K.; Hossain, M.B.; van der Helm, D.J. Org. Chem. 1983, 48, 3941-3945.
Schmitz, F.J.; DeGuzman, F.S.; Choi, Y.-H.; Hossain, M.B.; Rizvi, S.K.; van der Helm, D. Pure & Appl. Chem. 1990,62, 1393-1396.
Schmitz, F.J.; DeGuzman, F.S.; Hossain, M.B.; van der Helm, D. J. Org. Chem., 1991, 56, 804-808.
Schroeder 5 et al.. Effects of Acyclic Pyrimidine Nucleoside Analogues J. Med. Chem. 1981 ,24 1078-1083.
Scott WJ et al. J. Am. Chem. Soc., 1984, vol. 106, 4630.
Seebach et.al. Alkylation of Amino Acids Without Loss of Optical Activity . . . J.Am.Chem.Soc, vol. 105, No. 16, p. 5390-5398, 1983.
Sessa C et al, Trabectedin for Women with ovarian carcinoma after treatment with platinum and taxane fails, Journal of Clinical Oncology, vol. 23, No. 9, 2005.
Shimojima,H.Hayashi, 1H-2-Benzopyran-1-One Derivatives,Microbial Products With Pharmacol. Activity., Journal of Medicinal Chemistry, (1983), vol. 26, No. 10, p. 1370-1374.
Shirling B.E., and Gotlieb D., Int. J. Syst. Bacteriol. 16 313-340, 1966.
Sirohi B. et al., Lancet, (2004), vol. 363, pp. 875-887.
Skubitz, K.K. Cancer Investigation 2003, 21(2), 167-176.
Smith, Barry C. et al, Phytoplankton pigments accumulated by the Arctic surf clam, Mactromeris polynyma (Stimpson, 1860., Journal of Shellfish Research, (1992) vol. 11, No. 2, pp. 479-483.
Stierle, A.A.; Cardellina, J.H., II; Singelton, F.L. Tetrahedron Lett. 1991, 32, 4847-4848.
Stierle, A.C.; Cardellina, J.H., II; Strobel, G.A. Proc. Natl. Acad Sci. USA 1988, 85, 8008-8011.
Stierle, D.B.; Faulkner, D.J. J. Nat. Prod. 1991, 54, 1134-1136.
Still et al. Rapid Chromatographic Technique for Preparative Separations with Moderate Resolution.J. Org. Chem., 1978, vol. 43, 2923.
Stoffel, W. Ann. Rev. Biochem. 1971, 40, 57-82.
Sun, H. H. Cross, S. S.Gunasekera, M.; Koehn, F.E. Tetrahedron 1991, 47, 1185-1190.
Sun, H.H., Sakemi, S. J. Org. Chem. 1991, 56,4307-4308.
Sun, H.H.; Sakemi, S.; Burres, N.; McCarthy, P.J. Org. Chem. 1990, 55, 4964-4966.
T. K. Chakraborty et al, Total Synthesis of (+)-Crocacin D, Tetrahedron Lett., 2002, 43, pp. 2645-2648.
T. Terada et al., DNA Topomerase II Inhibitory Activity and the Structural Relationship of Podophyllotoxin Derivatives as Antitumor Agents, Chemical and Pharmaceutical Bulletin, vol. 40, No. 10, p. 2720-2727, 1992.
Takahashi N. et al, Sequence dependent enhancement of cytotoxicity produced by ecteinascidin 743 with doxorubicin or paclitaxel in soft tissue sarcoma cells Clinical Cancer Research, vol. 7, No. 10, 2001.
Takahashi, K.; Yazawa, K.; Kishi, K.; Mikami, Y.; Arai, T.; Kubo, A. J Antibiot. 1982. 35. 196-201.
Takeuchi, R. ; Tanabe, K. ; Tanaka, S. J. Org. Chem., 2000, vol. 65, 1558-1561.
Taylor, R.E.; Ciavarri, J.C.; Hearn, B.R., A Divergent Approach the Myriapoprones and Tedanolide Enantioselective Preparation of the Common Intermediate. Tetrahedron Lett.,1998, vol. 39, 9361.
Ter Haar E et al. Biochemistry, 1996, vol. 35,243-250.
Tetrahedron Asymmetry, vol. 19, pp. 500-511 (2008).
Tetrahedron, 1988, 44, 451.
Tetrahedron, 1992, 48, 341.
The Oncologist. 2002, 7 210-216.
Thoru Fukuyama et al., Stereocontrolled Total Synthesis of Saframycic B, J.Am.Chem.Soc., (1982), vol. 104, pp. 4957-4958.
Uchiyama H. et al, Blood., 1993, vol. 82, 3712-3720.
Urdiales et.al., Antiproliferative Effect of Dehydrodidemnin B Cancer Letters, vol. 102, Nos. 1 ,2 pp. 31-37, 1996.
Valoti G et al, Ecteinascidin-743, A New Marine Natural Product With Potent Antitumor Activity on Human Ovarian Carcinoma Xenografts, Clinical Cancer Research, vol. 4, No. 8, p. 1977-1983, 1998.
Van der Auwera P., Labbe M., MayberryW.R., Ferguson K.P., and Lambe D.W.Jr., J. Microbiol. Methods 4 265-275,1986.
Vervoort H, Fenical W, Epifanio RA. Tamandarins A and B new cytotoxic depsipeptides from a Brazilian ascidian of the family Didemnidae. J Org Chem. Feb. 11, 2000;65(3) 782-92.
W. Porter. Antineoplastic and antiherpetic activity of spermidine catecholamide iron chelators. Biochem. Bioph. vol. 121, No. 3, p. 848-854, 1984.
W.R. Roush et al, Org.Lett., 1999, vol. 1,95.
Whelan P The medical treatment of metastatic renal cell cancer EAU Update Series, vol. 1, No. 4, 2003, p. 237-246.
Wipf P, Synthetic Studies of Biologically Active Marine Cyclopeptides, Chemical Reviews, vol. 95, No. 6, pp. 2115-2134 (1995).
Wirth, D.D., et al., Maillard reaction of lactose and fluoxetine hydrochloride, a secondary amine, J. Pharm. Sci. 1998 87(1) pp. 31-39.
Witten, J.L.; Schaffer, M.H.; O'Shea, M.; Cook, J.C.; Hemling, M.E.; Rinehart, K.L., Jr. Biochem. Biophys. Res.Commun. 1984, 124, 350-358.
Wright et al. Antitumor Tetrahydroisoquinoline from the Colonial Ascidian Ecteinascidia turbinata. Alkaloids,J. Org. Chem., 1990, vol. 55, 4508-4512.
Y. Ikeda et al. The Journal of Antibiotics. vol. XXXVI, N°10, 1284, 1983.
Yazawa, K.; Asaoka, T.; Takahashi, K.; Mikami, Y.; Arai, T. J. Antibiot. 1982, 35, 915-917.
Yosief T et al, Asmarines A-C;three novel cytotoxic metabolites from the marine sponge *Raspailia sp.*, Tetrahedron Lett.; 1998; vol. 39 (20); pp. 3323-3326.
PharmaMar Infograph published on Apr. 24, 2018 in Spanish.
PharmaMar Infograph published on Apr. 24, 2018, English translation.
PharmaMar press release of Sep. 2017.
100th AACR Annual Meeting, Apr. 18-22, 2009, Denver, CO Abstract Nr. 4525.
100th AACR Annual Meeting, Apr. 18-22, 2009, Denver, CO, Abstract Nr. 2679.
26th EORTC-NCI-AACR Symposium on Molecular Targets and Cancer Therapeutics; Nov. 18-21, 2014, Barcelona, Spain, published in Eur. J. Cancer 2014, 50 (Suppl. 6), pp. 13-14, Abs. No. 23.
39th ESMO Congress, Sep. 26-30, 2014, Madrid, Spain, published in Ann. Oncol, 2014, 25(Suppl. 4), p. 146 Abs No. 482P.
50th ASCO Annual Meeting, May 30-Jun. 3, 2014, Chicago, IL, Abstract 5505.

(56) References Cited

OTHER PUBLICATIONS

51th ASCO Annual Meeting, May 29-Jun. 2, 2015, Chicago, IL, Abstract Nr. 7509.
51th ASCO Annual Meeting, May 29-Jun. 2, 2015, Chicago, IL, Abstract Nr. TPS26048.
A. Furstner et al, A new Titanium Mediated Approach to pyrroles First Synthesis of Lukianol A and Lamerilarin O Dimethyl Ether, Journal of organic chemistry, vol. 60, No. 20, 1995, p. 6637-6641.
A.Alexopoilos et al., Annals of Oncology 15 891-895, 2004.
Agric. Biol. Chem. 46(5) 1255-1259, 1982.
Alai, F.Q.; Liu, X.X.; McLaughlin, J.L. J.Nat. Prod 1999, 62, 504-540.
Alan C. Schroeder, Robert G. Hughes, Jr. and Alexander Bloch. Effects of Acyclic Pyrimidine NucleosideAnaloges. J. Med. Chem. 1991, 24 1078-1083.
Albericio, F. et al., Kahalide B. Synthesis of a natural cycldeosioeptide, Tetrahedron Letters, 2000, vol. 41, 9765-9769.
Andya et al Mechanisms of aggregate formation and carbohydrate excipient stabilization.. American Assoc of Pharm Sci 5(2) 21-31 (2003).
Annals of Oncology 10, 1113-1116 (1999).
Annals of oncology 13, 1737-1742 (2002).
Annals of oncology 15(3),440-449 (2004).
Annals of Oncology, 9, 981-987, 1998.
Arai, T.; Takahashi, K.; Ishiguro, K.; Yazawa, K. J. Antibiot. 1980, 33, 951-960.
Arai, T.; Yazawa, K.; Takahashi, K.; Maeda, A.; Mikami, Y. Antimicrob, Agent Chemother. 1985, 28, 5-11.
Arai, T; Takahashi, K; Kubo, A. J. Antibiot, 1977, 30, 1015-1018.
Asaoka, T.; Yazawa, K.; Mikami, Y. Arai, T.; Takahashi, K. J. Antibiot. 1982, 35, 1708-1710.
B Kunze et al, Crocacin, a New Electron Transport Inhibitor from Chondromyces crocatus (Myxobacteria), J. Antibiot., 1994.
Becerra et al. Chemical defenses of the sarcoglossan mollusk *Elysia rufescens* and its host Alga bryopsis sp. J.Chem. Ecol., 2001, vol. 27 (11), 2287-99.
Bergeron et al (Antineoplastic an antiherpetic activity of spermidine catecholamide iron chelators Biochem. Bioph. Res. Comm. 1984, 121(3), 848-854.
Bergmann, W.; Burke, D.C. J. Org, Chem. 1955, 20, 1501-1507.
Bergmann, W.; Burke, D.C. J. Org. Chern. 1956, 21, 226-228.
Bergmann, W.; Stempien, M.F., Jr. J. Org. Chem. 1957, 22, 1575-1577.
Berlinck, R.G.S.; Braekman, J.C.; Daloze, D.; Hallenga, K; Ottinger, R.; Bruno, I.; Riccio, R Tetrahedron Lett. 1990,31, 6531-6534.
Bobzin, S.C.; Faulkner, D. J J. Org. Chem. 1991, 56, 4403-4407.
Boyd M R et al, Stolonic acid a and b, J. Nat. Prod., (Sep. 8, 2000), vol. 63, pp. 1411-1413.
Breast Cancer Research and treatment 77, 185-188 (2003).
Brian M Gulledge et al, Microcystin analogues comprises only of Adda and a single additional amino acid retain moderate activity as PP1 PP2A inhibitors, Bioorg. & Med, Chem, Lett., 2003, vol. 13, No. 17, pp. 2907-2911.
Brown A P et al, Cancer Chemotherapy and Pharmacology vol. 50, No. 4, ISSN 0344-5704, pp. 333-333 (2002).
Bruening, R.C.; Oltz, E.M.; Furukawa, J.; Nakaninshi, K.; Kustin, K. J. Nat. Prod, 1986, 49, 193-204.
Byers, T. 9(CA Cancer Journal, vol. 49, No. 6 1999).
Cancer Investigation, vol. 21(2), pp. 167-176, 2003.
Chari, R.V. (2008) Targeted cancer therapy conferring specificity to cytotoxic drugs. Acc. Chem. Res. 41 , 98-107.
Chauhan D. et al, Blood., 1996, vol. 87,1104-1112.
Chem, Soc., 1988, 110, 1308.
Chern. Soc., 1988, 110, 1308.
Clinical Cancer Research 7, 3040-3046 (2001).
Clinical cancer research 7, 3251-3257 (2001).
Clinical Cancer Research, vol. 8, 75-85 2002).
Corey et al. Proc. Natl. Acad. Sci. USA, 1999, vol. 96, 3496-3501.
Corey, E.J., J. Am. Chem. Soc., (1996), vol. 118, pp. 9202-9203.
de Rocha et.al Natural Products in Anti-cancer therapy, Current Opinion in Pharmacology, vol. 1, p. 364-369, 2001.
Delaloge (Eur J Cancer) vol. 35 supp S271 Abst No. 1080 (1999).
D'Inacici et al., European Journal of Cancer, 38, Suppl.7. Nov. 2001, p. 34, abstract 97.
Depenbrock H; In vitro activity of Aplidine; a new marine-derived anti-cancer compound, on freshly explanted clonogenic human tumour cells and haematopoietic precursor cells, Br. J. Cancer, (1998).
Diliman, R.L.; Cardellina, J.H., II J. Nat. Prod. 1991, 54, 1159-1161.
Donald D. et al; Cancer Reasearch, 2002, vol. 62, 4256.
Donald S. et al, Cancer Research 2003, vol. 63, 5902-5908.
Drugs 62(8), 1185-1192 (2002).
Duran R et al, Minor Metabolites from the Ascidian Stolonica socialis and Cytotoxicity of Stolonoxides, Tetrahedron, (Aug. 11, 2000), vol. 56, No. 33, pp. 6031-6037 Aug. 11, 2000.
Durán, R.; Zubia; E. Ortega, M.J.; Naranjo, S.; Salva, J. Tetrahedron199 , 55, 13225-1-13232.
E.J.Corey,David Y.Gin, and Robert S. Kania, Enantioselective Total Synthesis of Ecteinascidin, J.Am.Chem. Soc.; (1996), vol. 118, pp. 9202-9203, XP002925428 [X].
EJ Martinez et al, PNAS, vol. 96, No. 7 (1999).
Elez, ME et. al. Clin. Cancer Res. 2014, 20(8), 2205-2214.
Erba E, Cell cycle phase perturbations and apoptosis in tumour cells induced by aplidine, Br J Cancer, (2002), vol. 86, pp. 1510-1517.
Erba, E. et.al., Cell Cycle phases perturbations induced by new natural marine compounds, Annals of Oncology, vol. 7, Supplement 1 #283 pp. 82, 1996.
Eur J. Cancer, 38,(7) 14th EORTC-NCI-AACR Symposiumon olecular Targets and Cancer Therapeutics,p. 34, abstract 97, (2002).
Eur J, Cancer, 45,1153-1161 (2009).
Eur J. Cancer, 48(15), 2361-2368 (2012).
Faircloth et al, Ann Oncol, 1996, vol. 7,34.
Faircloth et al. Methods in cell science, 1988, vol. 11 (4), 201-205.
Faircloth, G. et al., Dehydrodidemnin B (DDM) a new marine derived anticancer agent (MDA) with activity against experimental tumour models, 9th NCI-EORTC Symp New Drugs Cancer Ther (Mar. 12-15, Amsterdam) 1996, Abst 111.
Faircloth, G. et al., Preclinical development of aplidine, a novel marine-derived agent with potent antiturnour activity, 10th NCI-EORTC Symp New Drugs Cancer Ther (Jun. 16-19, Amsterdam) 1998, Abst 129.
Faircloth, G. et.al., Biological Activity of thiocoraline Annals of Oncology. vol. 7, Supplement 1 #112 p. 34, 1996.
Fenical, W. et al. J. Org. Chem., 2000, vol. 65,782-792.
Fontana A et al, Structure and absolute stereochemistry of stolonoxide A, a novel cyclic peroxide from the marine tunicate Stolonica socialis, Tetrahedron Letters, (Jan. 2000), vol. 41, No. 3, ISSN 0040-4039, pp. 429 (2000).
Fontana A et al. Tetrahedron, 2000, vol. 56, 7305-8.
Foster E.A., Nairaiamdes A and B, Two novel di-proline hetapeptides isolated from a Fijian Lissoclinum bistraturn Ascidian, Tetrahedron Letters, (1993), vol. 34, No. 18, pp. 2871-2874.
Foucault, A.P. Anal, Chem. 1991, 63, 569A-579A.
Frincke, J. M.;Faulkner, D. J. J. Am. Chem. Soc. 1982, 104, 265-269.
Fukuyama et al J Am Chem Soc vol. 104; p. 4957-4958 (1982).
Fukuyama et al., J. Am. Chem. Soc., 1982, Stereocontrolled Total Synthesis of (+)-Saframcin B, vol. 104, p. 4957.
Fukuyama et al., Total Synthesis of (+)—Saframycin A, J. Am. Chem. Soc., (1990), vol. 112, p. 3712.
G. Jou ; I. Gonzalez ; F. Albericio ; P.Lloyd-Williams ; E. Giralt, J. Org. Chem.,1997, vol. 62, 354-366.
Geldorf, Albert A et.al. Cytotoxicty and neurocytotoxicity of new marine anticancer agents.. Cancer Chemother. Pharmacol. vol. 44, p. 312-318, 1999.
Genin Michael J. et.al. Synthesis and Crystal Structure of Peptidomimetic Containing the . . . Journal of Organic Chemistry, vol. 58, No. 8 pp. 2334-2337, 1993.
Gerwick, W.H. Lipids 1996, 31, 1215-1231.

(56) References Cited

OTHER PUBLICATIONS

Giavazzi, Ecteinascidin-743, a New Marine Natural Product with Potent Antitumor Activity, Clinical Cancer Research, (1998), vol. 4, No. 8, pp. 1977-1983.
Gilbert Stork, KZ. Tetrahedron letters, 1989, vol. 30(17), 2173.
Goetz et al., The Absolute stereochemistry of Kahalalide F., Tetrahedron, 1999, vol. 55, 7739-7746.
Gomez-Fabre; P.M. et.al. Polamine contents of human breast cancer cells . . . Cancer Letters, vol. 113, Nos. 1,2 pp. 141-144, 1997.
Greenstein S. et al., Exp. Hematol, (2003), vol. 31, pp. 271-282.
Grode, S.H.; Cardeilina, J.H., II Lipids, 1983, 18, 889-893.
Gulavita, N.K.; Scheuer, P.J. J. Org. Chem. 1989, 54, 366-369.
Gulledge Brian M et al, Bioorganic & Medicinal Chemistry Letters, vol. 13, No. 17, I (2003).
Gunasekera SP et al. J. Org. Chem., 1990, vol. 55,4912-4915.
Gunawardana, P.P.; Kohmoto, S.; Burres, N.S. Tetrahedron Lett. 1989, 30,4359-4362.
Gunawardana, G.P.; Koehn, F. E.; Lee, A.Y.; Clardy, J.; He, H.-y.; Faulkner, D. J. J. Org. Chem. 1992, 57,1523-1526.
Gunawardana, G.P.; Kohmoto, S.; Gunasekera, S.P.; McConnell, O. J.; Koehn, F. E. J. Am. Chem. Soc. 1988, 110,4856-4858.
Gunawardana, G.P.; Kohmoto, S.; Gunasekera, S.P.; McConnell, O. J.; Koehn, F. E. J. Am. Chem. Soc. 1988, 110,4356-4358.
H Vervoort et al., Journal of Organic Chemistry, vol. 65, No. 3, pp. 782-792 (1999).
H.F. Hansen et al., ACTA Chemical Scandinavica, vol. 47, No. 12, pp. 1190-1200, (1993).
Hamada et.al. Efficient Total Synthesis of Didemnins A and B J.Am.Chem.Soc., vol. 111, p. 669-673 (1989).
Hamman et.al, J.Am.Chem.Soc., 1993, vol. 115, 5825-5826.
Hamman, M. et al. Kahalalides bioactive peptides from a marine mollusk *Elysia rufscens* and its algal diet Bryopsis sp. J.Org.Chem, 1996, vol. 61, 6594-6600.
Harris et.al. The World Health Organisation Classification of Haemotological Malignancies Report of the Clinical Advisory Committee Meeting Modern Pathology, vol. 13, No. 2, pp. 193-207, 2000.
Hasegawa T., Takizawa M., and Tanida S., J. Gen. Appl. Microbiol. 29 319-322, 1983.
He, H. -Y.; Faulkner, D. J. J. Org. Chem. 1989, 54, 5822-5824.
Hermann C et al, Total Synthesis of Hapalosin and Two Ring Expanded Analogs, Tetrahedron, 56(43), 8461-8471, (2000).
Hideshima T.et al, Cancer Res, 2001, vol. 61, 3071-3076.
Hung DT et al. Chem. Biol., 1996, vol. 3, 287-293.
I. Manzanares et al, Org. Lett., 2000, 2(16), 2545-2548.
Improved Tolerability of Chemotherapy in soft tissue sarcomas old and new strategies, Lara Maria Pasetto et al., Expert Rev. Anticancer Ther. 3(2), 167-178 (2003).
Ishii Keisuke et al, Syndrome of inappropriate secretion of antidiuretic hormone induced by intraarterial cisplatin chemotherapy, Gynecologic Oncology, vol. 87, No. 1, p. 150-151, 2002.
Ito, Y.J. Chromatogr. 1981, 214, 122-125.
Itoh, et al., Nature Medicine, vol. 5, No. 2, 1999.
Izbicka, In vitro antitumor acitivity of the novel marine agent, Ecteinascidin-743 (ET-743, NSC-648766) against human tumors explanted from patients, Annals of Oncology, (1998), vol. 9, No. 9, pp. 981-987, 1990.
J Am Chem Soc vol. 112, p. 3713-3715 (1990).
J. Am. Chem. Soc. (1996) 118, 9017-9023.
J. Am.Chem. Soc., 1992, 114, 1110.
J. Amer. Chem. Soc., 1991, 113, 4709.
J. Antibiotics 34(5) 611-613, 1981.
J. Luber Narod et al., Evaluation of the use of in vitro methodologies as tools for screening new compounds for potential in vivo toxicity, Toxicology In Vitro, (2001), vol. 15, pp. 571-577.
J. Med. Chem., 1989, 32, 1354.
J. Nat. Prod., 1990, 53, 771-792.
J. Org. Chem.(1992, 57, 6671).
J. Org. Chem., 1990, 55, 4512-4515.
J. Org. Chem., 1991, vol. 56, 1346.
Jaime Rodriguez et al., The Structures and Stereochemistry of Cytotoxic Sesquiterpene Quinones from Dactylospongia Elegans, Tetrahedron, (1992), vol. 48, No. 32 p. 6667-6668.
James M.F., et al., J.Am.Chem.Soc., 1982, vol. 104, 265-269.
Jares-Erijman, E.A.; Sakai, R.; Rinehart, K.L. J. Org. Chem. 1991, 56, 5712-5715.
Jiang et.al. Antitumour Activity of Didemnin B in the Human Tumour Stem Cell Assay, Cancer Chemotherapy and Pharmacology, 1983, 11 1-4.
Jimenez, C.; Crews, P. J. Nat. Prod. 1990, 53, 978-982.
Jimeno J., et al, Ann Oncol.,2002, vol. 13 (5) 65P.
Joc Org. Chem., 2000, vol. 65, 782-792.
JOC, 1997, vol. 62, 2-3.
Jou, Gemma et.al. Total Synthesis of Dehydrodideminin B, Journal of Organic Chemistry, vol. 62, No. 2, pp. 354-366, 1997.
Jouin et.al. Antieoplastic Activity of the Didemnin Congeners . . . Journal of Medicinal Chemistry, 1991, 34 486-491.
Journal of clinical oncology , 23(3), 576-584, 2005.
Journal of Clinical Oncology 28(19), 3107-3114 (2010).
Journal of Clinical Oncology, vol. 22(5) p. 890-900, 2004.
Journal of Clinical Oncology, vol. 22(8) p. 1480-1491, 2004.
Journal of Organic Chemistry, vol. 55 issued 1990, K. L. Rinehart et al, Ecteinascidins 729, 743, 759A, 759B, and 770 Potent Antitamor Agent from the Caribeen Tunicate Ecteinascidia Turbinata, pp. 4512-4515.
Journal of Organic Chemistry. vol. 55, No. 15 , Jul. 20, 1990 , Easton US pp. 4508-4512 A. E. Wright et al Antitumor tetrahydroisoquinoline alkaloids from the colonial ascidian Ecteinascidia turbinata.
K.L. Rinehart et al. J.Nat.Prod., 1995, vol. 58, 344.
Kan, Y.et al., Kahalalide K a new cyclic depsipeptide from the hawaiian green alga bryopsis species. J.Nat.Prod.,1999,vol. 62(8), 1169-72.
Kashman, Y.; Hirsh, S.; McConnell, O.J.; Ohtani, I.; Kusumi, T.; Kakisawa, H. J. Am. Chem. Soc. 1989, 111,31, 8925-8926.
Keifer, P.A.; Schwartz, R.E.; Koker, M.E.S.; Hughes, R.G., Jr.; Rittschoff, D.; Rinehart, K.L. J. Org. Chem. 1991,56, 2965-2975.
Keman, M.R.; Molinski, T.F.; Faulkner, D.J.J. Org. Chem. 1988, 53, 5014-5020.
Kerr D J et al Annals of Oncology vol. 11, No. 8, Aug. 1, 2000 (Aug. 1, 2000) , pp. 947-955.
Kofron, W.G., Baclawski, L.M., J. Org. Chem., (1976), vol. 41, p. 1879.
Kohmoto, S.; McConnell, O.J.; Wright, A.; Cross, S. Chem. Lett. 1987,1687-1690.
Kohomoto, S.; McConnell, O.J.*, Wright, A. Experientia 1988, 44, 85-86.
U.S. Appl. No. 10/485,536, dated May 18, 2005, Gallego et al.
U.S. Appl. No. 14/894,685, dated Nov. 30, 2015, Cuevas Marchante \* cited by examiner

ANTITUMORAL COMPOUNDS

FIELD OF THE INVENTION

The present invention relates to synthetic analogues of the ecteinascidins, particularly of ecteinascidin 736 (ET-736), pharmaceutical compositions containing them, methods for their manufacture and their use as antitumoral agents.

BACKGROUND OF THE INVENTION

The ecteinascidins are exceedingly potent antitumor agents isolated from the marine tunicate *Ecteinascidia turbinata*. One of these compounds, ET-743 of formula:

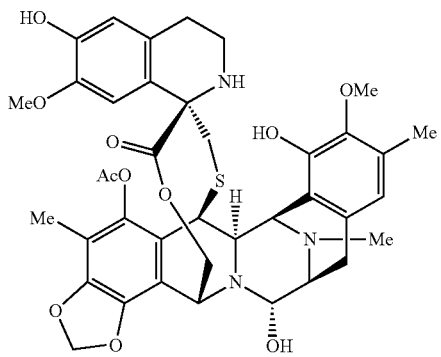 [SMILES: COc1cc2c(cc1O)CCN[C@]21CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

is being employed as an anticancer medicament, under the international nonproprietary name (INN) trabectedin, for the treatment of patients with advanced and metastatic soft tissue sarcoma (STS) after failure of anthracyclines and ifosfamide, or who are unsuited to receive such agents, and for the treatment of relapsed platinum-sensitive ovarian cancer in combination with pegylated liposomal doxorubicin.

Ecteinascidin 736 (ET-736) was first discovered by Rinehart and features a tetrahydro-β-carboline unit in place of the tetrahydroisoquinoline unit more usually found in the ecteinascidin compounds isolated from natural sources; See for example Sakai et al., *Proc. Natl. Acad. Sci. USA* 1992, vol. 89, 11456-11460.

ET-736

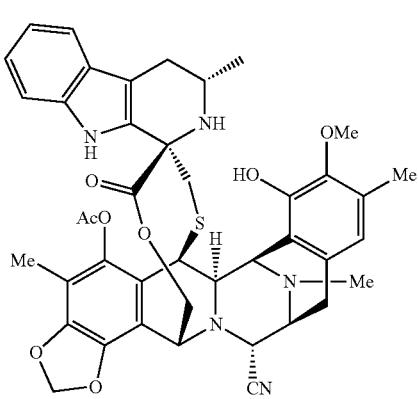

U.S. Pat. No. 5,149,804 describes Ecteinascidin 736 (ET-736), isolated from the Caribbean tunicate *Ecteinascidia turbinata*, and it structure. ET-736 protects mice in vivo at very low concentrations against P388 lymphoma, B16 melanoma, and Lewis lung carcinoma.

WO03014127 describes several synthetic analogues of ET-736 and their cytotoxic activity against tumoral cells. In particular, WO03014127 describes compounds A to D together with their cytotoxic activity against a panel of cancer cell lines.

A

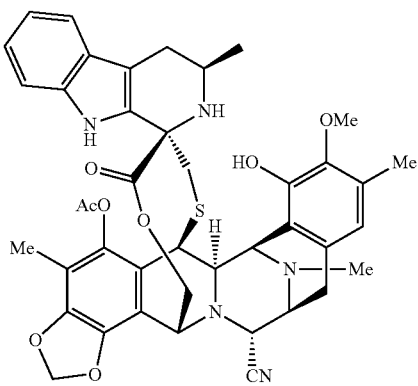

B

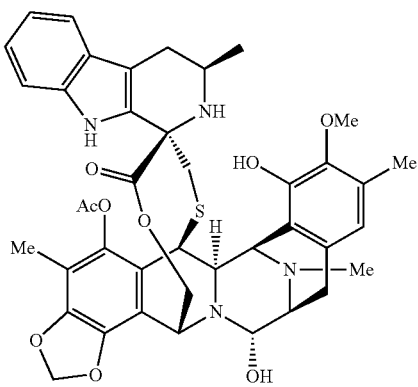

C

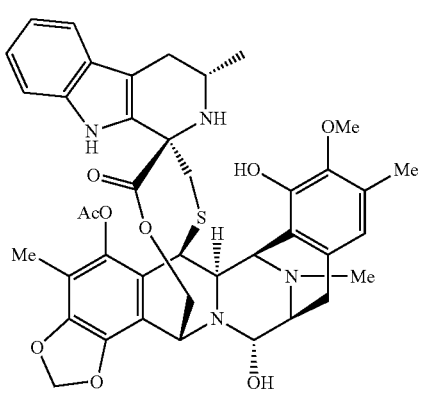

D

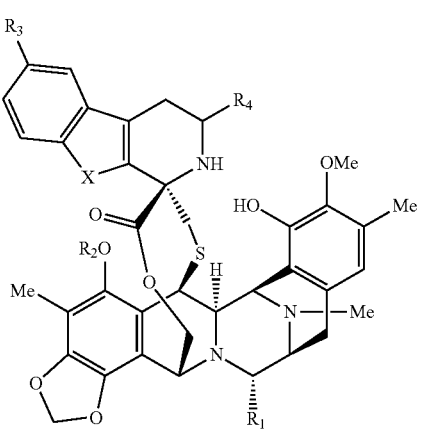

I

Another compound described in this patent application, PM01183, is currently in clinical trials for the treatment of cancer. PM01183 has the following chemical structure:

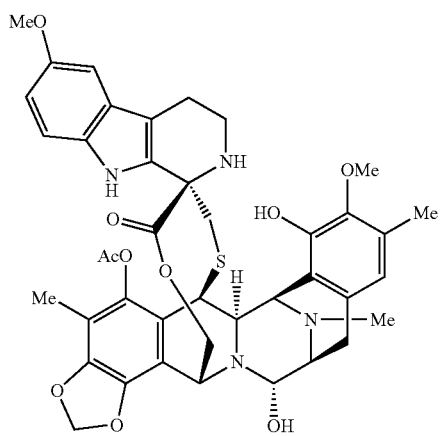 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

PM01183 has demonstrated a highly potent in vitro activity against solid and non-solid tumour cell lines as well as a significant in vivo activity in several xenografted human tumor cell lines in mice, such as those for breast, kidney and ovarian cancer. PM01183 exerts its anticancer effects through the covalent modification of guanines in the DNA minor groove that eventually give rise to DNA double-strand break, S-phase arrest and apoptosis in cancer cells.

Despite the positive results obtained in clinical applications in chemotherapy, the search in the field of ecteinascidin compounds is still open to the identification of new compounds with optimal features of activity, selectivity toward the tumour, with a reduced systemic toxicity and/or improved pharmacokinetic properties.

SUMMARY OF THE INVENTION

In a first aspect of the present invention there is provided a compound of formula I or a pharmaceutically acceptable salt or ester thereof:

wherein:
X is —NH— or —O—;
$R_1$ is —OH or —CN;
$R_2$ is a —C(=O)$R^a$ group;
$R_3$ is hydrogen or a —O$R^b$ group;
$R_4$ is selected from hydrogen, —CH$_2$OH, —CH$_2$OC(=O)$R^c$, —CH$_2$NH$_2$, and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino,
with the proviso that when $R_4$ is hydrogen then X is —O—.

There is also provided a compound of formula IC, or a pharmaceutically acceptable salt or ester thereof:

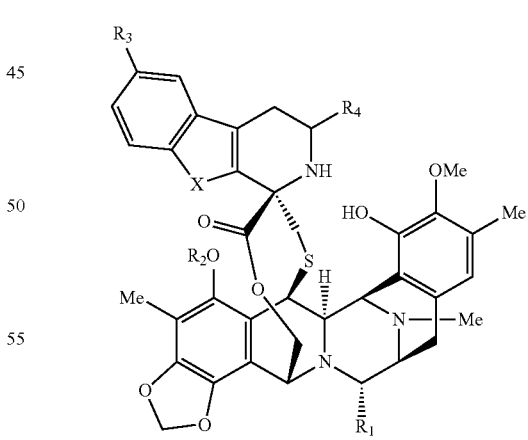

IC wherein:
X is —NH—;
$R_1$ is —OH or —CN;
$R_2$ is a —C(=O)$R^a$ group;
$R_3$ is hydrogen or a —O$R^b$ group;
$R_4$ is selected from —CH$_2$OH, —CH$_2$O—(C=O)$R^c$, —CH$_2$NH$_2$ and —CH$_2$NHProt$^{NH}$;

R$^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;
R$^b$ is selected from substituted or unsubstituted C$_1$-C$_{12}$ alkyl, substituted or unsubstituted C$_2$-C$_{12}$ alkenyl and substituted or unsubstituted C$_2$-C$_{12}$ alkynyl;
R$^c$ is selected from substituted or unsubstituted C$_1$-C$_{12}$ alkyl, substituted or unsubstituted C$_2$-C$_{12}$ alkenyl, and substituted or unsubstituted C$_2$-C$_{12}$ alkynyl; and
Prot$^{NH}$ is a protecting group for amino.

There is also provided a compound of formula ID, or a pharmaceutically acceptable salt or ester thereof:

ID

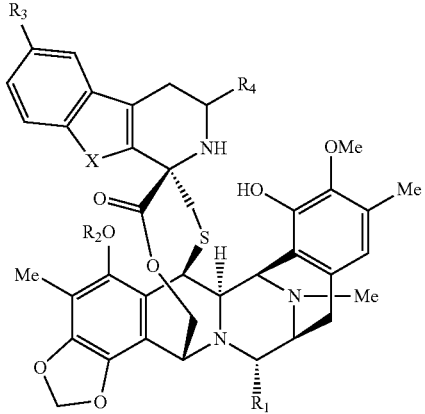

wherein:
X is —O—;
R$_1$ is —OH or —CN;
R$_2$ is a —C(=O)R$^a$ group;
R$_3$ is hydrogen or a —OR$^b$ group;
R$_4$ is selected from hydrogen, —CH$_2$OH, —CH$_2$O—(C=O)R$^c$, —CH$_2$NH$_2$ and —CH$_2$NHProt$^{NH}$;
R$^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;
R$^b$ is selected from substituted or unsubstituted C$_1$-C$_{12}$ alkyl, substituted or unsubstituted C$_2$-C$_{12}$ alkenyl and substituted or unsubstituted C$_2$-C$_{12}$ alkynyl;
R$^c$ is selected from substituted or unsubstituted C$_1$-C$_{12}$ alkyl, substituted or unsubstituted C$_2$-C$_{12}$ alkenyl, and substituted or unsubstituted C$_2$-C$_{12}$ alkynyl; and
Prot$^{NH}$ is a protecting group for amino.

There is also provided a compound of formula IE, or a pharmaceutically acceptable salt or ester thereof:

IE

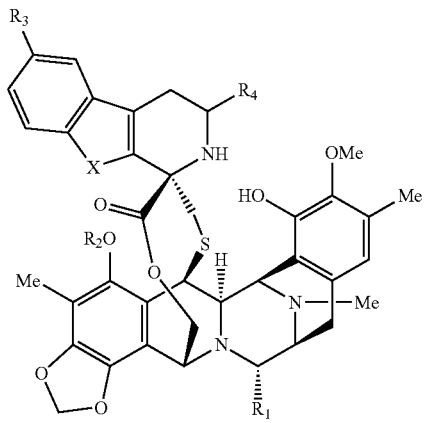

wherein:
X is —NH— or —O—;
R$_1$ is —OH or —CN;
R$_2$ is a —C(=O)R$^a$ group;
R$_3$ is hydrogen or a —OR$^b$ group;
R$_4$ is selected from —CH$_2$NH$_2$ and —CH$_2$NHProt$^{NH}$;
R$^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;
R$^b$ is selected from substituted or unsubstituted C$_1$-C$_{12}$ alkyl, substituted or unsubstituted C$_2$-C$_{12}$ alkenyl and substituted or unsubstituted C$_2$-C$_{12}$ alkynyl; and
Prot$^{NH}$ is a protecting group for amino.

There is also provided a compound of formula IA or a pharmaceutically acceptable salt or ester thereof:

IA

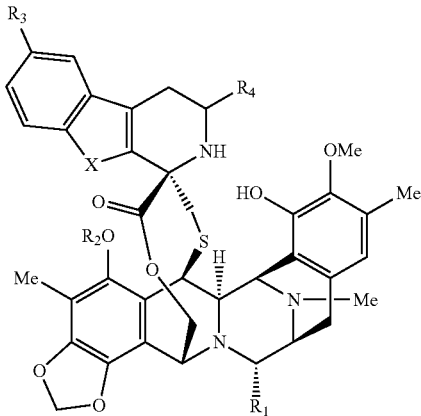

wherein:
X is —NH— or —O—;
R$_1$ is —OH or —CN;
R$_2$ is a —C(=O)R$^a$ group;
R$_3$ is hydrogen;
R$_4$ is selected from hydrogen, —CH$_2$OH, —CH$_2$O—(C=O)R$^c$, —CH$_2$NH$_2$ and —CH$_2$NHProt$^{NH}$;
R$^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;
R$^c$ is selected from substituted or unsubstituted C$_1$-C$_{12}$ alkyl, substituted or unsubstituted C$_2$-C$_{12}$ alkenyl, and substituted or unsubstituted C$_2$-C$_{12}$ alkynyl; and
Prot$^{NH}$ is a protecting group for amino;
with the proviso that when R$_4$ is hydrogen then X is —O—.

There is also provided a compound of formula IB or a pharmaceutically acceptable salt or ester thereof:

IB

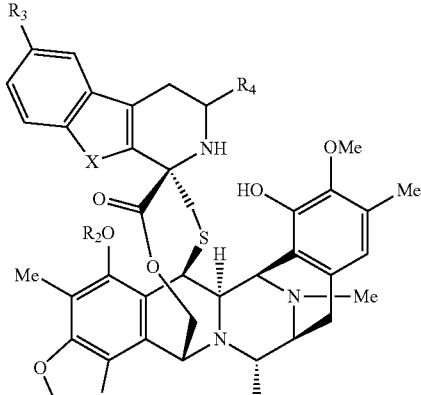

wherein:

X is —NH— or —O—;

$R_1$ is —OH or —CN;

$R_2$ is a —C(=O)$R^a$ group;

$R_3$ is a —$OR^b$ group;

$R_4$ is selected from hydrogen, —$CH_2OH$, —$CH_2O$—(C=O)$R^c$, —$CH_2NH_2$ and —$CH_2NHProt^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino;

with the proviso that when $R_4$ is hydrogen then X is —O—.

There is also provided a compound of formula IF or a pharmaceutically acceptable salt or ester thereof:

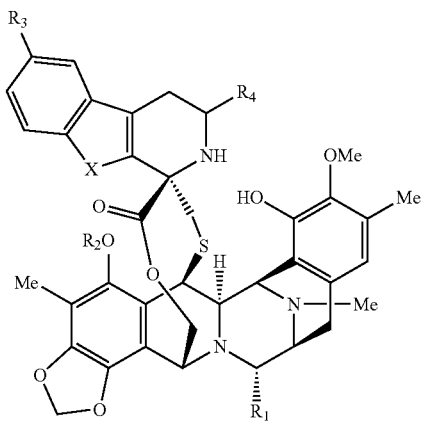

IF wherein:

X is —NH— or —O—;

$R_1$ is —OH;

$R_2$ is a —C(=O)$R^a$ group;

$R_3$ is hydrogen or a —$OR^b$ group;

$R_4$ is selected from hydrogen, —$CH_2OH$, —$CH_2OC$(=O)$R^c$, —$CH_2NH_2$, and —$CH_2NHProt^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino, with the proviso that when $R_4$ is hydrogen then X is —O—.

There is also provided a compound of formula IG or a pharmaceutically acceptable salt or ester thereof:

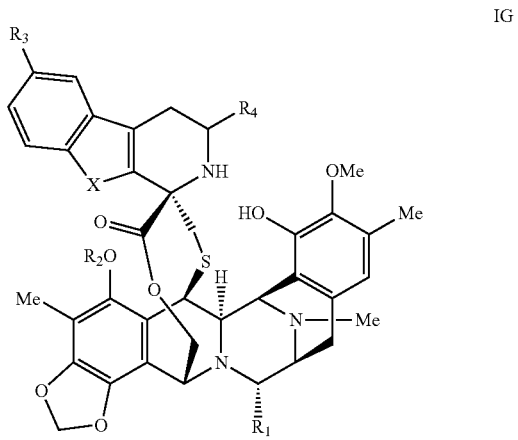

IG wherein:

X is —NH— or —O—;

$R_1$ is —OH or —CN;

$R_2$ is acetyl;

$R_3$ is hydrogen or a —$OR^b$ group;

$R_4$ is selected from hydrogen, —$CH_2OH$, —$CH_2OC$(=O)$R^c$, —$CH_2NH_2$, and —$CH_2NHProt^{NH}$;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino, with the proviso that when $R_4$ is hydrogen then X is —O—.

In a further aspect of the present invention, there is provided a pharmaceutical composition comprising a compound according to the present invention and a pharmaceutically acceptable carrier.

In a yet further aspect of the present invention, there is provided a dosage form comprising a pharmaceutical composition according to the present invention.

In a yet further aspect of the present invention, there is provided a compound, pharmaceutical composition or dosage form according to the present invention for use as a medicament.

In a yet further aspect of the present invention, there is provided a compound, pharmaceutical composition or dosage form according to the present invention for use in the treatment of cancer.

In a yet further aspect of the present invention, there is provided the use of a compound, pharmaceutical composition or dosage form according to the present invention for the manufacture of a medicament for the treatment of cancer.

In a yet further aspect of the present invention, there is provided a method for the prevention or treatment of cancer, comprising administering an effective amount of a compound according to the present invention, administering an effective amount of a pharmaceutical composition according to the present invention, or administering an effective amount of a dosage form according to the present invention to a patient in need thereof, notably a human.

In a yet further aspect of the present invention, there is provided the use of a compound according to the present invention for the treatment of cancer, or in the preparation of a medicament preferably for the treatment of cancer.

In a yet further aspect of the present invention, there is provided a kit comprising a therapeutically effective amount of a compound according to the present invention and a pharmaceutically acceptable carrier. The kit is for use in the treatment of cancer.

In a yet further aspect of the present invention, there is provided a process for obtaining compounds of formula I or a pharmaceutically acceptable salt or ester thereof, compounds of formula IA or a pharmaceutically acceptable salt or ester thereof, compounds of formula IB or a pharmaceutically acceptable salt or ester thereof, compounds of formula IC or a pharmaceutically acceptable salt or ester thereof, compounds of formula ID or a pharmaceutically acceptable salt or ester thereof, compounds of formula IE or a pharmaceutically acceptable salt or ester thereof, compounds of formula IF or a pharmaceutically acceptable salt or ester thereof, compounds of formula IG or a pharmaceutically acceptable salt or ester thereof; comprising the step of reacting a compound of formula II with a compound of formula III to give a compound of formula IV:

wherein (insofar as allowed by possible substituent groups):
X is —NH— or —O—;
$R_2$ is a —C(=O)$R^a$ group;
$R_3$ is hydrogen or a —O$R^b$ group;
$R_4$ is selected from hydrogen, —CH$_2$OH, —CH$_2$OC(=O)$R^c$, and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

The process may include the further step of replacing the cyano group in the compound of formula IV with a hydroxy group to give a compound of formula I, IA, IB, IC, ID, IE, IF, or IG where $R_1$ is OH.

DETAILED DESCRIPTION OF PREFERRED EMBODIMENTS

Figure 1:
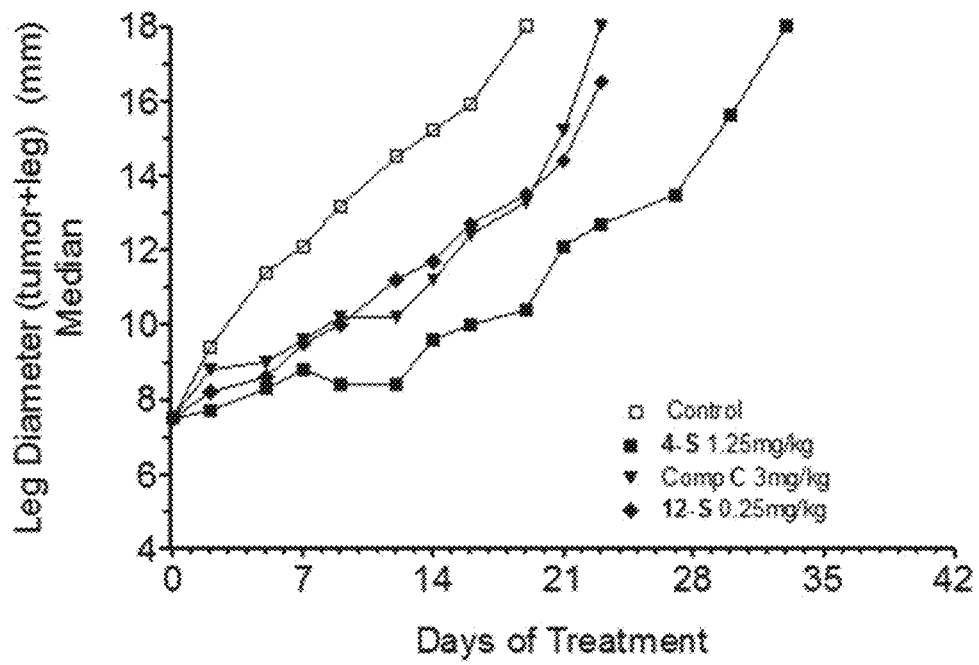
FIG. 1. Tumor total diameter evaluation of HT1080 tumors in mice treated with placebo, compound C, 4-S, and 12-S.

The following apply to all aspects of the present invention:

In the compounds of the present invention, the alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, n-propyl, isopropyl and butyl, including n-butyl, isobutyl, sec-butyl and tert-butyl are particularly preferred alkyl groups in the compounds of the present invention.

In the compounds of the present invention, the alkenyl groups may be branched or unbranched, have one or more double bonds and from 2 to about 12 carbon atoms. One more preferred class of alkenyl groups has from 2 to about 6 carbon atoms. Even more preferred are alkenyl groups having 2, 3 or 4 carbon atoms. Ethenyl, 1-propenyl, 2-propenyl, 1-methylethenyl, 1-butenyl, 2-butenyl, and 3-butenyl are particularly preferred alkenyl groups in the compounds of the present invention.

In the compounds of the present invention, the alkynyl groups may be branched or unbranched, have one or more triple bonds and from 2 to about 12 carbon atoms. One more preferred class of alkynyl groups has from 2 to about 6 carbon atoms. Even more preferred are alkynyl groups having 2, 3 or 4 carbon atoms.

Suitable aryl groups in the compounds of the present invention include single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups included substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated and/or fused rings and from 5 to about 18 ring atoms. Preferably heteroaromatic and heteroalicyclic groups contain from 5 to about 10 ring atoms, most preferably 5, 6, or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S and include, e.g., pyrrolidinyl, tetrahydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pirrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, protected amino, protected SH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, where each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. In addition, where there are more than one R' groups on a substituent, each R' may be the same or different.

In the compounds for the present invention, the halogen substituents include F, Cl, Br, and I.

The terms "pharmaceutically acceptable salt" and "ester" refers to any pharmaceutically acceptable salt or ester which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts can be carried out by methods known in the art.

For instance, pharmaceutically acceptable salts of the compounds provided herein are synthesized from the parent compounds, which contain a basic or acidic moiety, by conventional chemical methods. Generally, such salts are, for example, prepared by reacting the free acid or base of these compounds with a stoichiometric amount of the appropriate base or acid in water or in an organic solvent or in a mixture of both. Generally, nonaqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline or amorphous form either as free compounds or as solvates (e.g. hydrates) and it is intended that all forms are within the scope of the present invention. Methods of solvation are generally known within the art.

Stereoisomerism about the asymmetric carbons with unspecified stereochemistry is possible, therefore in such cases the asymmetric carbons can have (R) or (S) configuration. All diastereomers generated by a specific configuration of such asymmetric carbons in conjunction with the other asymmetric carbons present in the molecule, and mixtures thereof, are considered within the scope of the present invention. Stereoisomerism about the double bond (geometric isomerism) is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. Furthermore, compounds referred to herein may exist as atropoisomers. The single stereoisomers including diastereoisomers, geometric isomers and atropoisomers of the compounds referred to herein, and mixtures thereof fall within the scope of the present invention.

In addition, compounds referred to herein may exist in isotopically-labelled forms. All pharmaceutically acceptable salts, esters and isotopically labelled forms of the compounds referred to herein, and mixtures thereof, are considered within the scope of the present invention.

Protected forms of the compounds disclosed herein are considered within the scope of the present invention. Suitable protecting groups are well known for the skilled person in the art. A general review of protecting groups in organic chemistry is provided by Wuts, P G M and Greene T W in Protecting Groups in Organic Synthesis, $4^{th}$ Ed. Wiley-Interscience, and by Kocienski P J in Protecting Groups, $3^{rd}$ Ed. Georg Thieme Verlag. These references provide sections on protecting groups for OH, amino and SH groups. All these references are incorporated by reference in their entirety.

Within the scope of the present invention an OH protecting group is defined to be the O-bonded moiety resulting from the protection of the OH through the formation of a suitable protected OH group. Examples of such protected OH groups include ethers, silyl ethers, esters, sulfonates, sulfenates and sulfinates, carbonates, and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)

methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, O-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)-phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydropyranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenyl-methyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, 4,5-bis(ethoxycarbonyl)-[1,3]-dioxolan-2-yl, benzisothiazolyl S,S-dioxide. In the case of silyl ethers the protecting group for the OH can be selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy) ethoxy]disiloxane-1-yl, and fluorous silyl. In the case of esters the protecting group for the OH together with the oxygen atom of the unprotected OH to which it is attached form an ester that can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydro-xymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azido-butyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2-{[(4-methoxytrityl)thio]methylamino}methyl benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxy-butyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthio-methoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl-acetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH together with the oxygen atom of the unprotected OH to which it is attached form a sulfonate, sulfenate or sulfinates that can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, and dimethylphosphinothioyl. In the case of carbonates the protecting group for the OH together with the oxygen atom of the unprotected OH to which it is attached form a carbonate that can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino- 1-phenylethyl carbonate, phenacyl carbonate, 3',5'-dimethoxybenzoin carbonate, methyl dithiocarbonate, and S-benzyl thiocarbonate. And in the case of carbamates the protecting group for OH together with the oxygen atom of the unprotected OH to which it is attached forms a carbamate that can be selected from dimethyl thiocarbamate, N-phenyl carbamate, and N-methyl-N-(o-nitrophenyl) carbamate.

Within the scope of the present invention an amino protecting group is defined to be the N-bonded moiety resulting from the protection of the amino group through the formation of a suitable protected amino group. Examples of protected amino groups include carbamates, ureas, amides, heterocyclic systems, N-alkyl amines, N-alkenyl amines, N-alkynyl amines, N-aryl amines, imines, enamines, N-metal derivatives, N—N derivatives, N—P derivatives, N—Si derivatives, and N—S derivatives. In the case of carbamates the protecting group for the amino group together with the amino group to which it is attached form a carbamate that can be selected from methyl carbamate, ethyl carbamate, 9-fluorenylmethyl carbamate, 2,6-di-t-butyl-9-fluorenylmethyl carbamate, 2,7-bis(trimethylsilyl)fluorenylmethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate, 2-chloro-3-indenylmethyl carbamate, benz[f]inden-3-ylmethyl carbamate, 1,1-dioxobenzo[b]-thiophene-2-ylmethyl carbamate, 2-methylsulfonyl-3-phenyl-1-prop-2-enyl carbamate, 2,7-di-t-butyl-[9,(10,10-dioxo-10,10,10,10-tetrahydrothioxanthyl)]methyl carbamate, 2,2,2-trichloroethyl carbamate, 2-trimethylsilylethyl carbamate, (2-phenyl-2-trimethylsilyl)ethyl carbamate, 2-phenylethyl carbamate, 2-chloroethyl carbamate, 1,1-dimethyl-2-haloethyl carbamate, 1,1-dimethyl-2,2-dibromoethyl carbamate, 1,1-dimethyl-2,2,2-trichloroethyl carbamate, 2-(2'-pyridyl)ethyl carbamate, 2-(4'-pyridyl)ethyl carbamate, 2,2-bis(4'-nitrophenyl)ethyl carbamate, 2-[(2-nitrophenyl)dithio]-1-phenylethyl carbamate, 2-(N,N-dicyclohexylcarboxamido)ethyl carbamate, t-butyl carbamate, fluorous BOC carbamate, 1-adamantyl carbamate, 2-adamantyl carbamate, 1-(1-adamantyl)-1-methylethyl carbamate, 1-methyl-1-(4-byphenylyl)ethyl carbamate, 1-(3,5-di-t-butylphenyl)-1-methylethyl carbamate, triisopropylsilyloxy carbamate, vinyl carbamate, allyl carbamate, prenyl carbamate, 1-isopropylallyl carbamate, cinnamyl carbamate, 4-nitrocinnamyl carbamate, 3-(3'-pyridyl)prop-2-enyl carbamate, hexadienyl carbamate, propargyl carbamate, 1,4-but-2-ynyl biscarbamate, 8-quinolyl carbamate, N-hydroxypiperidinyl carbamate, alkyl dithiocarbamate, benzyl carbamate, 3,5-di-t-butylbenzyl carbamate, p-methoxybenzyl carbamate, p-nitrobenzyl carbamate, p-bromobenzyl carbamate, p-chlorobenzyl carbamate, 2,4-dichlorobenzyl carbamate, 4-methylsulfinylbenzyl carbamate, 4-trifluoromethylbenzyl carbamate, fluorous benzyl carbamate, 2-naphthylmethyl carbamate, 9-anthrylmethyl carbamate, diphenylmethyl carbamate, 4-phenylacetoxybenzyl carbamate, 4-azidobenzyl carbamate, 4-azidomethoxybenzyl carbamate, m-chloro-p-acyloxybenzyl carbamate, p-(dihydroxyboryl)-benzyl carbamate, 5-benzisoxazolylmethyl carbamate, 2-(trifluoromethyl)-6-chromonylmethyl carbamate, 2-methylthioethyl carbamate, 2-methylsulfonylethyl carbamate, 2-(p-toluenesulfonyl)ethyl carbamate, 2-(4-nitrophenylsulfonyl)ethyl carbamate, 2-(2,4-dinitrophenylsulfonyl)ethyl carbamate, 2-(4-trifluoromethylphenylsulfonyl)ethyl carbamate, [2-(1,3-dithianyl)]methyl carbamate, 2-phosphonioethyl carbamate, 2-[phenyl(methyl)sulfonio]ethyl carbamate, 1-methyl-1-(triphenylphosphonio)ethyl carbamate, 1,1-dimethyl-2-cyanoethyl carbamate, 2-dansylethyl carbamate, 2-(4-nitrophenyl)ethyl carbamate, 4-methylthiophenyl carbamate, 2,4-dimethylthiophenyl carbamate, m-nitrophenyl carbamate, 3,5-dimethoxybenzyl carbamate, 1-methyl-1-(3,5-dimethoxyphenyl)ethyl carbamate, α-methylnitropiperonyl carbamate, o-nitrobenzyl carbamate, 3,4-dimethoxy-6-nitrobenzyl carbamate, phenyl(o-nitrophenyl)methyl carbamate, 2-nitrophenylethyl carbamate, 6-nitroveratryl carbamate, 4-methoxyphenacyl carbamate, 3',5'-dimethoxybenzoin carbamate, 9-xanthenylmethyl carbamate, N-methyl-N-(o-nitrophenyl) carbamate, t-amyl carbamate, 1-methylcyclobutyl carbamate, 1-methylcyclohexyl carbamate, 1-methyl-1-cyclopropylmethyl carbamate, cyclobutyl carbamate, cyclopentyl carbamate, cyclohexyl carbamate, isobutyl carbamate, isobornyl carbamate, cyclopropylmethyl carbamate, p-decyloxybenzyl carbamate, diisopropylmethyl carbamate, 2,2-dimethoxy-carbonylvinyl carbamate, o-(N,N-dimethylcarboxamido)benzyl carbamate, 1,1-dimethyl-3-(N,N-dimethyl-carboxamido)propyl carbamate, butynyl carbamate, 1,1-dimethylpropynyl carbamate, 2-iodoethyl carbamate, 1-methyl-1-(4'-pyridyl)ethyl carbamate, 1-methyl-1-(p-phenylazophenyl)ethyl carbamate, p-(p'-methoxyphenylazo)benzyl carbamate, p-(phenylazo)benzyl carbamate, 2,4,6-trimethylbenzyl carbamate, isonicotinyl carbamate, 4-(trimethyl-ammonium) benzyl carbamate, p-cyanobenzyl carbamate, di(2-pyridyl)methyl carbamate, 2-furanylmethyl carbamate, phenyl carbamate, 2,4,6-tri-t-butylphenyl carbamate, 1-methyl-1-phenylethyl carbamate, and S-benzyl thiocarbamate. In the case of ureas the protecting groups for the amino group can be selected from phenothiazinyl-(10)-carbonyl, N'-p-toluenesulfonylaminocarbonyl, N'-phenylaminothiocarbonyl, 4-hydroxyphenylaminocarbonyl, 3-hydroxytryptaminocarbonyl, and N'-phenylaminothiocarbonyl. In the case of amides the protecting group for the amino together with the amino group to which it is attached form an amide that can be selected from formamide, acetamide, chloroacetamide, trichloroacetamide, trifluoroacetamide, phenylacetamide, 3-phenylpropanamide, pent-4-enamide, picolinamide, 3-pyridylcarboxamide, N-benzoylphenylalanyl amide, benzamide, p-phenylbenzamide, o-nitrophenylacetamide, 2,2-dimethyl-2-(o-nitrophenyl)acetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, o-nitrobenzamide, 3-(4-t-butyl-2,6-dinitrophenyl)-2,2-dimethylpropanamide, o-(benzoyloxymethyl)benzamide, 2-(acetoxymethyl)benzamide, 2-[(t-butyldiphenylsiloxy)methyl]benzamide, 3-(3',6'-dioxo-2',4',5'-trimethylcyclohexa-1',4'-diene)-3,3-dimethylpropionamide, o-hydroxy-trans-cinnamide, 2-methyl-2-(o-phenylazophenoxy)propanamide, 4-chlorobutanamide, aceto-acetamide, 3-(p-hydroxyphenyl)propanamide, (N-dithiobenzyloxycarbonylamino)acetamide, and N-acetylmethionine amide. In the case of heterocyclic systems the protecting group for the amino group together with the amino group to which it is attached form a heterocyclic system that can be selected from 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(triisopropylsiloxy)pyrrole, N-1,1,4,4-tetramethyldisilylazacyclopentane adduct, N-1,1,3,3-tetramethyl-1,3-disilaisoindoline, N-diphenylsilyldiethylene, N-5-substituted-1,3-dimethyl-1,3,5-triazacyclohexan-2-one, N-5-substituted-1,3-benzyl-1,3,5-triazacyclohexan-2-one, 1-substituted 3,5-dinitro-4-pyridone, and 1,3,5-dioxazine. In the case of N-alkyl, N-alkenyl, N-alkynyl or N-aryl amines the protecting group for the amino group can be selected from N-methyl, N-t-butyl, N-allyl, N-prenyl, N-cinnamyl, N-phenylallyl, N-propargyl, N-methoxymethyl, N-[2-(trimethylsilyl)ethoxy]methyl, N-3-acetoxypropyl, N-cyanomethyl, N-2-azanorbornenes, N-benzyl, N-4-methoxybenzyl, N-2,4-dimethoxybenzyl, N-2-hydroxybenzyl, N-ferrocenylmethyl, N-2,4-dinitrophenyl, o-methoxyphenyl, p-methoxyphenyl, N-9-phenylfluorenyl, N-fluorenyl, N-2-picolylamine N'-oxide, N-7-methoxycoumar-4-ylmethyl, N-diphenylmethyl, N-bis(4-methoxyphenyl)methyl, N-5-dibenzosuberyl, N-triphenylmethyl, N-(4-methylphenyl)diphenylmethyl, and N-(4-methoxyphenyl)diphenylmethyl. In the case of imines the protecting group for the amino group can be selected from N-1,1-dimethylthiomethylene, N-benzylidene, N-p-methoxybenzylidene, N-diphenylmethylene, N-[2-pyridyl)mesityl]methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene. In the case of enamines the protecting group for the amino group can be selected from N-(5,5-dimethyl-3-oxo-1-cyclohexenyl), N-2,7-dichloro-9-fluorenylmethylene, N-1-(4,4-dimethyl-2,6-dioxocyclohexylidene)ethyl, N-(1,3-dimethyl-2,4,6-(1H,3H,5H)-trioxopyrimidine-5-ylidene)-methyl, N-4,4,4-trifluoro-3-oxo-1-butenyl, and N-(1-isopropyl-4-nitro-2-oxo-3-pyrrolin-3-yl). In the case of N-metal derivatives the protecting group for the amino group can be selected from N-borane, N-diphenylborinic ester, N-diethylborinic ester, N-9-borabicyclononane, N-difluoroborinic ester, and 3,5-bis(trifluoromethyl)phenylboronic acid; and also including N-phenyl(pentacarbonylchromium)carbenyl, N-phenyl(pentacarbonyl-tungsten)carbenyl, N-methyl(pentacarbonylchromium)carbenyl, N-methyl(pentacarbonyltungsten)carbenyl, N-copper chelate, N-zinc chelate, and a 18-crown-6-derivative. In the case of N—N derivatives the protecting group for the amino group together with the amino group to which it is attached form a N—N derivative that can be selected from N-nitroamino, N-nitrosoamino, amine N-oxide, azide, triazene derivative, and N-trimethylsilylmethyl-N-benzylhydrazine. In the case of N—P derivatives the protected group for the amino group together with the amino group to which it is attached form a N—P derivative that can be selected from diphenylphosphinamide, dimethylthiophosphinamide, diphenylthiophosphinamide, dialkyl phosphoramidate, dibenzyl phosphoramidate, diphenyl phosphoramidate, and iminotriphenylphosphorane. In the case of N—Si derivatives the protecting group for the $NH_2$ can be selected from t-butyldiphenylsilyl and triphenylsilyl. In the case of N—S derivatives the protected amino group can be selected from N-sulfenyl or N-sulfonyl derivatives. The N-sulfenyl derivatives can be selected from benzenesulfenamide, 2-nitrobenzenesulfenamide, 2,4-dinitrobenzenesulfenamide, pentachlorobenzenesulfenamide, 2-nitro-4-methoxybenzenesulfenamide, triphenylmethylsulfenamide, 1-(2,2,2-trifluoro-1,1-diphenyl)ethylsulfenamide, and N-3-nitro-2-pyridinesulfenamide. The N-sulfonyl derivatives can be selected from methanesulfonamide, trifluoromethanesulfonamide, t-butylsulfonamide, benzylsulfonamide, 2-(trimethylsilyl) ethanesulfonamide, p-toluenesulfonamide, benzenesulfonamide, o-anisylsulfonamide, 2-nitrobenzenesulfonamide, 4-nitrobenzenesulfonamide, 2,4-dinitrobenzenesulfonamide, 2-naphthalenesulfonamide, 4-(4',8'-dimethoxynaphthylmethyl)benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzenesulfonamide, 2,6-dimethyl-4-methoxybenzenesulfonamide, pentamethylbenzenesulfonamide, 2,3,5,6-tetramethyl-4-methoxybenzenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, and 2,2,5,7,8-pentamethylchroman-6-sulfonamide.

Within the scope of the present invention a protecting group for SH is defined to be the S-bonded moiety resulting from the protection of the SH group through the formation of a suitable a protected SH group. Examples of such protected SH groups include thioethers, disulfides, silyl thioethers, thioesters, thiocarbonates, and thiocarbamates. In the case of thioethers the protecting group for the SH can be selected from S-alkyl, S-benzyl, S-p-methoxybenzyl, S-o-hydroxybenzyl, S-p-hydroxybenzyl, S-o-acetoxybenzyl, S-p-acetoxybenzyl, S-p-nitrobenzyl, S-o-nitrobenzyl, S-2,4,6-trimethylbenzyl, S-2,4,6-trimethoxybenzyl, S-4-picolyl, S-2-picolyl-N-oxide, S-2-quinolinylmethyl, S-9-anthrylmethyl, S-9-fluorenylmethyl, S-xanthenyl, S-ferrocenylmethyl, S-diphenylmethyl, S-bis(4-methoxyphenyl)methyl, S-5-dibenzosuberyl, S-triphenylmethyl, 4-methoxytrityl, S-diphenyl-4-pyridylmethyl, S-phenyl, S-2,4-dinitrophenyl, S-2-quinolyl, S-t-butyl, S-1-adamantyl, S-methoxymethyl, S-isobutoxymethyl, S-benzyloxymethyl, S-1-ethoxyethyl, S-2-tetrahydropyranyl, S-benzylthiomethyl, S-phenylthiomethyl, S-acetamidomethyl (Acm), 5-trimethylacetamidomethyl, S-benzamidomethyl, S-allyloxycarbonylaminomethyl, tetrafluoro-4-(N'-piperidino)-phenyl-N-allyloxycarbonylaminomethyl, S-phthalimidomethyl, S-phenylacetamidomethyl, S-acetylmethyl, S-carboxymethyl, 5-cyanomethyl, S-(2-nitro-1-phenyl)ethyl, S-2-(2,4-dinitrophenyl)ethyl, S-2-(4'-pyridyl)ethyl, S-2-cyanoethyl, S-2-(trimethylsilyl)ethyl, S-2,2-bis(carboethoxy)ethyl, S-(1-m-nitrophenyl-2-benzoyl)ethyl, S-2-phenylsulfonylethyl, S-1-(4-methylphenylsulfonyl)-2-methylprop-2-yl, and S-p-hydroxyphenacyl. In the case of disulfides the protected SH group can be selected from S-ethyl disulfide, S-t-butyl disulfide, S-2-nitrophenyl disulfide, S-2,4-dinitrophenyl disulfide, S-2-phenylazophenyl disulfide, S-2-carboxyphenyl disulfide, and S-3-nitro-2-pyridyl disulfide. In the case of silyl thioethers the protecting group for the SH can be selected from the list of groups that was listed above for the protection of OH with silyl ethers. In the case of thioesters the protecting group for the SH can be selected from S-acetyl, S-benzoyl, S-2-methoxyisobutyryl, S-trifluoroacetyl, S—N-[[p-biphenylyl)-isopropyloxy]carbonyl]-N-methyl-γ-aminothiobutyrate, and S—N-(t-butoxycarbonyl)-N-methyl-γ-aminothiobutyrate. In the case of thiocarbonate protecting group for the SH can be selected from S-2,2,2-trichloroethoxycarbonyl, S-t-butoxycarbonyl, S-benzyloxycarbonyl, S-p-methoxybenzyloxycarbonyl, and S-fluorenylmethylcarbonyl. In the case of thiocarbamate the protected SH group can be selected from S—(N-ethylcarbamate) and S—(N-methoxymethylcarbamate).

The mention of these groups should not be interpreted as a limitation of the scope of the invention, since they have been mentioned as a mere illustration of protecting groups for OH, amino and SH groups, but further groups having said function may be known by the skilled person in the art, and they are to be understood to be also encompassed by the present invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In an embodiment, the compound may be a compound of formula I or a pharmaceutically acceptable salt or ester thereof:

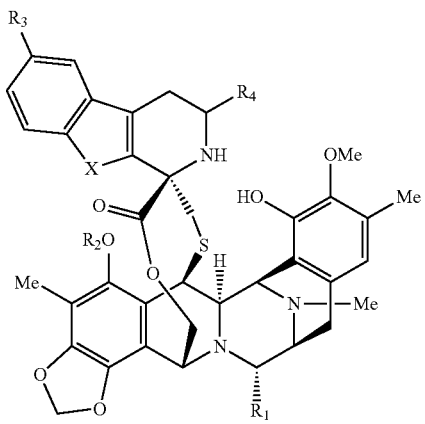

I wherein:

X is —NH— or —O—;

$R_1$ is —OH or —CN;

$R_2$ is a —C(=O)$R^a$ group;

$R_3$ is hydrogen or a —O$R^b$ group;

$R_4$ is selected from hydrogen, —CH$_2$OH, —CH$_2$OC(=O)$R^c$, —CH$_2$NH$_2$, and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino, with the proviso that when $R_4$ is hydrogen then X is —O—.

In a further embodiment, the compound of formula I may be a compound of formula IC, or a pharmaceutically acceptable salt or ester thereof:

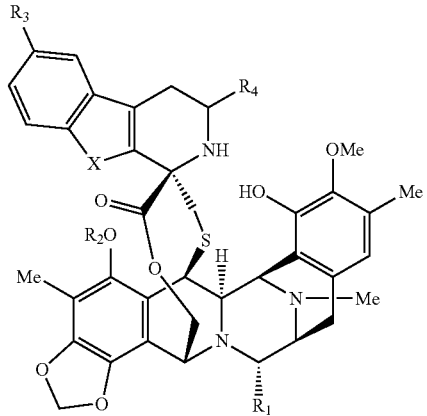

IC wherein:

X is —NH—;

$R_1$ is —OH or —CN;

$R_2$ is a —C(=O)$R^a$ group;

$R_3$ is hydrogen or a —O$R^b$ group;

$R_4$ is selected from —CH$_2$OH, —CH$_2$O—(C=O)$R^c$, —CH$_2$NH$_2$ and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino.

In a yet further embodiment, the compound of formula I may be a compound of formula ID, or a pharmaceutically acceptable salt or ester thereof:

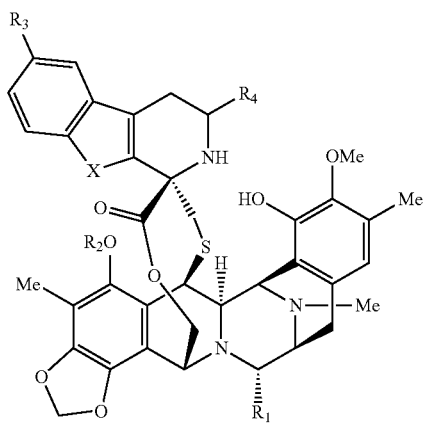

ID wherein:

X is —O—;

$R_1$ is —OH or —CN;

$R_2$ is a —C(=O)$R^a$ group;

$R_3$ is hydrogen or a —O$R^b$ group;

$R_4$ is selected from hydrogen, —CH$_2$OH, —CH$_2$O—(C=O)$R^c$, —CH$_2$NH$_2$ and —CH$_2$NHProt$^{NH}$;

$R^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;

$R^b$ is selected from substituted or unsubstituted C$_1$-C$_{12}$ alkyl, substituted or unsubstituted C$_2$-C$_{12}$ alkenyl and substituted or unsubstituted C$_2$-C$_{12}$ alkynyl;

$R^c$ is selected from substituted or unsubstituted C$_1$-C$_{12}$ alkyl, substituted or unsubstituted C$_2$-C$_{12}$ alkenyl, and substituted or unsubstituted C$_2$-C$_{12}$ alkynyl; and Prot$^{NH}$ is a protecting group for amino.

In a yet further embodiment, the compound of formula I may be a compound of formula IE, or a pharmaceutically acceptable salt or ester thereof:

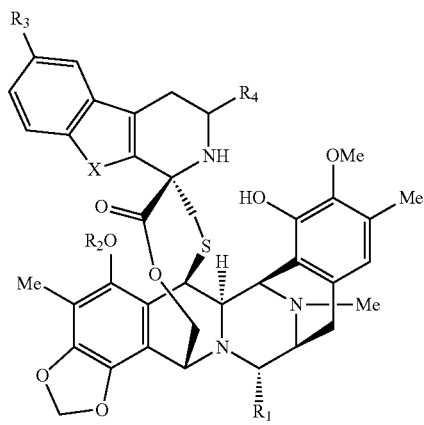

IE wherein:

X is —NH— or —O—;

$R_1$ is —OH or —CN;

$R_2$ is a —C(=O)$R^a$ group;

$R_3$ is hydrogen or a —O$R^b$ group;

$R_4$ is selected from —CH$_2$NH$_2$ and —CH$_2$NHProt$^{NH}$;

$R^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;

$R^b$ is selected from substituted or unsubstituted C$_1$-C$_{12}$ alkyl, substituted or unsubstituted C$_2$-C$_{12}$ alkenyl and substituted or unsubstituted C$_2$-C$_{12}$ alkynyl; and Prot$^{NH}$ is a protecting group for amino.

In a yet further embodiment, the compound of formula I may be a compound of formula IA or a pharmaceutically acceptable salt or ester thereof:

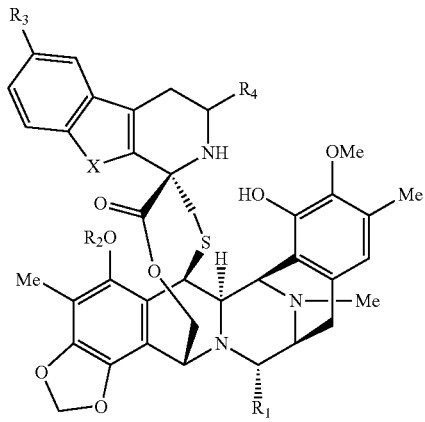

IA wherein:

X is —NH— or —O—;

$R_1$ is —OH or —CN;

$R_2$ is a —C(=O)$R^a$ group;

$R_3$ is hydrogen;

$R_4$ is selected from hydrogen, —CH$_2$OH, —CH$_2$O—(C=O)$R^c$, —CH$_2$NH$_2$ and —CH$_2$NHProt$^{NH}$;

$R^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;

$R^c$ is selected from substituted or unsubstituted C$_1$-C$_{12}$ alkyl, substituted or unsubstituted C$_2$-C$_{12}$ alkenyl, and substituted or unsubstituted C$_2$-C$_{12}$ alkynyl; and Prot$^{NH}$ is a protecting group for amino;

with the proviso that when $R_4$ is hydrogen then X is —O—.

In a yet further embodiment, the compound of formula I may be a compound of formula IB or a pharmaceutically acceptable salt or ester thereof:

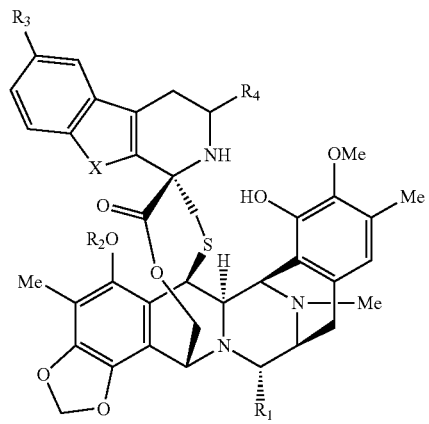

wherein:

X is —NH— or —O—;

$R_1$ is —OH or —CN;

$R_2$ is a —C(=O)$R^a$ group;

$R_3$ is a —O$R^b$ group;

$R_4$ is selected from hydrogen, —CH$_2$OH, —CH$_2$O—(C=O)$R^c$, —CH$_2$NH$_2$ and —CH$_2$NHProt$^{NH}$;

$R^a$ is selected from hydrogen, substituted or unsubstituted C$_1$-C$_{12}$ alkyl, substituted or unsubstituted C$_2$-C$_{12}$ alkenyl, and substituted or unsubstituted C$_2$-C$_{12}$ alkynyl;

$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino;

with the proviso that when $R_4$ is hydrogen then X is —O—.

In a yet further embodiment, the compound of formula I may be a compound of formula IF or a pharmaceutically acceptable salt or ester thereof:

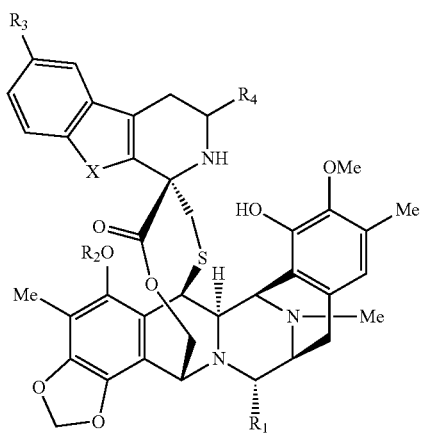

IF wherein:
X is —NH— or —O—;
$R_1$ is —OH;
$R_2$ is a —C(=O)$R^a$ group;
$R_3$ is hydrogen or a —OR$^b$ group;
$R_4$ is selected from hydrogen, —CH$_2$OH, —CH$_2$OC(=O)R$^c$, —CH$_2$NH$_2$, and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino,
with the proviso that when $R_4$ is hydrogen then X is —O—.

In a yet further embodiment, the compound of formula I may be a compound of formula IG or a pharmaceutically acceptable salt or ester thereof:

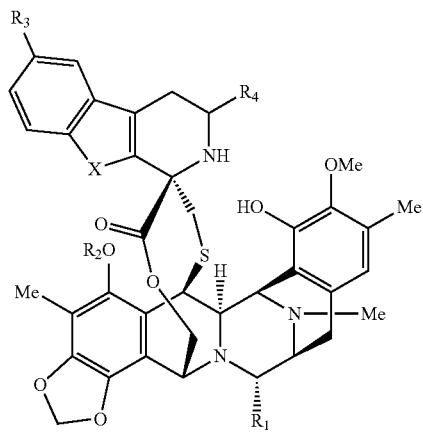

IG wherein:
X is —NH— or —O—;
$R_1$ is —OH or —CN;
$R_2$ is acetyl;
$R_3$ is hydrogen or a —OR$^b$ group;
$R_4$ is selected from hydrogen, —CH$_2$OH, —CH$_2$OC(=O)R$^c$, —CH$_2$NH$_2$, and —CH$_2$NHProt$^{NH}$;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino,
with the proviso that when $R_4$ is hydrogen then X is —O—.

Preferred compounds of the compounds of formula I, IA, IB, IC, ID, IE, IF, or IG, are those having general formula a or b, or a pharmaceutically acceptable salt or ester thereof:

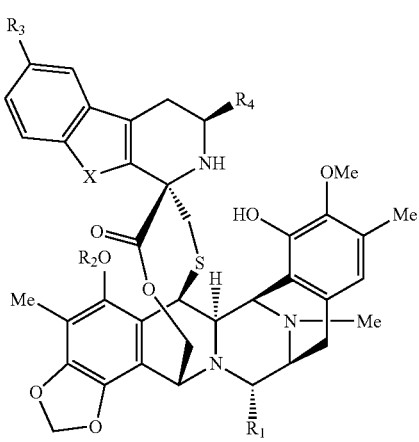

a

-continued

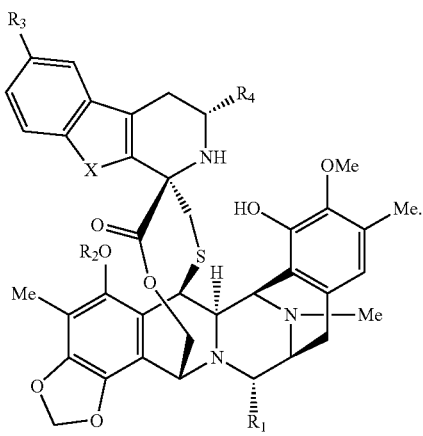

b

Note where the compounds have general formula a or b, $R_4$ may not be hydrogen.

Preferred compounds of the compounds of formula I, IA, IB, ID, IF, or IG may be those having formula c or a pharmaceutically acceptable salt or ester thereof:

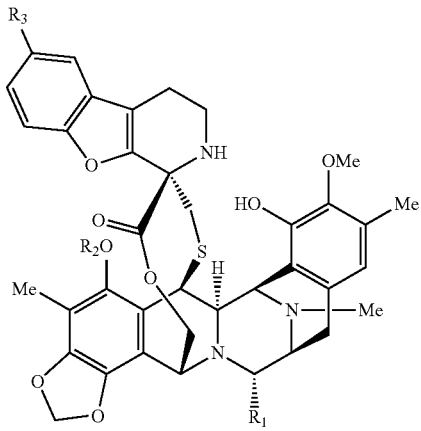

c wherein:
$R_1$ is —OH or —CN;
$R_2$ is a —C(=O)$R^a$ group;
$R_3$ is hydrogen or a —O$R^b$ group;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

Preferred compounds include compounds of general formula I, IA, IB, IE, IF, IG, Ia, IAa, IBa, IEa, IFa, IGa, Ib, IAb, IBb, IEb, IFb, and IGb, wherein:
X is —NH—;
and $R_1$; $R_2$; $R_3$; $R_4$; $R^a$; $R^b$; $R^c$; and Prot$^{NH}$ are as defined as above.

Preferred compounds include compounds of general formula I, IA, IB, IE, IF, IG, Ia, IAa, IBa, IEa, IFa, IGa, Ib, IAb, IBb, IEb, IFb, and IGb, wherein:
X is —O—;
and $R_1$; $R_2$; $R_3$; $R_4$; $R^a$; $R^b$; $R^c$; and Prot$^{NH}$ are as defined as above.

Further preferred compounds include compounds of general formula I, IA, IB, IC, ID, IE, IG, Ia, IAa, IBa, ICa, IDa, IEa, IGa, Ib, IAb, IBb, ICb, IDb, IEb, and IGb, wherein:
$R_1$ is —OH;
and X; $R_2$; $R_3$; $R_4$; $R^a$; $R^b$; $R^c$; and Prot$^{NH}$ are as defined as above.

Further preferred compounds include compounds of general formula I, IA, IB, IC, ID, IE, IF, Ia, IAa, IBa, ICa, IDa, IEa, IFa, Ib, IAb, IBb, ICb, IDb, IEb, and IFb, wherein:
$R_2$ is a —C(=O)$R^a$ group where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and X; $R_1$; $R_3$; $R_4$; $R^b$; $R^c$; and Prot$^{NH}$ are as defined as above.

Further preferred compounds include compounds of general formula I, IB, IC, ID, IE, IF, IG, Ia, IBa, ICa, IDa, IEa, IFa, IGa, Ib, IBb, ICb, IDb, IEb, IFb, and IGb, wherein:
$R_3$ is hydrogen or a —O$R^b$ group for compounds of formula I, IC, ID, IE, IF, IG, Ia, ICa, IDa, IEa, IFa, IGa, Ib, ICb, IDb, IEb, IFb, or IGb; and $R_3$ is a —O$R^b$ group of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and X; $R_1$; $R_2$; $R_4$; $R^a$; $R^c$; and Prot$^{NH}$ are as defined as above.

Further preferred compounds include compounds of general formula I, IA, IB, IC, ID, IE, IF, IG, Ia, IAa, IBa, ICa, IDa, IEa, IFa, IGa, Ib, IAb, IBb, ICb, IDb, IEb, IFb, and IGb, wherein:
$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, ID, IF, IG, Ia, IAa, IBa, ICa, IDa, IFa, IGa, Ib, IAb, IBb, ICb, IDb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —CH$_2$OH and —CH$_2$NH$_2$. More preferably, $R_4$ may be —CH$_2$NH$_2$. Most preferred $R_4$ is —CH$_2$OH;
and X; $R_1$; $R_2$; $R_3$; $R^a$; and $R^b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_1$ is —OH;
and $R_2$; $R_3$; $R_4$; $R^a$; $R^b$; $R^c$; and Prot$^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_2$ is a —C(=O)$R^a$ for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_1$; $R_3$; $R_4$; $R^b$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_3$ is hydrogen or a —O$R^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_1$; $R_2$; $R_4$; $R^a$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, or substituted or unsubstituted tert-butyl. Most preferred $R^c$ is methyl. More preferred $R_4$ is selected from CH$_2$OH and CH$_2$NH$_2$. More preferably, $R_4$ may be —CH$_2$NH$_2$. Most preferred $R_4$ is —CH$_2$OH;
and $R_1$; $R_2$; $R_3$; $R^a$; and $R^b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_1$ is —OH;
$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_3$; $R_4$; $R^b$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_1$ is —OH;
$R_3$ is hydrogen or a —O$R^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_2$; $R_4$; $R^a$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_1$ is —OH;
$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from CH$_2$OH and CH$_2$NH$_2$. More preferably, $R_4$ may be —CH$_2$NH$_2$. Most preferred $R_4$ is —CH$_2$OH;
and $R_2$; $R_3$; $R^a$; and $R^b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —O$R^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$; $R_4$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

X is —NH—;

$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from CH$_2$OH and CH$_2$NH$_2$. More preferably, $R_4$ may be —CH$_2$NH$_2$. Most preferred $R_4$ is —CH$_2$OH;

and $R_1$; $R_3$; and $R^b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

X is —NH—;

$R_3$ is hydrogen or a —OR$^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —OR$^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from CH$_2$OH and CH$_2$NH$_2$. More preferably, $R_4$ may be —CH$_2$NH$_2$. Most preferred $R_4$ is —CH$_2$OH;

and $R_1$; $R_2$; and $R^a$; are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

X is —NH—;

$R_1$ is —OH;

$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —OR$^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —OR$^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_4$; $R^c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

X is —NH—;

$R_1$ is —OH;

$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from CH$_2$OH and CH$_2$NH$_2$. More preferably, $R_4$ may be —CH$_2$NH$_2$. Most preferred $R_4$ is —CH$_2$OH;

and $R_3$; and $R^b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —O$R^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
$R_4$ is selected from —$CH_2OH$, —$CH_2OC(=O)R^c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from $CH_2OH$ and $CH_2NH_2$. More preferably, $R_4$ may be —$CH_2NH_2$. Most preferred $R_4$ is —$CH_2OH$;
and $R_1$ is as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:
X is —NH—;
$R_1$ is —OH;
$R_2$ is a —C(=O)$R^a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —O$R^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
$R_4$ is selected from —$CH_2OH$, —$CH_2OC(=O)R^c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R^c$ is methyl. More preferred $R_4$ is selected from $CH_2OH$ and $CH_2NH_2$. More preferably, $R_4$ may be —$CH_2NH_2$. Most preferred $R_4$ is —$CH_2OH$.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_1$ is —OH;
and $R_2$; $R_3$; $R_4$; $R^a$; $R^b$; $R^c$; and Prot$^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_2$ is a —C(=O)$R^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_1$; $R_3$; $R_4$; $R^b$; $R^c$; and Prot$^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_3$ is hydrogen or a —O$R^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —O$R^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ is hydrogen and methoxy, being hydrogen the most preferred $R_3$ group;
and $R_1$; $R_2$; $R_4$; $R^a$; $R^c$; and Prot$^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;

$R_4$ is selected from —$CH_2OH$, —$CH_2OC(=O)R^c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —$CH_2OH$ and $CH_2NH_2$. More preferably, $R_4$ may be —$CH_2NH_2$. Most preferred $R_4$ is —$CH_2OH$; and $R_1$; $R_2$; $R_3$; $R^a$; and $R^b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_1$ is —OH;
$R_2$ is a —$C(=O)R^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_3$; $R_4$; $R^b$; $R^c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_1$ is —OH;
$R_3$ is hydrogen or a —$OR^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_2$; $R_4$; $R^a$; $R^c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_1$ is —OH;
$R_4$ is selected from —$CH_2OH$, —$CH_2OC(=O)R^c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —$CH_2OH$ and $CH_2NH_2$. More preferably, $R_4$ may be —$CH_2NH_2$. Most preferred $R_4$ is —$CH_2OH$;
and $R_2$; $R_3$; $R^a$; and $R^b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_2$ is a —$C(=O)R^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —$OR^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR^b$ group for compounds of formula IB, IBa or IBb; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_1$; $R_4$; $R^c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_2$ is a —$C(=O)R^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_4$ is selected from —$CH_2OH$, —$CH_2OC(=O)R^c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;
and $R_1$; $R_3$; and $R^b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

X is —O—;

$R_3$ is hydrogen or a —OR$^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —OR$^b$ group for compounds of formula IB, IBa or IBb; where R$^b$ is a substituted or unsubstituted $C_1$-$C_6$ alkyl. Particularly preferred R$^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —CH$_2$OH, —CH$_2$OC(=O)R$^c$, —CH$_2$NH$_2$, and —CH$_2$NHProt$^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —CH$_2$NH$_2$, and —CH$_2$NHProt$^{NH}$ for compounds of formula IE, IEa or IEb; where R$^c$ is a substituted or unsubstituted $C_1$-$C_6$ alkyl. Particularly preferred R$^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred R$^c$ is methyl. More preferred $R_4$ is selected from —CH$_2$OH and —CH$_2$NH$_2$. More preferably, $R_4$ may be —CH$_2$NH$_2$. Most preferred $R_4$ is —CH$_2$OH; and $R_1$; $R_2$; and R$^a$; are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

X is —O—;

$R_1$ is —OH;

$R_2$ is a —C(=O)R$^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where R$^a$ is a substituted or unsubstituted $C_1$-$C_6$ alkyl. Particularly preferred R$^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —OR$^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —OR$^b$ group for compounds of formula IB, IBa or IBb; where R$^b$ is a substituted or unsubstituted $C_1$-$C_6$ alkyl. Particularly preferred R$^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group; and $R_4$; R$^c$; and Prot$^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

X is —O—;

$R_1$ is —OH;

$R_2$ is a —C(=O)R$^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where R$^a$ is a substituted or unsubstituted $C_1$-$C_6$ alkyl. Particularly preferred R$^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —CH$_2$OH, —CH$_2$OC(=O)R$^c$, —CH$_2$NH$_2$, and —CH$_2$NHProt$^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —CH$_2$NH$_2$, and —CH$_2$NHProt$^{NH}$ for compounds of formula IE, IEa or IEb; where R$^c$ is a substituted or unsubstituted $C_1$-$C_6$ alkyl. Particularly preferred R$^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred R$^c$ is methyl. More preferred $R_4$ is selected from —CH$_2$OH and —CH$_2$NH$_2$. More preferably, $R_4$ may be —CH$_2$NH$_2$. Most preferred $R_4$ is —CH$_2$OH; and $R_3$; and R$^b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

X is —O—;

$R_2$ is a —C(=O)R$^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where R$^a$ is a substituted or unsubstituted $C_1$-$C_6$ alkyl. Particularly preferred R$^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —OR$^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —OR$^b$ group for compounds of formula IB, IBa or IBb; where R$^b$ is a substituted or unsubstituted $C_1$-$C_6$ alkyl. Particularly preferred R$^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —CH$_2$OH, —CH$_2$OC(=O)R$^c$, —CH$_2$NH$_2$, and —CH$_2$NHProt$^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —CH$_2$NH$_2$, and —CH$_2$NHProt$^{NH}$ for compounds of formula IE, IEa or IEb; where R$^c$ is a substituted or unsubstituted $C_1$-$C_6$ alkyl. Particularly preferred R$^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —CH$_2$OH and —CH$_2$NH$_2$. More preferably, $R_4$ may be —CH$_2$NH$_2$. Most preferred $R_4$ is —CH$_2$OH; and $R_1$ is as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:
X is —O—;
$R_1$ is —OH;
$R_2$ is a —C(=O)$R^a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R^a$ is a substituted or unsubstituted C$_1$-C$_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —OR$^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —OR$^b$ group for compounds of formula IB, IBa or IBb; where $R^b$ is a substituted or unsubstituted C$_1$-C$_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
$R_4$ is selected from —CH$_2$OH, —CH$_2$OC(=O)$R^c$, —CH$_2$NH$_2$, and —CH$_2$NHProt$^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted C$_1$-C$_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from —CH$_2$OH and —CH$_2$NH$_2$. More preferably, $R_4$ may be —CH$_2$NH$_2$. Most preferred $R_4$ is —CH$_2$OH.

Further preferred compounds include compounds of general formula Ic, IAc, IBc, IDc, and IGc wherein:
$R_1$ is —OH;
and $R_2$; $R_3$; $R^a$ and $R^b$ are as defined as above.

Further preferred compounds include compounds of general formula Ic, IAc, IBc, IDc, IFc, and IGc, wherein:
$R_2$ is a —C(=O)$R^a$ group for compounds of formula Ic, IAc, IBc, IDc, or IFc; and $R_2$ is acetyl for compounds of formula IGc; where $R^a$ is a substituted or unsubstituted C$_1$-C$_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_1$; $R_3$; $R^b$ are as defined as above.

Further preferred compounds include compounds of general formula Ic, IAc, IBc, IDc, IFc, and IGc, wherein:
$R_3$ is hydrogen or a —OR$^b$ group for compounds of formula Ic, IDc, IFc, or IGc; $R_3$ is hydrogen for compounds of formula IAc; and $R_3$ is a —OR$^b$ group for compounds of formula IBc; where $R^b$ is a substituted or unsubstituted C$_1$-C$_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_1$; $R_2$; and $R^a$ are as defined as above.

Further preferred compounds include compounds of general formula Ic, IAc, IBc, IDc, IFc, and IGc, wherein:
$R_1$ is —OH;
$R_2$ is a —C(=O)$R^a$ group for compounds of formula Ic, IAc, IBc, IDc, or IFc; and $R_2$ is acetyl for compounds of formula IGc; where $R^a$ is a substituted or unsubstituted C$_1$-C$_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
and $R_3$; and $R^b$ are as defined as above.

Further preferred compounds include compounds of general formula Ic, IAc, IBc, IDc, IFc, and IGc, wherein:
$R_1$ is —OH;
$R_3$ is hydrogen or a —OR$^b$ group for compounds of formula Ic, IDc, IFc, or IGc; $R_3$ is hydrogen for compounds of formula IAc; and $R_3$ is a —OR$^b$ group for compounds of formula IBc; where $R^b$ is a substituted or unsubstituted C$_1$-C$_6$ alkyl. Particularly preferred $R^b$ is selected from substituted or unsubstituted methyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;
and $R_2$; and $R^a$ are as defined as above.

Further preferred compounds include compounds of general formula Ic, IAc, IBc, IDc, IFc, and IGc, wherein:
$R_2$ is a —C(=O)$R^a$ group for compounds of formula Ic, IAc, IBc, IDc, or IFc; and $R_2$ is acetyl for compounds of formula IGc; where $R^a$ is a substituted or unsubstituted C$_1$-C$_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;
$R_3$ is hydrogen or a —OR$^b$ group for compounds of formula Ic, IDc, IFc, or IGc; $R_3$ is hydrogen for compounds of formula IAc; and $R_3$ is a —OR$^b$ group for compounds of formula IBc; where $R^b$ is a substituted or unsubstituted C$_1$-C$_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$ is as defined as above.

Further preferred compounds include compounds of general formula Ic, IAc, IBc, IDc, IFc, and IGc, wherein:

$R_1$ is —OH;

$R_2$ is a —C(=O)$R^a$ group for compounds of formula Ic, IAc, IBc, IDc, or IFc; and $R_2$ is acetyl for compounds of formula IGc; where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —O$R^b$ group for compounds of formula Ic, IDc, IFc, or IGc; $R_3$ is hydrogen for compounds of formula IAc; and $R_3$ is a —O$R^b$ group for compounds of formula IBc; where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group.

The following preferred substituents (where allowed by possible substituent groups) apply to compounds of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, Ic, IAc, IBc, IDc, IFc, and IGc:

In compounds of the present invention, particularly preferred $R_1$ is —OH.

In compounds of the present invention, particularly preferred $R_2$ is a —C(=O)$R^a$ group where $R^a$ is a substituted or unsubstituted $C_1$-$C_6$ alkyl. Particularly preferred $R^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl.

In compounds of the present invention, particularly preferred $R_3$ is hydrogen or a —O$R^b$ group where $R^b$ is a substituted or unsubstituted $C_1$-$C_6$ alkyl. Particularly preferred $R^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group.

In compounds of the present invention, particularly preferred $R_4$ is selected from H, —CH$_2$OH, —CH$_2$OC(=O)$R^c$, —CH$_2$NH$_2$, and —CH$_2$NHProt$^{NH}$ where $R^c$ is a substituted or unsubstituted $C_1$-$C_6$ alkyl. Particularly preferred $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from H, CH$_2$OH and CH$_2$NH$_2$. Most preferred $R_4$ is —CH$_2$OH.

In compounds of general formula I, IA, IB, IC, ID, IE, IF, IG, Ia, IAa, IBa, ICa, IDa, IEa, IFa, IGa, Ib, IAb, IBb, ICb, IDb, IEb, IFb, and IGb particularly preferred $R_4$ is selected from —CH$_2$OH, —CH$_2$OC(=O)$R^c$, —CH$_2$NH$_2$, and —CH$_2$NHProt$^{NH}$ for compounds of formula I, IA, IB, IC, ID, IF, IG, Ia, IAa, IBa, ICa, IDa, IFa, IGa, Ib, IAb, IBb, ICb, IDb, IFb, or IGb; and $R_4$ is selected from —CH$_2$NH$_2$, and —CH$_2$NHProt$^{NH}$ for compounds of formula IE, IEa or IEb; where $R^c$ is a substituted or unsubstituted $C_1$-$C_6$ alkyl. Particularly preferred $R^c$ is a substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R^c$ is methyl. More preferred $R_4$ is selected from CH$_2$OH and CH$_2$NH$_2$. Most preferred $R_4$ is —CH$_2$OH.

Being particularly preferred compounds of formula Ia, IAa, IBa, ICa, IDa, IFa, IGa when $R_4$ is —CH$_2$OH or —CH$_2$OC(=O)$R^c$ and compounds of formula Ib, IAb, IBb, ICb, IDb, IEb, IFb, IGb when $R_4$ is —CH$_2$NH$_2$ or —CH$_2$NHProt$^{NH}$.

In compounds of the present invention, particularly preferred X is —NH—.

Alternatively, in compounds of the present invention, particularly preferred X is —O—.

Preferred compounds according to the present invention include:

Compounds of formula I, IA, IB, IC, ID, IF, IG, Ia, IAa, IBa, ICa, IDa, IFa, IGa, Ib, IAb, IBb, ICb, IDb, IFb, and IGb wherein:

$R_4$ is selected from —CH$_2$OH and —CH$_2$OC(=O)$R^c$;

Being particularly preferred compounds of formula Ia, IAa, IBa, ICa, IDa, IFa, and IGa and/or compounds where $R_4$ is —CH$_2$OH.

Compounds of formula I, IA, IB, IC, ID, IE IF, IG, Ia, IAa, IBa, ICa, IDa, IEa, IFa, IGa, Ib, IAb, IBb, ICb, IDb, IEb, IFb, and IGb wherein $R_4$ is selected from —CH$_2$NH$_2$ and —CH$_2$NHProt$^{NH}$; and Prot$^{NH}$ is a protecting group for amino.

Being particularly preferred compounds of formula Ib, IAb, IBb, ICb, IDb, IEb, IFb, and IGb and/or compounds where $R_4$ is —CH$_2$NH$_2$.

Compounds of formula Ic, IAc, IBc, IDc, IFc, IGc wherein $R_2$ is a —C(=O)$R^a$ group for compounds of formula Ic, IAc, IBc, IDc, or IFc; and $R_2$ is acetyl for compounds of formula IGc;

$R_3$ is hydrogen or a —O$R^b$ group for compounds of formula Ic, IDc, IFc, IGc; $R_3$ is hydrogen for compounds of formula IAc; or $R_3$ is a —O$R^b$ group for compounds of formula IBc;

$R^a$ is selected from hydrogen, and substituted or unsubstituted $C_1$-$C_6$ alkyl; and $R^b$ is substituted or unsubstituted $C_1$-$C_6$ alkyl.

Particularly preferred compounds according to the present invention include:

Compounds of formula I, IA, IB, IC, IF, IG, Ia, IAa, IBa, ICa, IFa, IGa, Ib, IAb, IBb, ICb, IFb, and IGb wherein X is —NH—;

$R_4$ is selected from —CH$_2$OH, and —CH$_2$OC(=O)$R^c$; and $R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

Being more preferred compounds of formula Ia, IAa, IBa, ICa, IFa, IGa and/or compounds where $R_4$ is —$CH_2OH$.

Compounds of formula I, IA, IB, ID, IF, IG, Ia, IAa, IBa, IDa, IFa, IGa, Ib, IAb, IBb, IDb, IFb, and IGb wherein X is —O—;

$R_4$ is selected from —$CH_2OH$ and —$CH_2OC(=O)R^c$; and $R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

Being more preferred compounds of formula Ia, IAa, IBa, IDa, IFa, IGa and/or compounds where $R_4$ is —$CH_2OH$.

Compounds of formula I, IA, IB, IC, IE, IF, IG, Ia, IAa, IBa, ICa, IEa, IFa, IGa, Ib, IAb, IBb, ICb, IEb, IFb, and IGb wherein X is —NH—;

$R_4$ is selected from —$CH_2NH_2$ and —$CH_2NHProt^{NH}$; and $Prot^{NH}$ is a protecting group for amino.

Being more preferred compounds of formula Ib, IAb, IBb, ICb, IEb, IFb, IGb and/or compounds where $R_4$ is —$CH_2NH_2$.

Compounds of formula I, IA, IB, ID, IE, IF, IG, Ia, IAa, IBa, IDa, IEa, IFa, IGa, Ib, IAb, IBb, IDb, IEb, IFb, and IGb wherein X is —O—;

$R_4$ is selected from —$CH_2NH_2$ and —$CH_2NHProt^{NH}$; and $Prot^{NH}$ is a protecting group for amino.

Being more preferred compounds of formula Ib, IAb, IBb, IDb, IEb, IFb, IGb and/or compounds where $R_4$ is —$CH_2NH_2$.

Compounds of formula I, IA, IB, IC, ID, IF, IG, Ia, IAa, IBa, ICa, IDa, IFa, IGa, Ib, IAb, IBb, ICb, IDb, IFb, IGb wherein $R_2$ is a —$C(=O)R^a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or a —$OR^b$ group for compounds of formula I, IC, ID, IF, IG, Ia, ICa, IDa, IFa, IGa, Ib, ICb, IDb, IFb, or IGb; $R_3$ is hydrogen for compounds of formula IA, IAa or IAb; or $R_3$ is a —$OR^b$ group for compounds of formula IB, IBa or IBb;

$R_4$ is selected from —$CH_2OH$, and —$CH_2OC(=O)R^c$;

$R^a$ is selected from hydrogen, and substituted or unsubstituted $C_1$-$C_6$ alkyl;

$R^b$ is substituted or unsubstituted $C_1$-$C_6$ alkyl; and $R^c$ is substituted or unsubstituted $C_1$-$C_6$ alkyl.

Being more preferred compounds of formula Ia, IAa, IBa, ICa, IDa, IFa, IGa and/or compounds where $R_4$ is —$CH_2OH$.

Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein $R_2$ is a —$C(=O)R^a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or a —$OR^b$ group for compounds of formula I, IC, ID, IE, IF, IG, Ia, ICa, IDa, IEa, IFa, IGa, Ib, ICb, IDb, IEb, IFb, or IGb; $R_3$ is hydrogen for compounds of formula IA, IAa or IAb; or $R_3$ is a —$OR^b$ group for compounds of formula IB, IBa or IBb;

$R_4$ is selected from —$CH_2NH_2$ and —$CH_2NHProt^{NH}$;

$R^a$ is selected from hydrogen, and substituted or unsubstituted $C_1$-$C_6$ alkyl;

$R^b$ is substituted or unsubstituted $C_1$-$C_6$ alkyl; and $Prot^{NH}$ is a protecting group for amino.

Being more preferred compounds of formula Ib, IAb, IBb, ICb, IDb, IEb, IFb, IGb and/or compounds where $R_4$ is —$CH_2NH_2$.

Compounds of formula Ic, IAc, IBc, IDc, IFc, IGc wherein $R_2$ is a —$C(=O)R^a$ group for compounds of formula Ic, IAc, IBc, IDc, or IFc; and $R_2$ is acetyl for compounds of formula IGc;

$R_3$ is hydrogen or a —$OR^b$ group for compounds of formula Ic, IDc, IFc, IGc; $R_3$ is hydrogen for compounds of formula IAc; or $R_3$ is a —$OR^b$ group for compounds of formula IBc;

$R^a$ is substituted or unsubstituted $C_1$-$C_6$ alkyl; and $R^b$ is substituted or unsubstituted $C_1$-$C_6$ alkyl.

More preferred compounds according to the present invention include

Compounds of formula I, IA, IB, IC, IF, IG, Ia, IAa, IBa, ICa, IFa, IGa, Ib, IAb, IBb, ICb, IFb, and IGb wherein X is —NH—;

$R_2$ is a —$C(=O)R^a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;

$R_3$ is hydrogen or a —$OR^b$ group for compounds of formula I, IC, IF, IG, Ia, ICa, IFa, IGa, Ib, ICb, IFb, or IGb; $R_3$ is hydrogen for compounds of formula IA, IAa or IAb; or $R_3$ is a —$OR^b$ group for compounds of formula IB, IBa or IBb;

$R_4$ is —$CH_2OH$;

$R^a$ is selected from hydrogen and substituted or unsubstituted $C_1$-$C_6$ alkyl; and $R^b$ is substituted or unsubstituted $C_1$-$C_6$ alkyl.

Being particularly more preferred compounds of formula Ia, IAa, or IBa, ICa, IFa, IGa.

Compounds of formula I, IA, IB, ID, IF, IG, Ia, IAa, IBa, IDa, IFa, IGa, Ib, IAb, IBb, IDb, IFb, and IGb wherein X is —O—;

$R_2$ is a —$C(=O)R^a$ group for compounds of formula I, IA, IB, ID, IF, Ia, IAa, IBa, IDa, IFa, Ib, IAb, IBb, IDb, or IFb; and $R_2$ is acetyl for compounds of formula IG, IGa or IGb;

$R_3$ is hydrogen or a —$OR^b$ group for compounds of formula I, ID, IF, IG, Ia, IDa, IFa, IGa, Ib, IDb, IFb, or IGb; $R_3$ is hydrogen for compounds of formula IA, IAa or IAb;

or $R_3$ is a —$OR^b$ group for compounds of formula IB, IBa or IBb;

$R_4$ is —$CH_2OH$;

$R^a$ is selected from hydrogen and substituted or unsubstituted $C_1$-$C_6$ alkyl; and $R^b$ is substituted or unsubstituted $C_1$-$C_6$ alkyl.

Being particularly more preferred compounds of formula Ia, IAa, IBa, IDa, IFa, or IGa.

Compounds of formula I, IA, IB, IC, IE, IF, IG, Ia, IAa, IBa, ICa, IEa, IFa, IGa, Ib, IAb, IBb, ICb, IEb, IFb, and IGb wherein X is —NH—;

$R_2$ is a —$C(=O)R^a$ group for compounds of formula I, IA, IB, IC, IE, IF, Ia, IAa, IBa, ICa, IEa, IFa, Ib, IAb, IBb, ICb, IEb or IFb; and $R_2$ is acetyl for compounds of formula IG, IGa or IGb;
$R_3$ is hydrogen or a $-OR^b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa or IAb; or $R_3$ is a $-OR^b$ group for compounds of formula IB, IBa or IBb;
$R_4$ is selected from $-CH_2NH_2$ and $-CH_2NHProt^{NH}$;
$R^a$ is selected from hydrogen and substituted or unsubstituted $C_1$-$C_6$ alkyl;
$R^b$ is substituted or unsubstituted $C_1$-$C_6$ alkyl; and
$Prot^{NH}$ is a protecting group for amino.
Being particularly more preferred compounds of formula Ib, IAb, IBb, ICb, IEb, IFb, IGb and/or compounds where $R_4$ is $-CH_2NH_2$
Compounds of formula I, IA, IB, ID, IE, IF, IG, Ia, IAa, IBa, IDa, IEa, IFa, IGa, Ib, IAb, IBb, IDb, IEb, IFb, and IGb wherein
X is $-O-$;
$R_2$ is a $-C(=O)R^a$ group for compounds of formula I, IA, IB, ID, IE, IF, Ia, IAa, IBa, IDa, IEa, IFa, Ib, IAb, IBb, IDb, IEb or IFb; and $R_2$ is acetyl for compounds of formula IG, IGa or IGb;
$R_3$ is hydrogen or a $-OR^b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa or IAb; or $R_3$ is a $-OR^b$ group for compounds of formula IB, IBa or IBb;
$R_4$ is selected from $-CH_2NH_2$ and $-CH_2NHProt^{NH}$;
$R^a$ is selected from hydrogen and substituted or unsubstituted $C_1$-$C_6$ alkyl;
$R^b$ is substituted or unsubstituted $C_1$-$C_6$ alkyl; and
$Prot^{NH}$ is a protecting group for amino.
Being particularly more preferred compounds of formula Ib, IAb, IBb, IDb, IEb, IFb, IGb and/or compounds where $R_4$ is $CH_2NH_2$.
Compounds of formula I, IA, IB, IC, ID, IF, IG, Ia, IAa, IBa, ICa, IDa, IFa, IGa, Ib, IAb, IBb, ICb, IDb, IFb, and IGb wherein
$R_2$ is a $-C(=O)R^a$ group for compounds of formula I, IA, IB, IC, ID, IF, Ia, IAa, IBa, ICa, IDa, IFa, Ib, IAb, IBb, ICb, IDb or IFb; and $R_2$ is acetyl for compounds of formula IG, IGa or IGb;
$R_3$ is hydrogen or a $-OR^b$ group for compounds of formula I, IC, ID, IF, IG, Ia, ICa, IDa, IFa, IGa, Ib, ICb, IDb, IFb, or IGb; $R_3$ is hydrogen for compounds of formula IA, IAa or IAb; or $R_3$ is a $-OR^b$ group for compounds of formula IB, IBa or IBb;
$R_4$ is $-CH_2OH$;
$R^a$ is substituted or unsubstituted $C_1$-$C_6$ alkyl; and
$R^b$ is substituted or unsubstituted $C_1$-$C_6$ alkyl.
Being particularly more preferred compounds of formula Ia, IAa, IBa, ICa, IDa, IFa, or IGa.
Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein
$R_2$ is a $-C(=O)R^a$ group for compounds of formula I, IA, IB, IC, ID, IE, IF, Ia, IAa, IBa, ICa, IDa, IEa, IFa, Ib, IAb, IBb, ICb, IDb, IEb or IFb; and $R_2$ is acetyl for compounds of formula IG, IGa or IGb;
$R_3$ is hydrogen or a $-OR^b$ group for compounds of formula I, IC, ID, IE, IF, IG, Ia, ICa, IDa, IEa, IFa, IGa, Ib, ICb, IDb, IEb, IFb, or IGb; $R_3$ is hydrogen for compounds of formula IA, IAa or IAb; or $R_3$ is a $-OR^b$ group for compounds of formula IB, IBa or IBb;
$R_4$ is selected from $-CH_2NH_2$ and $-CH_2NHProt^{NH}$;
$R^a$ is substituted or unsubstituted $C_1$-$C_6$ alkyl;
$R^b$ is substituted or unsubstituted $C_1$-$C_6$ alkyl; and
$Prot^{NH}$ is a protecting group for amino.
Being particularly more preferred compounds of formula Ib, IAb, IBb, ICb, IDb, IEb, IFb, IGb and/or compounds where $R_4$ is $-CH_2NH_2$.
Compounds of formula I, IA, IB, IC, IF, IG, Ia, IAa, IBa, ICa, IFa, IGa, Ib, IAb, IBb, ICb, IFb, and IGb wherein
X is $-NH-$;
$R_2$ is a $-C(=O)R^a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;
$R_3$ is hydrogen or a $-OR^b$ group for compounds of formula I, IC, IF, IG, Ia, ICa, IFa, IGa, Ib, ICb, IFb, or IGb; $R_3$ is hydrogen for compounds of formula IA, IAa or IAb; or $R_3$ is a $-OR^b$ group for compounds of formula IB, IBa or IBb;
$R_4$ is $-CH_2OC(=O)R^c$;
$R^a$ is selected from hydrogen and substituted or unsubstituted $C_1$-$C_6$ alkyl;
$R^b$ is substituted or unsubstituted $C_1$-$C_6$ alkyl; and
$R^c$ is a substituted or unsubstituted $C_1$-$C_6$ alkyl.
Being more preferred compounds of formula Ia, IAa, IBa, ICa, IFa, or IGa.
Compounds of formula Ic, IAc, IBc, IDc, IFc, and IGc wherein
$R_2$ is a $-C(=O)R^a$ group for compounds of formula Ic, IAc, IBc, IDc, or IFc; and $R_2$ is acetyl for compounds of formula IGc;
$R_3$ is hydrogen or methoxy for compounds of formula Ic, IDc, IFc, or IGc; $R_3$ is hydrogen for compounds of formula IAc; or $R_3$ is methoxy for compounds of formula IBc; and
$R^a$ is substituted or unsubstituted $C_1$-$C_6$ alkyl.
Particularly more preferred compounds according to the present invention include:
Compounds of formula I, IA, IB, IC, IF, IG, Ia, IAa, IBa, ICa, IFa, IGa, Ib, IAb, IBb, ICb, IFb, and IGb wherein
X is $-NH-$;
$R_2$ is a $-C(=O)R^a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;
$R_3$ is hydrogen or methoxy for compounds of formula I, IC, IF, IG, Ia, ICa, IFa, IGa, Ib, ICb, IFb, or IGb; $R_3$ is hydrogen for compounds of formula IA, IAa or IAb; and
$R_3$ is methoxy for compounds of formula IB, IBa or IBb;
$R_4$ is $-CH_2OH$; and
$R^a$ is substituted or unsubstituted $C_1$-$C_6$ alkyl.
Being even more preferred compounds of formula Ia, IAa, IBa, ICa, IFa, IGa.
Compounds of formula I, IA, IB, ID, IF, IG, Ia, IAa, IBa, IDa, IFa, IGa, Ib, IAb, IBb, IDb, IFb, and IGb wherein
X is $-O-$;
$R_2$ is a $-C(=O)R^a$ group for compounds of formula I, IA, IB, ID, IF, Ia, IAa, IBa, IDa, IFa, Ib, IAb, IBb, IDb, or IFb; and $R_2$ is acetyl for compounds of formula IG, IGa or IGb;
$R_3$ is hydrogen or methoxy for compounds of formula I, ID, IF, IG, Ia, IDa, IFa, IGa, Ib, IDb, IFb, or IGb; $R_3$ is hydrogen for compounds of formula IA, IAa or IAb; or $R_3$ is methoxy for compounds of formula IB, IBa or IBb;
$R_4$ is $-CH_2OH$; and
$R^a$ is substituted or unsubstituted $C_1$-$C_6$ alkyl.

Being even more preferred compounds of formula Ia, IAa, IBa, IDa, IEa, IFa, IGa.

Compounds of formula I, IA, IB, IC, IE, IF, IG, Ia, IAa, IBa, ICa, IEa, IFa, IGa, Ib, IAb, IBb, ICb, IEb, IFb, and IGb wherein X is —NH—;

$R_2$ is a —C(=O)$R^a$ group for compounds of formula I, IA, IB, IC, IE, IF, Ia, IAa, IBa, ICa, IEa, IFa, Ib, IAb, IBb, ICb, IEb or IFb; and $R_2$ is acetyl for compounds of formula IG, IGa or IGb;

$R_3$ is hydrogen or methoxy for compounds of formula I, IC, IE, IF, IG, Ia, ICa, IEa, IFa, IGa, Ib, ICb, IEb, IFb, or IGb; $R_3$ is hydrogen for compounds of formula IA, IAa or IAb; or $R_3$ is methoxy for compounds of formula IB, IBa or IBb;

$R_4$ is selected from —CH$_2$NH$_2$ and —CH$_2$NHProt$^{NH}$;

$R^a$ is substituted or unsubstituted $C_1$-$C_6$ alkyl; and

Prot$^{NH}$ is a protecting group for amino.

Being even more preferred compounds of formula Ib, IAb, IBb, ICb, IEb, IFb, IGb and/or compounds where $R_4$ is —CH$_2$NH$_2$.

Compounds of formula I, IA, IB, ID, IE, IF, IG, Ia, IAa, IBa, IDa, IEa, IFa, IGa, Ib, IAb, IBb, IDb, IEb, IFb, and IGb wherein X is —O—;

$R_2$ is a —C(=O)$R^a$ group for compounds of formula I, IA, IB, ID, IE, IF, Ia, IAa, IBa, IDa, IEa, IFa, Ib, IAb, IBb, IDb, IEb or IFb; and $R_2$ is acetyl for compounds of formula IG, IGa or IGb;

$R_3$ is hydrogen or methoxy for compounds of formula I, ID, IE, IF, IG, Ia, IDa, IEa, IFa, IGa, Ib, IDb, IEb, IFb, or IGb; $R_3$ is hydrogen for compounds of formula IA, IAa or IAb; or $R_3$ is methoxy for compounds of formula IB, IBa or IBb;

$R_4$ is selected from —CH$_2$NH$_2$ and —CH$_2$NHProt$^{NH}$;

$R^a$ is substituted or unsubstituted $C_1$-$C_6$ alkyl; and

Prot$^{NH}$ is a protecting group for amino.

Being even more preferred compounds of formula Ib, IAb, IBb, IDb, IEb, IFb, IGb and/or compounds where $R_4$ is —CH$_2$NH$_2$.

Compounds of formula I, IA, IB, IC, ID, IF, IG, Ia, IAa, IBa, ICa, IDa, IFa, IGa, Ib, IAb, IBb, ICb, IDb, IFb, and IGb wherein $R_2$ is a —C(=O)$R^a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or methoxy for compounds of formula I, IC, ID, IF, IG, Ia, ICa, IDa, IFa, IGa, Ib, ICb, IDb, IFb, and IGb; $R_3$ is hydrogen for compounds of formula IA, IAa or IAb; or $R_3$ is methoxy for compounds of formula IB, IBa or IBb;

$R_4$ is —CH$_2$OH; and $R^a$ is selected from methyl, ethyl, n-propyl, isopropyl and butyl, including n-butyl, sec-butyl, isobutyl and tert-butyl.

Being even more preferred compounds of formula Ia, IAa, IBa, ICa, IDa, IEa, IFa, or IGa.

Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein $R_2$ is a —C(=O)$R^a$ group for compounds of formula I, IA, IB, IC, ID, IE, IF, Ia, IAa, IBa, ICa, IDa, IEa, IFa, Ib, IAb, IBb, ICb, IDb, IEb or IFb; and $R_2$ is acetyl for compounds of formula IG, IGa or IGb;

$R_3$ is hydrogen or a methoxy for compounds of formula I, IC, ID, IE, IF, IG, Ia, ICa, IDa, IEa, IFa, IGa, Ib, ICb, IDb, IEb, IFb, and IGb; $R_3$ is hydrogen for compounds of formula IA, IAa or IAb; or $R_3$ is methoxy for compounds of formula IB, IBa or IBb;

$R_4$ is selected from —CH$_2$NH$_2$ and —CH$_2$NHProt$^{NH}$;

$R^a$ is selected from methyl, ethyl, n-propyl, isopropyl and butyl, including n-butyl, sec-butyl, isobutyl and tert-butyl; and Prot$^{NH}$ is a protecting group for amino.

Being even more preferred compounds of formula Ib, IAb, IBb, ICb, IDb, IEb, IFb, IGb and/or compounds where $R_4$ is —CH$_2$NH$_2$.

Compounds of formula Ic or IAc, IDc, IFc, and IGc wherein $R_2$ is a —C(=O)$R^a$ group for compounds of formula Ic, IAc, IDc, or IFc; and $R_2$ is acetyl for compounds of formula IGc;

$R_3$ is hydrogen; and $R^a$ is selected from methyl, ethyl, n-propyl, isopropyl and butyl, including n-butyl, sec-butyl, isobutyl and tert-butyl.

Compounds of formula Ic, IBc, IDc, IFc, and IGc wherein $R_2$ is a —C(=O)$R^a$ group for compounds of formula Ic, IBc, IDc, or IFc; and $R_2$ is acetyl for compounds of formula IGc;

$R_3$ is methoxy; and $R^a$ is selected from methyl, ethyl, n-propyl, isopropyl and butyl, including n-butyl, sec-butyl, isobutyl and tert-butyl.

Even more preferred compounds according to the present invention include:

Compounds of formula I, IA, IC, IF, IG, Ia, IAa, ICa, IFa, IGa, Ib, IAb, ICb, IFb, and IGb wherein X is —NH—;

$R_2$ is acetyl;

$R_3$ is hydrogen; and $R_4$ is —CH$_2$OH.

Being most preferred compounds of formula Ia, IAa, ICa, IFa, or IGa.

Compounds of formula I, IA, ID, IF, IG, Ia, IAa, IDa, IFa, IGa, Ib, IAb, IDb, IFb, and IGb wherein X is —O—;

$R_2$ is acetyl;

$R_3$ is hydrogen; and $R_4$ is —CH$_2$OH.

Being most preferred compounds of formula Ia, IAa, IDa, IFa, or IGa

Compounds of formula I, IA, IC, IE, IF, IG, Ia, IAa, ICa, IEa, IFa, IGa, Ib, IAb, ICb, IEb, IFb, and IGb wherein X is —NH—;

$R_2$ is acetyl;

$R_3$ is hydrogen; and $R_4$ is —CH$_2$NH$_2$.

Being most preferred compounds of formula Ib, IAb, ICb, IEb, IFb, or IGb.

Compounds of formula I, IA, ID, IE, IF, IG, Ia, IAa, IDa, IEa, IFa, IGa, Ib, IAb, IDb, IEb, IFb, and IGb wherein X is —O—;

$R_2$ is acetyl;

$R_3$ is hydrogen; and $R_4$ is —CH$_2$NH$_2$.

Being most preferred compounds of formula Ib, IAb, IDb, IEb, IFb, or IGb.

Compounds of formula I, IA, IC, ID, IF, IG, Ia, IAa, ICa, IDa, IFa, IGa, Ib, IAb, ICb, IDb, IFb, and IGb wherein $R_2$ is acetyl;

$R_3$ is hydrogen; and $R_4$ is —CH$_2$OH.

Being most preferred compounds of formula Ia, IAa, ICa, IDa, IFa or IGa.

Compounds of formula I, IA, IC, ID, IF, IG, Ia, IAa, ICa, IDa, IFa, IGa, Ib, IAb, ICb, IDb, IFb, and IGb wherein R$_1$ is —OH;

R$_2$ is acetyl;

R$_3$ is hydrogen; and

R$_4$ is —CH$_2$OH.

Being most preferred compounds of formula Ia, IAa, ICa, IDa, IFa or IGa.

Compounds of formula I, IA, IC, ID, IE, IF, IG, Ia, IAa, ICa, IDa, IEa, IFa, IGa, Ib, IAb, ICb, IDb, IEb, IFb, and IGb wherein R$_2$ is acetyl;

R$_3$ is hydrogen; and

R$_4$ is —CH$_2$NH$_2$.

Being most preferred compounds of formula Ib, IAb, ICb, IDb, IEb, IFb, or IGb.

Compounds of formula Ic or IAc, IDc, IFc, IGc wherein

R$_2$ is acetyl; and

R$_3$ is hydrogen.

Compounds of formula Ic or IBc, IDc, IFc, IGc wherein

R$_2$ is acetyl; and

R$_3$ is methoxy.

A compound according to the present invention of formula:

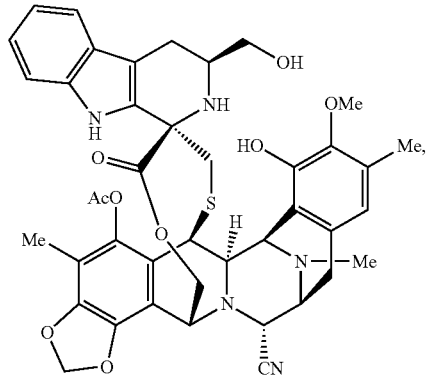

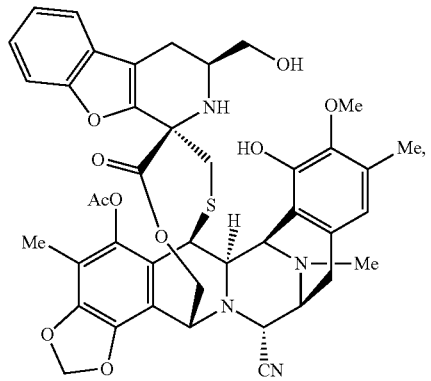

-continued

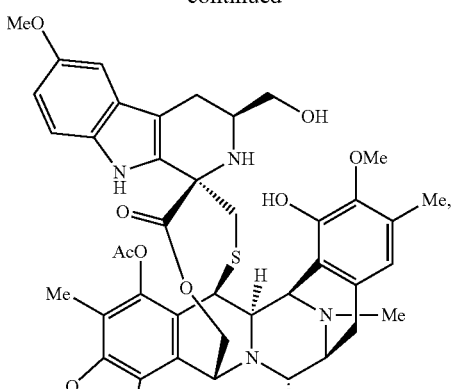

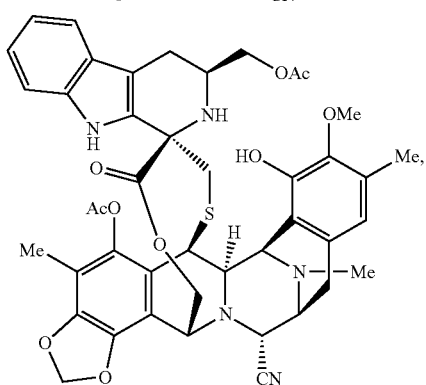

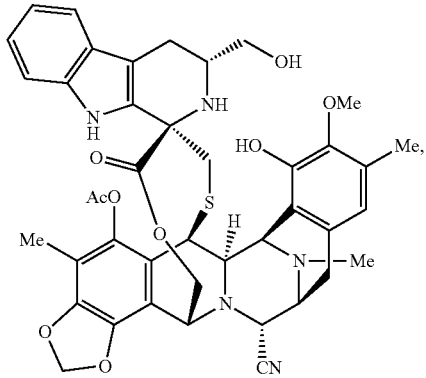

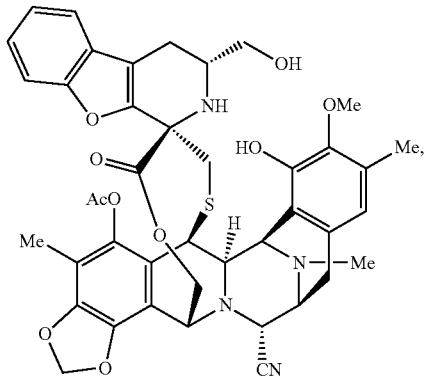

51
-continued
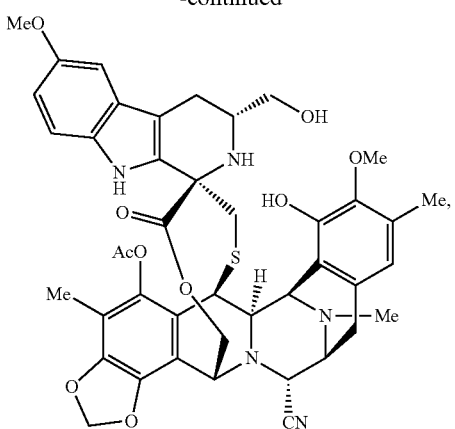
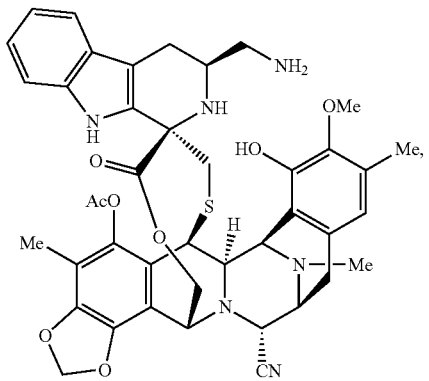
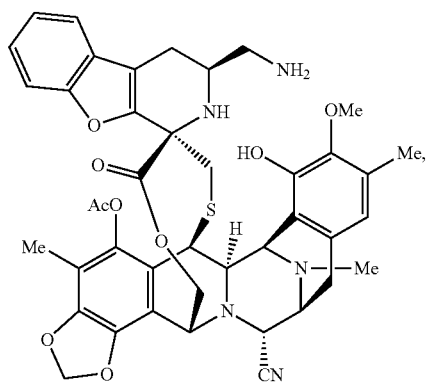
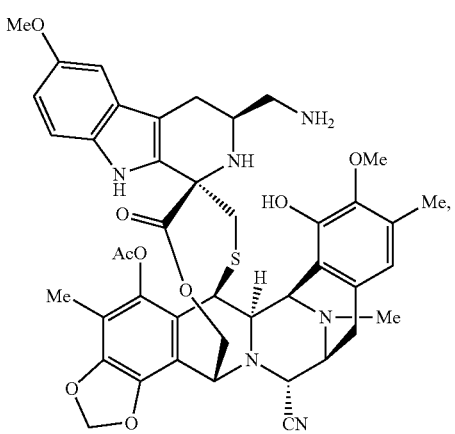
52
-continued
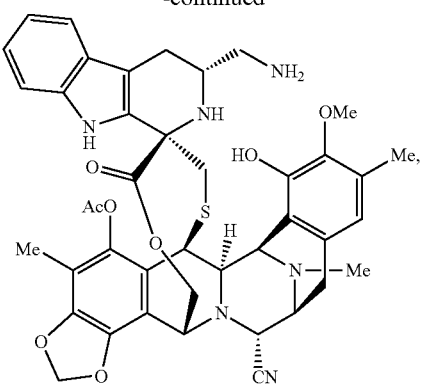
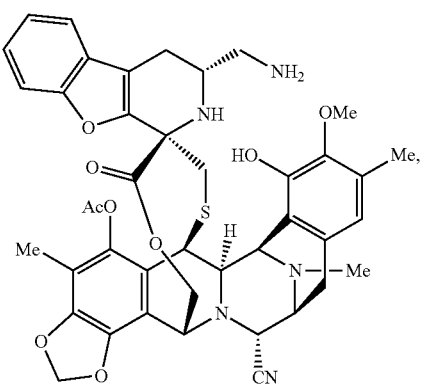
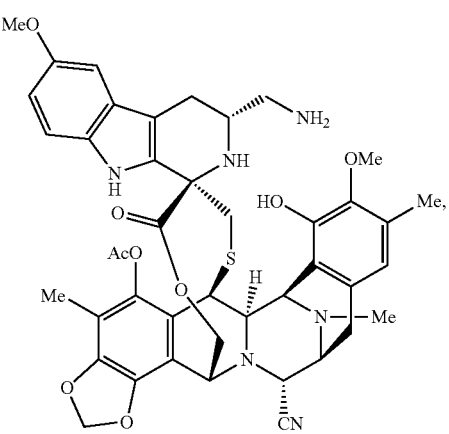
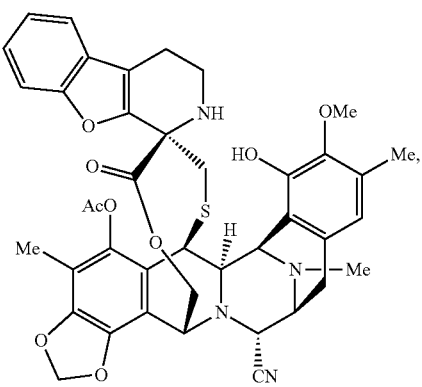

53
-continued
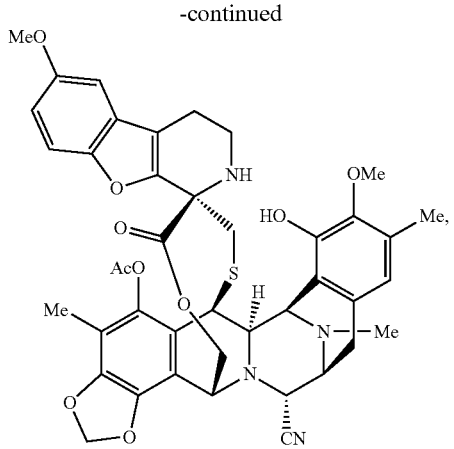
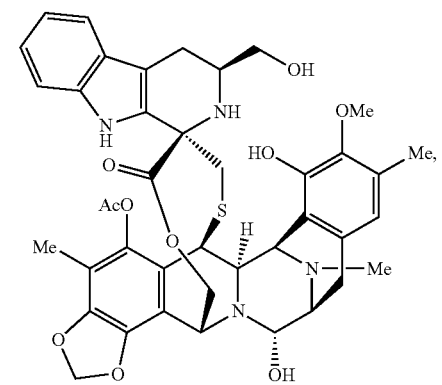
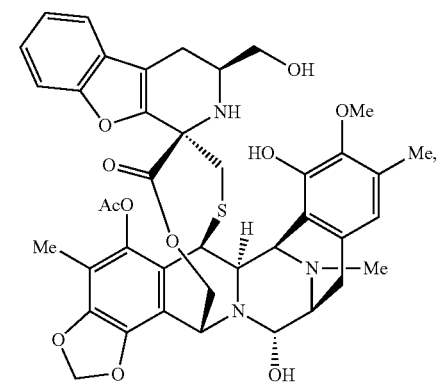
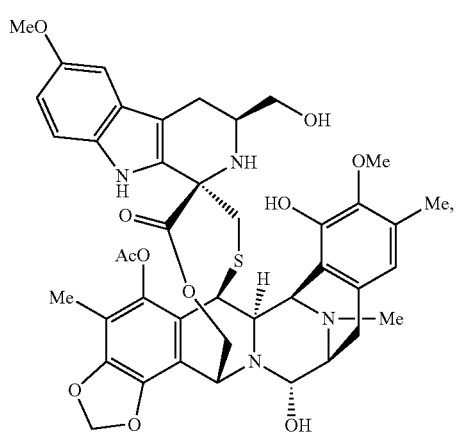
54
-continued
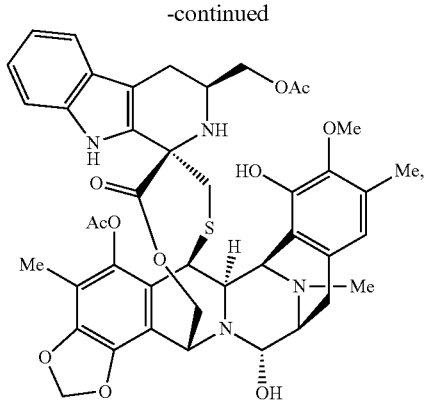
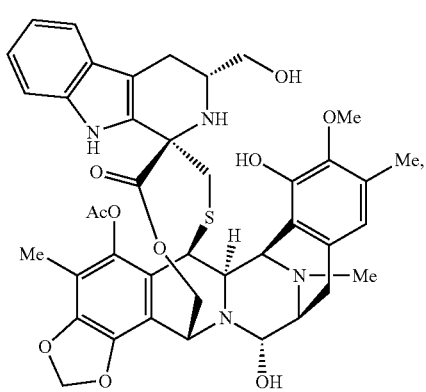
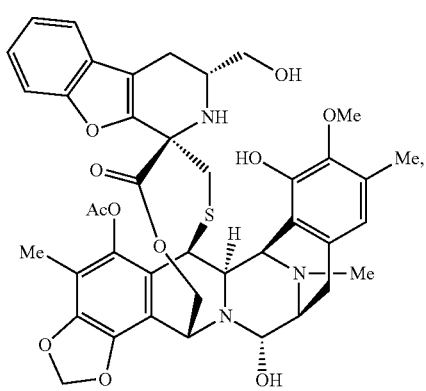
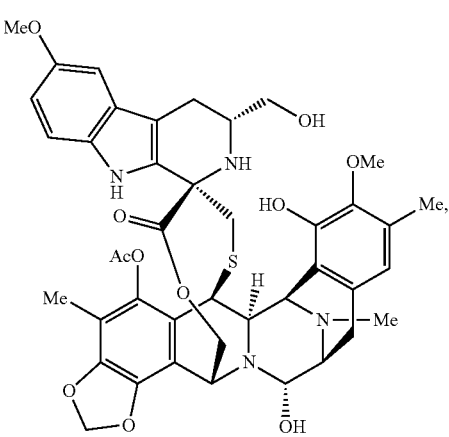

-continued
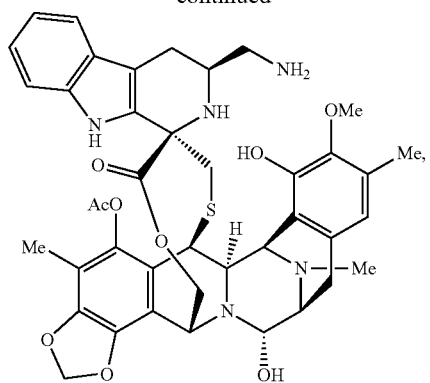
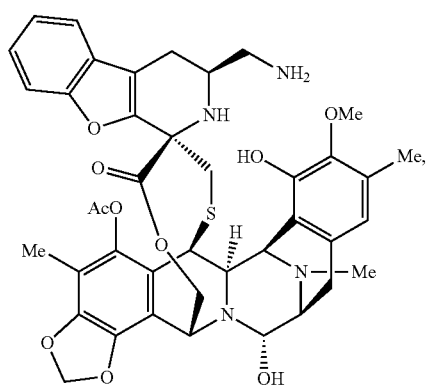
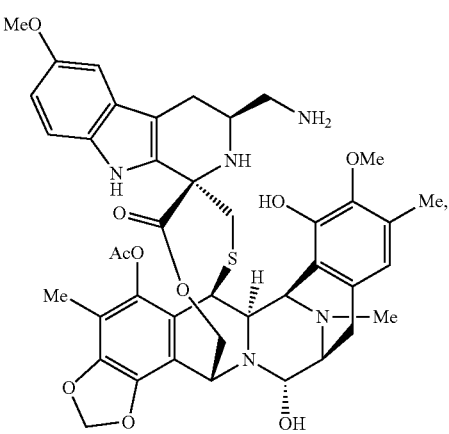
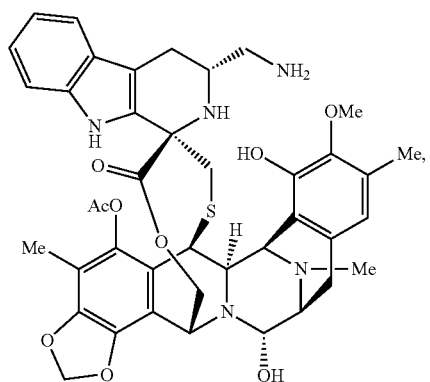
-continued
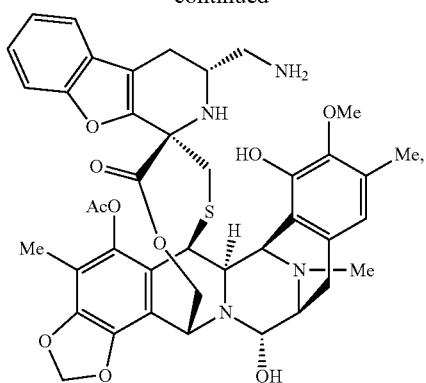
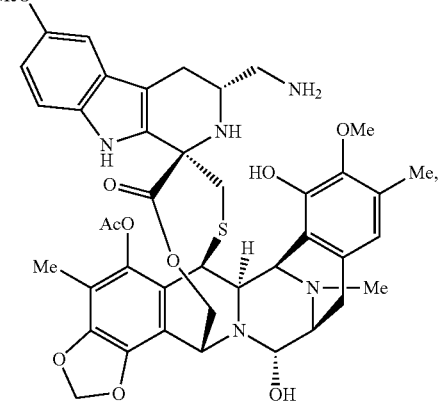
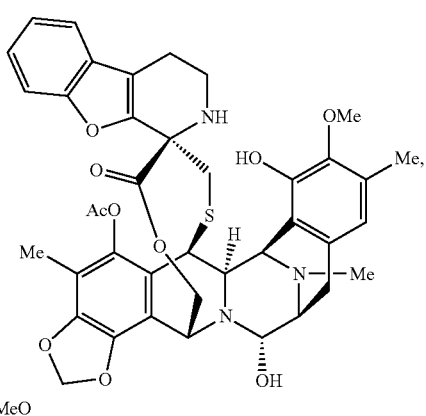
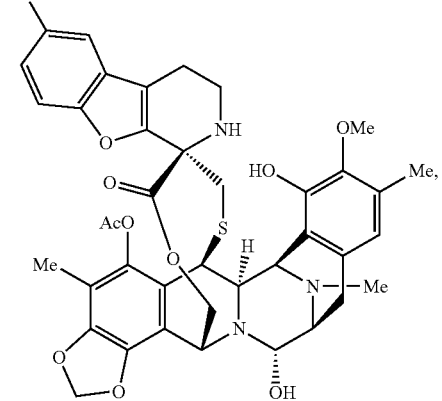
or a pharmaceutically acceptable salt or ester thereof.

Being particularly preferred a compound of formula:
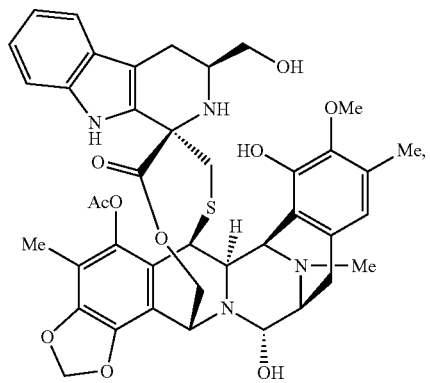
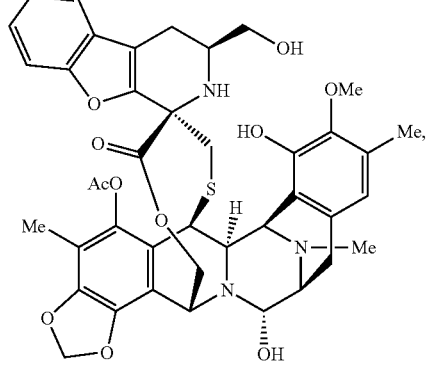
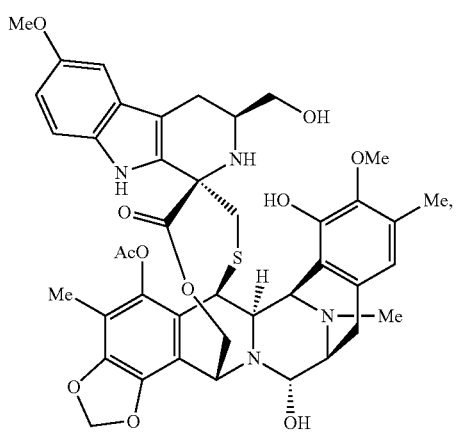
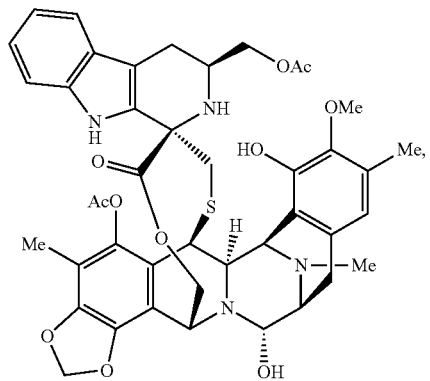
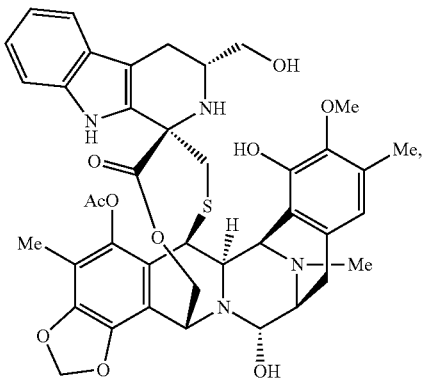
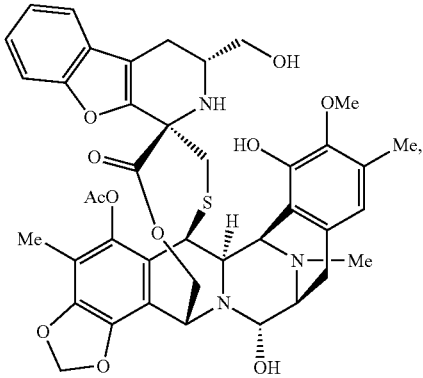
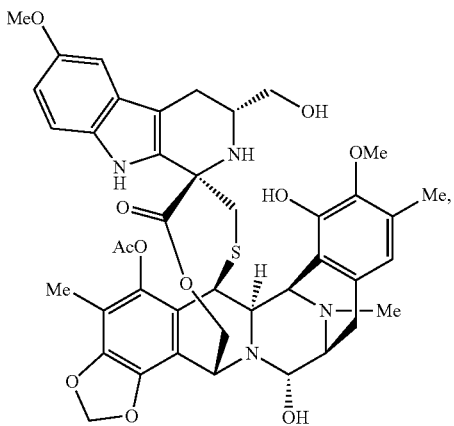
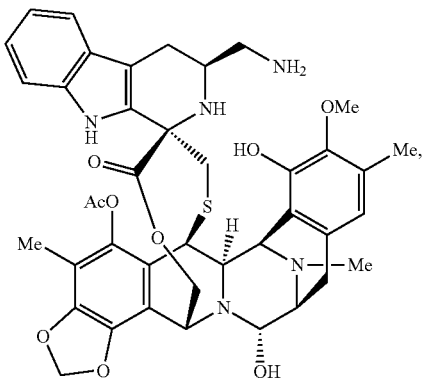

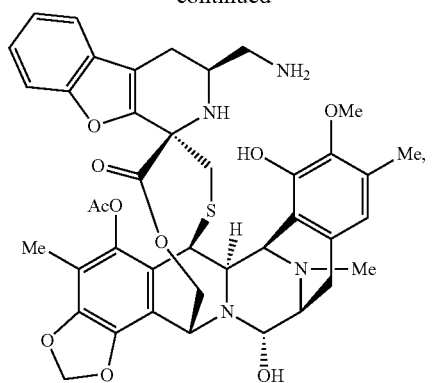
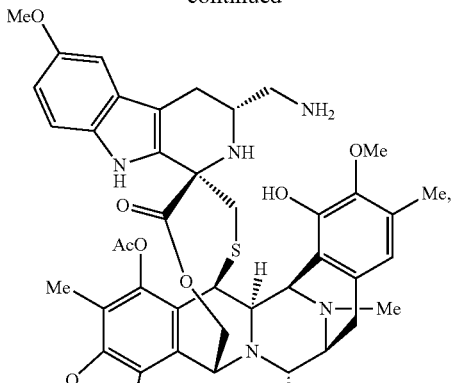
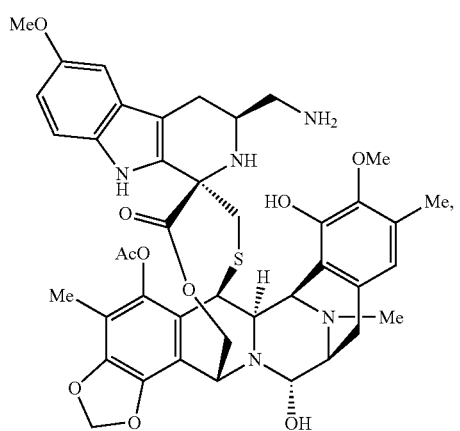
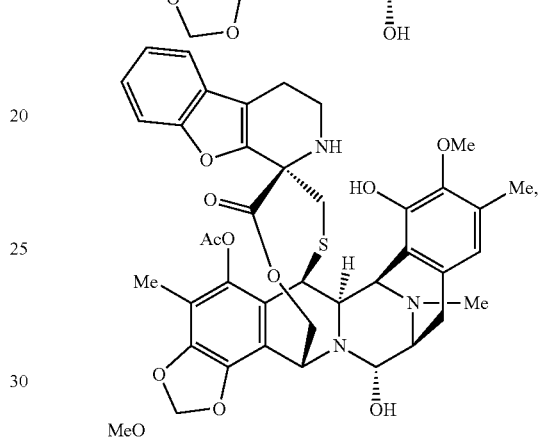
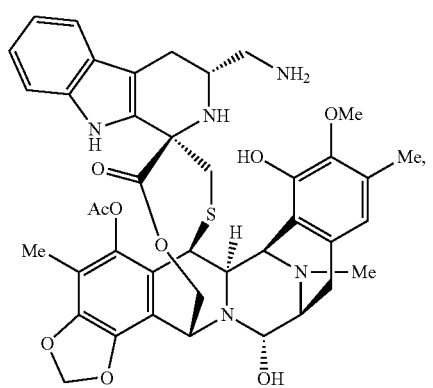
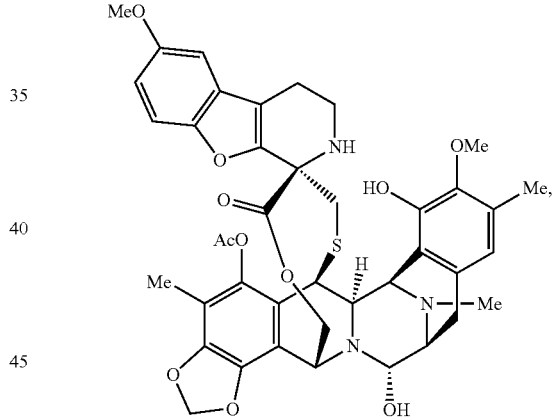
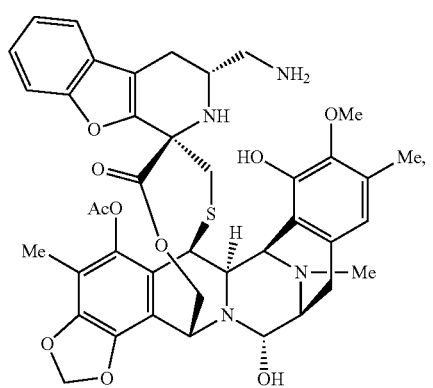
or a pharmaceutically acceptable salt or ester thereof
A compound according to the present invention of formula:
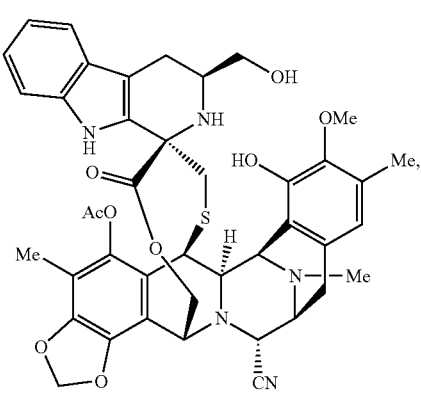

61
-continued
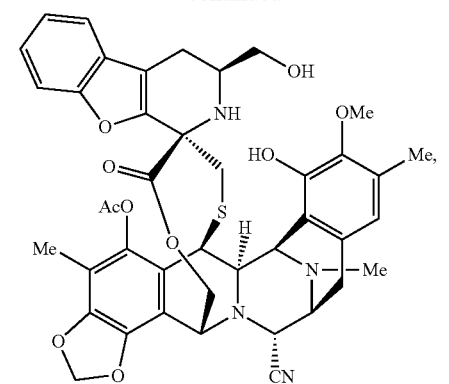
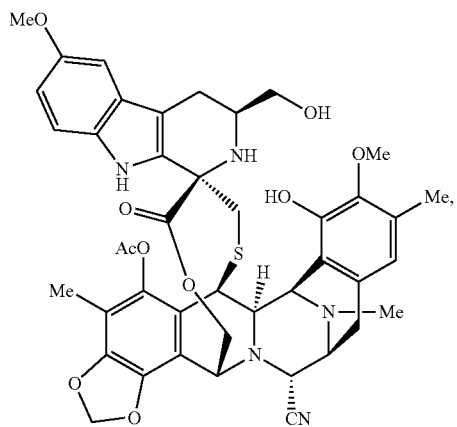
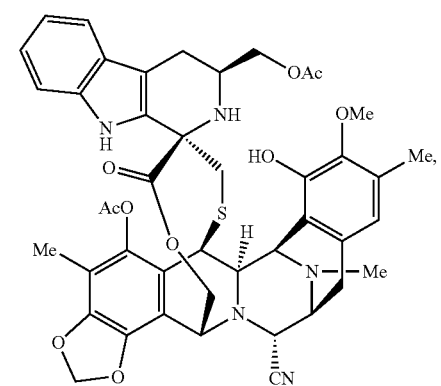
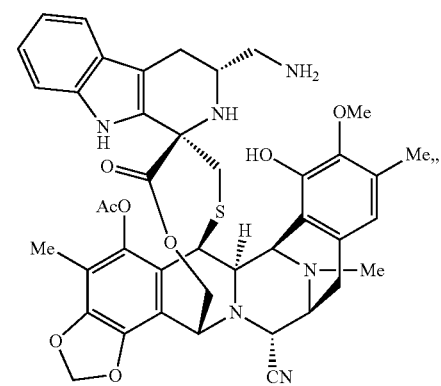
62
-continued
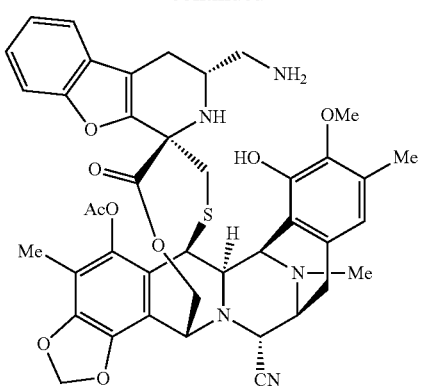
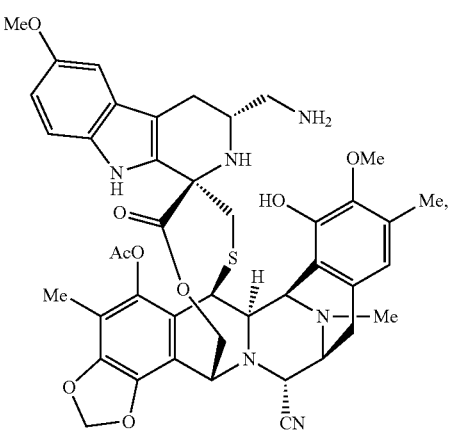
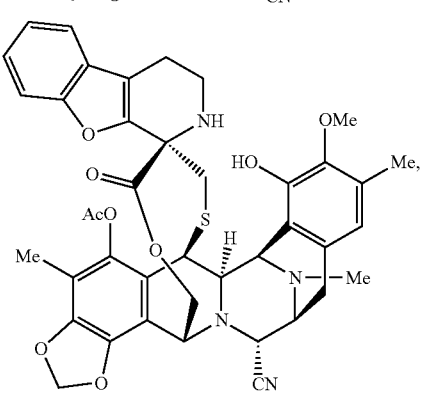
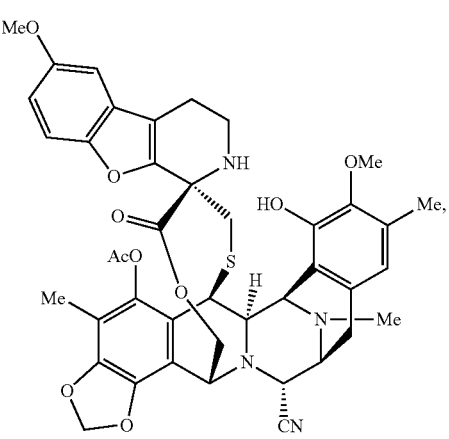 [SMILES: COc1ccc2oc3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1C#N)N2C)OCO4]

| 63 -continued | 64 -continued |
|---|---|
| 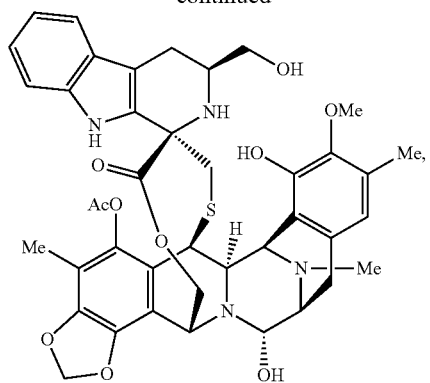 | 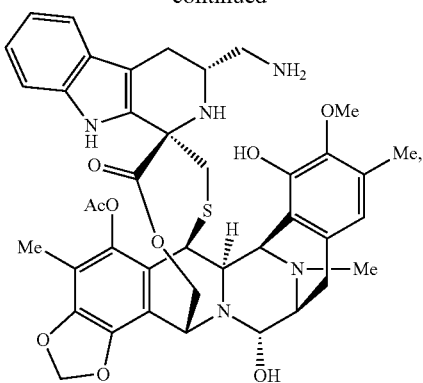 |
| 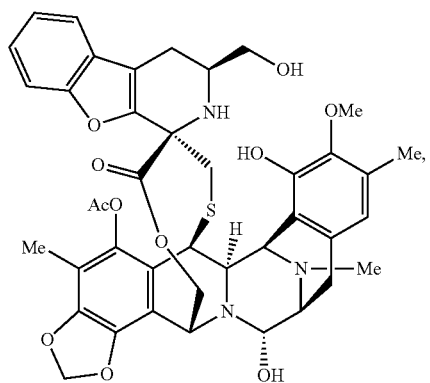 | 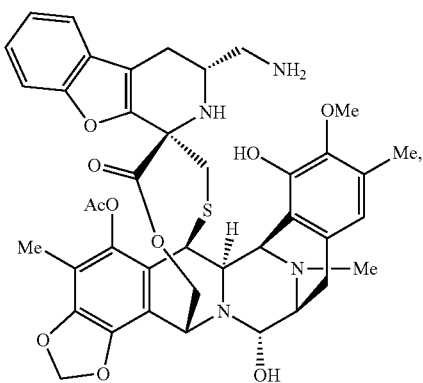 |
| 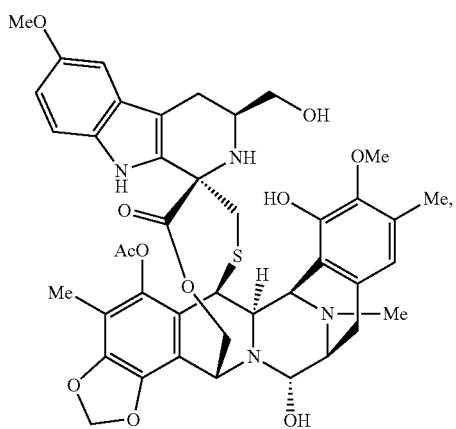 | 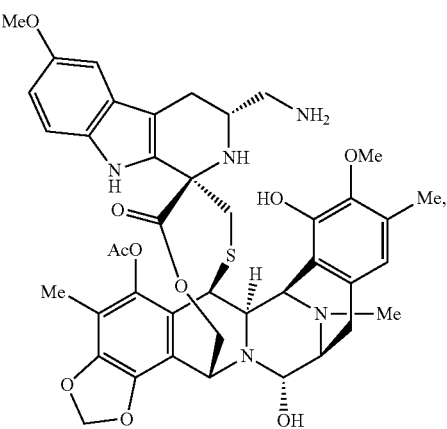 |
| 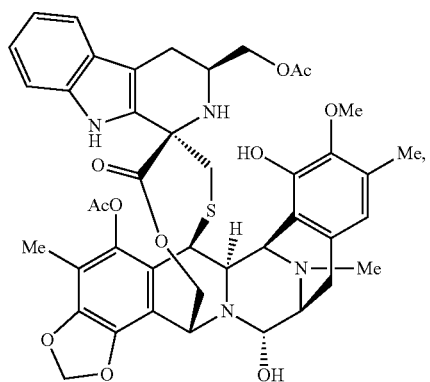 | 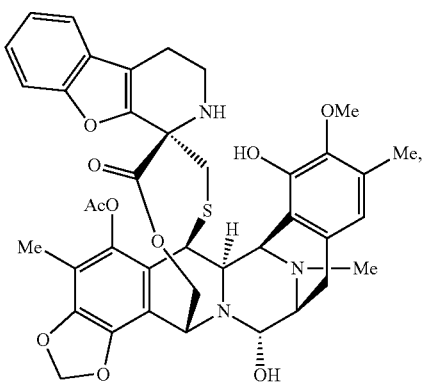 |

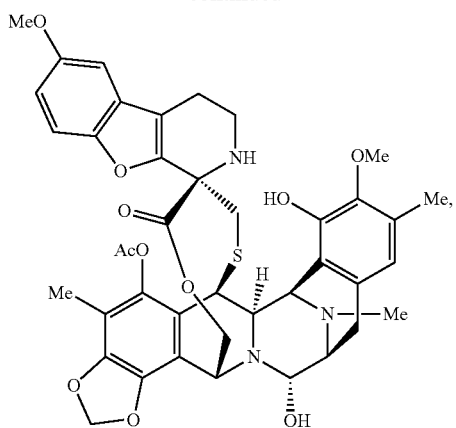 [SMILES: COc1ccc2oc3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]
or a pharmaceutically acceptable salt or ester thereof.
Being particularly preferred a compound of formula:
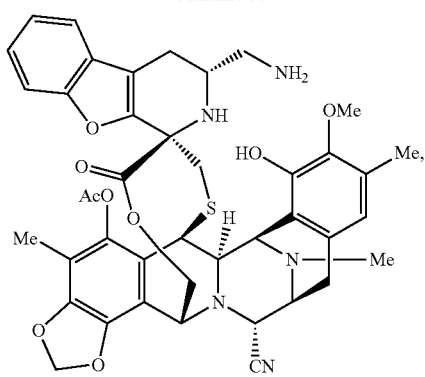
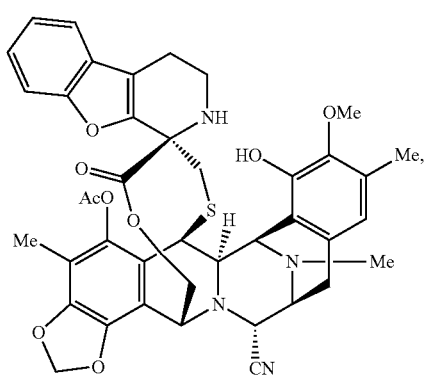
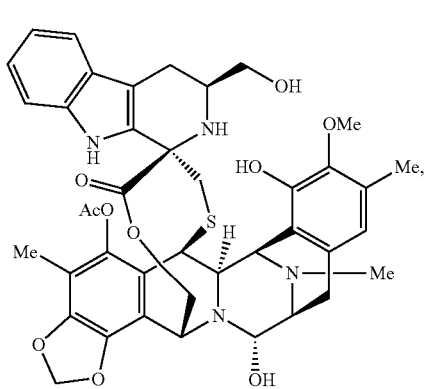
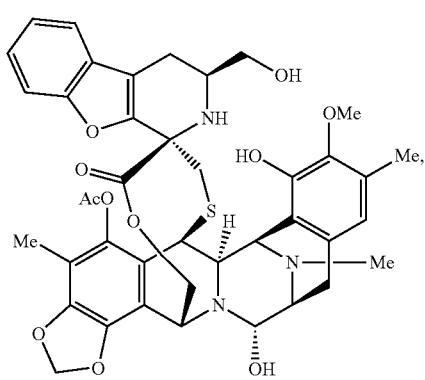

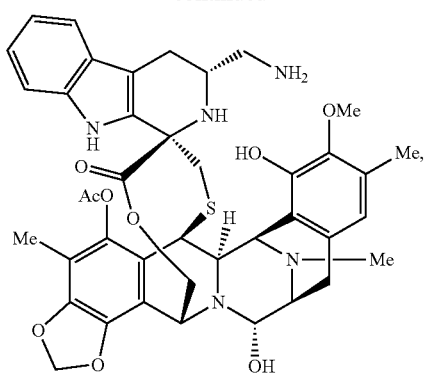
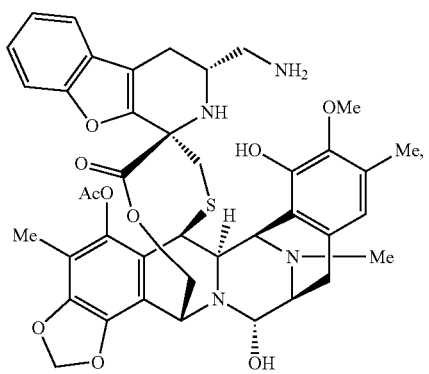
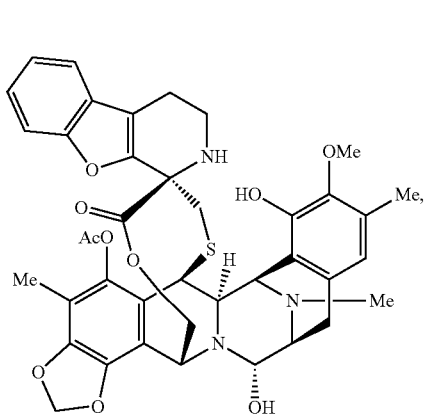
or a pharmaceutically acceptable salt or ester thereof.
Being more preferred a compound of formula:
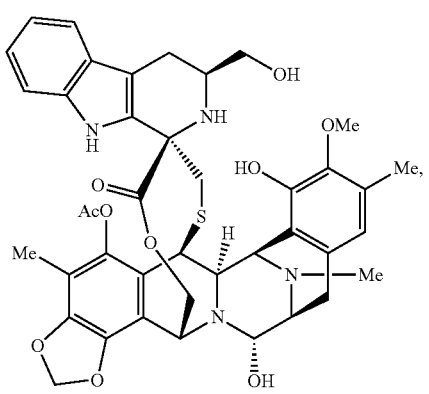
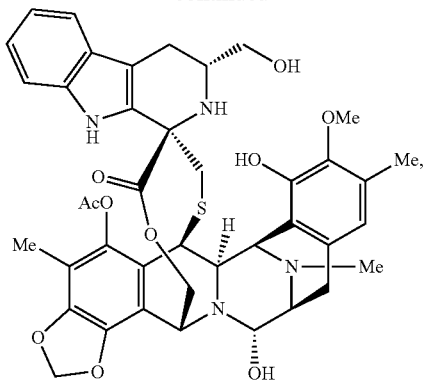
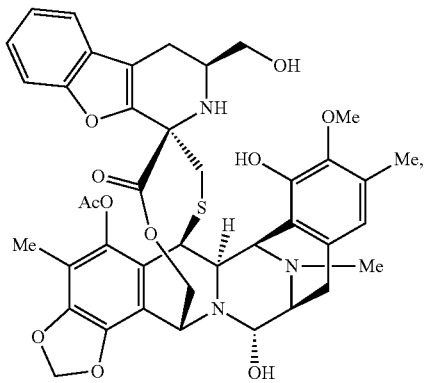
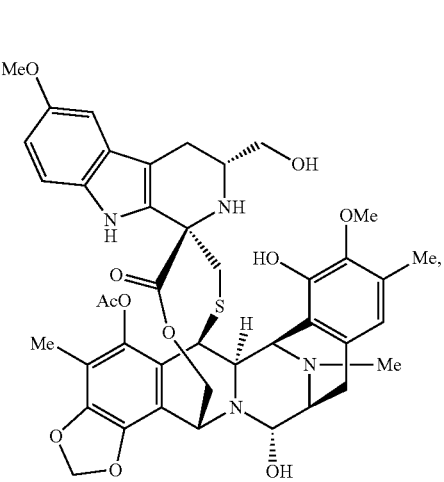
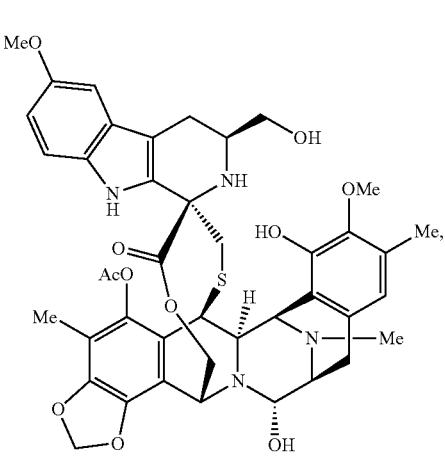

-continued
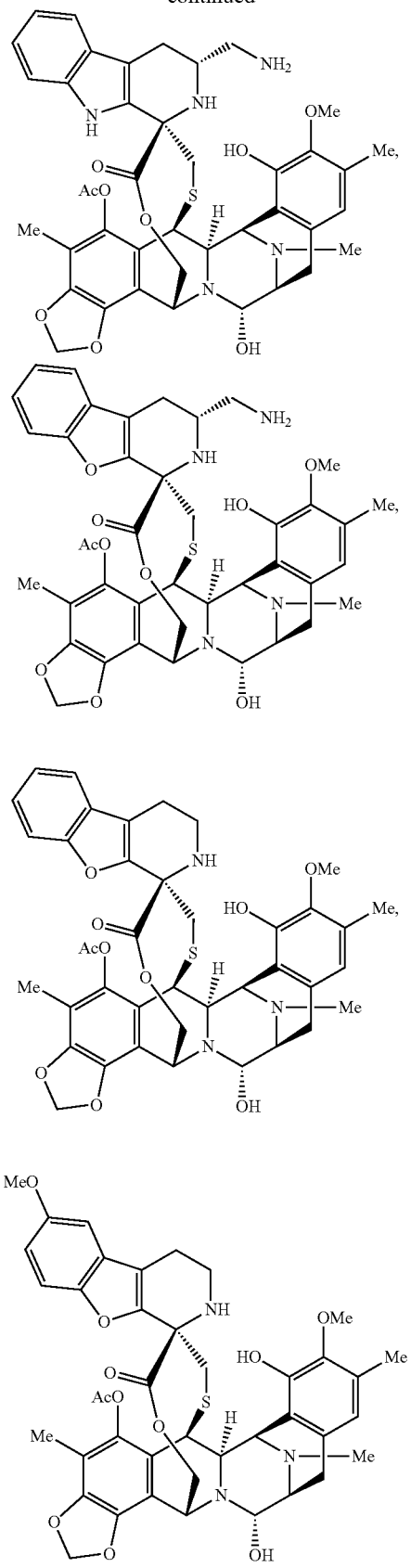
or a pharmaceutically acceptable salt or ester thereof.
Being even more preferred compounds according to the present invention are compounds of formula:
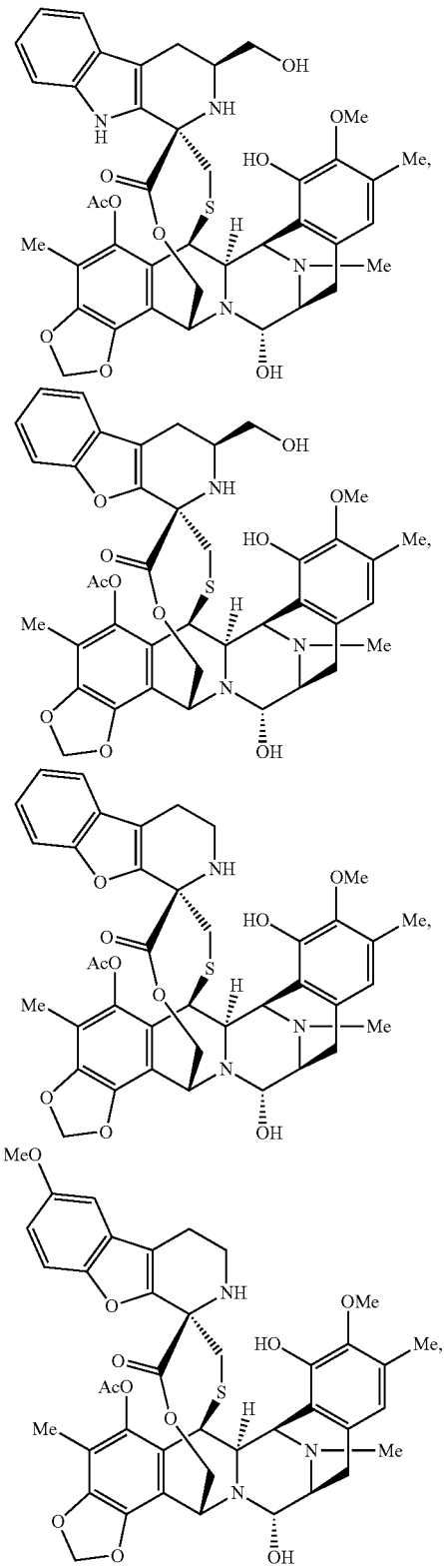
or a pharmaceutically acceptable salt or ester thereof.

The most preferred compounds according to the present invention are compounds of formula:

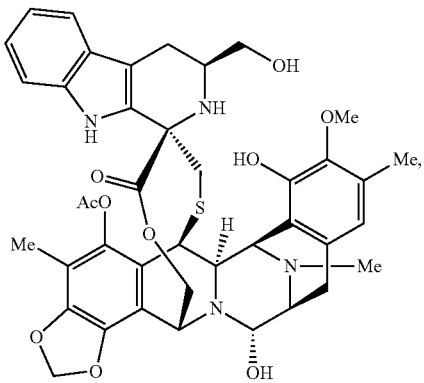

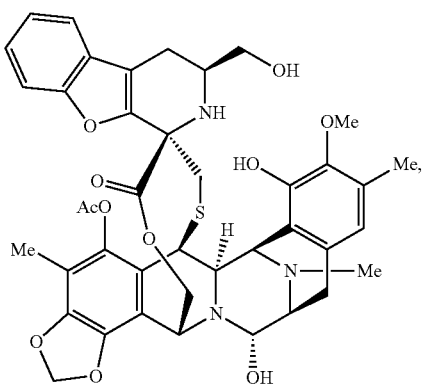

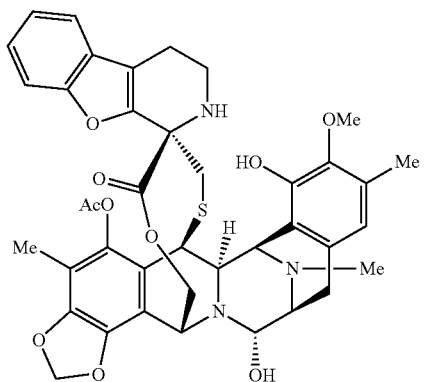

or a pharmaceutically acceptable salt or ester thereof.

In additional preferred embodiments, the preferences described above for the different substituents are combined. The present invention is also directed to such combinations of preferred substitutions (where allowed by possible substituent groups) in compounds of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, Ic, IAc, IBc, IDc, IFc or IGc according to the present invention.

An important feature of the above-described compounds is their bioactivity and in particular their cytotoxic activity. In this regard, we have surprisingly found that the compounds of the present invention show an enhanced antitumor activity, as it is shown in Examples 27 and 29 to 40.

Compositions Comprising a Compound of Formula I, IA, IB, IC, ID, IE, IF, IG, Ia, IAa, IBa, ICa, IDa, IEa, IFa, IGa, Ib, IAb, IBb, ICb, IDb, IEb, IFb, IGb, Ic, IAc, IBc, IDc, IFc or IGc of the Invention and Uses Thereof In a further embodiment of the present invention, there is provided a pharmaceutical composition comprising a compound according to the present invention and a pharmaceutically acceptable carrier. Examples of the administration form include without limitation oral, topical, parenteral, sublingual, rectal, vaginal, ocular and intranasal. Parenteral administration includes subcutaneous injections, intravenous, intramuscular, intrasternal injection or infusion techniques. Preferably the compositions are administered parenterally. Pharmaceutical compositions of the invention can be formulated so as to allow a compound according to the present invention to be bioavailable upon administration of the composition to an animal, preferably human. Compositions can take the form of one or more dosage units, where for example, a tablet can be a single dosage unit, and a container of a compound according to the present invention may contain the compound in liquid or in aerosol form and may hold a single or a plurality of dosage units.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, or liquid so as to provide an aerosol composition useful in, for example inhalatory administration. Powders may also be used for inhalation dosage forms. The term "carrier" refers to a diluent, adjuvant or excipient, with which the compound according to the present invention is administered. Such pharmaceutical carriers can be liquids, such as water and oils including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, disaccharides, and the like. In addition, auxiliary, stabilizing, thickening, lubricating and coloring agents can be used. In one embodiment, when administered to an animal, the compounds and compositions according to the present invention, and pharmaceutically acceptable carriers are sterile. Water is a preferred carrier when the compounds according to the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more for the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agent such as sucrose or saccharin; a flavoring agent such as peppermint, methyl salicylate or orange flavoring; and a coloring agent.

When the composition is in the form of a capsule (e.g. a gelatin capsule), it can contain, in addition to materials of the above type, a liquid carrier such as polyethylene glycol, cyclodextrins or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the compounds according to the present invention are administered intravenously. Infusion times of up to 24 hours are preferred to be used, more preferably 1 to 12 hours, with 1 to 6 hours being most preferred. Short infusion times which allow treatment to be carried out without an overnight stay in a hospital are especially desirable. However, infusion may be 12 to 24 hours or even longer if required. Infusion may be carried out at suitable intervals of, for example, 1 to 4 weeks.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The amount of the compound according to the present invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgement of the practitioner and each patient's circumstances.

The compositions comprise an effective amount of a compound of the present invention such that a suitable dosage will be obtained. The correct dosage of the compounds will vary according to the particular formulation, the mode of application, and its particular site, host and the disease being treated, e.g. cancer and, if so, what type of tumor. Other factors like age, body weight, sex, diet, time of administration, rate of excretion, condition of the host, drug combinations, reaction sensitivities and severity of the disease should be taken into account. Administration can be carried out continuously or periodically within the maximum tolerated dose.

Typically, the amount is at least about 0.01% of a compound of the present invention, and may comprise at least 80%, by weight of the composition. When intended for oral administration, this amount can be varied to range from about 0.1% to about 80% by weight of the composition. Preferred oral compositions can comprise from about 4% to about 50% of the compound of the present invention by weight of the composition.

Preferred compositions of the present invention are prepared so that a parenteral dosage unit contains from about 0.01% to about 10% by weight of the compound of the present invention. More preferred parenteral dosage unit contains about 0.5% to about 5% by weight of the compound of the present invention.

For intravenous administration, the composition is suitable for doses from about 0.1 mg/kg to about 250 mg/kg of the animal's body weight, preferably from about 0.1 mg/kg and about 20 mg/kg of the animal's body weight, and more preferably from about 1 mg/kg to about 10 mg/kg of the animal's body weight.

The compound of the present invention, can be administered by any convenient route, for example by infusion or bolus injection, by absorption through epithelial or mucocutaneous linings.

In specific embodiments, it can be desirable to administer one or more compounds of the present invention, or compositions locally to the area in need of treatment. In one embodiment, administration can be by direct injection at the site (or former site) of a cancer, tumor or neoplastic or pre-neoplastic tissue.

Pulmonary administration can also be employed, e.g. by use of an inhaler or nebulizer, and formulation with an aerosolizing agent, or via perfusion in a fluorocarbon or synthetic pulmonary surfactant. In certain embodiments, the compound of the present invention can be formulated as a suppository, with traditional binders and carriers such as triglycerides.

The present compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a compound of the present invention with water, or other physiologically suitable diluent, such as phosphate buffered saline, so as to form a solution. A surfactant can be added to facilitate the formation of a homogeneous solution or suspension.

Preferred compositions according to the present invention include:
 Pharmaceutical compositions comprising a compound of the present invention and a disaccharide. Particularly preferred disaccharides are selected from lactose, trehalose, sucrose, maltose, isomaltose, cellobiose, isosaccharose, isotrehalose, turanose, melibiose, gentiobiose, and mixtures thereof
 Lyophilised pharmaceutical compositions comprising a compound of the present invention and a disaccharide. Particularly preferred disaccharides are selected from lactose, trehalose, sucrose, maltose, isomaltose, cellobiose, isosaccharose, isotrehalose, turanose, melibiose, gentiobiose, and mixtures thereof.

The ratio of the active substance to the disaccharide in embodiments of the present invention is determined according to the solubility of the disaccharide and, when the formulation is freeze dried, also according to the freezedryability of the disaccharide. It is envisaged that this active substance:disaccharide ratio (w/w) can be about 1:10 in some embodiments, about 1:20 in other embodiments, about 1:50 in still other embodiments. It is envisaged that other embodiments have such ratios in the range from about 1:5 to about 1:500, and still further embodiments have such ratios in the range from about 1:10 to about 1:500.

The composition comprising a compound of the present invention may be lyophilized. The composition comprising a compound of the present invention is usually presented in a vial which contains a specified amount of such compound.

We have found that the compounds of the present invention and compositions of the present invention are particularly effective in the treatment of cancer.

Thus, as described earlier, the present invention provides a method of treating a patient in need thereof, notably a human, affected by cancer which comprises administering to the affected individual a therapeutically effective amount of a compound or composition according to the present invention. The present invention provides a compound or composition for use as medicament. The present invention provides a compound or composition for use in the treatment of cancer, and more preferably a cancer selected from lung cancer, including non-small cell lung cancer and small cell lung cancer, colon cancer, breast cancer, pancreas cancer, sarcoma, ovarian cancer, prostate cancer and gastric cancer.

Thus, the compounds and compositions according to the present invention are useful for inhibiting the multiplication, or proliferation, of a tumor cell or cancer cell, or for treating cancer in an animal.

The compounds and compositions according to the present invention show excellent activity in the treatment of cancers such as lung cancer including non-small cell lung cancer and small cell lung cancer, colon cancer, breast cancer, pancreas cancer, sarcoma, ovarian cancer, prostate cancer and gastric cancer. Most preferred cancers are selected from lung cancer including non-small cell lung cancer and small cell lung cancer, breast cancer, pancreas cancer and colorectal cancer.

In the present application, by "cancer" it is meant to include tumors, neoplasias and any other malignant disease having as cause malignant tissue or cells.

The term "treating", as used herein, unless otherwise indicated, means reversing, attenuating, alleviating or inhibiting the progress of the disease or condition to which such term applies, or one or more symptoms of such disorder or condition. The term "treatment", as used herein, unless otherwise indicated, refers to the act of treating as "treating" is defined immediately above.

The compounds and compositions according to the present invention can be administered to an animal that has also undergone surgery as treatment for the cancer. In one embodiment of the present invention, the additional method of treatment is radiation therapy.

In a specific embodiment of the present invention, the compound or composition according to the present invention is administered concurrently with radiation therapy. In another specific embodiment, the radiation therapy is administered prior or subsequent to administration of the compound or composition of the present invention, preferably at least an hour, three hours, five hours, 12 hours, a day, a week, a month, more preferably several months (e.g. up to three months) prior or subsequent to administration of a compound or composition of the present invention.

Any radiation therapy protocol can be used depending upon the type of cancer to be treated. For example, but not by way of limitation, x-ray radiation can be administered; in particular, high-energy megavoltage (radiation of greater than 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In a further embodiment of the present invention, there is provided a kit comprising a therapeutically effective amount of a compound according to the present invention and a pharmaceutically acceptable carrier.

In one embodiment, the kit according to this embodiment is for use in the treatment of cancer, and more preferably a cancer selected from lung cancer, including non-small cell lung cancer and small cell lung cancer, colon cancer, breast cancer, pancreas cancer, sarcoma, ovarian cancer, prostate cancer and gastric cancer.

In a further embodiment of the present invention, there is provided a process for obtaining a compound of formula I, IA, IB, IC, ID, IE, IF, IG, Ia, IAa, IBa, ICa, IDa, IEa, IFa, IGa, Ib, IAb, IBb, ICb, IDb, IEb, IFb, or IGb, or a pharmaceutically acceptable salt or ester thereof, comprising the step of reacting a compound of formula II with a compound of formula III to give a compound of formula IV:

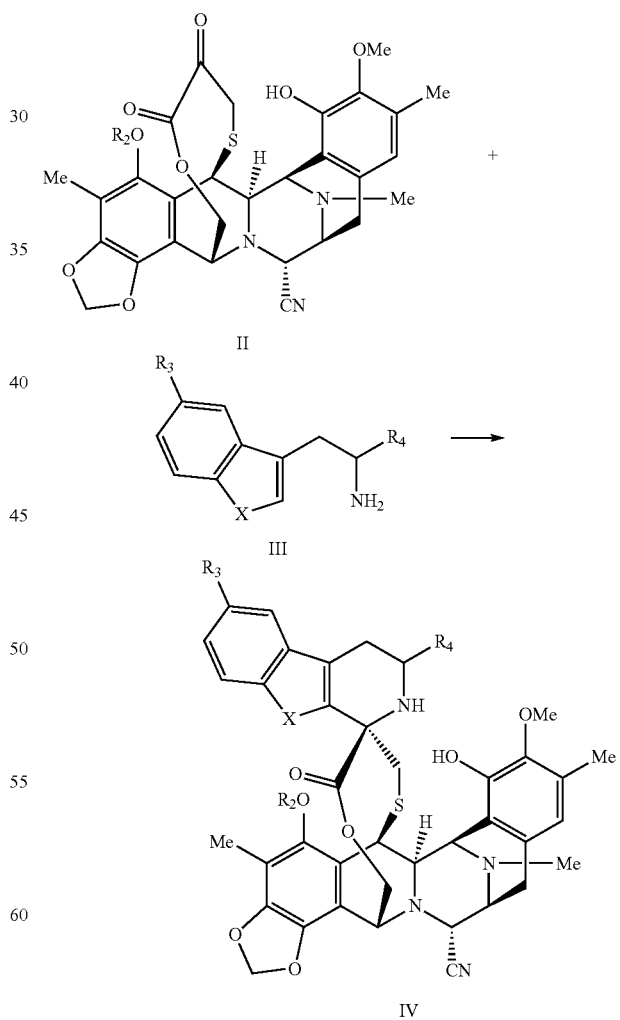

wherein (where allowed by possible substituent groups):
X is —NH— or —O—;

$R_2$ is a —C(=O)$R^a$ group;

$R_3$ is hydrogen or a —O$R^b$ group;

$R_4$ is selected from hydrogen, —CH$_2$OH, —CH$_2$OC(=O)$R^c$ and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino;

with the proviso that when $R_4$ is hydrogen then X is —O—.

It is particularly preferred that, when $R_4$ is —CH$_2$NHProt$^{NH}$ in the compound of formula IV, the process further comprises the step of deprotecting such amino group to provide a compound of formula I, IA, IB, IC, ID, IE, IG, Ia, IAa, IBa, ICa, IDa, IEa, IGa, Ib, IAb, IBb, ICb, IDb, IEb, or IGb wherein $R_4$ is —CH$_2$NH$_2$ and $R_1$ is cyano.

In a more preferred embodiment, the process further comprises the step of replacing the cyano group in the compound of formula IV or in the compound of formula I, IA, IB, IC, ID, IE, IG, Ia, IAa, IBa, ICa, IDa, IEa, IGa, Ib, IAb, IBb, ICb, IDb, IEb, or IGb where $R_4$ is —CH$_2$NH$_2$ and $R_1$ is cyano with a hydroxy group to give a compound of formula I, IA, IB, IC, ID, IE, IF, IG, Ia, IAa, IBa, ICa, IDa, IEa, IFa, IGa, Ib, IAb, IBb, ICb, IDb, IEb, IFb or IGb where $R_1$ is OH:

Preferred processes according to the present invention include:

A process that employs a compound of formula II wherein:

$R_2$ is a —C(=O)$R^a$ group where $R^a$ is substituted or unsubstituted $C_1$-$C_{12}$ alkyl. Particularly preferred $R^a$ is a substituted or unsubstituted $C_1$-$C_6$ alkyl. More preferred $R^a$ is a substituted or unsubstituted alkyl group selected from methyl, ethyl, n-propyl, isopropyl, and butyl, including n-butyl, sec-butyl, isobutyl and tert-butyl, being methyl the most preferred $R^a$ group.

A process wherein the compound of formula III is selected from a compound of formula IIIa, IIIb and IIIc:

IIIa

IIIb

-continued

IIIc wherein

X is selected from —NH— and —O—;

$R_3$ is selected from hydrogen and O$R^b$ where $R^b$ is substituted or unsubstituted $C_1$-$C_{12}$ alkyl. Particularly preferred $R^b$ is a substituted or unsubstituted $C_1$-$C_6$ alkyl. More preferred $R^b$ is a substituted or unsubstituted alkyl group selected from methyl, ethyl, n-propyl, isopropyl, and butyl, including n-butyl, sec-butyl, isobutyl and tert-butyl. More preferred $R^3$ is hydrogen or methoxy. Most preferred $R^3$ is hydrogen;

$R^4$ is selected from —CH$_2$OH and —CH$_2$NHProt$^{NH}$ where Prot$^{NH}$ is a protecting group for amino.

It is particularly preferred that the compound of formula III is a compound of formula IIIa or IIIb.

A process that employs a compound of formula III, IIIa or IIIb wherein $R_4$ is —CH$_2$OH.

Being preferred a process that employs a compound of formula IIIa or IIIb wherein $R_4$ is as defined above.

Being more preferred a process that employs a compound of formula IIIa wherein $R_4$ is as defined above.

A process that employs a compound of formula III, IIIa or IIIb wherein $R_4$ is —CH$_2$NHProt$^{NH}$.

Being preferred a process that employs a compound of formula IIIa or IIIb wherein $R_4$ is as defined above.

Being more preferred a process that employs a compound of formula IIIb wherein $R_4$ is as defined above.

EXAMPLES

Compound 1 was prepared as described in Example 20 of WO 01/87895.

Reference compounds A, B, C, D, E, F, ET-736, and PM01183 were prepared as described in WO 03/014127 (Compounds 19, 18, 44, 43, 2, 1, 26, and 27 respectively).

Example 1

A)

-continued

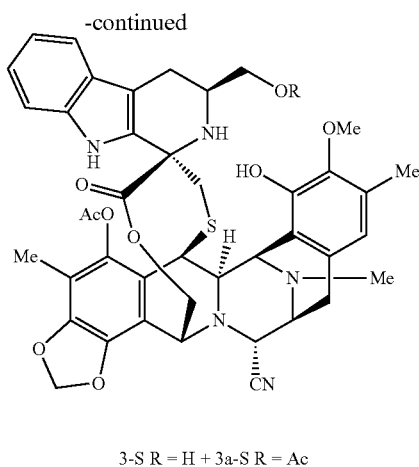

3-S R = H + 3a-S R = Ac

To a solution of 1 (0.5 g, 0.80 mmol) in acetic acid (20 mL, 0.04 M) was added L-tryptophanol (2-S) (533 mg, 3.0 mmol, Sigma-Aldrich). The reaction mixture was stirred at 23° C. for 16 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered and concentrated under vacuum. Flash chromatography (Hexane:EtOAc, 1:1) gave compounds 3-S (616 mg, 97%) and 3a-S (12 mg, 2%).

3-S $R_f$=0.50 (Hexane:EtOAc, 1:1).

$^1$H NMR (300 MHz, $CDCl_3$): δ 7.71 (s, 1H), 7.36 (dd, J=7.9, 1.0 Hz, 1H), 7.27 (dd, J=8.2, 0.9 Hz, 1H), 7.13 (ddd, J=8.3, 7.0, 1.2 Hz, 1H), 7.03 (ddd, J=8.0, 7.0, 1.0 Hz, 1H), 6.62 (s, 1H), 6.26 (d, J=1.4 Hz, 1H), 6.04 (d, J=1.3 Hz, 1H), 5.75 (s, 1H), 5.14 (dd, J=11.7, 1.2 Hz, 1H), 4.60 (s, 1H), 4.41 (s, 1H), 4.36-4.24 (m, 2H), 4.21 (d, J=2.7 Hz, 1H), 3.82 (s, 3H), 3.52 (s, 1H), 3.50-3.47 (m, 1H), 3.45 (dq, J=8.4, 2.2 Hz, 1H), 3.35 (t, J=10.1 Hz, 1H), 3.01-2.78 (m, 5H), 2.62 (dd, J=15.3, 4.7 Hz, 1H), 2.41 (s, 1H), 2.38 (s, 3H), 2.37-2.31 (m, 1H), 2.28 (s, 3H), 2.17 (s, 3H), 2.06 (s, 3H).

ESI-MS m/z: 794.2 $(M+H)^+$.

3a-S $R_f$=0.70 (Hexane:EtOAc, 1:1).

$^1$H NMR (500 MHz, $CDCl_3$): δ 7.83 (s, 1H), 7.38 (dt, J=7.9, 0.9 Hz, 1H), 7.25 (dt, J=8.3, 0.9 Hz, 1H), 7.11 (ddd, J=8.2, 7.1, 1.2 Hz, 1H), 7.02 (ddd, J=8.0, 7.0, 1.0 Hz, 1H), 6.62 (s, 1H), 6.24 (d, J=1.4 Hz, 1H), 6.03 (d, J=1.3 Hz, 1H), 5.79 (s, 1H), 5.13 (d, J=11.7 Hz, 1H), 4.60 (s, 1H), 4.39 (s, 1H), 4.36-4.22 (m, 3H), 4.17-4.09 (m, 1H), 3.91 (dd, J=10.5, 8.6 Hz, 1H), 3.83 (s, 3H), 3.51-3.41 (m, 2H), 3.04-2.92 (m, 3H), 2.72 (dd, J=15.1, 4.0 Hz, 1H), 2.54-2.41 (m, 2H), 2.38 (s, 3H), 2.35-2.30 (m, 1H), 2.29 (s, 3H), 2.21-2.16 (m, 1H), 2.18 (s, 3H), 2.12 (s, 3H); 2.05 (s, 3H).

$^{13}$C NMR (101 MHz, $CDCl_3$): δ 171.2, 170.7, 168.6, 147.5, 145.8, 143.0, 141.1, 140.4, 135.6, 130.1, 129.5, 126.7, 122.2, 121.2, 120.9, 119.4, 118.4, 118.2, 118.2, 113.6, 113.5, 110.9, 110.0, 109.1, 102.1, 91.4, 67.2, 63.4, 61.3, 60.4, 59.7, 59.1, 54.8, 54.6, 47.7, 42.0, 41.6, 31.6, 24.0, 22.6, 21.0, 15.9, 14.2, 9.7.

ESI-MS m/z: 836.2 $(M+H)^+$.

B)

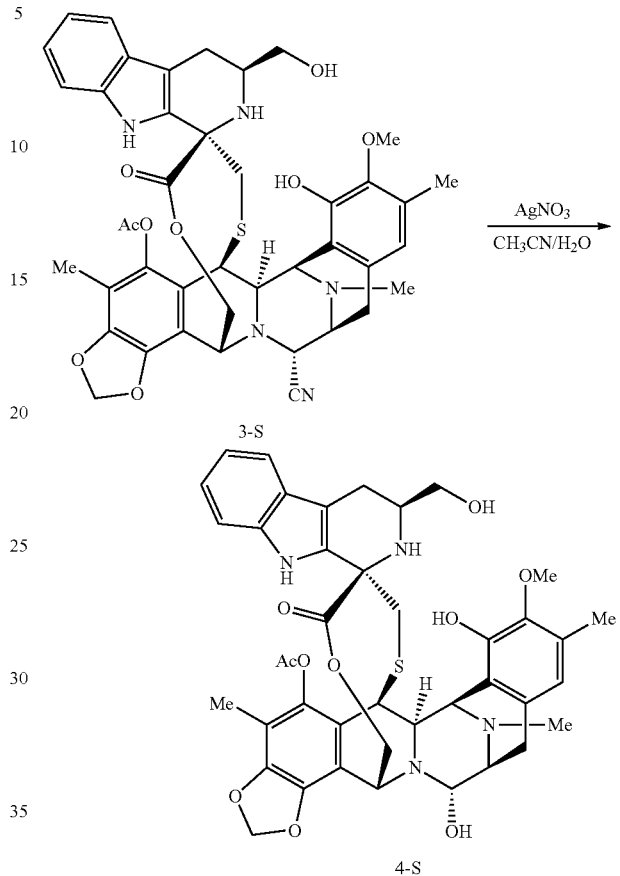

To a solution of 3-S (616 mg, 0.77 mmol) in $CH_3CN:H_2O$ (1.39:1, 51 mL, 0.015 M) was added $AgNO_3$ (3.40 g, 23.3 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to give 4-S (471 mg, 78%).

$R_f$=0.50 ($CH_2Cl_2:CH_3OH$, 9:1).

$^1$H NMR (500 MHz, $CDCl_3$): δ 7.71 (s, 1H), 7.36 (dd, J=7.8, 1.1 Hz, 1H), 7.26 (dd, J=7.8, 1.1 Hz, 1H), 7.12 (ddd, J=8.2, 7.0, 1.2 Hz, 1H), 7.03 (ddd, J=8.0, 7.1, 1.0 Hz, 1H), 6.64 (s, 1H), 6.23 (d, J=1.3 Hz, 1H), 6.01 (d, J=1.4 Hz, 1H), 5.75 (s, 1H), 5.25 (d, J=11.4 Hz, 1H), 4.92 (s, 1H), 4.52 (br s, 3H), 4.22 (dd, J=11.4, 2.2 Hz, 1H), 4.19 (s, 1H), 3.83 (s, 3H), 3.54 (br s, 2H), 3.35 (t, J=10.2 Hz, 1H), 3.26 (s, 1H), 3.01-2.93 (m, 3H), 2.88 (br s, 3H), 2.63 (dd, J=15.2, 4.8 Hz, 1H), 2.38 (s, 3H), 2.36-2.31 (m, 2H), 2.28 (s, 3H), 2.05 (s, 3H).

$^{13}$C NMR (126 MHz, $CDCl_3$): δ 171.9, 168.6, 147.5, 145.4, 142.9, 141.2, 140.7, 135.5, 130.4, 126.8, 122.3, 122.0, 121.3, 119.4, 118.4, 115.2, 112.8, 111.0, 110.0, 109.6, 101.8, 81.9, 76.8, 65.2, 62.8, 62.5, 60.4, 58.1, 57.9, 55.9, 55.1, 53.4, 51.6, 41.8, 41.3, 39.6, 24.1, 23.8, 20.5, 15.8, 9.7.

ESI-MS m/z: 767.3 $(M-H_2O+H)^+$.

(+)-HR-ESI-TOF-MS m/z 767.2788 $[M-H_2O+H]^+$ (Calcd. for $C_{41}H_{43}N_4O_9S$: 767.2745).

Example 2

B')

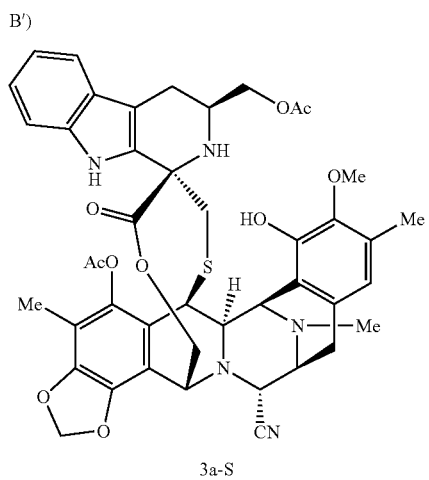

3a-S

AgNO₃
CH₃CN/H₂O
→

A)

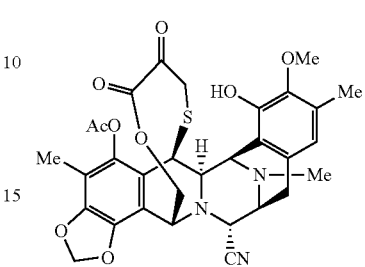

1

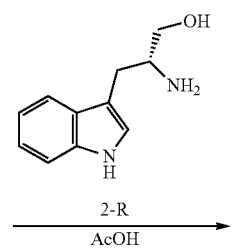

2-R
AcOH
→

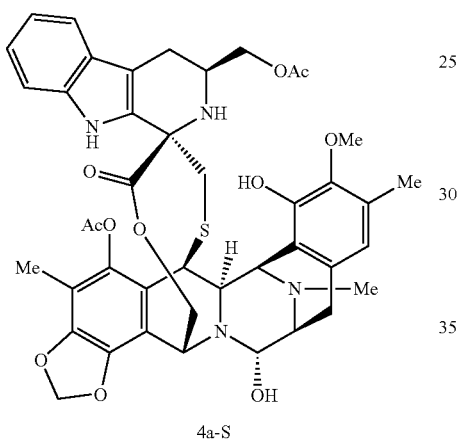

4a-S

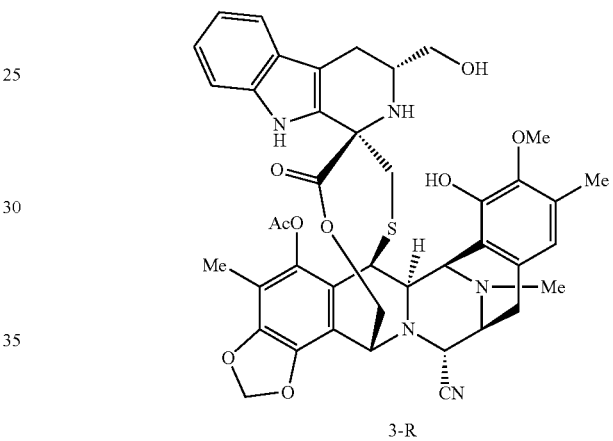

3-R

To a solution of 3a-S (30 mg, 0.035 mmol) in CH₃CN:H₂O (1.39:1, 2.4 mL, 0.015 M) was added AgNO₃ (180 mg, 1.07 mmol). After 3 h at 23° C., the reaction mixture was quenched with a mixture 1:1 of saturated aqueous solutions of NaCl and NaHCO₃, stirred for 15 min, diluted with CH₂Cl₂, stirred for 5 min, and extracted with CH₂Cl₂. The combined organic layers were dried over anhydrous Na₂SO₄, filtered, and concentrated under vacuum. The residue obtained was purified by flash chromatography (CH₂Cl₂:CH₃OH, from 99:1 to 85:15) to give 4a-S (24 mg, 83%).

$R_f$=0.60 (CH₂Cl₂:CH₃OH, 9:1).

¹H NMR (400 MHz, CDCl₃): δ 7.81 (s, 1H), 7.37 (d, J=7.8 Hz, 1H), 7.30-7.21 (m, 1H), 7.06 (dddd, J=34.7, 8.0, 7.1, 1.1 Hz, 2H), 6.63 (s, 1H), 6.22 (d, J=1.3 Hz, 1H), 6.02 (dd, J=12.9, 1.4 Hz, 1H), 5.74 (s, 1H), 5.25-5.21 (m, 1H), 4.89 (d, J=8.7 Hz, 1H), 4.55-4.45 (m, 2H), 4.30-4.18 (m, 1H), 4.14 (dd, J=10.5, 4.2 Hz, 1H), 4.00-3.88 (m, 2H), 3.82 (s, 3H), 3.56-3.44 (m, 2H), 3.23 (d, J=9.0 Hz, 1H), 2.95 (d, J=15.7 Hz, 2H), 2.87-2.78 (m, 2H), 2.71 (dd, J=15.0, 3.9 Hz, 1H), 2.48 (dd, J=15.1, 9.6 Hz, 1H), 2.37 (s, 3H), 2.35-2.29 (m, 1H), 2.28 (s, 3H), 2.22-2.16 (m, 1H), 2.15 (s, 3H), 2.12 (s, 3H), 2.03 (s, 3H).

ESI-MS m/z: 809.2 (M–H₂O+H)⁺.

To a solution of 1 (0.5 g, 0.80 mmol) in acetic acid (20 mL, 0.04 M) was added D-tryptophanol (2-R) (533 mg, 3.0 mmol, Sigma-Aldrich). The reaction mixture was stirred at 23° C. for 16 h and then acetic acid was evaporated. An aqueous saturated solution of NaHCO₃ was added and the mixture was extracted with CH₂Cl₂. The combined organic layers were dried over anhydrous Na₂SO₄, filtered, and concentrated under vacuum. Flash chromatography (Hexane:EtOAc, 1:1) gave compound 3-R (479 mg, 75%).

$R_f$=0.44 (Hexane:EtOAc, 1:1).

¹H NMR (400 MHz, CDCl₃): δ 7.61 (s, 1H), 7.39 (d, J=7.8 Hz, 1H), 7.29 (d, J=9.6 Hz, 1H), 7.12 (t, J=7.3 Hz, 1H), 7.03 (t, J=7.3 Hz, 1H), 6.60 (s, 1H), 6.25 (s, 1H), 6.03 (s, 1H), 5.75 (s, 1H), 5.04 (d, J=11.7 Hz, 1H), 4.62 (s, 1H), 4.37 (s, 1H), 4.32-4.25 (m, 1H), 4.22 (d, J=2.7 Hz, 1H), 4.19-4.09 (m, 1H), 3.82 (s, 3H), 3.77 (s, 1H), 3.64 (d, J=9.0 Hz, 1H), 3.49-3.41 (m, 2H), 3.02-2.90 (m, 2H), 2.60-2.52 (m, 2H), 2.45 (d, J=14.7 Hz, 2H), 2.40 (s, 3H), 2.28 (s, 3H), 2.22-2.14 (m, 2H), 2.18 (s, 3H), 2.10 (m, 3H).

ESI-MS m/z: 794.3 (M+H)⁺.

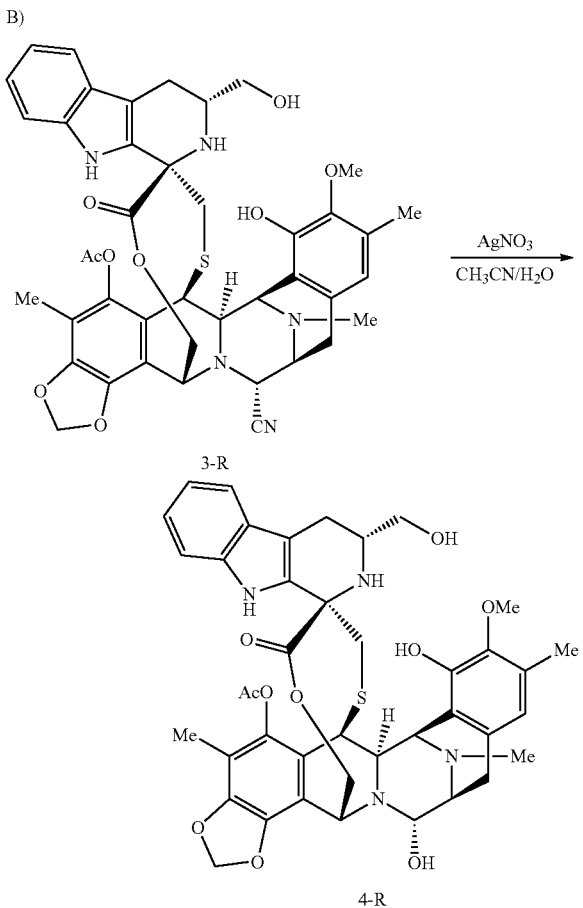

To a solution of 3-R (479 mg, 0.60 mmol) in $CH_3CN:H_2O$ (1.39:1, 40 mL, 0.015 M) was added $AgNO_3$ (3.03 g, 18.1 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to afford 4-R (428 mg, 91%).

$R_f$=0.45 ($CH_2Cl_2:CH_3OH$, 9:1).

$^1$H NMR (400 MHz, $CDCl_3$): δ 7.62 (s, 1H), 7.39 (d, J=8.1 Hz, 1H), 7.28 (d, J=8.1 Hz, 1H), 7.11 (ddd, J=8.2, 7.0, 1.2 Hz, 1H), 7.02 (ddd, J=7.9, 7.1, 1.0 Hz, 1H), 6.61 (s, 1H), 6.22 (d, J=1.3 Hz, 1H), 5.99 (d, J=1.3 Hz, 1H), 5.73 (s, 1H), 5.17 (dd, J=11.5, 1.2 Hz, 1H), 4.86 (s, 1H), 4.56-4.47 (m, 2H), 4.17 (dd, J=5.1, 1.6 Hz, 1H), 4.08 (dd, J=11.5, 2.1 Hz, 1H), 3.81 (s, 3H), 3.78 (d, J=3.8 Hz, 1H), 3.64 (dd, J=10.8, 3.8 Hz, 2H), 3.51 (d, J=5.1 Hz, 1H), 3.48-3.43 (m, 2H), 3.24 (d, J=8.6 Hz, 1H), 3.00-2.80 (m, 2H), 2.57 (s, 1H), 2.55-2.43 (m, 1H), 2.40 (s, 3H), 2.27 (s, 3H), 2.19-2.12 (m, 1H), 2.16 (s, 3H), 2.08 (s, 3H).

$^{13}$C NMR (101 MHz, $CDCl_3$): δ 171.8, 168.6, 147.6, 145.4, 143.0, 141.3, 140.7, 136.0, 131.1, 130.0, 129.6, 126.6, 122.1, 121.6, 121.2, 119.4, 118.4, 115.6, 112.9, 111.1, 110.6, 101.8, 81.7, 65.8, 62.7, 61.8, 60.4, 60.3, 57.9, 57.8, 56.1, 55.0, 52.1, 42.2, 41.3, 41.1, 23.8, 23.4, 20.5, 15.7, 9.8.

ESI-MS m/z: 767.6 $(M-H_2O+H)^+$.

(+)-HR-ESI-TOF-MS m/z: 767.2799 $[M-H_2O+H]^+$ (Calcd. for $C_{41}H_{43}N_4O_9S$: 767.2745).

Example 3. Synthesis of allyl N—[(R)-(2-amino-3-(1H-indol-3-yl)propyl)]carbamate (9-R)

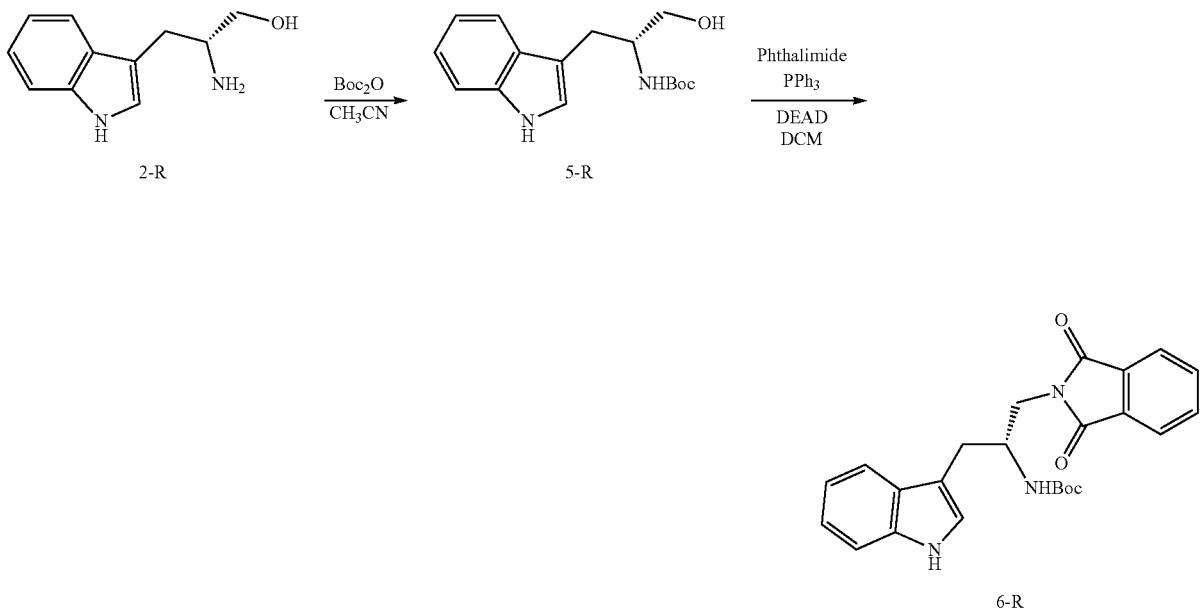

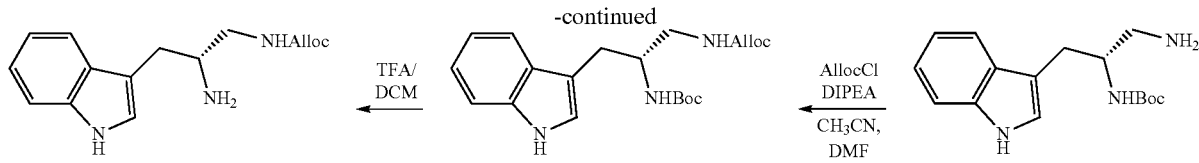

A)

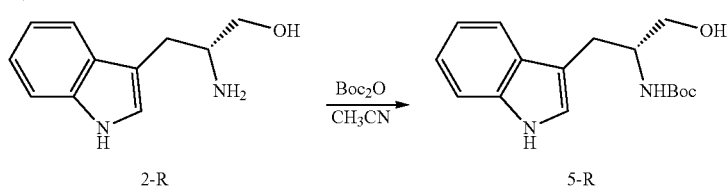

To a solution of D-tryptophanol (2-R) (2.0 g, 10.4 mmol) in CH$_3$CN (42 mL, 4 mL/mmol) was added di-tert-butyl dicarbonate (4.6 g, 20.8 mmol). The reaction mixture was stirred at 23° C. for 3 h and concentrated under vacuum. Flash chromatography (CH$_2$Cl$_2$:CH$_3$OH from 99:1 to 85:15) to afford 5-R (2.2 g, 73%).

R$_f$=0.5 (CH$_2$Cl$_2$:CH$_3$OH, 9:1).

$^1$H NMR (400 MHz, CDCl$_3$): δ 8.13 (s, 1H), 7.67 (dd, J=7.8, 1.1 Hz, 1H), 7.38 (dd, J=8.1, 1.3 Hz, 1H), 7.29-7.10 (m, 2H), 7.06 (s, 1H), 4.82 (s, 1H), 4.00 (s, 1H), 3.71 (dd, J=11.0, 3.8 Hz, 1H), 3.62 (dd, J=11.0, 5.5 Hz, 1H), 3.01 (d, J=6.7 Hz, 2H), 2.14 (s, 1H), 1.44 (s, 9H).

B)

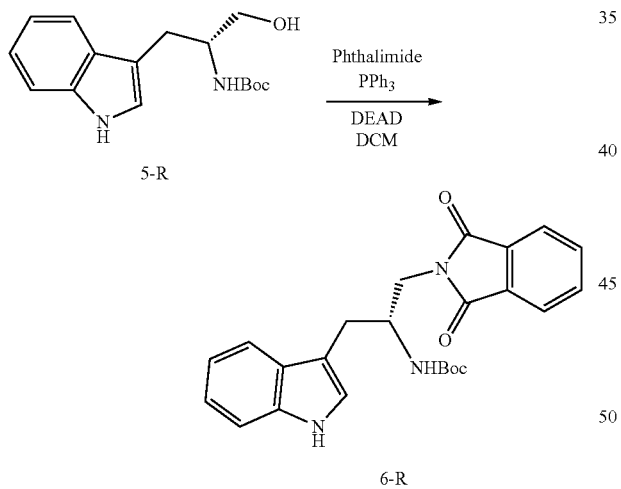

To a solution of 5-R (2.4 g, 8.2 mmol) in CH$_2$Cl$_2$ (50 mL, 6 mL/mmol) was added phthalimide (2.7 g, 18.2 mmol), triphenylphosphine (4.8 g, 18.2 mmol) and the mixture was cooled at 0° C. A solution of diethyl azodicarboxylate solution in CH$_2$Cl$_2$ (25 mL, 3 mL/mmol) was added for 15 min. The reaction was stirred at 23° C. for 16 h, concentrated under vacuum. The residue obtained was purified by flash chromatography (CH$_2$Cl$_2$:CH$_3$OH, from 99:1 to 85:15) to afford 6-R (3.3 g, 96%).

R$_f$=0.7 (CH$_2$Cl$_2$:CH$_3$OH, 9:1).

$^1$H NMR (400 MHz, CDCl$_3$): δ 8.50 (s, 1H), 7.81 (dd, J=5.5, 3.1 Hz, 2H), 7.66 (dd, J=5.6, 3.2 Hz, 2H), 7.60 (d, J=7.8 Hz, 1H), 7.35 (d, J=8.0 Hz, 1H), 7.19-7.04 (m, 3H), 4.81 (s, 1H), 4.40 (s, 1H), 3.83 (dd, J=13.9, 3.7 Hz, 1H), 3.72 (dd, J=13.9, 9.9 Hz, 1H), 3.08-3.01 (m, 2H), 1.23 (s, 9H).

C)

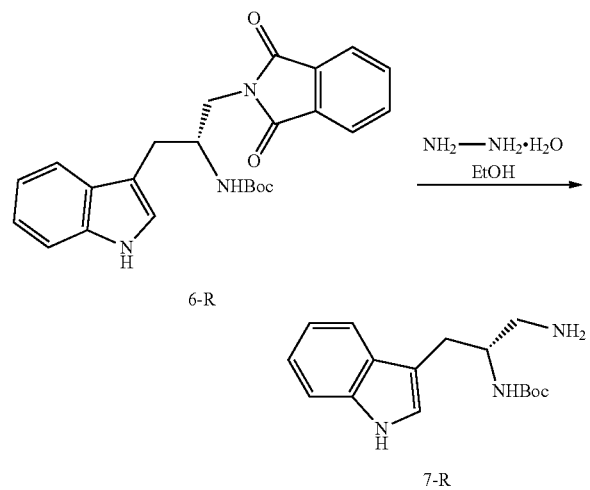

To a solution of 6-R (3.25 g, 7.74 mmol) in ethanol (231 mL, 30 mL/mmol) was added hydrazine monohydrate (37 mL, 774 mmol). The reaction mixture was stirred at 80° C. in sealed tube for 2.25 h, concentrated under vacuum. Flash chromatography (EtOAc:CH$_3$OH, from 100:1 to 50:50) afforded 7-R (2.15 g, 96%).

R$_f$=0.2 (EtOAc:CH$_3$OH, 6:4).

$^1$H NMR (400 MHz, CD$_3$OD): δ 7.60 (d, J=7.9 Hz, 1H), 7.33 (d, J=8.1 Hz, 1H), 7.13-7.04 (m, 2H), 7.05-6.96 (m, 1H), 4.02-3.94 (m, 1H), 2.99-2.87 (m, 3H), 2.78 (dd, J=13.1, 9.7 Hz, 1H), 1.39 (s, 9H).

ESI-MS m/z: 290.2 (M+H)$^+$.

D)

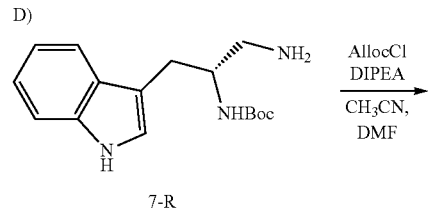

-continued

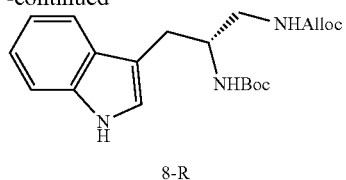

8-R

To a solution of 7-R (2.15 g, 7.4 mmol) in CH$_3$CN (74 mL, 10 mL/mmol) and DMF (7.4 mL, 1 mL/mmol) was added N,N-diisopropylethylamine (1.06 mL, 5.9 mmol) and allyl chloroformate (7.9 mL, 74 mmol). The reaction was stirred at 23° C. for 16 h. The mixture was diluted with EtOAc, NH$_4$Cl was added and the mixture was extracted with EtOAc. The combined organic layers were dried over anhydrous Na$_2$SO$_4$, filtered, and concentrated under vacuum. The residue obtained was purified by flash chromatography (Hexane:EtOAc, from 100:1 to 1:100) to afford 8-R (1.69 g, 61%).

R$_f$=0.4 (Hexane:EtOAc, 1:1).

$^1$H NMR (400 MHz, CDCl$_3$): δ 8.25 (s, 1H), 7.62 (d, J=7.8 Hz, 1H), 7.35 (dd, J=8.1, 0.9 Hz, 1H), 7.16 (dddd, J=27.8, 8.0, 7.0, 1.1 Hz, 2H), 7.04 (d, J=2.4 Hz, 1H), 5.90 (ddt, J=17.3, 10.7, 5.6 Hz, 1H), 5.34-5.22 (m, 1H), 5.20 (dt, J=10.5, 1.4 Hz, 1H), 5.12 (s, 1H), 4.82 (s, 1H), 4.55 (dq, J=5.4, 1.7 Hz, 2H), 4.02 (s, 1H), 3.35 (dt, J=10.0, 4.7 Hz, 1H), 3.21 (s, 1H), 2.95 (ddd, J=21.6, 15.4, 9.1 Hz, 2H), 1.42 (s, 9H).

ESI-MS m/z: 274.3 (M−Boc+H)$^+$.

E)

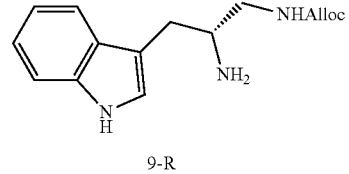

8-R

To a solution of 8-R (1.30 g, 3.50 mmol) in CH$_2$Cl$_2$ (58 mL, 16.6 mL/mmol) was added trifluoroacetic acid (30 mL, 8.3 mL/mmol). The reaction mixture was stirred at 23° C. for 1.5 h, concentrated under vacuum to give crude 9-R which was used in the next steps without further purification.

R$_f$=0.2 (CH$_2$Cl$_2$:CH$_3$OH, 9:1).

$^1$H NMR (400 MHz, CDCl$_3$): δ 7.95 (s, 1H), 7.53 (d, J=7.8 Hz, 1H), 7.36 (d, J=8.1 Hz, 1H), 7.17 (s, 1H), 7.09 (t, J=7.5 Hz, 1H), 7.03 (t, J=7.5 Hz, 1H), 5.87 (ddt, J=16.4, 10.8, 5.6 Hz, 1H), 5.34-5.13 (m, 2H), 4.50 (d, J=5.5 Hz, 2H), 3.62 (bs, 1H), 3.42 (dd, J=14.9, 3.9 Hz, 1H), 3.36-3.20 (m, 1H), 3.11-3.00 (m, 2H).

ESI-MS m/z: 274.3 (M+H)$^+$.

Example 4. Synthesis of allyl N—[(S)-(2-amino-3-(1H-indol-3-yl)propyl)]carbamate (9-S)

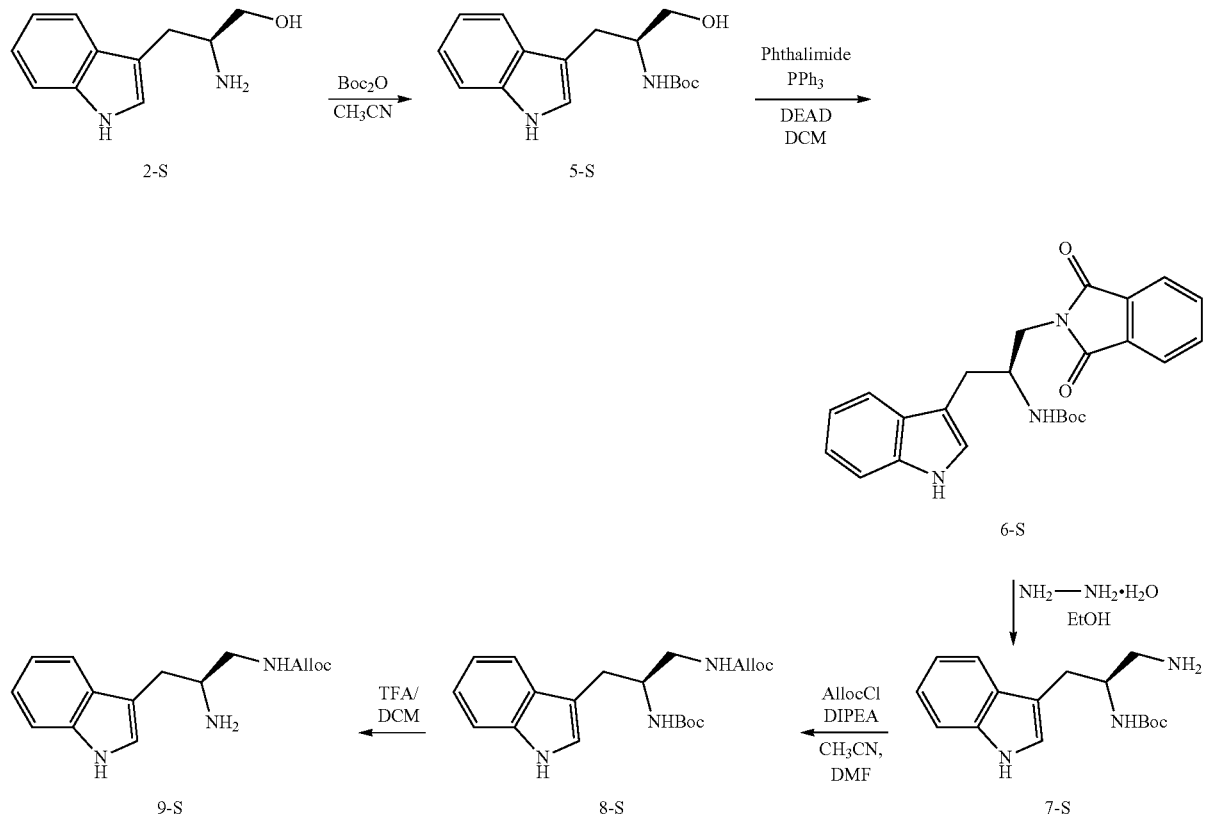

A)

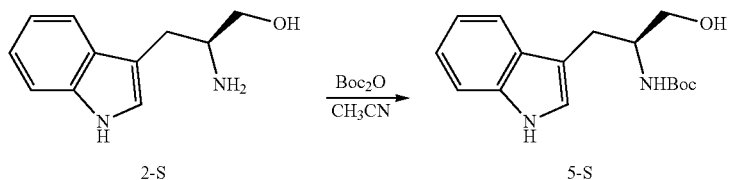

To a solution of L-tryptophanol (2-S) (2.0 g, 10.4 mmol) in $CH_3CN$ (42 mL, 4 mL/mmol) was added Di-tert-butyl dicarbonate (4.6 g, 20.8 mmol). The reaction mixture was stirred at 23° C. for 3 h, concentrated under vacuum. Flash chromatography ($CH_2Cl_2$:$CH_3OH$, from 99:1 to 85:15) to afford 5-S (2.24 g, 73%).

$R_f$=0.5 ($CH_2Cl_2$:$CH_3OH$, 9:1).

$^1$H NMR (400 MHz, $CDCl_3$): δ 8.10 (s, 1H), 7.65 (dd, J=7.8, 1.1 Hz, 1H), 7.37 (dd, J=8.1, 1.3 Hz, 1H), 7.23-7.11 (m, 2H), 7.06 (s, 1H), 4.81 (s, 1H), 3.99 (s, 1H), 3.70 (dd, J=11.0, 3.8 Hz, 1H), 3.61 (dd, J=11.0, 5.5 Hz, 1H), 3.00 (d, J=6.7 Hz, 2H), 2.01 (s, 1H), 1.42 (s, 9H).

B)

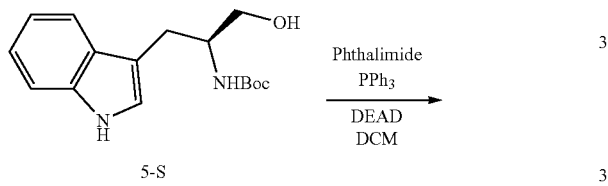

To a solution of 5-S (1.2 g, 4.13 mmol) in $CH_2Cl_2$ (24.8 mL, 6 mL/mmol) was added phthalimide (1.33 g, 9.1 mmol), triphenylphosphine (2.4 g, 9.1 mmol) and the mixture was cooled at 0° C. A solution of diethyl azodicarboxylate solution (3 mL, 10.32 mmol) in $CH_2Cl_2$ (12.4 mL, 3 mL/mmol) was added for 15 min. The reaction was stirred at 23° C. for 16 h, concentrated under vacuum. The residue obtained was purified by flash chromatography ($CH_2Cl_2$:$CH_3OH$, from 99:1 to 85:15) to afford 6-S (2.8 g, >100%).

$R_f$=0.7 ($CH_2Cl_2$:$CH_3OH$, 9:1).

$^1$H NMR (400 MHz, $CDCl_3$): δ 8.49 (s, 1H), 7.80 (dd, J=5.4, 3.1 Hz, 2H), 7.66 (dd, J=5.6, 3.2 Hz, 2H), 7.60 (d, J=7.8 Hz, 1H), 7.34 (d, J=8.0 Hz, 1H), 7.21-7.04 (m, 3H), 4.74 (s, 1H), 4.42 (s, 1H), 3.83 (dd, J=13.9, 3.7 Hz, 1H), 3.72 (dd, J=13.9, 9.9 Hz, 1H), 3.10-3.01 (m, 2H), 1.23 (s, 9H).

C)

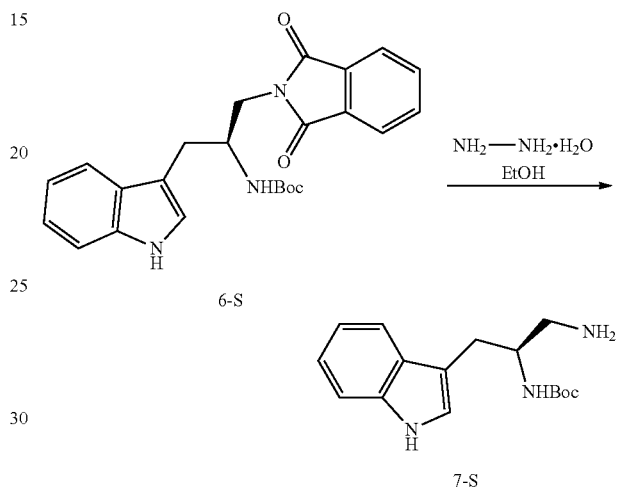

To a solution of 6-S (0.86 g, 2.07 mmol) in ethanol (72 mL, 36 mL/mmol) was added hydrazine monohydrate (10 mL, 207 mmol). The reaction mixture was stirred at 80° C. in sealed tube for 2.25 h, concentrated under vacuum. Flash chromatography (EtOAc:$CH_3OH$, from 100:1 to 50:50) to afford 7-S (1.0 g, 84%).

$R_f$=0.2 (EtOAc:$CH_3OH$, 6:4).

$^1$H NMR (400 MHz, $CD_3OD$): δ 7.61 (d, J=7.9 Hz, 1H), 7.35 (d, J=8.1 Hz, 1H), 7.13-6.97 (m, 2H), 7.09 (s, 1H), 4.06-3.96 (m, 1H), 3.01-2.76 (m, 4H), 1.38 (s, 9H).

ESI-MS m/z: 290.3 (M+H)$^+$.

D)

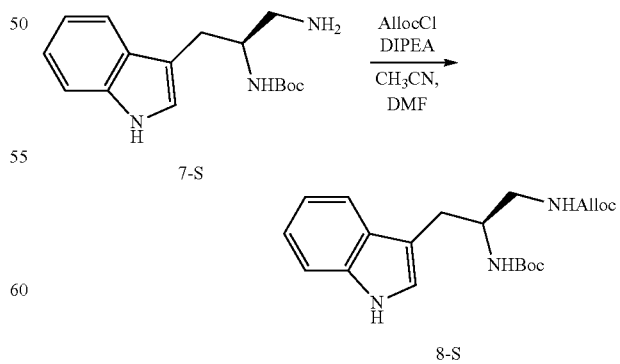

To a solution of 7-S (0.95 g, 3.3 mmol) in $CH_3CN$ (33 mL, 10 mL/mmol) and DMF (3.3 mL, 1 mL/mmol) was added N,N-diisopropylethylamine (0.5 mL, 2.6 mmol) and allyl chloroformate (3.5 mL, 33 mmol). The reaction was stirred at 23° C. for 20 h. The mixture was diluted with EtOAc, NH₄Cl was added and the mixture was extracted with EtOAc. The combined organic layers were dried over anhydrous Na₂SO₄, filtered, and concentrated under vacuum. The residue obtained was purified by flash chromatography (Hexane:EtOAc, from 100:1 to 1:100) to afford 8-S (0.88 g, 73%).

$R_f$=0.5 (Hexane:EtOAc, 1:1).

¹H NMR (400 MHz, CDCl₃): δ 8.17 (s, 1H), 7.63 (d, J=7.8 Hz, 1H), 7.20 (dd, J=8.1, 0.9 Hz, 1H), 7.13 (dddd, J=27.8, 8.0, 7.0, 1.1 Hz, 2H), 7.06 (d, J=2.4 Hz, 1H), 5.90 (ddt, J=17.3, 10.7, 5.6 Hz, 1H), 5.31-5.18 (m, 2H), 5.09 (s, 1H), 4.80 (s, 1H), 4.59-4.52 (m, 2H), 4.03 (s, 1H), 3.37 (dt, J=10.0, 4.7 Hz, 1H), 3.21 (s, 1H), 3.05-2.87 (m, 2H), 1.42 (s, 9H).

ESI-MS m/z: 274.3 (M-Boc+H)⁺.

E)

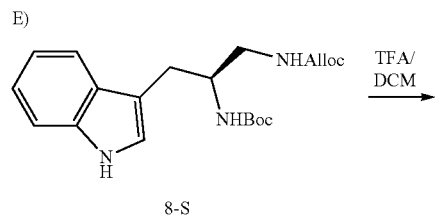

8-S

TFA/ DCM

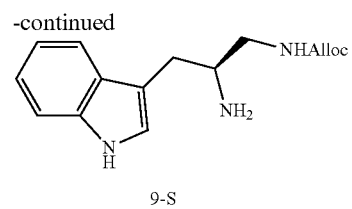

9-S

To a solution of 8-S (0.875 g, 2.3 mmol) in CH₂Cl₂ (38 mL, 16.6 mL/mmol) was added trifluoroacetic acid (19 mL, 8.3 mL/mmol). The reaction mixture was stirred at 23° C. for 2 h, concentrated under vacuum to give crude 9-S which was used in the next steps without further purification.

$R_f$=0.2 (CH₂Cl₂:CH₃OH, 9:1).

¹H NMR (400 MHz, CD₃OD): δ 7.56 (d, J=7.8 Hz, 1H), 7.37 (d, J=8.1 Hz, 1H), 7.21 (s, 1H), 7.13 (t, J=7.5 Hz, 1H), 7.05 (t, J=7.5 Hz, 1H), 5.94 (ddt, J=16.4, 10.8, 5.6 Hz, 1H), 5.34-5.16 (m, 2H), 4.56 (d, J=5.5 Hz, 2H), 3.60 (bs, 1H), 3.43 (dd, J=14.9, 3.9 Hz, 1H), 3.37-3.31 (m, 1H), 3.14-2.99 (m, 2H).

ESI-MS m/z: 274.3 (M+H)⁺.

Example 5

A)

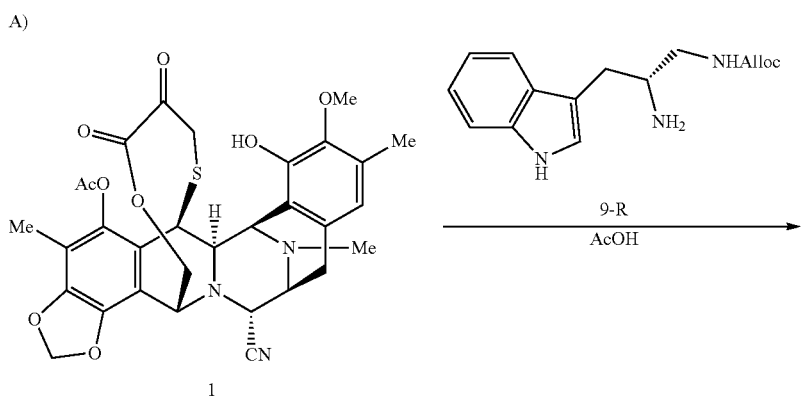

1

9-R
AcOH

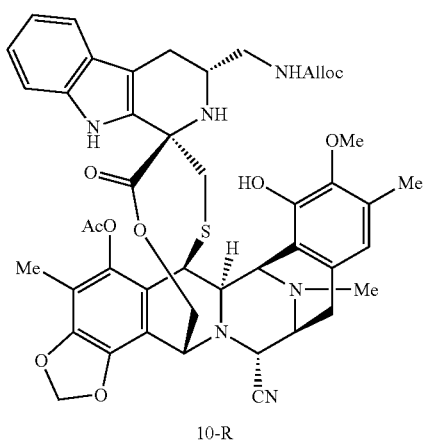

10-R

To a solution of 1 (1.45 g, 2.33 mmol) in acetic acid (58 mL, 0.08 M) was added 9-R (0.95 g, 3.50 mmol). The reaction mixture was stirred a 50° C. for 18 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$. Flash chromatography (Hexane:EtOAc, 1:1) gives compound 10-R (1.3 g, 64%).

R$_f$=0.5 (Hexane:EtOAc, 1:1).

$^1$H NMR (400 MHz, CDCl$_3$): δ 7.66 (s, 1H), 7.36 (d, J=7.9 Hz, 1H), 7.27 (d, J=7.9 Hz, 1H), 7.10 (ddd, J=8.3, 7.0, 1.3 Hz, 1H), 7.01 (td, J=7.5, 7.0, 1.0 Hz, 1H), 6.62 (s, 1H), 6.23 (d, J=1.4 Hz, 1H), 6.01 (d, J=1.4 Hz, 1H), 5.99-5.89 (m, 1H), 5.79 (s, 1H), 5.44-5.21 (m, 2H), 5.14-4.99 (m, 2H), 4.63 (ddd, J=7.3, 4.4, 1.5 Hz, 2H), 4.36 (s, 1H), 4.33-4.24 (m, 1H), 4.29-4.26 (m, 1H), 4.21 (d, J=2.7 Hz, 1H), 4.19-4.13 (m, 3H), 3.80 (s, 3H), 3.56 (s, 1H), 3.48-3.43 (m, 3H), 3.27 (dt, J=13.2, 4.0 Hz, 1H), 3.04-2.88 (m, 2H), 2.56 (dd, J=15.2, 3.8 Hz, 1H), 2.49-2.35 (m, 2H), 2.31 (s, 3H), 2.28 (s, 3H), 2.17 (s, 3H), 2.07 (s, 3H).

ESI-MS m/z: 877.3 (M+H)$^+$.

with EtOAc. The combined organic layers were dried over anhydrous Na$_2$SO$_4$, filtered, and concentrated under vacuum. Flash chromatography (Hexane:EtOAc, from 100:1 to 1:100 and EtOAc:CH$_3$OH, from 100:1 to 1:100) to afford 11-R (440 mg, 82%).

R$_f$=0.5 (CH$_2$Cl$_2$:CH$_3$OH, 1:1).

$^1$H NMR (400 MHz, CDCl$_3$): δ 7.64 (s, 1H), 7.38 (d, J=7.9 Hz, 1H), 7.29 (d, J=8.1 Hz, 1H), 7.11 (ddt, J=8.3, 7.0, 1.4 Hz, 1H), 7.03 (ddt, J=8.3, 7.0, 1.4 Hz, 1H), 6.58 (s, 1H), 6.24 (d, J=1.5 Hz, 1H), 6.02 (d, J=1.5 Hz, 1H), 5.02 (d, J=11.8 Hz, 1H), 4.63 (s, 1H), 4.36 (s, 1H), 4.28 (d, J=5.1 Hz, 1H), 4.21 (d, J=2.2 Hz, 1H), 4.16 (s, 1H), 3.80 (s, 3H), 3.51-3.39 (m, 4H), 3.32-3.13 (m, 3H), 2.95 (d, J=8.9 Hz, 2H), 2.89-2.76 (m, 2H), 2.73-2.57 (m, 1H), 2.42 (d, J=14.8 Hz, 1H), 2.36 (s, 3H), 2.25 (s, 3H), 2.16 (s, 3H), 2.09 (s, 3H).

ESI-MS m/z: 793.2 (M+H)$^+$.

C)

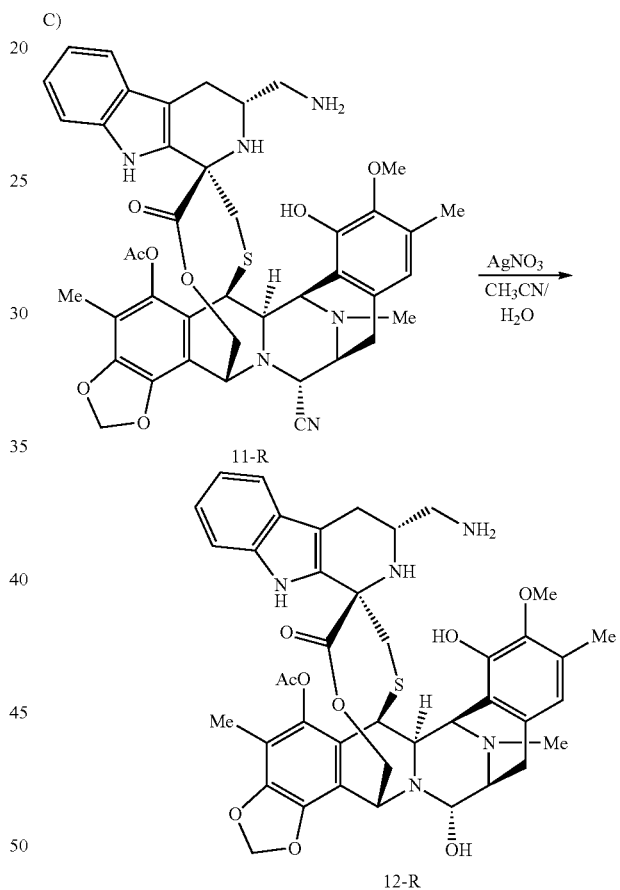

B)

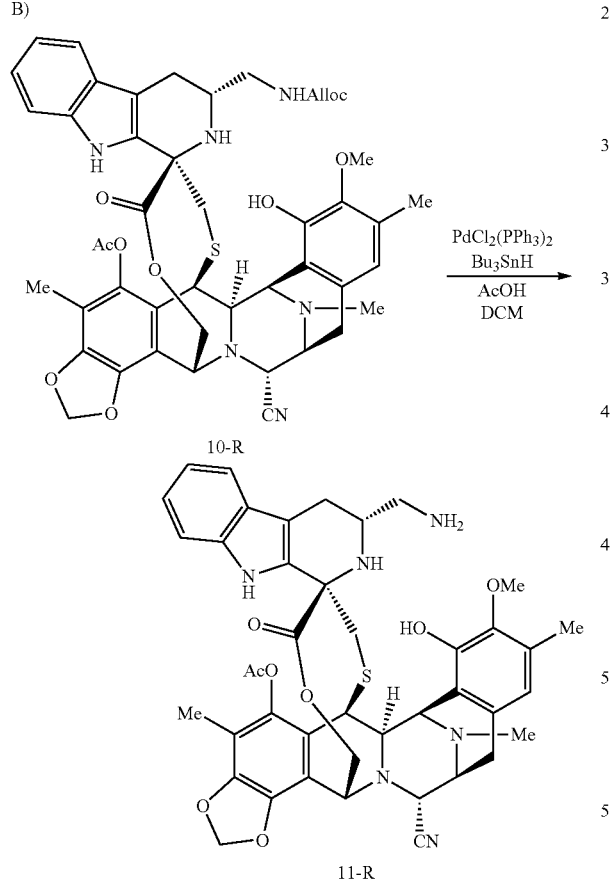

To a solution of 10-R (600 mg, 0.68 mmol) in CH$_2$Cl$_2$ (12 mL, 18 mL/mmol) was added bis(triphenylphosphine)palladium(II) dichloride (77 mg, 0.1 mmol) and acetic acid (0.4 mL, 6.8 mmol). Tributyltin hydride (1.1 mL, 4.08 mmol) was added at 0° C., the reaction mixture was stirred at 0° C. for 0.5 h and concentrated under vacuum. The crude obtained was diluted with EtOAc, saturated aqueous solution of NH$_4$Cl was added, and the mixture was extracted To a solution of 11-R (850 mg, 1.07 mmol) in CH$_3$CN: H$_2$O (1.39:1, 70 mL, 0.015 M) was added AgNO$_3$ (3.64 g, 21.4 mmol). After 17 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 12-R (553 mg, 66%).

R$_f$=0.3 (CH$_2$Cl$_2$:CH$_3$OH, 9:1).

$^1$H NMR (500 MHz, CDCl$_3$): δ 7.60 (s, 1H), 7.38 (d, J=7.9 Hz, 1H), 7.28 (d, J=7.9 Hz, 1H), 7.11 (ddt, J=8.3, 7.1, 1.2 Hz, 1H), 7.02 (ddt, J=8.3, 7.1, 1.2 Hz, 1H), 6.58 (s, 1H), 6.22 (s, 1H), 6.00 (s, 1H), 5.16 (d, J=11.5 Hz, 1H), 4.87 (s, 1H), 4.54 (s, 1H), 4.51 (d, J=3.3 Hz, 1H), 4.17 (d, J=5.4 Hz, 1H), 4.07 (dd, J=11.3, 2.2 Hz, 1H), 3.81 (s, 3H), 3.52 (d, J=5.1 Hz, 1H), 3.24 (d, J=8.8 Hz, 2H), 2.99-2.78 (m, 4H), 2.66 (dd, J=14.9, 3.5 Hz, 1H), 2.49-2.39 (m, 2H), 2.38 (s, 3H), 2.28 (m, 2H), 2.25 (s, 3H), 2.21-2.16 (m, 2H), 2.15 (s, 3H), 2.08 (s, 3H).

$^{13}$C NMR (101 MHz, CD$_3$OD): δ 171.7, 169.4, 148.7, 145.9, 143.7, 141.4, 140.9, 136.9, 130.8, 130.0, 129.7, 126.0, 121.4, 121.0, 119.7, 119.1, 118.4, 117.5, 114.9, 110.8, 107.5, 106.4, 102.1, 91.3, 63.2, 60.0, 59.0, 58.6, 55.3, 54.6, 52.7, 52.4, 48.4, 45.8, 42.5, 40.2, 24.5, 23.2, 19.2, 15.0, 8.2.

ESI-MS m/z: 766.2 (M–H$_2$O+H)$^+$.

(+)-HR-ESI-TOF-MS m/z: 766.2972 [M–H$_2$O+H]$^+$ (Calcd. for C$_{41}$H$_{44}$N$_5$O$_8$S$^+$: 766.2905).

C')

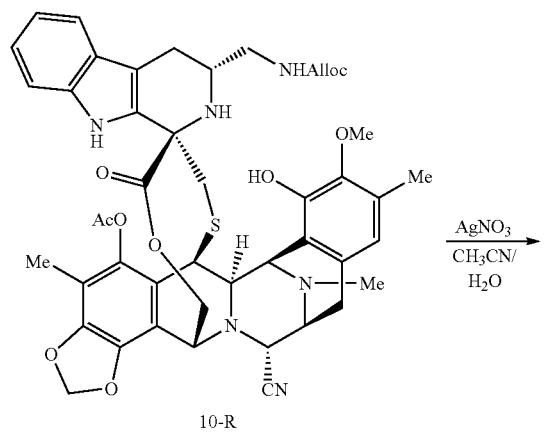

To a solution of 10-R (700 mg, 0.8 mmol) in CH$_3$CN:H$_2$O (1.39:1, 87.5 mL, 0.015 M) was added AgNO$_3$ (2.66 g, 16 mmol). After 20 h at 23° C., the reaction mixture was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 13-R (438 mg, 63%).

Rf=0.40 (CH$_2$Cl$_2$:CH$_3$OH, 9:1).

$^1$H NMR (400 MHz, CDCl$_3$): δ 7.64 (s, 1H), 7.37 (d, J=7.9 Hz, 1H), 7.32-7.20 (m, 1H), 7.11 (t, J=7.7 Hz, 1H), 7.01 (t, J=7.4 Hz, 1H), 6.62 (s, 1H), 6.21 (s, 1H), 6.05-5.90 (m, 1H), 5.99 (s, 1H), 5.75 (d, J=6.0 Hz, 1H), 5.40-5.07 (m, 4H), 4.88 (d, J=14.7 Hz, 1H), 4.68-4.50 (m, 3H), 4.28-4.13 (m, 1H), 4.08 (dt, J=11.4, 2.4 Hz, 1H), 3.83 (s, 3H), 3.68-3.40 (m, 4H), 3.37-3.19 (m, 2H), 2.98-2.79 (m, 2H), 2.59-2.36 (m, 3H), 2.29 (s, 3H), 2.27 (s, 3H), 2.14 (s, 3H), 2.10-2.16 (m, 1H), 2.08 (s, 3H).

ESI-MS m/z: 850.3 (M–H$_2$O+H)$^+$.

Example 6

A)

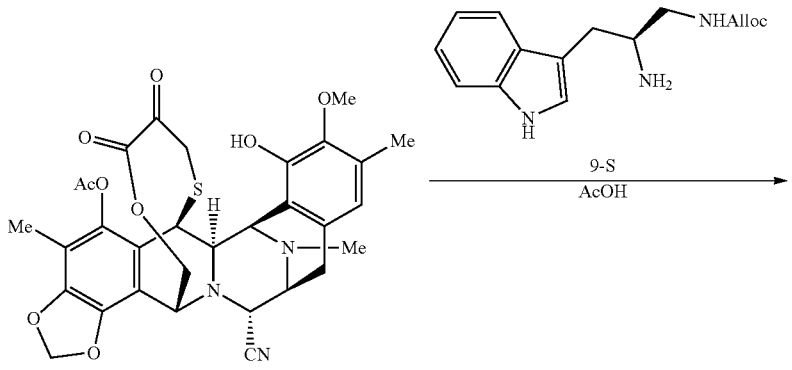

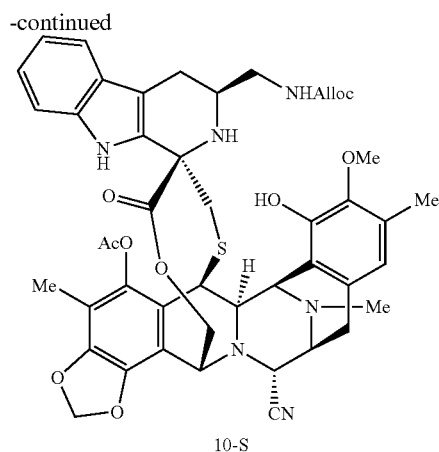

10-S

To a solution of 1 (955 mg, 1.5 mmol) in acetic acid (37.5 mL, 0.08 M) was added 9-S (627 mg, 2.29 mmol). The reaction mixture was stirred a 50° C. for 18 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$. Flash chromatography (Hexane:EtOAc, 1:1) gives compound 10-S (756 mg, 58%).

R$_f$=0.4 (Hexane:EtOAc, 1:1).

$^1$H NMR (400 MHz, CDCl$_3$): δ 7.78 (s, 1H), 7.36 (d, J=7.9 Hz, 1H), 7.24 (d, J=7.9 Hz, 1H), 7.10 (ddd, J=8.3, 7.0, 1.3 Hz, 1H), 7.01 (td, J=7.5, 7.0, 1.0 Hz, 1H), 6.68 (s, 1H), 6.23 (d, J=1.4 Hz, 1H), 6.01 (d, J=1.4 Hz, 1H), 6.07-5.93 (m, 1H), 5.82 (s, 1H), 5.41-5.19 (m, 2H), 5.1 (d, J=11.7 Hz, 1H), 4.66 (dt, J=5.9, 1.3 Hz, 1H), 4.57 (s, 1H), 4.37 (s, 1H), 4.33-4.20 (m, 3H), 3.81 (s, 3H), 3.46 (d, J=4.2 Hz, 2H), 3.22-3.13 (m, 1H), 3.11-2.88 (m, 4H), 2.66 (dd, J=15.2, 4.2 Hz, 1H), 2.51 (dd, J=15.3, 6.0 Hz, 1H), 2.43-2.32 (m, 2H), 2.31 (s, 3H), 2.26 (s, 3H), 2.19 (s, 3H), 2.04 (s, 3H).

ESI-MS m/z: 877.3 (M+H)$^+$.

B)

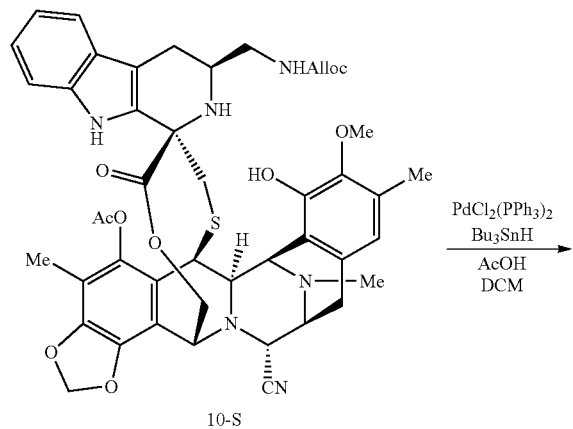

10-S

PdCl$_2$(PPh$_3$)$_2$
Bu$_3$SnH
AcOH
DCM
→

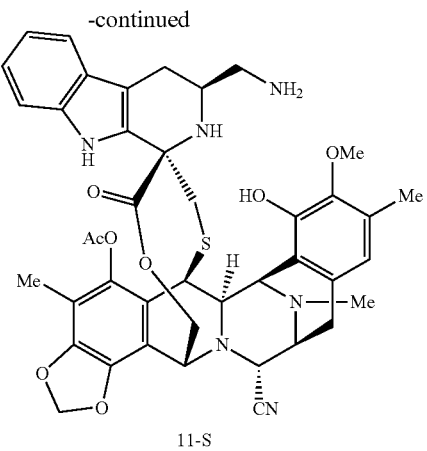

11-S

To a solution of 10-S (650 mg, 0.72 mmol) in CH$_2$Cl$_2$ (13.3 mL, 18 mL/mmol) was added bis(triphenylphosphine)palladium(II) dichloride (83 mg, 0.11 mmol) and acetic acid (0.42 mL, 7.4 mmol). Tributyltin hydride (1.2 mL, 4.4 mmol) was added at 0° C., the reaction mixture was stirred at 23° C. for 0.5 h, and concentrated under vacuum. Flash chromatography (Hexane:EtOAc, from 100:1 to 1:100 and EtOAc:CH$_3$OH, from 100:1 to 1:100) to afford 11-S (445 mg, 78%).

R$_f$=0.5 (CH$_2$Cl$_2$:CH$_3$OH, 1:1).

$^1$H NMR (400 MHz, CDCl$_3$): δ 7.74 (s, 1H), 7.36 (d, J=7.9 Hz, 1H), 7.26 (d, J=8.1 Hz, 1H), 7.12 (ddt, J=8.3, 7.0, 1.4 Hz, 1H), 7.02 (ddt, J=8.3, 7.0, 1.4 Hz, 1H), 6.62 (s, 1H), 6.26 (d, J=1.5 Hz, 1H), 6.04 (d, J=1.5 Hz, 1H), 5.12 (d, J=11.8 Hz, 1H), 4.59 (s, 1H), 4.42 (s, 1H), 4.36-4.17 (m, 3H), 3.81 (s, 3H), 3.51-3.39 (m, 3H), 2.98-2.75 (m, 4H), 2.69-2.60 (m, 2H), 2.47 (d, J=16.1 Hz, 1H), 2.38 (s, 3H), 2.35-2.17 (m, 2H), 2.28 (s, 3H), 2.13 (s, 3H), 2.04 (s, 3H).

ESI-MS m/z: 793.3 (M+H)$^+$.

C)

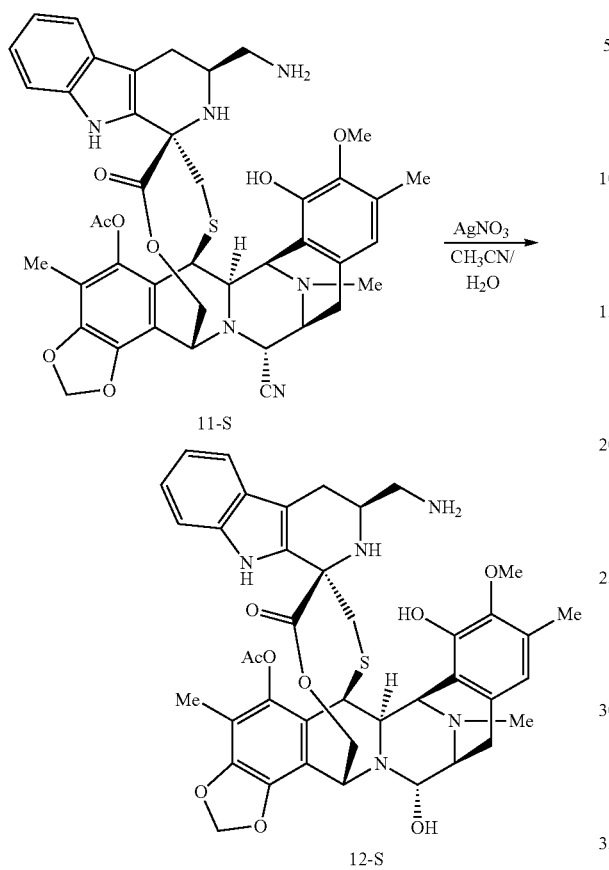

11-S

12-S

To a solution of 11-S (435 mg, 0.55 mmol) in CH$_3$CN:H$_2$O (1.39:1, 38.5 mL, 0.015 M) was added AgNO$_3$ (1.84 g, 11 mmol). After 24 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 12-S (152 mg, 35%).

R$_f$=0.2 (CH$_2$Cl$_2$:CH$_3$OH, 9:1).

$^1$H NMR (500 MHz, CD$_3$OD): δ 7.34 (dd, J=7.7, 1.5 Hz, 1H), 7.28 (dd, J=7.7, 1.5 Hz, 1H), 7.04 (ddt, J=8.2, 7.0, 1.1 Hz, 1H), 6.95 (ddt, J=8.2, 7.0, 1.2 Hz, 1H), 6.55 (s, 1H), 6.31-6.25 (m, 1H), 6.15-6.05 (m, 1H), 5.31 (d, J=11.4 Hz, 1H), 4.91 (s, 1H), 4.64 (s, 1H), 4.40-4.19 (m, 3H), 3.76 (s, 3H), 3.64 (d, J=5.2 Hz, 1H), 3.44 (d, J=9.0 Hz, 1H), 3.03-2.85 (m, 4H), 2.85-2.65 (m, 2H), 2.59 (d, J=15.6 Hz, 1H), 2.52-2.39 (m, 2H), 2.37 (s, 3H), 2.27 (s, 3H), 2.09 (s, 3H), 2.00 (s, 3H).

$^{13}$C NMR (126 MHz, CD$_3$OD): δ 171.4, 169.3, 148.6, 145.8, 143.5, 141.2, 140.8, 136.5, 131.2, 130.3, 129.5, 126.3, 121.6, 121.2, 119.8, 119.4, 118.6, 117.5, 114.9, 111.0, 107.5, 107.4, 102.2, 91.1, 63.5, 60.5, 59.2, 58.5, 55.3, 54.7, 53.4, 52.7, 48.6, 44.7, 42.7, 39.9, 24.3, 23.4, 19.2, 15.1, 8.2. ESI-MS m/z: 766.2 (M–H$_2$O+H)$^+$.

(+)-HR-ESI-TOF-MS m/z: 766.2958 [M–H$_2$O+H]$^+$ (Calcd. for C$_{41}$H$_{44}$N$_5$O$_8$S: 766.2905).

C')

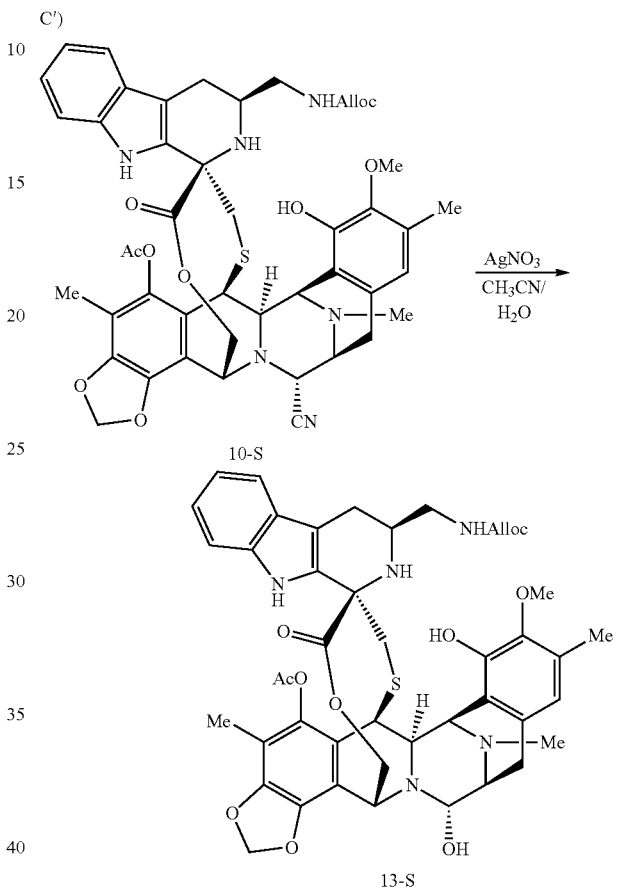

10-S

13-S

To a solution of 10-S (5 mg, 0.006 mmol) in CH$_3$CN:H$_2$O (1.39:1, 0.5 mL, 0.015 M) was added AgNO$_3$ (29 mg, 0.17 mmol). After 20 h at 23° C., the reaction mixture was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 13-S (5 mg, 100%).

R$_f$=0.40 (CH$_2$Cl$_2$:CH$_3$OH, 9:1).

$^1$H NMR (400 MHz, CDCl$_3$): δ 7.75 (s, 1H), 7.37 (d, J=7.9 Hz, 1H), 7.32-7.20 (m, 1H), 7.12 (t, J=7.7 Hz, 1H), 7.02 (t, J=7.4 Hz, 1H), 6.84 (s, 1H), 6.24 (s, 1H), 6.08-5.97 (m, 1H), 6.01 (s, 1H), 5.87 (s, 1H), 5.42-5.19 (m, 4H), 4.88 (s, 1H), 4.69-4.65 (m, 2H), 4.58 (s, 1H), 4.28-4.13 (m, 2H), 3.84 (s, 3H), 3.68-3.40 (m, 2H), 3.24-3.15 (m, 2H), 3.08-2.90 (m, 2H), 2.73-2.57 (m, 2H), 2.53-2.37 (m, 3H), 2.34 (s, 3H), 2.25 (s, 3H), 2.14 (s, 3H), 2.10-2.16 (m, 1H), 2.03 (s, 3H). ESI-MS m/z: 850.3 (M–H$_2$O+H)$^+$.

Example 7. Synthesis of Reference Compounds 14-S and 15-S

A)

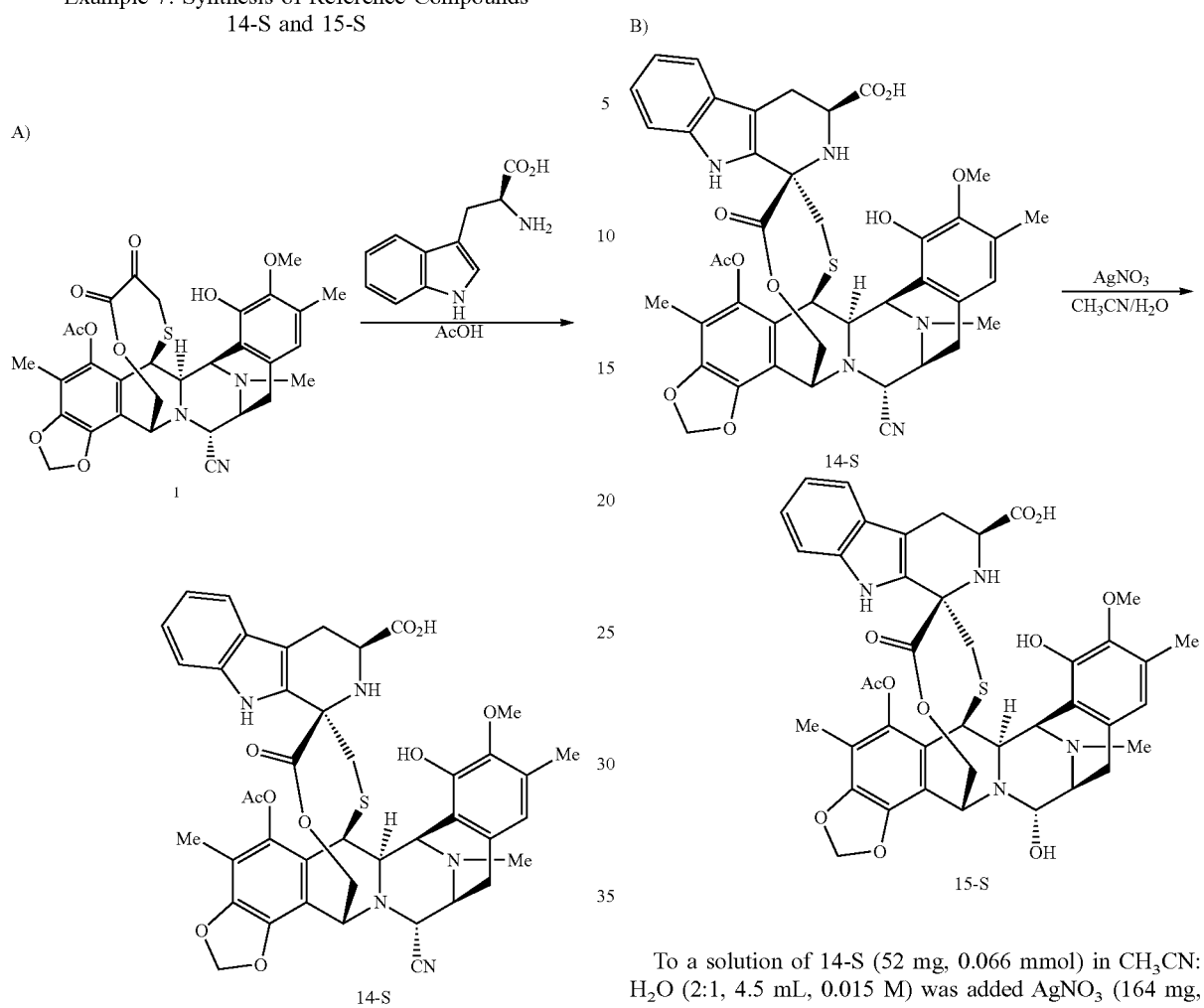

B)

To a solution of 1 (50 mg, 0.08 mmol) in acetic acid (1 mL, 0.08 M) was added L-tryptophan (50 mg, 0.24 mmol). The reaction mixture was stirred at 50° C. for 17 h and then acetic acid was evaporated. An aqueous saturated solution of NaHCO₃ was added and the mixture was extracted with CH₂Cl₂. The combined organic layers were dried over anhydrous Na₂SO₄, filtered and concentrated under vacuum. Flash chromatography (CH₂Cl₂:CH₃OH, from 99:1 to 80:20) gave compound 14-S (58 mg, 90%).

$R_f$=0.20 (CH₂Cl₂:CH₃OH, 10:1).

¹H NMR (400 MHz, CDCl₃): δ 7.77 (s, 1H), 7.39 (d, J=7.9 Hz, 1H), 7.25 (d, J=7.9 Hz, 1H), 7.13 (ddd, J=8.2, 7.0, 1.2 Hz, 1H), 7.04 (td, J=7.5, 7.1, 1.0 Hz, 1H), 6.56 (s, 1H), 6.24 (d, J=1.3 Hz, 1H), 6.03 (d, J=1.3 Hz, 1H), 5.15 (d, J=11.7 Hz, 1H), 4.62 (s, 1H), 4.43 (s, 1H), 4.35 (dd, J=11.7, 2.1 Hz, 1H), 4.28 (dd, J=5.2, 1.6 Hz, 1H), 4.20 (s, 1H), 3.78 (s, 3H), 3.52-3.41 (m, 4H), 3.07-2.88 (m, 2H), 2.91-2.80 (m, 2H), 2.42-2.21 (m, 2H), 2.35 (s, 3H), 2.27 (s, 3H), 2.14 (s, 3H), 2.04 (s, 3H).

ESI-MS m/z: 808.6 (M+H)⁺.

To a solution of 14-S (52 mg, 0.066 mmol) in CH₃CN: H₂O (2:1, 4.5 mL, 0.015 M) was added AgNO₃ (164 mg, 1.45 mmol). After 20 h at 23° C., a mixture 1:1 of saturated aqueous solutions of NaCl and NaHCO₃ was added, stirred for 15 min, diluted with CH₂Cl₂, stirred for 30 min, and extracted with CH₂Cl₂. The combined organic layers were dried over anhydrous Na₂SO₄, filtered and concentrated under vacuum. The residue obtained was purified by flash chromatography (CH₂Cl₂:CH₃OH, from 99:1 to 70:30) to afford 15-S (18 mg, 35%).

$R_f$=0.15 (CH₂Cl₂:CH₃OH, 9:1).

¹H NMR (400 MHz, CD₃OD): δ 7.76 (s, 1H), 7.40 (d, J=7.8 Hz, 1H), 7.25 (d, J=7.8 Hz, 1H), 7.14 (t, J=7.4 Hz, 1H), 7.04 (t, J=7.4 Hz, 1H), 6.58 (s, 1H), 6.23 (d, J=1.3 Hz, 1H), 6.01 (d, J=1.3 Hz, 1H), 5.28 (d, J=12.7 Hz, 1H), 4.95 (s, 1H), 4.53 (s, 1H), 4.28 (dd, J=11.4, 2.0 Hz, 1H), 4.21 (s, 1H), 3.80 (s, 3H), 3.58 (s, 1H), 3.52-3.47 (m, 2H), 3.28 (s, 1H), 3.03 (dd, J=15.8, 5.2 Hz, 1H), 2.91-2.82 (m, 3H), 2.44 (d, J=15.4 Hz, 1H), 2.36 (s, 3H), 2.35-2.31 (m, 1H), 2.28 (s, 3H), 2.15 (s, 3H), 2.03 (s, 3H).

¹³C NMR (101 MHz, CDCl₃): δ 173.7, 171.2, 168.7, 147.5, 145.7, 142.8, 141.2, 140.8, 135.6, 129.8, 126.3, 122.8, 121.5, 121.2, 119.9, 118.6, 117.7, 115.0, 111.1, 101.9, 81.5, 66.8, 62.9, 60.4, 57.9, 55.8, 55.1, 52.3, 42.3, 41.3, 38.3, 31.9, 29.4, 28.9, 24.5, 24.0, 23.8, 22.7, 20.5, 16.0, 9.7.

ESI-MS m/z: 781.6 (M–H₂O+H)⁺.

(+)-HR-ESI-TOF-MS m/z: 781.2610 [M–H₂O+H]⁺ (Calcd. for C₄₁H₄₁N₄O₁₀S: 781.2538).

Example 8

A) Synthesis of (S)-5-methoxy-tryptophanol (17-S)

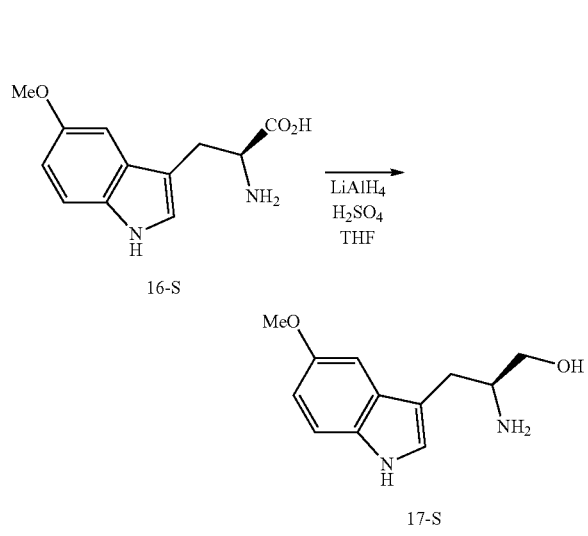

B) Synthesis of (R)-5-methoxy-tryptophanol (17-R)

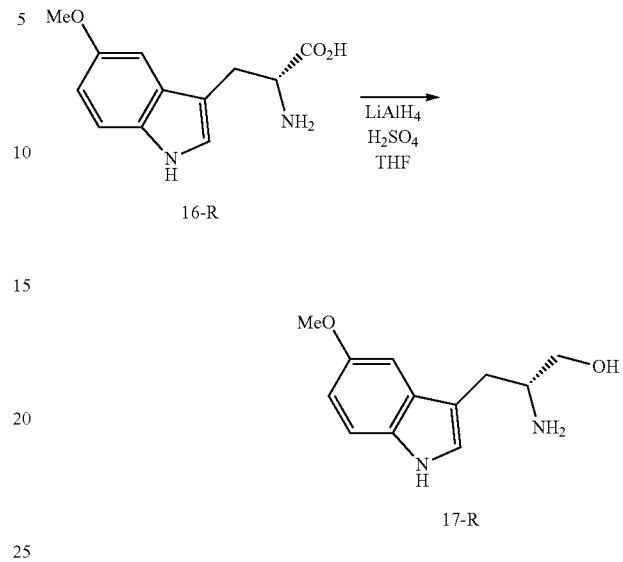

To a solution of LiAlH$_4$ (23.4 mL, 1.0 M in THF, 23.4 mmol) at −40° C. was added carefully H$_2$SO$_4$ (0.31 mL, 5.57 mmol) and a suspension of 5-methoxy-L-tryptophan (16-S) (1.0 g, 4.26 mmol, Chem-Impex) in THF (13.4 mL, 0.3 M). The reaction mixture was left evolution at 23° C., heated for 3 h at 80° C. and 18 h at 23° C. Cool at −21° C. the reaction mixture was quenched carefully with NaOH 2N until basic pH. EtOAc was added and the mixture filtered through Celite® and washed with CH$_3$OH. The crude was concentrated under vacuum to give 17-S as a crude which was used in the next step without further purification.

R$_f$=0.2 (CH$_2$Cl$_2$:CH$_3$OH, 4:1).

$^1$H NMR (400 MHz, CDCl$_3$): δ 7.19 (dt, J=8.8, 0.7 Hz, 1H), 7.06-7.00 (m, 2H), 6.72 (dd, J=8.8, 2.4 Hz, 1H), 3.77 (s, 3H), 3.63-3.48 (m, 1H), 3.42-3.33 (m, 1H), 3.17-3.06 (m, 1H), 2.86 (ddt, J=14.3, 6.1, 0.8 Hz, 1H), 2.66 (dd, J=14.3, 7.5 Hz, 1H).

ESI-MS m/z: 221.4 (M+H)$^+$.

To a solution of LiAlH$_4$ (11.7 mL, 1.0 M in THF, 11.7 mmol) at −40° C. was added carefully H$_2$SO$_4$ (0.31 mL, 5.75 mmol) and a suspension of 5-methoxy-D-tryptophan (16-R) (0.5 g, 2.13 mmol, Aldrich) in THF (6.7 mL, 0.3 M). The reaction mixture was left evolution at 23° C., heated for 3.5 h at 80° C. and 18 h at 23° C. Cool at −21° C. the reaction mixture was quenched carefully with NaOH 2N until basic pH. EtOAc was added and the mixture filtered through Celite® and washed with CH$_3$OH. The crude was concentrated under vacuum to give 17-R as a crude which was used in the next step without further purification.

R$_f$=0.2 (CH$_2$Cl$_2$:CH$_3$OH, 4:1).

$^1$H NMR (400 MHz, CD$_3$OD): δ 7.20 (d, J=8.9 Hz, 1H), 7.06-6.96 (m, 2H), 6.71 (dd, J=8.8, 2.5 Hz, 1H), 3.75 (s, 3H), 3.62-3.52 (m, 1H), 3.37 (dd, J=10.8, 7.0 Hz, 1H), 3.09 (br s, 1H), 2.82 (dd, J=14.3, 5.9 Hz, 1H), 2.62 (dd, J=14.4, 7.6 Hz, 1H).

ESI-MS m/z: 221.6 (M+H)$^+$.

Example 9

A)

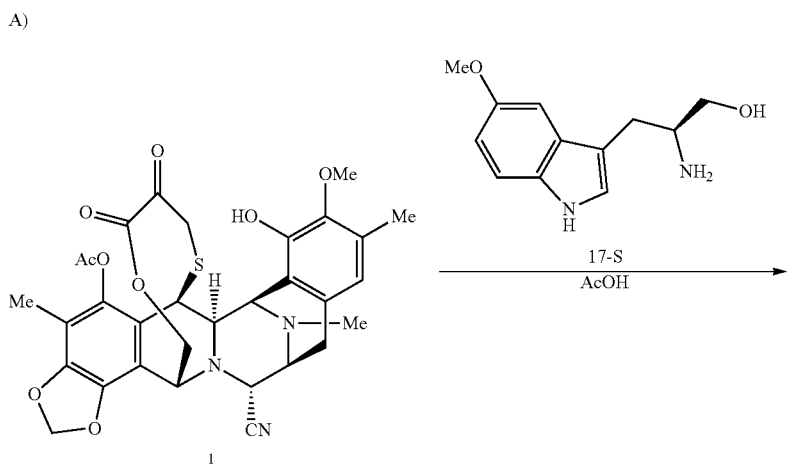

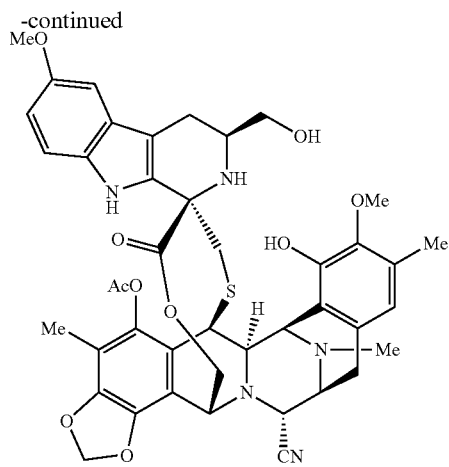

18-S

To a solution of 1 (530 mg, 0.85 mmol) in acetic acid (10.6 mL, 0.08 M) was added 17-S (469 mg, 2.13 mmol). The reaction mixture was stirred at 50° C. for 18 h and then acetic acid was evaporated. An aqueous saturated solution of NaHCO₃ was added and the mixture was extracted with CH₂Cl₂. The combined organic layers were dried over anhydrous Na₂SO₄, filtered, and concentrated under vacuum. Flash chromatography (Hexane:EtOAc, 1:1) gave compound 18-S (420 mg, 60%).

$R_f$=0.3 (Hexane:EtOAc, 1:1).

¹H NMR (400 MHz, CD₃OD): δ 7.13 (d, J=8.8 Hz, 1H), 6.80 (d, J=2.4 Hz, 1H), 6.66 (dd, J=8.8, 2.5 Hz, 1H), 6.51 (s, 1H), 6.27 (s, 1H), 6.11 (s, 1H), 5.21 (d, J=11.7 Hz, 1H), 4.67 (s, 1H), 4.49-4.29 (m, 4H), 3.75 (s, 3H), 3.73 (s, 3H), 3.47 (t, J=5.8 Hz, 3H), 3.37 (d, J=5.1 Hz, 1H), 3.01-2.81 (m, 2H), 2.75 (d, J=7.4 Hz, 1H), 2.66 (dd, J=15.1, 4.1 Hz, 1H), 2.55-2.35 (m, 4H), 2.34 (s, 3H), 2.28 (s, 3H), 2.11 (s, 3H), 1.99 (s, 3H).

ESI-MS m/z: 824.3 (M+H)⁺.

B)

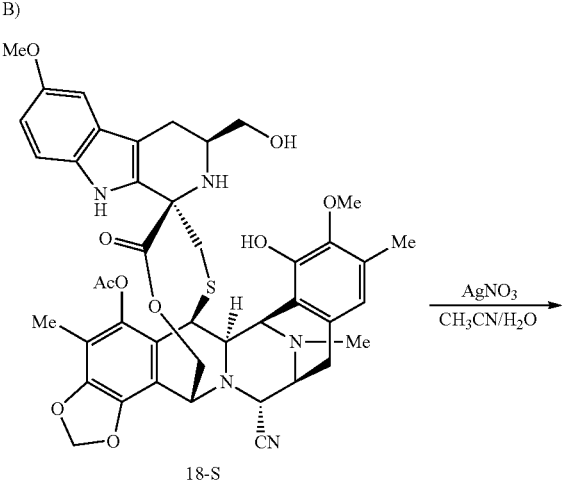

18-S

→ AgNO₃ / CH₃CN/H₂O

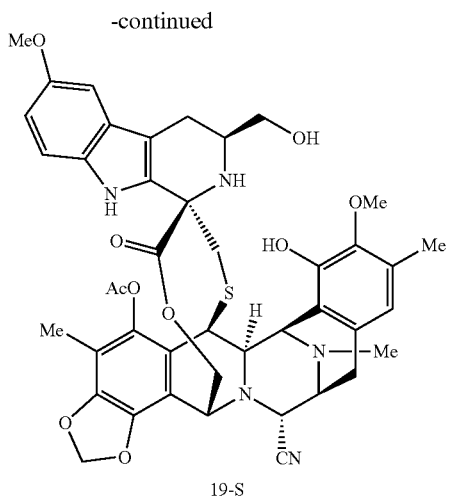

19-S

To a solution of 18-S (420 mg, 0.519 mmol) in CH₃CN:H₂O (1.39:1, 36 mL, 0.015 M) was added AgNO₃ (2.60 g, 15.3 mmol). After 3 h at 23° C., the reaction mixture was quenched with a mixture 1:1 of saturated aqueous solutions of NaCl and NaHCO₃, stirred for 15 min, diluted with CH₂Cl₂, stirred for 5 min, and extracted with CH₂Cl₂. The combined organic layers were dried over anhydrous Na₂SO₄, filtered, and concentrated under vacuum. The residue obtained was purified by flash chromatography (CH₂Cl₂:CH₃OH, from 99:1 to 85:15) to obtain 19-S (250 mg, 60%).

$R_f$=0.45 (CH₂Cl₂:CH₃OH, 9:1).

¹H NMR (500 MHz, CD₃OD): δ 7.15 (dd, J=8.9, 0.6 Hz, 1H), 6.82 (dd, J=2.4, 0.6 Hz, 1H), 6.68 (dd, J=8.8, 2.5 Hz, 1H), 6.54 (s, 1H), 6.27 (d, J=1.3 Hz, 1H), 6.08 (d, J=1.3 Hz, 1H), 5.30 (d, J=11.5 Hz, 1H), 4.62 (s, 1H), 4.34 (dd, J=11.4, 2.0 Hz, 1H), 4.31-4.27 (m, 2H), 3.76 (s, 3H), 3.75 (s, 3H), 3.66-3.58 (m, 1H), 3.55-3.45 (m, 2H), 3.42 (d, J=7.8 Hz, 1H), 2.93-2.73 (m, 3H), 2.68 (dd, J=15.1, 4.2 Hz, 1H), 2.54 (d, J=15.4 Hz, 1H), 2.42 (dd, J=15.1, 10.1 Hz, 2H), 2.35 (s, 3H), 2.29 (s, 3H), 2.09 (s, 3H), 2.00 (s, 3H).

¹³C NMR (126 MHz, CD₃OD): δ 172.7, 170.8, 155.1, 149.9, 147.2, 145.0, 142.6, 142.2, 133.1, 132.4, 132.1, 131.3, 128.1, 122.5, 121.6, 120.3, 116.4, 113.0, 112.9, 111.4, 109.0, 103.6, 100.8, 92.5, 66.6, 65.0, 61.7, 60.4, 59.9, 56.7, 56.1, 54.8, 54.1, 51.7, 44.1, 41.3, 30.7, 25.4, 24.7, 20.6, 16.3, 9.5.

ESI-MS m/z: 798.1 $(M-H_2O+H)^+$.

(+)-HR-ESI-TOF-MS m/z: 797.2899 $[M-H_2O+H]^+$ (Calcd. for $C_{42}H_{45}N_4O_{10}S$ 797.2851).

Example 10

A)

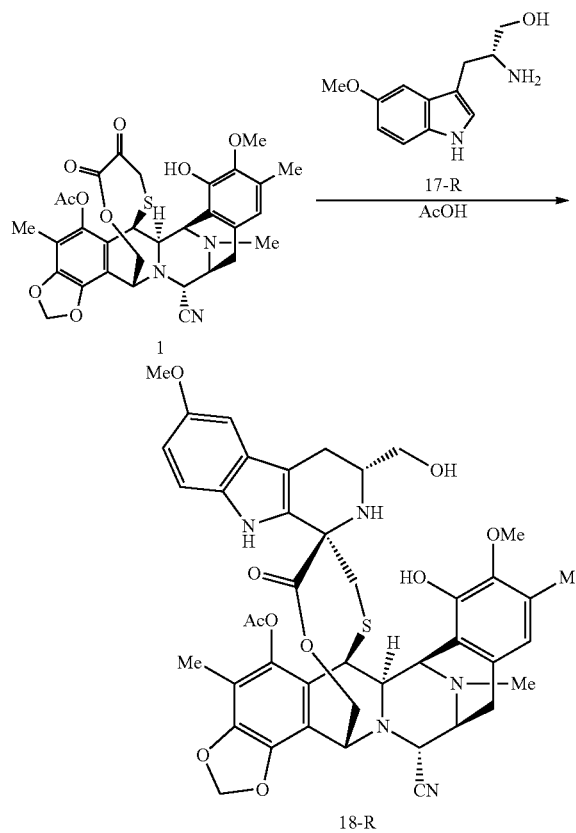

B)

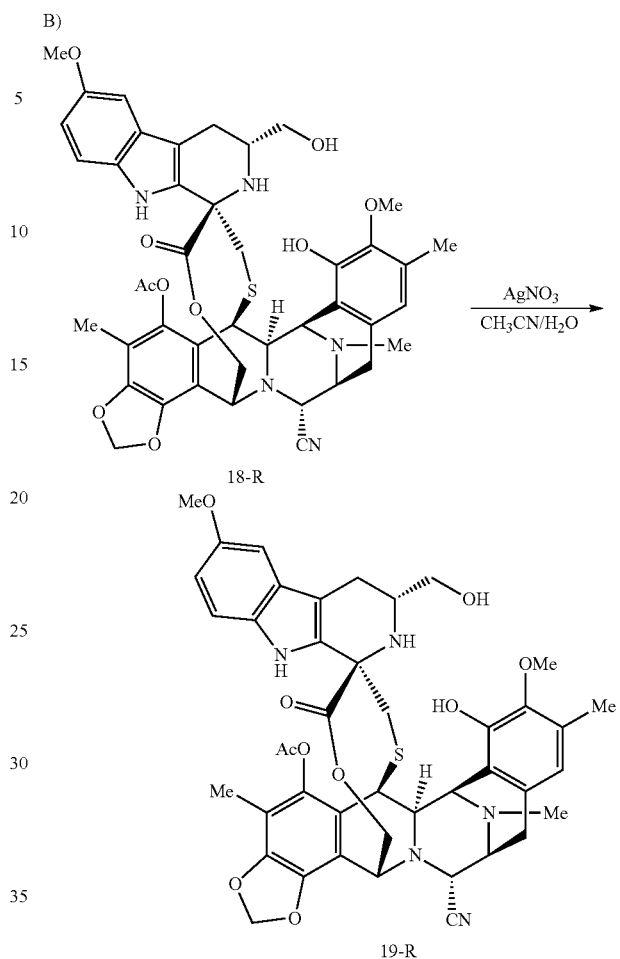

To a solution of 1 (311 mg, 0.50 mmol) in acetic acid (6.25 mL, 0.08 M) was added 17-R (220 mg, 1.0 mmol). The reaction mixture was stirred at 50° C. for 18 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, 1:1) gave compound 18-R (280 mg, 68%).

$R_f$=0.3 (Hexane:EtOAc, 1:1).

$^1$H NMR (400 MHz, CDCl$_3$): δ 7.53 (s, 1H), 7.18 (d, J=8.7 Hz, 1H), 6.82 (d, J=2.4 Hz, 1H), 6.78 (dd, J=8.6, 2.3 Hz, 1H), 6.60 (s, 1H), 6.23 (s, 1H), 6.02 (s, 1H), 5.76 (s, 1H), 5.04 (d, J=11.7 Hz, 1H), 4.62 (s, 1H), 4.36 (s, 1H), 4.28 (d, J=5.0 Hz, 1H), 4.24-4.09 (m, 3H), 3.81 (s, 3H), 3.79 (s, 3H), 3.64 (s, 1H), 3.47-3.40 (m, 3H), 3.01-2.90 (m, 2H), 2.53 (d, J=6.9 Hz, 2H), 2.45-2.41 (m, 1H), 2.40 (s, 3H), 2.27 (s, 3H), 2.22-2.14 (m, 1H), 2.18 (s, 3H), 2.06 (s, 3H).

ESI-MS m/z: 824.3 $(M+H)^+$.

To a solution of 18-R (330 mg, 0.40 mmol) in CH$_3$CN: H$_2$O (1.39:1, 28 mL, 0.015 M) was added AgNO$_3$ (2.04 g, 12.0 mmol). After 3 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to obtain 19-R (224 mg, 69%).

$R_f$=0.44 (CH$_2$Cl$_2$:CH$_3$OH, 9:1).

$^1$H NMR (500 MHz, CD$_3$OD): δ 7.14 (dd, J=8.8, 0.5 Hz, 1H), 6.83 (d, J=2.5 Hz, 1H), 6.68 (dd, J=8.8, 2.5 Hz, 1H), 6.59 (s, 1H), 6.26 (d, J=1.4 Hz, 1H), 6.07 (d, J=1.4 Hz, 1H), 5.21 (d, J=11.5 Hz, 1H), 4.68-4.55 (m, 1H), 4.32-4.25 (m, 2H), 4.12 (dd, J=11.5, 2.1 Hz, 1H), 3.75 (s, 3H), 3.74 (s, 3H), 3.60 (d, J=5.2 Hz, 1H), 3.57-3.45 (m, 3H), 3.41 (d, J=8.8 Hz, 1H), 2.97-2.83 (m, 3H), 2.73 (dd, J=15.0, 3.4 Hz, 1H), 2.69 (d, J=14.9 Hz, 1H), 2.34 (s, 3H), 2.30 (s, 3H), 2.20 (dd, J=15.1, 10.4 Hz, 1H), 2.12 (s, 3H), 2.11-2.08 (m, 1H), 2.05 (s, 3H).

$^{13}$C NMR (126 MHz, CD$_3$OD): δ 173.0, 170.8, 155.0, 149.8, 147.3, 145.0, 142.8, 142.3, 133.5, 133.1, 132.2, 132.1, 131.1, 130.5, 127.8, 122.5, 121.7, 120.0, 116.4, 113.5, 112.9, 111.4, 110.2, 103.5, 100.9, 92.6, 66.8, 64.5, 61.3, 60.4, 60.0, 56.8, 56.1, 55.9, 54.1, 44.1, 41.3, 25.6, 24.5, 20.6, 16.2, 9.6.

ESI-MS m/z: 797.4 $(M-H_2O+H)^+$.

(+)-HR-ESI-TOF-MS m/z: 797.2896 $[M-H_2O+H]^+$ (Calcd. for $C_{42}H_{45}N_4O_{10}S$ 797.2851).

Example 11. Synthesis of allyl N—[(S)-2-amino-3-(5-methoxy-1H-indol-3-yl)propyl)]carbamate (24-S)
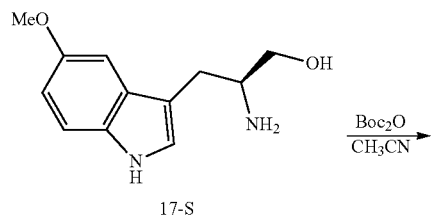
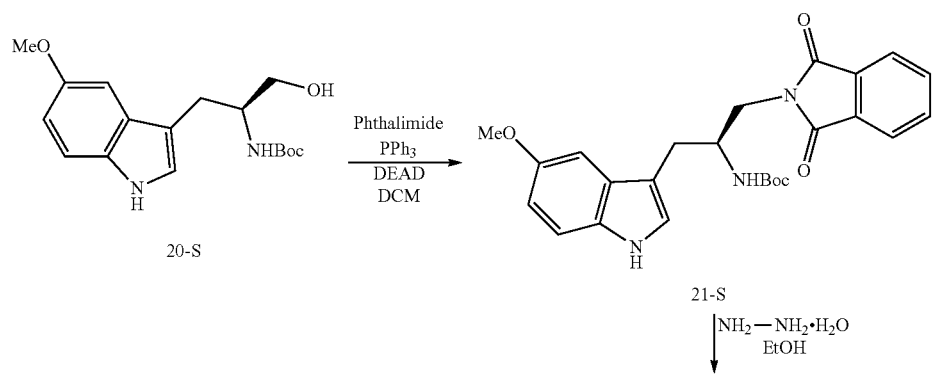
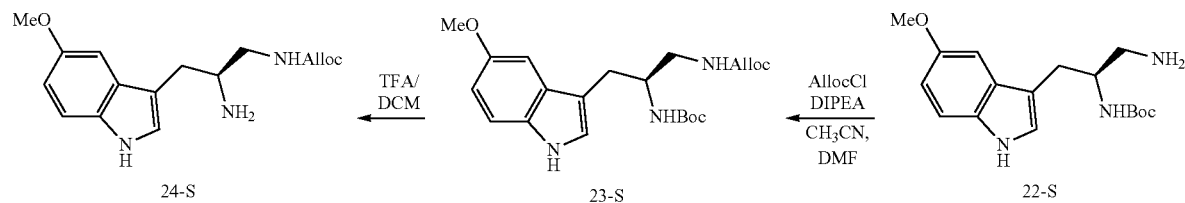
A)
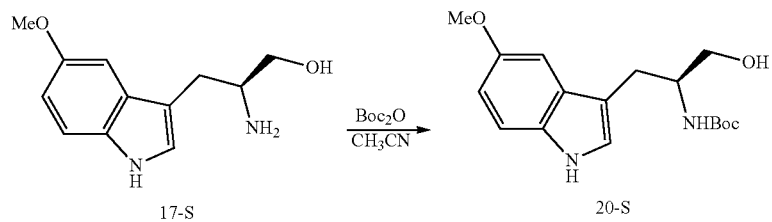

To a solution of 17-S (6.9 g, 31.4 mmol) in CH₃CN (126 mL, 4 mL/mmol) was added di-tert-butyl dicarbonate (13.7 g, 62.8 mmol). The reaction mixture was stirred at 23° C. for 5.5 h, concentrated under vacuum. Flash chromatography (CH$_2$Cl$_2$:CH$_3$OH, from 99:1 to 85:15) gives 20-S (4.5 g, 45%).

R$_f$=0.6 (CH$_2$Cl$_2$:CH$_3$OH, 9:1).

$^1$H NMR (400 MHz, CDCl$_3$): δ 8.04 (s, 1H), 7.25 (d, J=8.4 Hz, 1H), 7.10 (d, J=2.4 Hz, 1H), 7.03 (s, 1H), 6.87 (dd, J=8.8, 2.5 Hz, 1H), 4.83 (s, 1H), 3.98 (s, 1H), 3.87 (s, 3H), 3.73-3.58 (m, 2H), 2.96 (d, J=6.6 Hz, 2H), 1.42 (s, 9H).

B)

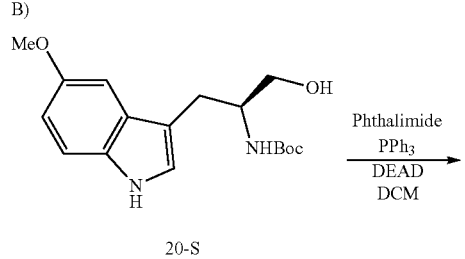

To a solution of 20-S (4.5 g, 14 mmol) in CH$_2$Cl$_2$ (84 mL, 6 mL/mmol) was added phthalimide (4.5 g, 30.9 mmol), triphenylphosphine (8.1 g, 30.9 mmol) and the mixture was cooled at 0° C. A solution of 40% of diethyl azodicarboxylate in CH$_2$Cl$_2$ (10.4 mL, 35 mmol) was added for 15 min. The reaction was stirred at 23° C. for 18 h, concentrated under vacuum. The residue obtained was purified by flash chromatography (Hexane:EtOAc, from 99:1 to 85:15) to yield 21-S (5.8 g, 92%).

R$_f$=0.55 (Hexane:EtOAc, 1:1).

$^1$H NMR (400 MHz, CDCl$_3$): δ 8.48 (s, 1H), 7.78 (dd, J=5.5, 3.1 Hz, 2H), 7.69-7.61 (m, 2H), 7.21 (d, J=8.8 Hz, 1H), 7.06 (dd, J=18.5, 2.4 Hz, 2H), 6.81 (dd, J=8.8, 2.4 Hz, 1H), 4.87 (s, 1H); 4.39 (s, 1H), 3.87 (s, 3H), 3.83-3.66 (m, 2H), 2.98 (d, J=6.1 Hz, 2H), 1.20 (s, 9H).

C)

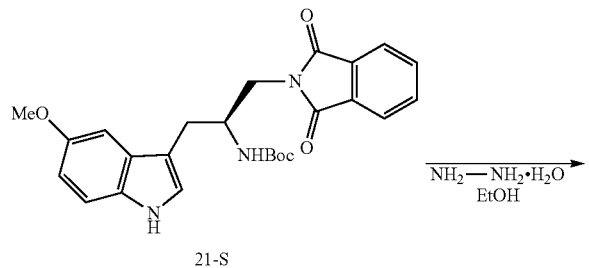

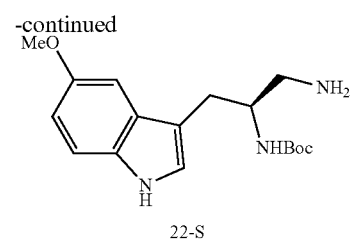

To a solution of 21-S (6.29 g, 14 mmol) in ethanol (420 mL, 30 mL/mmol) was added hydrazine monohydrate (61.1 mL, 1260 mmol). The reaction mixture was stirred at 80° C. in sealed tube for 2 h, concentrated under vacuum. Flash chromatography (CH$_2$Cl$_2$:CH$_3$OH, from 100:1 to 50:50) affords 22-S (4.2 g, 95%).

R$_f$=0.1 (CH$_2$Cl$_2$:CH$_3$OH, 8:2).

$^1$H NMR (400 MHz, CDCl$_3$): δ 7.22 (d, J=8.8 Hz, 1H), 7.12 (d, J=2.4 Hz, 1H), 7.06 (s, 1H), 6.76 (dd, J=8.8, 2.4 Hz, 1H), 4.06-3.97 (m, 1H), 3.82 (s, 3H), 3.06-2.82 (m, 4H), 1.37 (s, 9H).

D)

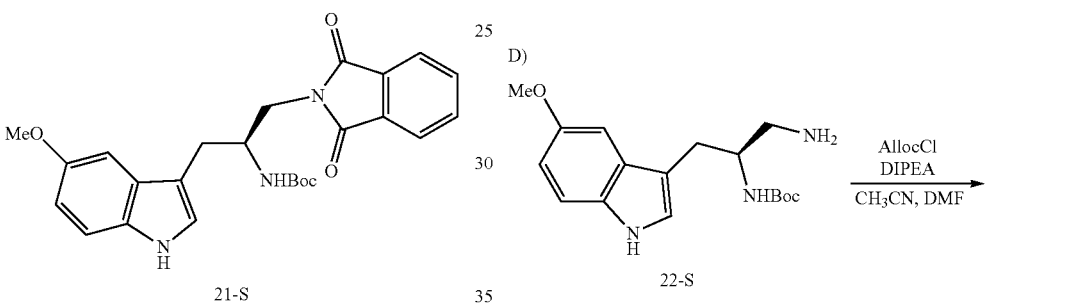

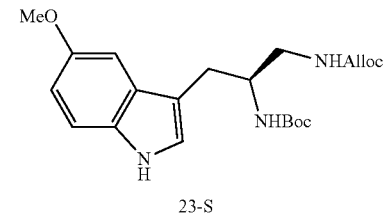

To a solution of 22-S (4.0 g, 12.52 mmol) in CH$_3$CN (125 mL, 10 mL/mmol) and DMF (12 mL, 1 mL/mmol) was added N,N-diisopropylethylamine (1.8 mL, 10 mmol) and allyl chloroformate (13.3 mL, 125 mmol). The reaction was stirred at 23° C. for 5 h. The mixture was diluted with EtOAc and NH$_4$Cl was added and the mixture was extracted with EtOAc. The combined organic layers were dried over anhydrous Na$_2$SO$_4$, filtered, and concentrated under vacuum. The residue obtained was purified by flash chromatography (Hexane:EtOAc, from 100:1 to 1:100) to obtain 23-S (2.65 g, 52%).

R$_f$=0.5 (Hexane:EtOAc, 1:1).

$^1$H NMR (400 MHz, CDCl$_3$): δ 8.11 (s, 1H), 7.28-7.20 (m, 1H), 7.04 (d, J=13.1 Hz, 2H), 6.85 (dd, J=8.9, 2.4 Hz, 1H), 5.97-5.82 (m, 1H), 5.33-5.24 (m, 1H), 5.19 (dt, J=10.4, 1.3 Hz, 1H), 5.11 (s, 1H), 4.82 (s, 1H), 4.55 (d, J=5.6 Hz, 2H), 4.01 (s, 1H), 3.86 (s, 3H), 3.37 (d, J=13.7 Hz, 1H), 3.21 (s, 1H), 2.89 (dd, J=14.5, 7.0 Hz, 1H), 1.41 (s, 9H).

E)
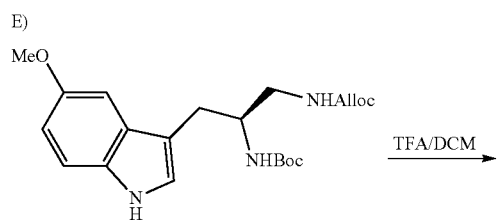
To a solution of 23-S (2.60 g, 6.44 mmol) in CH$_2$Cl$_2$ (106 mL, 16.6 mL/mmol) was added trifluoroacetic acid (54 mL, 8.3 mL/mmol). The reaction mixture was stirred at 23° C. for 1.5 h, concentrated under vacuum to afford 24-S (3.9 g, 100%).
R$_f$=0.1 (CH$_2$Cl$_2$:CH$_3$OH, 9:1).
$^1$H NMR (400 MHz, CD$_3$OD): δ 8.27 (s, 1H), 7.25 (dd, J=9.0, 2.4 Hz, 1H), 7.10 (s, 1H), 6.96 (d, J=2.3 Hz, 1H), 6.87 (dd, J=9.0, 2.4 Hz, 1H), 5.81 (ddt, J=16.3, 10.9, 5.7 Hz, 1H), 5.23 (dd, J=19.3, 13.6 Hz, 2H), 4.49 (d, J=5.9 Hz, 2H), 3.82 (s, 3H), 3.81-3.55 (m, 1H), 3.62-3.39 (m, 2H), 3.08 (qd, J=15.1, 7.3 Hz, 2H).
Example 12
A)
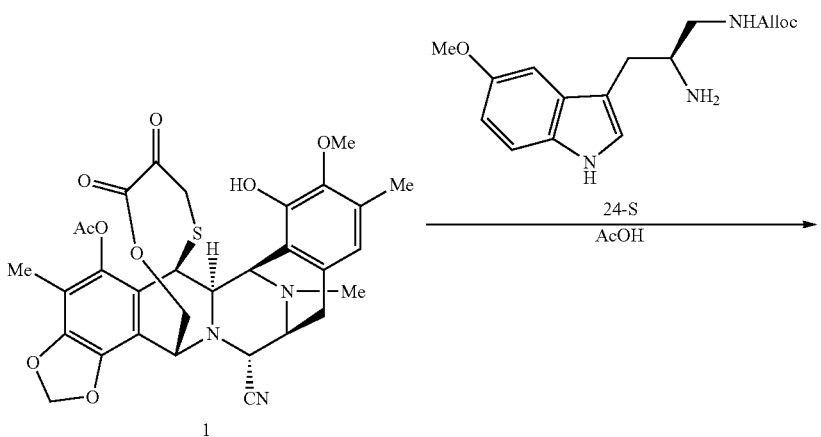
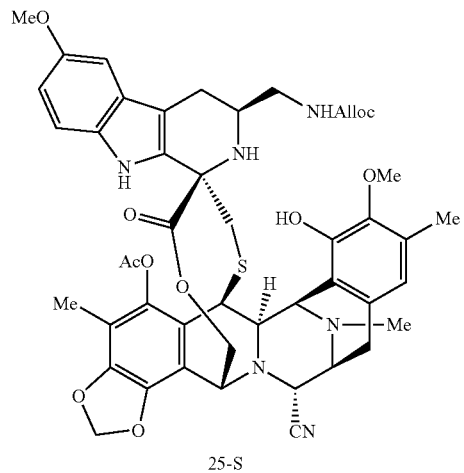

To a solution of 1 (120 mg, 0.19 mmol) in acetic acid (6 mL, 0.08 M) was added 24-S (117 mg, 0.35 mmol). The reaction mixture was stirred at 23° C. for 18 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, 1:1) gives compound 25-S (95 mg, 54%).

R$_f$=0.4 (Hexane:EtOAc, 1:1).

$^1$H NMR (400 MHz, CDCl$_3$): δ 7.64 (s, 1H), 7.14 (d, J=8.8 Hz, 1H), 6.80 (s, 1H), 6.77 (d, J=8.8 Hz, 1H), 6.68 (s, 1H), 6.24 (s, 1H), 6.03 (s, 1H), 6.02-5.93 (m, 1H), 5.76 (s, 1H), 5.38 (d, J=10.5 Hz, 1H), 5.26 (d, J=10.5 Hz, 1H), 5.11 (d, J=11.7 Hz, 1H), 4.66 (d, J=5.6 Hz, 2H), 4.57 (s, 1H), 4.37 (s, 1H), 4.33-4.19 (m, 3H), 3.82 (s, 3H), 3.79 (s, 3H), 3.46 (s, 2H), 3.17 (s, 1H), 3.10-2.90 (m, 3H), 2.68-2.45 (m, 2H), 2.38-2.33 (m, 1H), 2.32 (s, 3H), 2.27 (s, 3H), 2.16 (s, 3H), 2.04 (s, 2H).

ESI-MS m/z: 907.1 (M+H)$^+$.

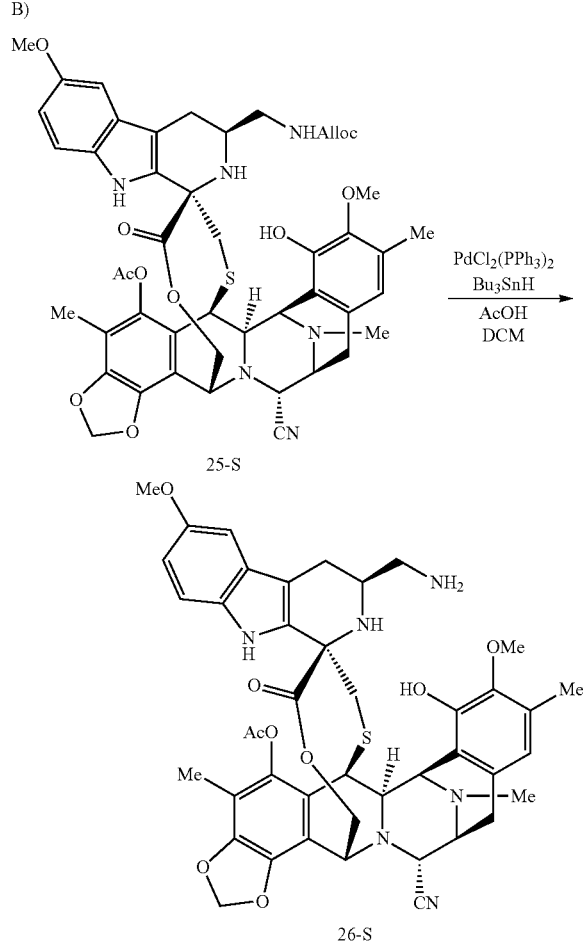

To a solution of 25-S (90 mg, 0.1 mmol) in CH$_2$Cl$_2$ (2 mL, 18 mL/mmol) was added bis(triphenylphosphine)palladium (II)dichloride (12 mg, 0.1 mmol) and acetic acid (0.056 mL, 0.99 mmol). Tributyltin hydride (0.16 mL, 0.60 mmol) was added at 0° C., the reaction mixture was stirred at 0° C. for 0.5 h, and concentrated under vacuum. Flash chromatography (Hexane:EtOAc, from 100:1 to 1:100 and EtOAc:CH$_3$OH, from 100:1 to 1:100) to afford 26-S (75 mg, 92%).

R$_f$=0.25 (CH$_2$Cl$_2$:CH$_3$OH, 1:1).

$^1$H NMR (400 MHz, CDCl$_3$): δ 7.62 (s, 1H), 7.15 (d, J=9.3 Hz, 1H), 6.81-6.76 (m, 2H), 6.72 (s, 1H), 6.25 (d, J=1.2 Hz, 1H), 6.03 (d, J=1.2 Hz, 1H), 5.12 (d, J=11.7 Hz, 1H), 4.57 (s, 1H), 4.41 (s, 1H), 4.36-4.24 (m, 2H), 4.20 (d, J=11.7 Hz, 1H), 3.82 (s, 3H), 3.79 (s, 3H), 3.44 (dd, J=22.0, 7.1 Hz, 2H), 3.08-2.78 (m, 4H), 2.73-2.64 (m, 2H), 2.41-2.22 (m, 3H), 2.28 (s, 3H), 2.25-2.15 (m, 1H), 2.14 (s, 3H), 2.08 (s, 3H), 2.04 (s, 3H).

ESI-MS m/z: 823.3 (M+H)$^+$.

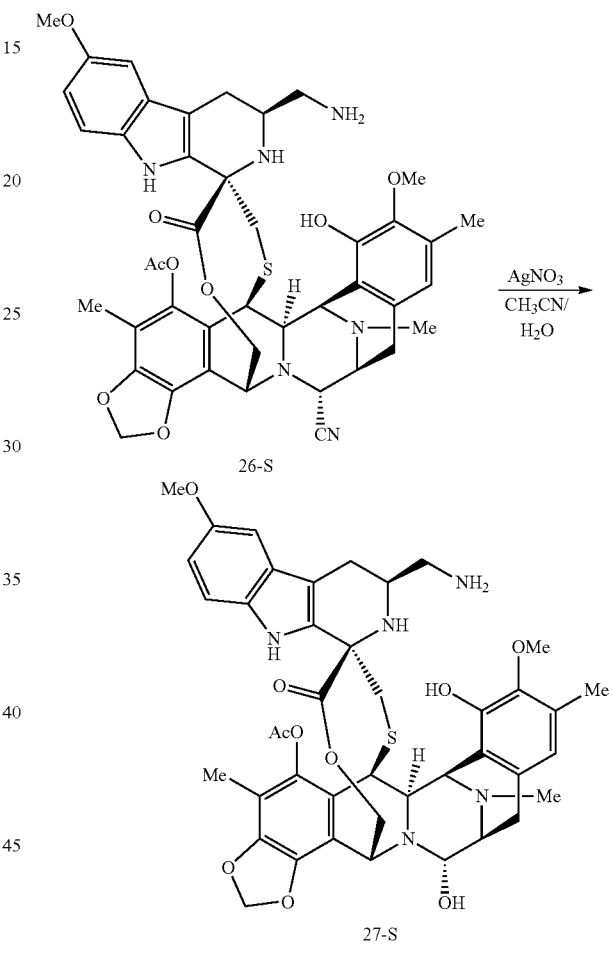

To a solution of 26-S (70 mg, 0.085 mmol) in CH$_3$CN:H$_2$O (1.39:1, 6 mL, 0.015 M) was added AgNO$_3$ (335 mg, 1.7 mmol). After 18 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 27-S (23 mg, 33%).

R$_f$=0.2 (CH$_2$Cl$_2$:CH$_3$OH, 9:1).

$^1$H NMR (400 MHz, CDCl$_3$): δ 7.62 (s, 1H), 7.15 (d, J=7.8 Hz, 1H), 6.78 (s, 1H), 6.75 (d, J=7.8 Hz, 1H), 6.21 (d, J=1.5 Hz, 1H), 6.01 (d, J=1.5 Hz, 1H), 5.78 (s, 1H), 5.22 (d, J=11.5 Hz, 1H), 4.90 (s, 1H), 4.58-4.42 (m, 3H), 4.29-4.10 (m, 2H), 3.84-3.80 (m, 1H), 3.83 (s, 3H), 3.79 (s, 3H), 3.53-3.48 (m, 2H), 3.22 (d, J=8.7 Hz, 1H), 3.12 (s, 1H), 3.02 (d, J=12.8 Hz, 1H), 2.89-2.64 (m, 3H), 2.46 (s, 3H), 2.42-2.34 (m, 2H), 2.27 (s, 3H), 2.12 (s, 3H), 2.03 (s, 3H).
$^{13}$C NMR (126 MHz, CDCl$_3$): δ 172.1, 168.7, 154.0, 147.6, 145.6, 143.0, 141.2, 140.8, 131.6, 130.6, 129.6, 127.1, 121.8, 120.9, 118.4, 115.2, 112.5, 111.8, 101.8, 100.2, 81.5, 62.6, 60.6, 58.0, 57.8, 56.0, 55.8, 55.0, 42.3, 41.4, 31.9, 29.7, 27.8, 26.9, 25.6, 24.0, 22.7, 20.5, 16.0, 14.1, 13.6, 9.7.
ESI-MS m/z: 796.3 (M–H$_2$O+H)$^+$.
(+)-HR-ESI-TOF-MS m/z: 796.3062 [M–H$_2$O+H]$^+$ (Calcd. for C$_{42}$H$_{46}$N$_5$O$_9$S 796.3011).
Example 13. Synthesis of allyl N—[(R)-2-amino-3-(5-methoxy-1H-indol-3-yl)propyl]carbamate (24-R)
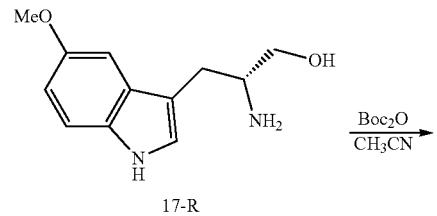
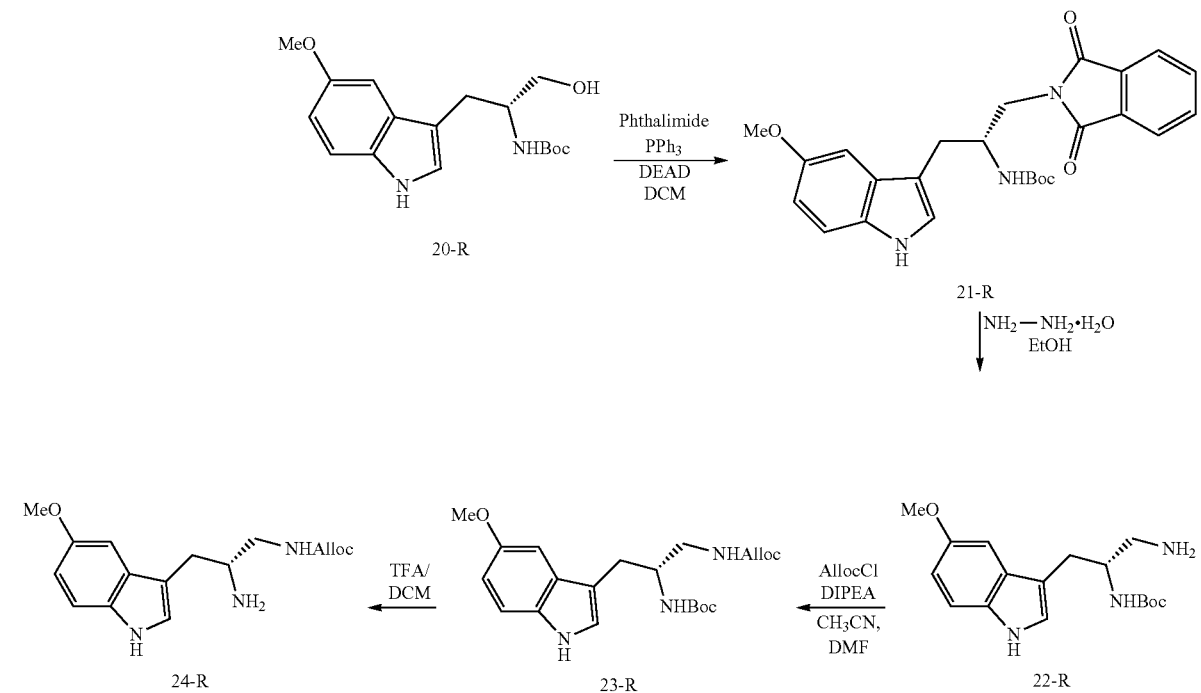
A)
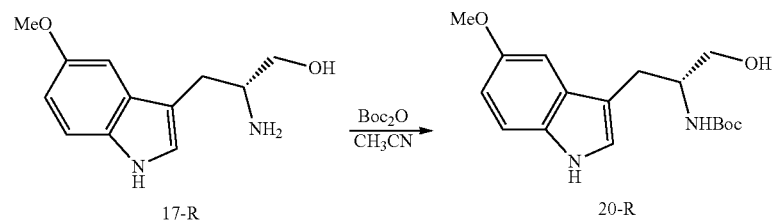

To a solution of 17-R (2.35 g, 10.7 mmol) in CH$_3$CN (43 mL, 4 mL/mmol) was added di-tert-butyl dicarbonate (4.67 g, 21.4 mmol). The reaction mixture was stirred at 23° C. for 2.5 h, concentrated under vacuum. Flash chromatography (CH$_2$Cl$_2$:CH$_3$OH, from 99:1 to 85:15) afforded 20-R (1.7 g, 50%).

R$_f$=0.6 (CH$_2$Cl$_2$:CH$_3$OH, 9:1).

$^1$H NMR (400 MHz, CDCl$_3$): δ 8.05 (s, 1H), 7.25 (d, J=8.9 Hz, 1H), 7.09 (d, J=2.4 Hz, 1H), 7.02 (d, J=2.4 Hz, 1H), 6.86 (dd, J=8.8, 2.4 Hz, 1H), 4.83 (s, 1H), 3.98 (s, 1H), 3.87 (s, 3H), 3.69 (td, J=9.2, 7.5, 5.3 Hz, 1H), 3.61 (dd, J=10.9, 5.6 Hz, 1H), 2.95 (d, J=6.8 Hz, 2H), 1.42 (s, 9H).

B)

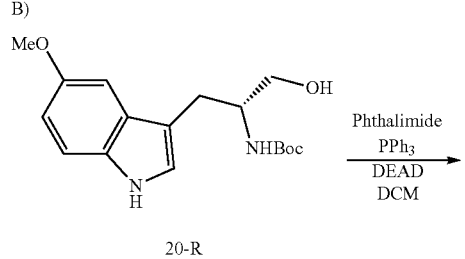

20-R

Phthalimide
PPh$_3$
DEAD
DCM

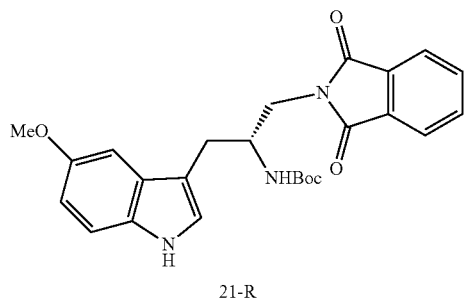

21-R

To a solution of 20-R (1.7 g, 5.3 mmol) in CH$_2$Cl$_2$ (32 mL, 6 mL/mmol) was added phthalimide (1.72 g, 11.7 mmol), triphenylphosphine (3.06 g, 11.7 mmol) and the mixture was cooled at 0° C. A solution of 40% of diethyl azodicarboxylate in CH$_2$Cl$_2$ (4.0 mL, 13.2 mmol) was added for 15 min. The reaction was stirred at 23° C. for 16 h, concentrated under vacuum. The residue obtained was purified by flash chromatography (Hexane:EtOAc, from 99:1 to 85:15) to afford 21-R (2.0 g, 84%).

R$_f$=0.45 (Hexane:EtOAc, 1:1).

$^1$H NMR (400 MHz, CDCl$_3$): δ 8.31 (s, 1H), 7.80 (dd, J=5.4, 3.0 Hz, 2H), 7.67 (dd, J=5.4, 3.0 Hz, 2H), 7.30-7.12 (m, 2H), 7.08 (dd, J=15.2, 2.4 Hz, 1H), 6.84 (dd, J=8.8, 2.4 Hz, 1H), 4.85 (d, J=9.2 Hz, 1H), 4.43 (q, J=5.3 Hz, 1H), 3.86 (s, 3H), 3.83-3.68 (m, 2H), 3.01 (d, J=5.4 Hz, 2H), 1.22 (s, 9H).

C)

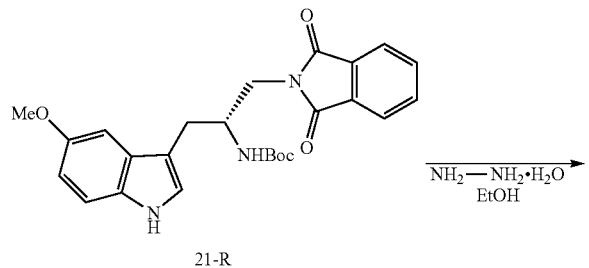

21-R

NH$_2$—NH$_2$·H$_2$O
EtOH

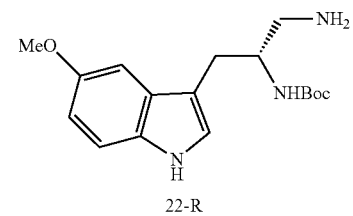

22-R

To a solution of 21-R (2.0 g, 4.45 mmol) in ethanol (133 mL, 30 mL/mmol) was added hydrazine monohydrate (21.6 mL, 445 mmol). The reaction mixture was stirred at 80° C. in sealed tube for 2 h, concentrated under vacuum. Flash chromatography (CH$_2$Cl$_2$:CH$_3$OH, from 100:1 to 50:50) to afford 22-R (1.15 g, 81%).

R$_f$=0.1 (CH$_2$Cl$_2$:CH$_3$OH, 8:2).

$^1$H NMR (400 MHz, CDCl$_3$): δ 7.21 (d, J=8.8 Hz, 1H), 7.12 (s, 1H), 7.05 (s, 1H), 6.75 (dd, J=8.8, 2.4 Hz, 1H), 3.95 (ddd, J=10.7, 8.7, 5.4 Hz, 1H), 3.82 (s, 3H), 2.98-2.79 (m, 3H), 2.75 (dd, J=13.1, 9.4 Hz, 1H), 1.37 (s, 9H).

D)

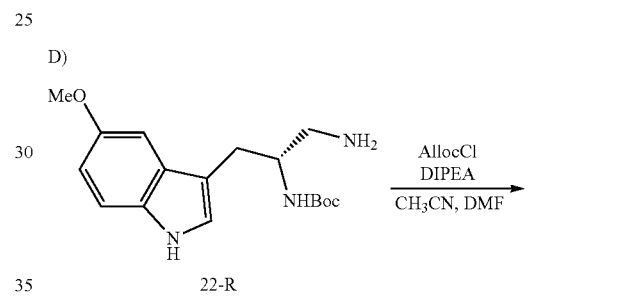

22-R

AllocCl
DIPEA
CH$_3$CN, DMF

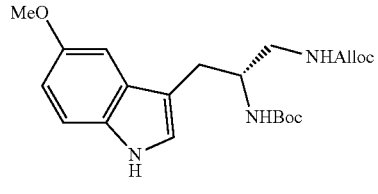

23-R

To a solution of 22-R (1.1 g, 3.4 mmol) in CH$_3$CN (34 mL, 10 mL/mmol) and DMF (3.4 mL, 1 mL/mmol) was added N,N-diisopropylethylamine (0.5 mL, 2.7 mmol) and allyl chloroformate (3.7 mL, 34 mmol). The reaction was stirred at 23° C. for 19 h. The mixture was diluted with EtOAc and NH$_4$Cl was added and the mixture was extracted with EtOAc. The combined organic layers were dried over anhydrous Na$_2$SO$_4$, filtered, and concentrated under vacuum. The residue obtained was purified by flash chromatography (Hexane:EtOAc, from 100:1 to 1:100) to afford 23-R (0.95 g, 69%).

R$_f$=0.5 (Hexane:EtOAc, 1:1).

$^1$H NMR (400 MHz, CDCl$_3$): δ 8.55 (s, 1H), 7.20 (d, J=8.8 Hz, 1H), 7.05 (s, 1H), 6.98-6.87 (m, 1H), 6.82 (dt, J=8.8, 1.8 Hz, 1H), 5.96-5.81 (m, 1H), 5.37-5.22 (m, 2H), 5.22-5.14 (m, 1H), 5.02-4.97 (m, 1H), 4.60-4.47 (m, 2H), 4.00 (s, 1H), 3.84 (s, 3H), 3.31 (s, 1H), 3.19 (s, 1H), 2.88 (td, J=14.5, 13.3, 5.9 Hz, 2H), 1.40 (s, 9H).

E)
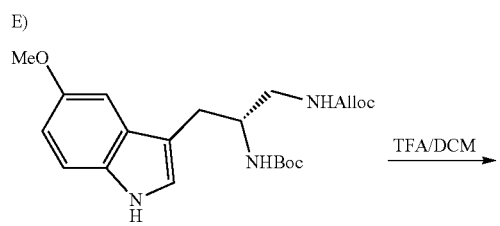
To a solution of 23-R (0.94 g, 2.3 mmol) in CH$_2$Cl$_2$ (39 mL, 16.6 mL/mmol) was added trifluoroacetic acid (19 mL, 8.3 mL/mmol). The reaction mixture was stirred at 23° C. for 1.5 h, concentrated under vacuum to afford 24-R (0.72 g, 100%).
R$_f$=0.1 (CH$_2$Cl$_2$:CH$_3$OH, 9:1).
$^1$H NMR (400 MHz, CD$_3$OD): δ 7.27 (d, J=8.8, 1H), 7.18 (s, 1H), 7.04 (d, J=2.4 Hz, 1H), 6.80 (ddd, J=8.8, 2.4, 0.9 Hz, 1H), 5.95 (ddt, J=16.4, 10.8, 5.5 Hz, 1H), 5.32 (d, J=17.1 Hz, 1H), 5.20 (d, J=10.5 Hz, 1H), 4.60-4.53 (m, 2H), 3.83 (s, 3H), 3.59 (dt, J=11.4, 5.5 Hz, 1H), 3.47-3.30 (m, 2H), 3.13-2.94 (m, 2H).
Example 14
A)
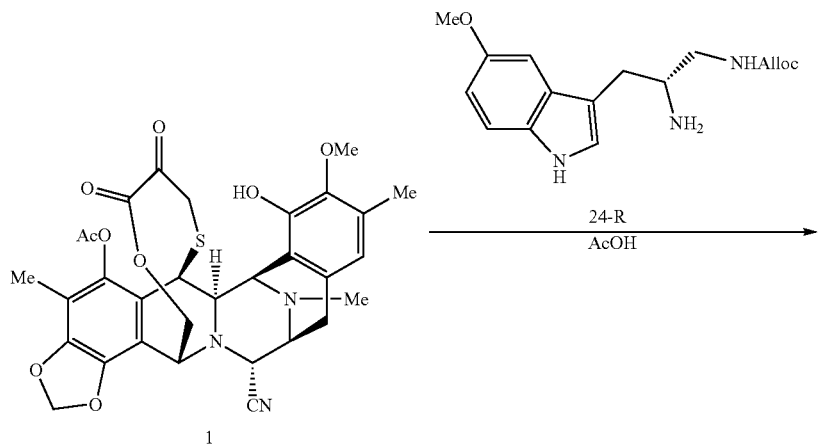
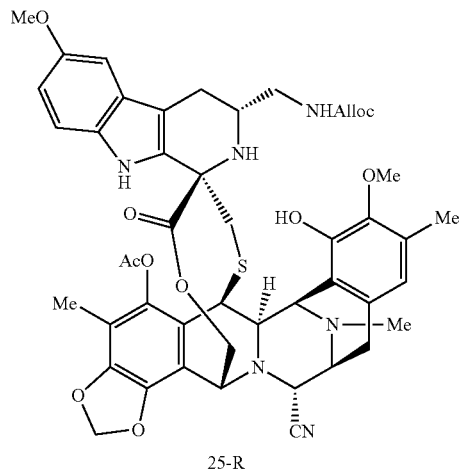

To a solution of 1 (0.71 g, 1.14 mmol) in acetic acid (45 mL, 0.08 M) was added 24-R (0.54 mg, 1.8 mmol). The reaction mixture was stirred at 23° C. for 7 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, 1:1) gives compound 25-R (670 mg, 65%).

R$_f$=0.4 (Hexane:EtOAc, 1:1).

$^1$H NMR (400 MHz, CDCl$_3$): δ 7.52 (s, 1H), 7.17 (d, J=8.8 Hz, 1H), 6.83-6.73 (m, 2H), 6.61 (s, 1H), 6.23 (d, J=1.0 Hz, 1H), 6.02 (d, J=1.0 Hz, 1H), 6.05-5.89 (m, 1H), 5.75 (s, 1H), 5.44-5.30 (m, 1H), 5.25 (d, J=10.4 Hz, 1H), 5.13-4.99 (m, 2H), 4.71-4.59 (m, 2H), 4.36 (s, 1H), 4.30-4.07 (m, 3H), 3.80 (s, 3H), 3.79 (s, 3H), 3.61-3.53 (m, 1H); 3.48-3.41 (m, 3H), 3.26 (dt, J=13.3, 3.8 Hz, 1H), 3.04-2.88 (m, 2H), 2.52 (dd, J=14.9, 3.7 Hz, 1H), 2.46-2.35 (m, 2H), 2.31 (s, 3H), 2.29 (s, 3H), 2.16 (s, 3H), 2.12-2.02 (m, 1H), 2.09 (s, 3H).

ESI-MS m/z: 907.3 (M+H)$^+$.

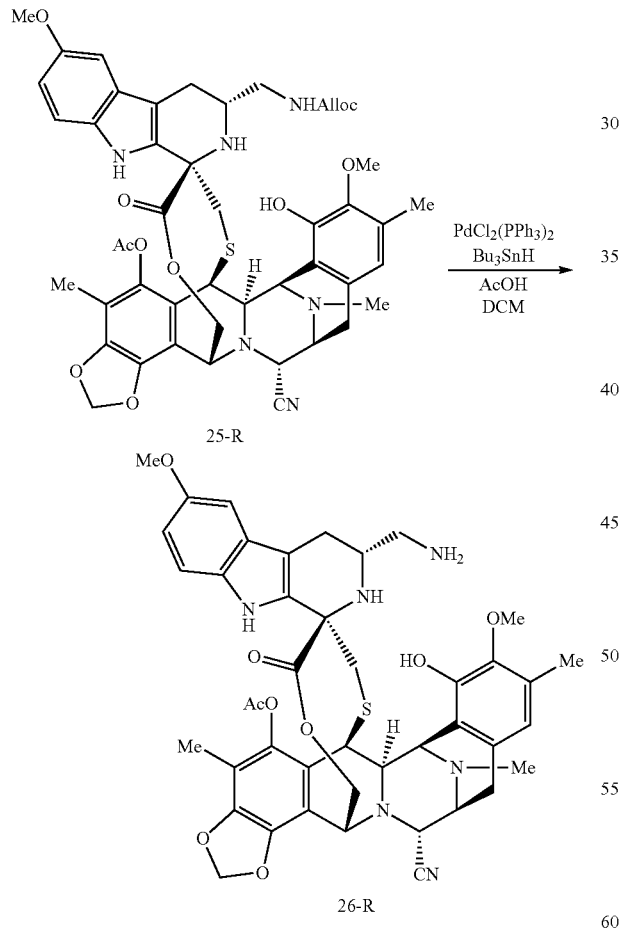

To a solution of 25-R (745 mg, 0.82 mmol) in CH$_2$Cl$_2$ (15 mL, 18 mL/mmol) was added bis(triphenylphosphine)palladium(II) dichloride (92 mg, 0.1 mmol) and acetic acid (0.47 mL, 8.2 mmol). Tributyltin hydride (1.33 mL, 4.9 mmol) was added at 0° C., the reaction mixture was stirred at 0° C. for 0.75 h and concentrated under vacuum. Flash chromatography (Hexane:EtOAc, from 100:1 to 1:100 and EtOAc:CH$_3$OH, from 100:1 to 1:100) to afford 26-R (680 mg, >100%).

R$_f$=0.25 (CH$_2$Cl$_2$:CH$_3$OH, 1:1).

$^1$H NMR (400 MHz, CDCl$_3$): δ 7.57 (s, 1H), 7.16 (d, J=8.8 Hz, 1H), 6.85-6.72 (m, 2H), 6.57 (s, 1H), 6.21 (d, J=1.4 Hz, 1H), 6.00 (d, J=1.3 Hz, 1H), 5.05-4.97 (m, 1H), 4.63 (s, 1H), 4.35 (s, 1H), 4.31-4.09 (m, 4H), 3.80 (s, 3H), 3.78 (s, 3H), 3.50-3.40 (m, 3H), 3.24 (dq, J=9.9, 5.3 Hz, 1H), 2.95 (s, 1H), 2.91-2.75 (m, 2H), 2.62 (dd, J=14.8, 3.6 Hz, 1H), 2.43-2.28 (m, 2H), 2.36 (s, 3H), 2.25 (s, 3H), 2.22-2.14 (m, 1H), 2.15 (s, 3H), 2.08 (s, 3H).

ESI-MS m/z: 823.3 (M+H)$^+$.

C)

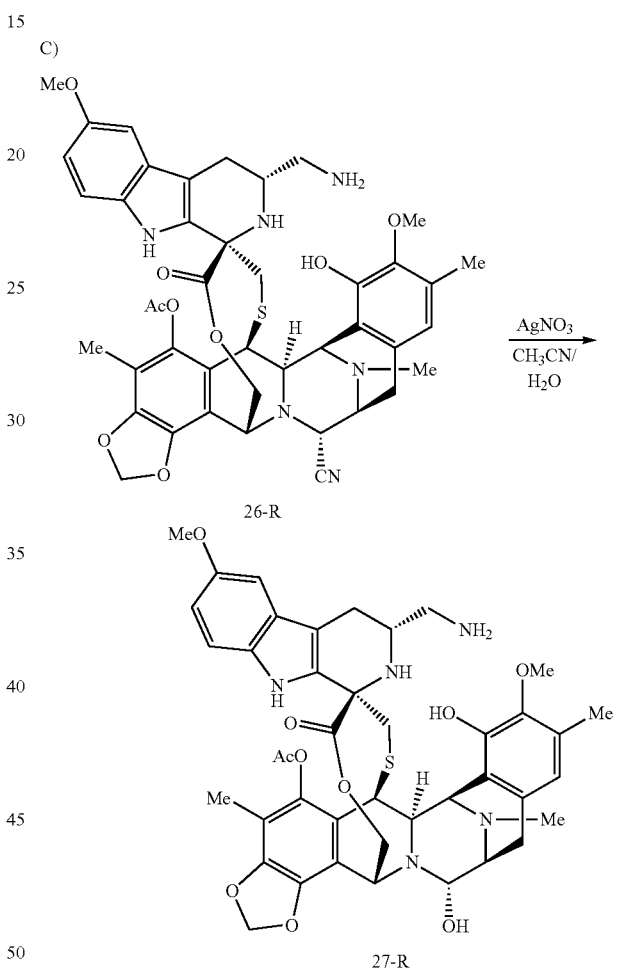

To a solution of 26-R (660 mg, 0.80 mmol) in CH$_3$CN:H$_2$O (1.39:1, 56 mL, 0.015 M) was added AgNO$_3$ (2.70 g, 16.0 mmol). After 16.5 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give 27-R (271 mg, 42%).

R$_f$=0.1 (CH$_2$Cl$_2$:CH$_3$OH, 9:1).

$^1$H NMR (400 MHz, CDCl$_3$): δ 7.46 (s, 1H), 7.16 (d, J=8.9 Hz, 1H), 6.83 (s, 1H), 6.72 (d, J=8.9 Hz, 1H), 6.58 (s, 1H), 6.20 (d, J=1.8 Hz, 1H), 5.99 (d, J=1.8 Hz, 1H), 5.76 (s,

1H), 5.15 (d, J=11.4 Hz, 1H), 4.86 (s, 1H), 4.52 (m, 2H), 4.17 (d, J=5.3 Hz, 1H), 4.07 (d, J=11.4 Hz, 1H), 3.80 (s, 3H), 3.78 (s, 3H), 3.55-3.43 (m, 2H), 3.32-3.20 (m, 2H), 3.01-2.82 (m, 4H), 2.68-2.59 (m, 1H), 2.44-2.31 (m, 1H), 2.38 (s, 3H), 2.30-2.19 (m, 1H), 2.26 (s, 3H), 2.15 (s, 3H), 2.07 (s, 3H).

$^{13}$C NMR (101 MHz, CD$_3$OD): δ 171.7, 171.3, 153.8, 153.3, 148.0, 147.6, 145.4, 145.4, 143.1, 141.3, 140.7, 131.6, 131.4, 131.2, 129.3, 126.8, 121.6, 120.9, 118.3, 115.6, 112.2, 111.8, 101.8, 100.2, 81.7, 63.5, 63.1, 61.7, 58.0, 57.8, 56.1, 55.8, 55.0, 42.2, 42.1, 41.4, 41.0, 25.1, 23.8, 20.5, 16.0, 9.7.

ESI-MS m/z: 796.3 (M−H$_2$O+H)$^+$.

(+)-HR-ESI-TOF-MS m/z: 796.3045 [M−H$_2$O+H]$^+$ (Calcd. for C$_{42}$H$_{46}$N$_5$O$_9$S 796.3011).

Example 15. Synthesis of Reference Compounds 28-S and 29-S

A)

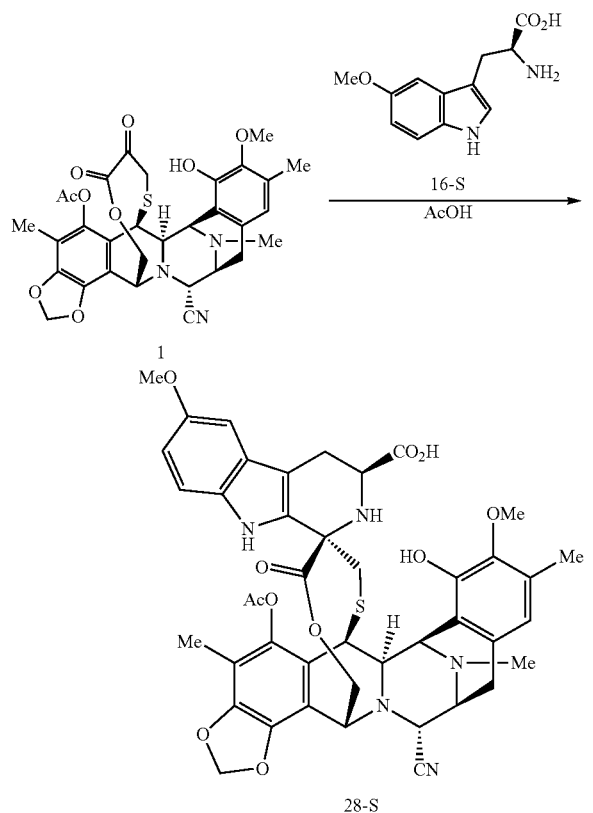

To a solution of 1 (450 mg, 0.72 mmol) in acetic acid (9 mL, 0.08 M) was added 16-S (675 mg, 2.88 mmol). The reaction mixture was stirred a 52° C. for 3 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (CH$_2$Cl$_2$:CH$_3$OH, from 99:1 to 80:20) gave compound 28-S (400 mg, 66%).

R$_f$=0.35 (CH$_2$Cl$_2$:CH$_3$OH, 10:1).

$^1$H NMR (400 MHz, CDCl$_3$): δ 7.65 (s, 1H), 7.15 (d, J=8.7 Hz, 1H), 6.85-6.76 (m, 2H), 6.57 (s, 1H), 6.25 (d, J=1.4 Hz, 1H), 6.04 (d, J=1.3 Hz, 1H), 5.16 (d, J=11.7 Hz, 1H), 4.62 (s, 1H), 4.44 (s, 1H), 4.35 (dd, J=11.7, 2.0 Hz, 1H), 4.29 (dd, J=5.2, 1.6 Hz, 1H), 4.22 (d, J=2.7 Hz, 1H), 3.80 (s, 3H), 3.79 (s, 3H), 3.52-3.43 (m, 3H), 3.02-2.81 (m, 4H), 2.41-2.31 (m, 2H), 2.36 (s, 3H), 2.29 (s, 3H), 2.15 (s, 3H), 2.05 (s, 3H).

ESI-MS m/z: 838.6 (M+H)$^+$.

B)

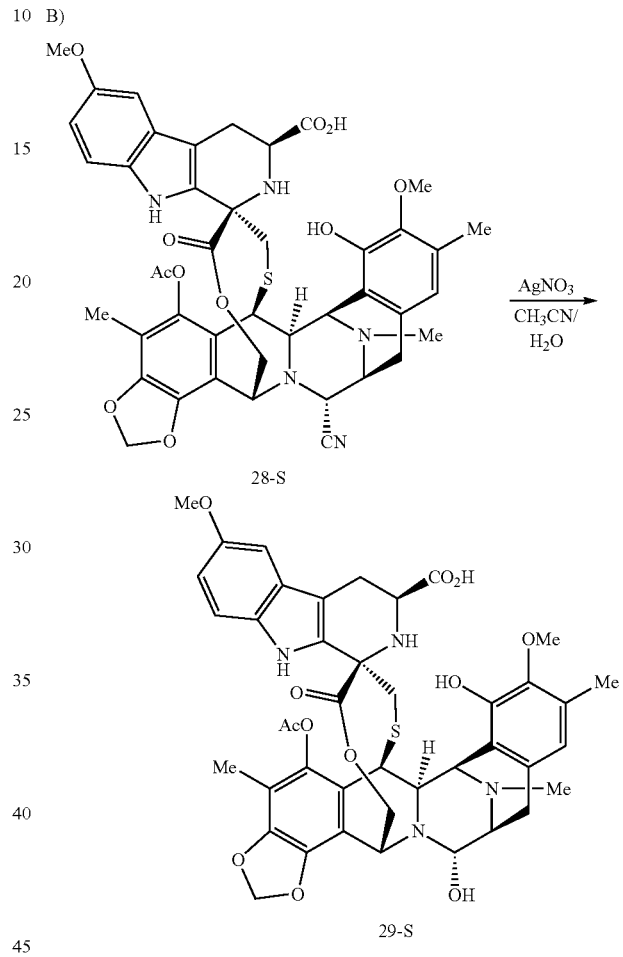

To a solution of 28-S (400 mg, 0.48 mmol) in CH$_3$CN:H$_2$O (2:1, 33 mL, 0.015 M) was added AgNO$_3$ (1.20 g, 7.16 mmol). After 16 h at 23° C., a mixture 1:1 of saturated aqueous solutions of NaCl and NaHCO$_3$ was added, stirred for 15 min, diluted with CH$_2$Cl$_2$, stirred for 30 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 70:30) to afford 29-S (179 mg, 45%).

R$_f$=0.25 (CH$_2$Cl$_2$:CH$_3$OH, 9:1).

$^1$H NMR (500 MHz, CD$_3$OD): δ 7.17 (d, J=8.9 Hz, 1H), 6.83 (d, J=2.4 Hz, 1H), 6.70 (dd, J=8.9, 2.4 Hz, 1H), 6.66 (s, 1H), 6.29 (d, J=1.3 Hz, 1H), 6.10 (d, J=1.3 Hz, 1H), 5.32 (d, J=11.6 Hz, 1H), 4.65 (s, 1H), 4.57 (s, 1H), 4.48 (s, 1H), 4.38 (dd, J=11.7, 2.1 Hz, 1H), 3.75 (s, 3H), 3.73 (s, 3H), 3.41-3.35 (m, 1H), 3.16-2.91 (m, 5H), 2.71 (dd, J=15.3, 11.4 Hz, 1H), 2.54 (s, 1H), 2.42-2.36 (m, 2H), 2.38 (s, 3H), 2.37 (s, 3H), 2.28 (s, 3H), 1.99 (s, 3H).

$^{13}$C NMR (126 MHz, CDCl$_3$): δ 171.3, 170.6, 155.2, 149.8, 147.5, 145.4, 142.8, 142.4, 133.0, 131.8, 130.0, 128.0, 122.2, 121.8, 115.5, 113.9, 113.3, 113.2, 111.4, 109.1, 103.8, 100.9, 91.6, 65.4, 61.9, 60.3, 59.4, 57.1, 56.4, 56.2, 55.2, 53.4, 43.7, 40.8, 38.3, 30.7, 26.4, 24.7, 20.4, 16.5, 9.6.

ESI-MS m/z: 811.3 (M–H$_2$O+H)$^+$.

(+)-HR-ESI-TOF-MS m/z: 811.2682 [M–H$_2$O+H]$^+$ (Calcd. for C$_{42}$H$_{43}$N$_4$O$_{11}$S 811.2644).

Example 16. Synthesis of Reference Compounds 28-R and 29-R

A)

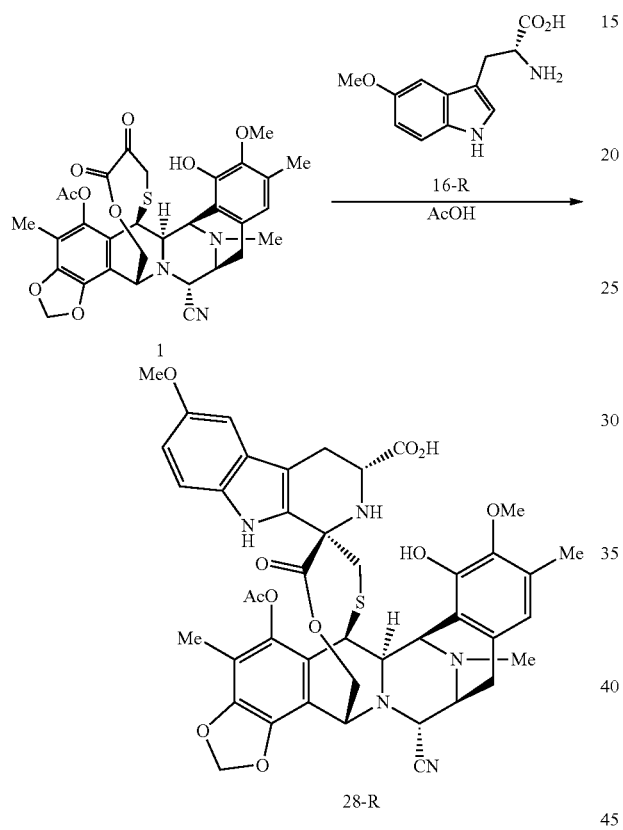

B)

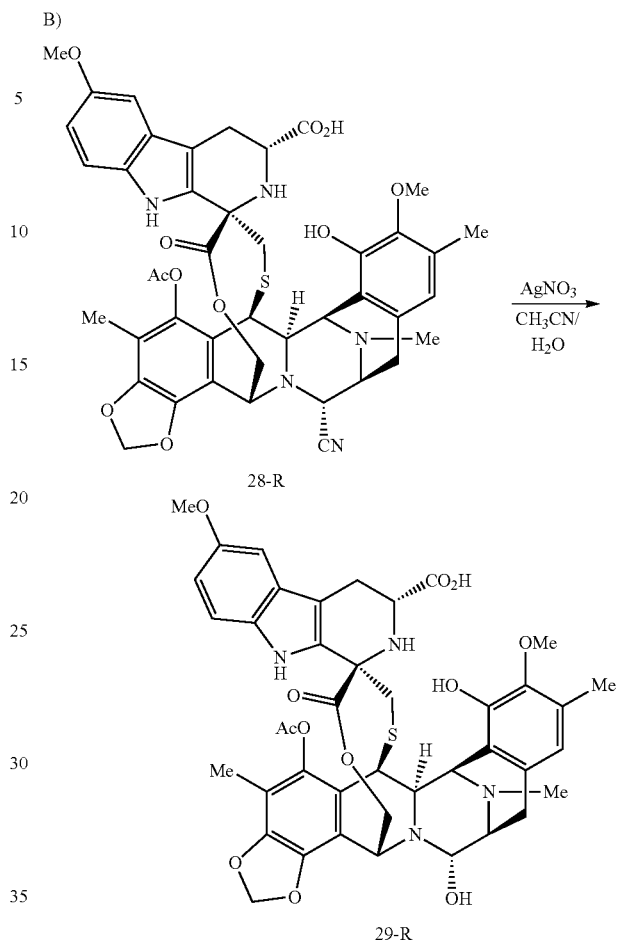

To a solution of 1 (50 mg, 0.08 mmol) in acetic acid (1 mL, 0.08 M) was added 16-R (66 mg, 0.3 mmol). The reaction mixture was stirred at 50° C. for 6 h and then acetic acid was evaporated. An aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (CH$_2$Cl$_2$:CH$_3$OH, from 99:1 to 80:20) gave compound 28-R (50 mg, 75%).

R$_f$=0.20 (CH$_2$Cl$_2$:CH$_3$OH, 10:1).

$^1$H NMR (400 MHz, CDCl$_3$): 7.63 (s, 1H), 7.16 (d, J=8.8 Hz, 1H), 6.81 (d, J=2.4 Hz, 1H), 6.77 (dd, J=8.8, 2.3 Hz, 1H), 6.56 (s, 1H), 6.21 (d, J=1.2 Hz, 1H), 6.00 (d, J=1.2 Hz, 1H), 5.77 (s, 1H), 5.00 (d, J=11.8 Hz, 1H), 4.63 (s, 1H), 4.35 (s, 1H), 4.27 (d, J=5.0 Hz, 1H), 4.22-4.04 (m, 3H), 3.79 (s, 3H), 3.77 (s, 3H), 3.48-3.40 (m, 2H), 3.00 (dd, J=15.3, 4.8 Hz, 1H), 2.92 (d, J=5.4 Hz, 2H), 2.71 (dd, J=15.3, 10.1 Hz, 1H), 2.46 (d, J=14.9 Hz, 1H), 2.34 (s, 3H), 2.26 (s, 3H), 2.21 (d, J=15.0 Hz, 1H), 2.15 (s, 3H), 2.07 (s, 3H).

ESI-MS m/z: 838.8 (M+H)$^+$.

To a solution of 28-R (50 mg, 0.06 mmol) in CH$_3$CN:H$_2$O (2:1, 4.2 mL, 0.015M) was added AgNO$_3$ (304 mg, 1.80 mmol). After 3 h at 23° C., a mixture 1:1 of saturated aqueous solutions of NaCl and NaHCO$_3$ was added, stirred for 15 min, diluted with CH$_2$Cl$_2$, stirred for 30 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH from 99:1 to 70:30) to afford 29-R (30 mg, 60%).

R$_f$=0.15 (CH$_2$Cl$_2$:CH$_3$OH, 9:1).

$^1$H NMR (400 MHz, CDCl$_3$): 7.68 (s, 1H), 7.14 (d, J=8.8 Hz, 1H), 6.80 (d, J=2.4 Hz, 1H), 6.76 (dd, J=8.8, 2.4 Hz, 1H), 6.57 (s, 1H), 6.17 (d, J=1.3 Hz, 1H), 5.95 (d, J=1.3 Hz, 1H), 5.75 (s, 1H), 5.12 (d, J=11.5 Hz, 1H), 4.85 (s, 1H), 4.56-4.46 (m, 2H), 4.17 (s, 1H), 4.10 (dd, J=9.9, 4.9 Hz, 1H), 4.05 (dd, J=11.4, 2.0 Hz, 1H), 3.78 (s, 3H), 3.76 (s, 3H), 3.51 (s, 1H), 3.48-3.42 (m, 2H), 3.23 (s, 1H), 3.00 (dd, J=15.3, 4.9 Hz, 1H), 2.90-2.77 (m, 2H), 2.71 (dd, J=15.2, 9.9 Hz, 1H), 2.48 (d, J=14.6 Hz, 1H), 2.34 (s, 3H), 2.25 (s, 3H), 2.20 (d, J=14.6 Hz, 1H), 2.14 (s, 3H), 2.05 (s, 3H).

$^{13}$C NMR (101 MHz, CDCl$_3$): 175.6, 171.0, 168.7, 154.1, 147.3, 145.6, 143.1, 141.3, 140.8, 131.1, 130.4, 126.5, 121.9, 121.5, 121.3, 115.5, 112.9, 112.7, 112.0, 109.1, 101.9, 100.2, 81.5, 62.8, 61.7, 60.4, 57.9, 57.8, 56.0, 55.8, 54.8, 53.4, 42.5, 41.2, 40.3, 29.7, 24.6, 23.8, 20.5, 15.9, 9.8.

ESI-MS m/z: 811.6 (M–H$_2$O+H)$^+$.

(+)-HR-ESI-TOF-MS m/z: 811.2687 [M–H$_2$O+H]$^+$ (Calcd. for C$_{42}$H$_{43}$N$_4$O$_{11}$S 811.2644).

Example 17

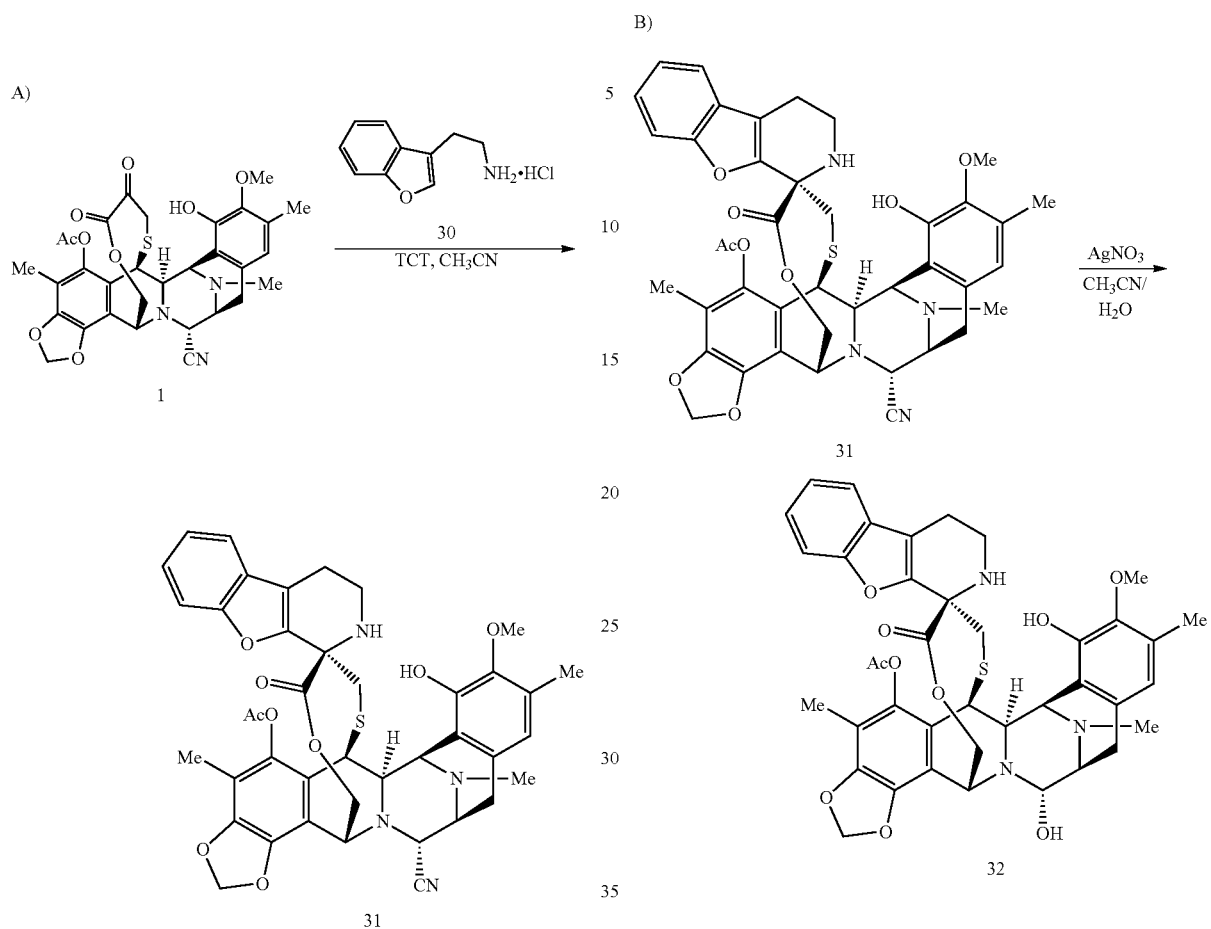

To a solution of compound 1 (2.0 g, 3.21 mmol) in acetonitrile (200 mL, 0.01 M) was added 2-benzofuran-3-yl-ethylamine hydrochloride (30) (1.90 g, 9.65 mmol, Sigma Aldrich) and cyanuric chloride (TCT) (200 mg, 10%). The reaction mixture was stirred at 85° C. for 24 h and then aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, from 9:1 to 1:9) gives compound 31 (1.95 g, 79%).

R$_f$=0.5 (Hexane:EtOAc, 1:1).

$^1$H NMR (400 MHz, CDCl$_3$): δ 7.38-7.36 (m, 2H), 7.19-7.10 (m, 2H), 6.64 (s, 1H), 6.20 (d, J=1.5 Hz, 1H), 6.05 (d, J=1.5 Hz, 1H), 5.76 (s, 1H), 5.05 (d, J=11.7 Hz, 1H), 4.54 (s, 1H), 4.33-4.24 (m, 2H), 4.23-4.16 (m, 2H), 3.81 (s, 3H), 3.49-3.38 (m, 2H), 3.28-3.21 (m, 1H), 3.06-2.78 (m, 5H), 2.57-2.50 (m, 2H), 2.37 (s, 3H), 2.27 (s, 3H), 2.21 (m, 3H), 2.08 (s, 3H).

ESI-MS m/z: 765.3 (M+H)$^+$.

To a solution of compound 31 (380 mg, 0.49 mmol) in CH$_3$CN:H$_2$O (1.39:1, 25 mL, 0.015 M) was added AgNO$_3$ (1.30 g, 7.45 mmol). After 5 h at 23° C., a mixture 1:1 of saturated aqueous solutions of NaCl and NaHCO$_3$ was added, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to afford compound 32 (175 mg, 47%).

R$_f$=0.40 (CH$_2$Cl$_2$:CH$_3$OH, 9:1).

$^1$H NMR (400 MHz, CDCl$_3$): δ 7.35 (ddd, J=10.7, 7.6, 1.1 Hz, 2H), 7.14 (dtd, J=19.7, 7.3, 1.3 Hz, 2H), 6.65 (s, 1H), 6.16 (d, J=1.5 Hz, 1H), 6.01 (d, J=1.5 Hz, 1H), 5.75 (s, 1H), 5.15 (dd, J=11.5, 1.2 Hz, 1H), 4.80 (s, 1H), 4.48 (d, J=3.2 Hz, 1H), 4.44 (s, 1H), 4.20-4.06 (m, 2H), 3.81 (s, 1H), 3.50 (d, J=18.8 Hz, 1H), 3.30 (ddd, J=12.6, 7.9, 5.1 Hz, 1H), 3.22 (d, J=9.1 Hz, 1H), 2.99 (d, J=17.9 Hz, 1H), 2.84 (dd, J=19.2, 12.0 Hz, 3H), 2.59-2.49 (m, 2H), 2.36 (s, 3H), 2.27 (s, 3H), 2.21-2.14 (m, 1H), 2.18 (s, 3H), 2.06 (s, 3H).

$^{13}$C NMR (101 MHz, CDCl$_3$): δ 171.2, 168.7, 154.4, 150.0, 147.9, 145.5, 142.9, 140.9, 140.8, 131.3, 129.0, 127.7, 123.7, 122.2, 121.2, 120.8, 118.9, 118.3, 115.5, 113.5, 111.7, 101.7, 82.1, 62.7, 61.7, 60.3, 57.8, 57.4, 55.9, 55.0, 42.2, 41.3, 39.7, 38.2, 29.7, 23.7, 21.3, 20.6, 15.9, 9.7.

ESI-MS m/z: 738.6 (M–H$_2$O+H)$^+$.

(+)-HR-ESI-TOF-MS m/z: 756.2654 [M+H]$^+$ (Calcd. for C$_{40}$H$_{42}$N$_3$O$_{10}$S 756.2585).

Example 18

A)

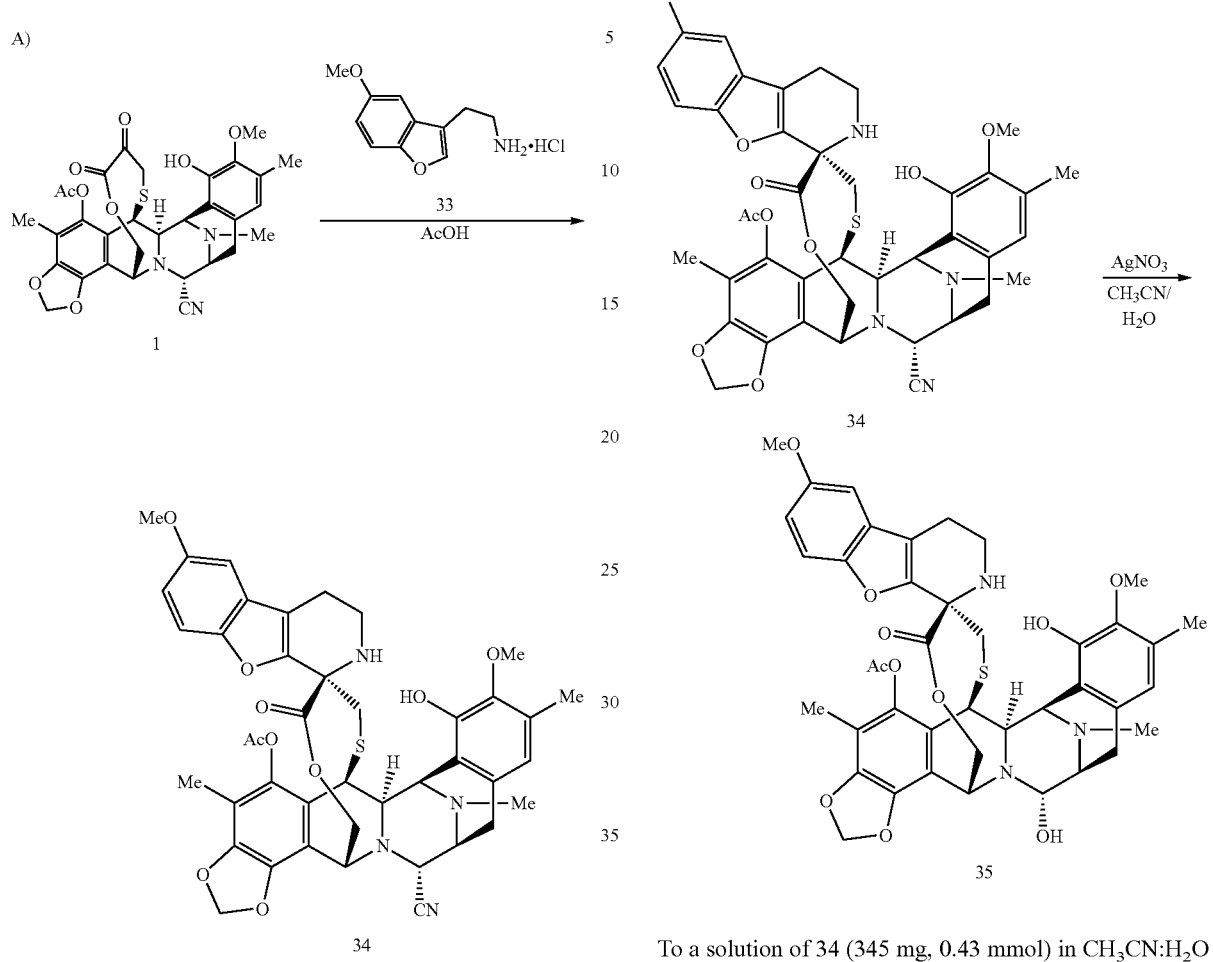

B)

To a solution of 1 (500 mg, 0.80 mmol) in acetic acid (10 mL, 0.08 M) was added 2-(5-methoxybenzofuran-3-yl)-ethylamine hydrochloride (33) (Diverchim, ref: DW04590) (444 mg, 1.60 mmol). The reaction mixture was stirred at 50° C. for 6 days and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) affords 34 (270 mg, 43%).

$R_f$=0.3 (Hexane:EtOAc, 1:1).

$^1$H NMR (400 MHz, $CDCl_3$): δ 7.25 (d, J=9.1 Hz, 1H), 6.80-6.73 (m, 2H), 6.63 (s, 1H), 6.18 (d, J=1.4 Hz, 1H), 6.03 (d, J=1.4 Hz, 1H), 5.78 (s, 1H), 5.03 (dd, J=11.5, 1.3 Hz, 1H), 4.52 (s, 1H), 4.29 (s, 1H), 4.26 (dd, J=4.7, 1.5 Hz, 1H), 4.23-4.16 (m, 2H), 3.80 (s, 3H), 3.78 (s, 3H), 3.46-3.43 (m, 1H), 3.43-3.37 (m, 1H), 3.24 (s, 1H), 3.03 (d, J=18.0 Hz, 1H), 2.91 (dd, J=17.9, 9.2 Hz, 1H), 2.87-2.72 (m, 2H), 2.53-2.47 (m, 1H), 2.36 (s, 3H), 2.27 (s, 3H), 2.20 (s, 3H), 2.06 (s, 3H).

ESI-MS m/z: 795.8 $(M+H)^+$.

To a solution of 34 (345 mg, 0.43 mmol) in $CH_3CN:H_2O$ (1.39:1, 30 mL, 0.015 M) was added $AgNO_3$ (2.20 g, 13.0 mmol). After 3 h at 23° C., a mixture 1:1 of saturated aqueous solutions of NaCl and $NaHCO_3$ was added, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to obtain 35 (175 mg, 51%).

$R_f$=0.35 ($CH_2Cl_2:CH_3OH$, 9:1).

$^1$H NMR (500 MHz, $CD_3OD$): δ 7.27 (d, J=9.0 Hz, 1H), 6.90 (d, J=2.6 Hz, 1H), 6.80 (dd, J=9.0, 2.6 Hz, 1H), 6.57 (s, 1H), 6.23 (d, J=1.2 Hz, 1H), 6.05 (d, J=1.2 Hz, 1H), 5.23 (d, J=11.5 Hz, 1H), 4.27-4.08 (m, 4H), 3.77 (s, 3H), 3.75 (s, 3H), 3.63 (d, J=14.1 Hz, 2H), 3.40-3.34 (m, 2H), 2.93-2.87 (m, 5H), 2.80 (d, J=15.5 Hz, 1H), 2.57-2.54 (m, 2H), 2.34 (s, 3H), 2.30 (s, 3H), 2.14 (s, 3H), 2.05 (s, 3H).

$^{13}$C NMR (126 MHz, $CD_3OD$): δ 171.9, 170.6, 157.5, 147.0, 145.0, 142.3, 141.0, 132.2, 131.1, 129.1, 122.2, 120.9, 120.2, 116.3, 115.1, 114.0, 112.7, 111.4, 103.5, 102.7, 92.9, 62.0, 60.3, 59.8, 59.4, 56.5, 56.2, 56.0, 54.0, 43.8, 41.2, 40.7, 30.8, 30.3, 28.7, 24.5, 21.6, 20.6, 16.2, 9.6.

ESI-MS m/z: 768.6 $(M-H_2O+H)^+$.

(+)-HR-ESI-TOF-MS m/z: 768.2630 $[M-H_2O+H]^+$ (Calcd. for $C_{41}H_{42}N_3O_{10}S$ 768.2585).

Example 19

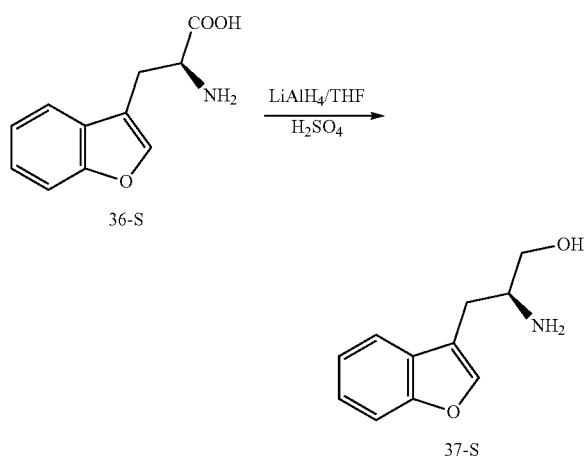

To a solution of LiAlH₄ (148 mL, 1.0 M in THF, 148 mmol) at −40° C. was added carefully H₂SO₄ (7.14 mL, 72.9 mmol) and a suspension of (S)-2-amino-3-(benzofuran-3-yl)propanoic acid (36-S) (prepared as described in *Tetrahedron Asymmetry* 2008, 19, 500-511) (5.54 g, 26.9 mmol) in THF (85 mL, 0.003 M). The reaction mixture was left evolution at 23° C., heated at 80° C. for 3 h and 18 h at 23° C. Cool at −21° C. the reaction mixture was quenched carefully with NaOH 2N until basic pH. EtOAc was added and the mixture filtered through Celite® and washed with CH₃OH. The crude was concentrated under vacuum to afford compound 37-S (3.93 g, >100%).

$R_f$=0.1 (CH₂Cl₂:CH₃OH, 4:1).

¹H NMR (400 MHz, CD₃OD): δ 7.67-7.62 (m, 1H), 7.61 (s, 1H), 7.51-7.41 (m, 1H), 7.34-7.18 (m, 2H), 3.69-3.48 (m, 1H), 3.44 (dd, J=10.8, 6.6 Hz, 1H), 3.18 (dtd, J=7.4, 6.4, 4.6 Hz, 1H), 2.88 (ddd, J=14.4, 6.1, 1.0 Hz, 1H), 2.68 (ddd, J=14.4, 7.5, 0.9 Hz, 1H).

Example 20

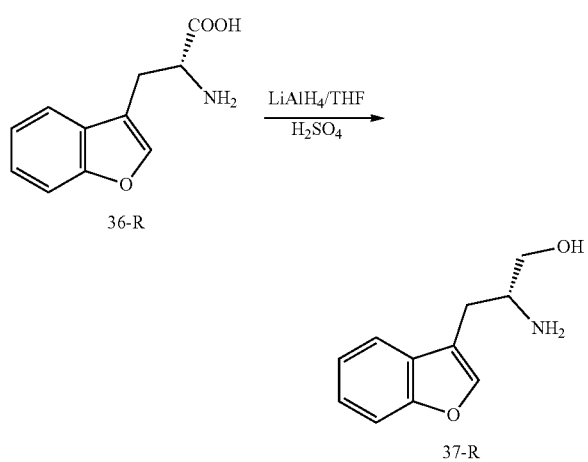

To a solution of LiAlH₄ (118 mL, 1.0 M in THF, 118 mmol) at −40° C. was added carefully H₂SO₄ (3.1 mL, 57.8 mmol) and a suspension of (R)-2-amino-3-(benzofuran-3-yl)propanoic acid (36-R) (prepared as described in *Tetrahedron Asymmetry* 2008, 19, 500-511) (4.4 g, 21.4 mmol) in THF (67.4 mL, 0.003 M). The reaction mixture was left evolution at 23° C., heated at 80° C. for 3 h and 18 h at 23° C. Cool at −21° C. the reaction mixture was quenched carefully with NaOH 2N until basic pH. EtOAc was added and the mixture filtered through Celite® and washed with CH₃OH. The crude was concentrated under vacuum. Flash chromatography (CH₂Cl₂:CH₃OH, from 99:1 to 85:15, Silice amine) to afford compound 37-R (2.77 g, 68%).

$R_f$=0.1 (CH₂Cl₂:CH₃OH, 4:1).

¹H NMR (400 MHz, CD₃OD): δ 7.63-7.52 (m, 1H), 7.56 (s, 1H), 7.46-7.33 (m, 1H), 7.21 (dtd, J=19.9, 7.3, 1.3 Hz, 2H), 3.57 (dd, J=10.7, 4.6 Hz, 1H), 3.42 (dd, J=10.8, 6.6 Hz, 1H), 3.15 (dtd, J=7.6, 6.3, 4.6 Hz, 1H), 2.84 (ddd, J=14.4, 6.0, 1.0 Hz, 1H), 2.64 (ddd, J=14.4, 7.5, 0.9 Hz, 1H).

Example 21

A)

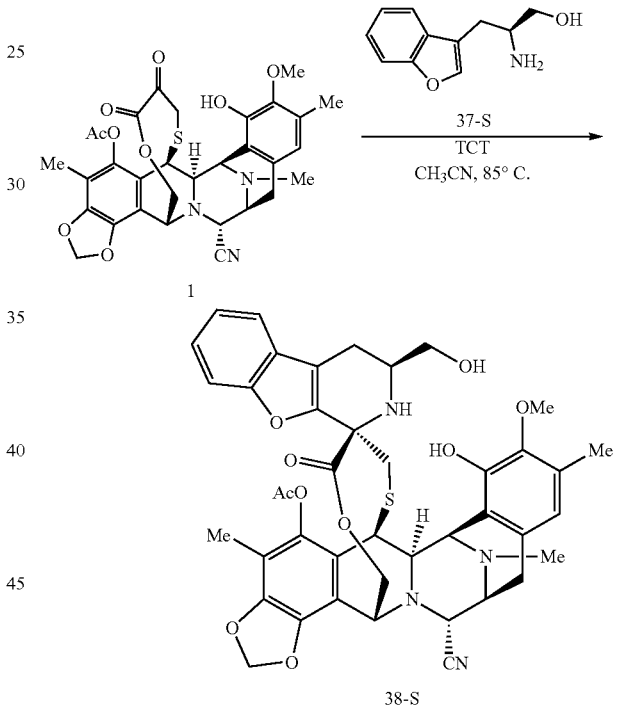

To a solution of compound 1 (850 mg, 1.36 mmol) in CH₃CN (136 mL, 0.01 M) was added (S)-2-amino-3-(benzofuran-3-yl)propan-1-ol (37-S) (1.30 g, 6.83 mmol and cyanuric chloride (TCT) (170 mg, 20%). The reaction mixture was stirred at 85° C. for 24 h and then aqueous saturated solution of NaHCO₃ was added and the mixture was extracted with CH₂Cl₂. The combined organic layers were dried over anhydrous Na₂SO₄, filtered, and concentrated under vacuum. Flash chromatography (Hexane:EtOAc, from 9:1 to 1:9) gives compound 38-S (750 mg, 69%).

$R_f$=0.25 (Hexane:EtOAc, 1:1).

¹H NMR (400 MHz, CDCl₃): δ 7.39-7.33 (m, 1H), 7.33-7.29 (m, 1H), 7.20 (ddd, J=8.3, 7.2, 1.4 Hz, 1H), 7.14 (td, J=7.4, 1.0 Hz, 1H), 6.61 (s, 1H), 6.21 (d, J=1.4 Hz, 1H), 6.06 (d, J=1.4 Hz, 1H), 5.74 (s, 1H), 5.08 (d, J=11.2 Hz, 1H), 4.58 (s, 1H), 4.37 (s, 1H), 4.32-4.23 (m, 2H), 4.19 (d, J=2.7

Hz, 1H), 3.81 (s, 3H), 3.52-3.41 (m, 3H), 3.36-3.29 (m, 1H), 3.13 (d, J=9.8 Hz, 1H), 3.00-2.81 (m, 3H), 2.57 (dd, J=15.7, 4.9 Hz, 1H), 2.50 (d, J=15.2 Hz, 1H), 2.37 (s, 3H), 2.31-2.25 (m, 1H), 2.29 (s, 3H), 2.16 (s, 3H), 2.10 (d, J=7.2 Hz, 1H), 2.05 (s, 3H).

ESI-MS m/z: 795.2 (M)$^+$.

$^{13}$C NMR (126 MHz, CDCl$_3$): δ 172.0, 170.7, 156.1, 150.6, 149.9, 147.1, 145.0, 142.4, 142.2, 132.0, 131.4, 128.7, 125.5, 123.8, 122.6, 121.6, 120.1, 116.5, 114.4, 112.3, 103.5, 92.6, 66.0, 65.1, 62.2, 60.4, 59.7, 56.6, 56.1, 54.8, 54.1, 51.6, 44.0, 41.3, 38.3, 30.8, 24.8, 20.6, 16.3, 9.6.

ESI-MS m/z: 768.2 (M–H$_2$O+H)$^+$.

(+)-HR-ESI-TOF-MS m/z: 768.2652 [M–H$_2$O+H]$^+$ (Calcd. for C$_{41}$H$_{42}$N$_3$O$_{10}$S 768.2585).

Example 22

A)

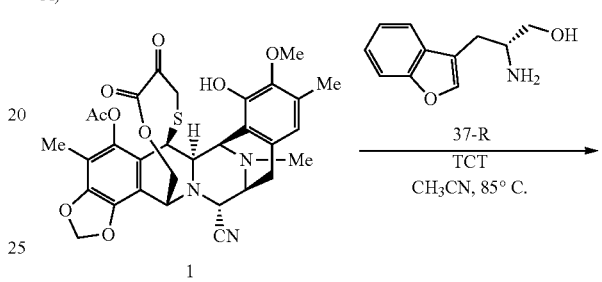

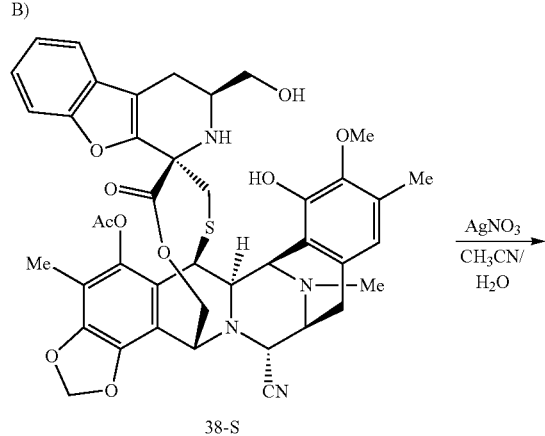

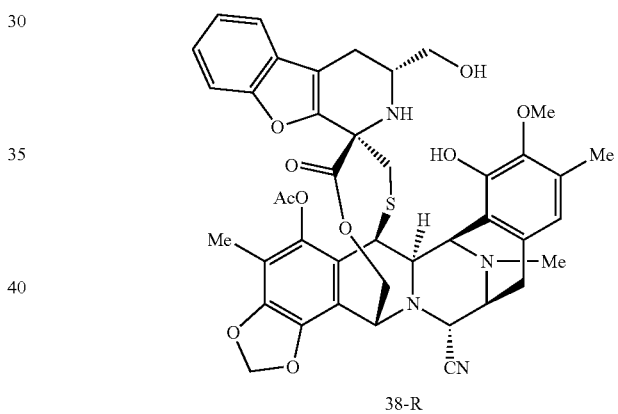

To a solution of compound 38-S (890 mg, 1.12 mmol) in CH$_3$CN:H$_2$O (1.39:1, 75 mL, 0.015 M) was added AgNO$_3$ (4.70 g, 28.0 mmol). After 18 h at 23° C., a mixture 1:1 of saturated aqueous solutions of NaCl and NaHCO$_3$ was added, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to afford compound 39-S (500 mg, 57%).

R$_f$=0.30 (CH$_2$Cl$_2$:CH$_3$OH, 9:1).

$^1$H NMR (400 MHz, CDCl$_3$): δ 7.38-7.33 (m, 1H), 7.33-7.28 (m, 1H), 7.23-7.16 (m, 1H), 7.16-7.09 (m, 1H), 6.62 (s, 1H), 6.18 (d, J=1.4 Hz, 1H), 6.03 (d, J=1.4 Hz, 1H), 5.71 (s, 1H), 5.19 (d, J=11.2 Hz, 1H), 4.85 (s, 1H), 4.49 (s, 2H), 4.24-4.10 (m, 3H), 3.81 (s, 3H), 3.54 (d, J=4.9 Hz, 1H), 3.49 (d, J=2.3 Hz, 3H), 3.33 (t, J=10.1 Hz, 2H), 3.22 (s, 1H), 2.98 (s, 1H), 2.84 (d, J=7.6 Hz, 2H), 2.62-2.53 (m, 2H), 2.37 (s, 3H), 2.30-2.24 (m, 1H), 2.28 (s, 3H), 2.14 (s, 3H), 2.04 (s, 3H).

To a solution of compound 1 (100 mg, 0.16 mmol) in CH$_3$CN (16 mL, 0.01 M) was added (R)-2-amino-3-(benzofuran-3-yl)propan-1-ol (37-R) (307 mg, 1.6 mmol) and cyanuric chloride (TCT) (40 mg, 40%). The reaction mixture was stirred at 85° C. for 44 h and then aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, from 9:1 to 1:9) gives compound 38-R (95 mg, 75%).

R$_f$=0.3 (Hexane:EtOAc, 1:1).

$^1$H NMR (400 MHz, CDCl$_3$): δ 7.42-7.27 (m, 2H), 7.28-7.09 (m, 2H), 6.58 (s, 1H), 6.20 (d, J=1.4 Hz, 1H), 6.05 (d, J=1.4 Hz, 1H), 5.79 (s, 1H), 5.00 (d, J=11.4 Hz, 1H), 4.59 (s, 1H), 4.34 (s, 1H), 4.31-4.16 (m, 4H), 3.80 (s, 3H), 3.79-3.76 (m, 1H), 3.63 (s, 1H), 3.54-3.40 (m, 4H), 2.99-2.87 (m, 2H), 2.68 (d, J=15.0 Hz, 1H), 2.56-2.47 (m, 1H), 2.38 (s, 3H), 2.27 (s, 3H), 2.17 (s, 3H), 2.07 (s, 3H).

ESI-MS m/z: 795.2 (M+H)$^+$.

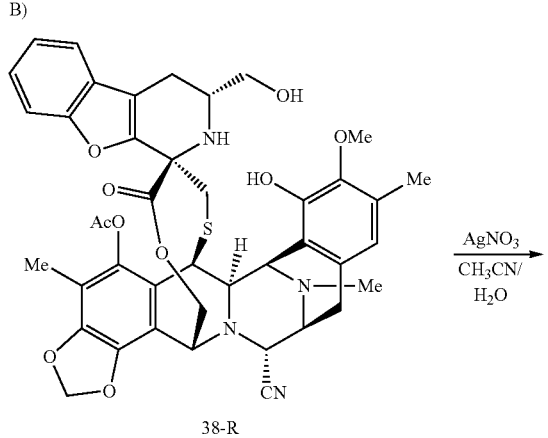

To a solution of compound 38-R (95 mg, 0.11 mmol) in CH$_3$CN:H$_2$O (1.39:1, 11 mL, 0.015 M) was added AgNO$_3$ (601 mg, 3.58 mmol). After 18 h at 23° C., a mixture 1:1 of saturated aqueous solutions of NaCl and NaHCO$_3$ was added, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to afford compound 39-R (66 mg, 70%).

R$_f$=0.3 (CH$_2$Cl$_2$:CH$_3$OH, 9:1).

$^1$H NMR (400 MHz, CDCl$_3$): δ 7.39-7.31 (m, 2H), 7.23-7.07 (m, 2H), 6.59 (s, 1H), 6.17 (d, J=1.4 Hz, 1H), 6.01 (d, J=1.4 Hz, 1H), 5.75 (s, 1H), 5.12 (dd, J=11.3, 1.2 Hz, 1H), 4.84 (s, 1H), 4.56-4.43 (m, 2H), 4.19-4.07 (m, 3H), 3.79 (s, 3H), 3.83-3.74 (m, 1H), 3.66-3.51 (m, 3H), 3.24 (s, 1H), 2.99-2.79 (m, 2H), 2.75-2.64 (m, 1H), 2.59-2.43 (m, 2H), 2.38 (s, 3H), 2.27 (s, 3H), 2.16 (s, 3H), 2.07 (s, 3H).

$^{13}$C NMR (101 MHz, CD$_3$OD): δ 170.5, 169.1, 154.9, 148.9, 148.5, 145.7, 143.6, 141.1, 140.8, 130.6, 129.9, 127.1, 124.1, 122.4, 122.4, 121.2, 120.3, 118.7, 118.2, 115.1, 113.6, 110.9, 102.1, 91.1, 65.0, 63.3, 60.2, 59.0, 58.4, 55.4, 54.5, 52.7, 52.3, 42.5, 38.7, 29.4, 23.5, 23.2, 19.1, 14.8, 8.3.

ESI-MS m/z: 768.2 (M–H$_2$O+H)$^+$.

(+)-HR-ESI-TOF-MS m/z: 767.2628 [M–H$_2$O+H]$^+$ (Calcd. for C$_{41}$H$_{42}$N$_3$O$_{10}$S 768.2585).

Example 23. Synthesis of allyl-N—[(S)-2-amino-3-(benzofuran-3-yl)propyl]carbamate (44-S)

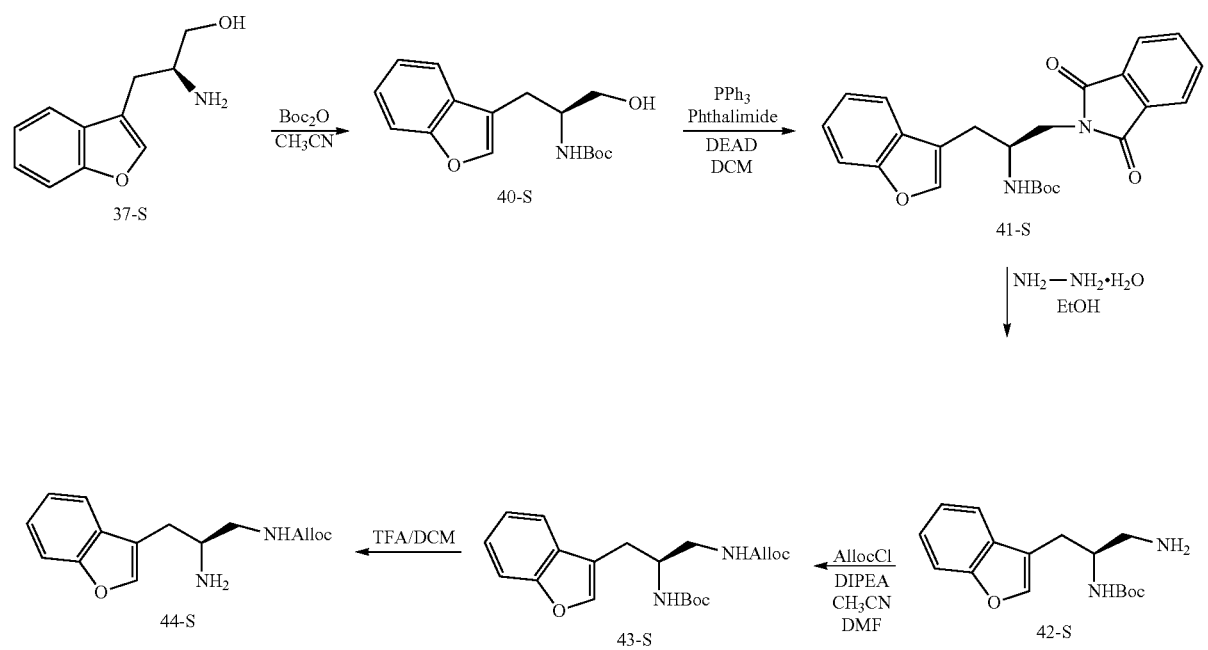

A)

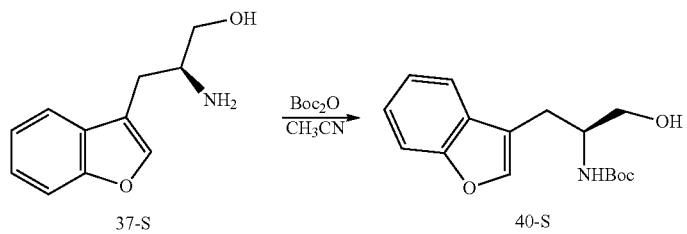

To a solution of compound 37-S (1.0 g, 5.22 mmol) in CH$_3$CN (21 mL, 4 mL/mmol) was added di-tert-butyl dicarbonate (2.28 g, 10.4 mmol). The reaction mixture was stirred at 23° C. for 2 h, concentrated under vacuum. Flash chromatography (CH$_2$Cl$_2$:CH$_3$OH, from 99:1 to 85:15) to afford compound 40-S (0.5 g, 33%).

R$_f$=0.7 (CH$_2$Cl$_2$:CH$_3$OH, 9:1).

$^1$H NMR (400 MHz, CDCl$_3$): δ 7.64 (d, J=7.6 Hz, 1H), 7.49 (s, 1H), 7.46 (d, J=7.6 Hz, 1H), 7.36-7.19 (m, 2H), 4.94 (s, 1H), 3.98 (s, 1H), 3.71-3.56 (m, 2H), 2.93 (d, J=6.9 Hz, 2H), 1.41 (s, 9H).

B)

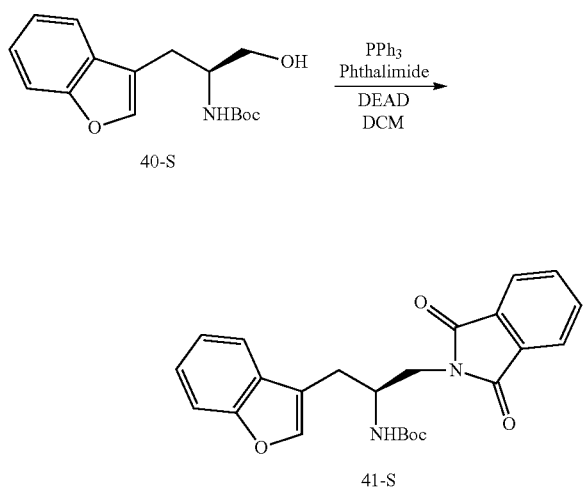

To a solution of compound 40-S (0.5 g, 1.71 mmol) in CH$_2$Cl$_2$ (11 mL, 6 mL/mmol) was added phthalimide (0.55 g, 3.77 mmol), Triphenylphosphine (0.99 g, 3.77 mmol) and the mixture was cooled at 0° C. A solution of 40% of Diethyl azodicarboxylate in CH$_2$Cl$_2$ (1.26 mL, 4.29 mmol) was added for 15 min. The reaction was stirred at 23° C. for 18 h, concentrated under vacuum. The residue obtained was purified by flash chromatography (Hexane:EtOAc, from 99:1 to 40:60) to afford compound 41-S (0.68 g, 94%).

R$_f$=0.8 (CH$_2$Cl$_2$:CH$_3$OH, 9:1).

$^1$H NMR (400 MHz, CDCl$_3$): δ 7.89-7.79 (m, 2H), 7.83-7.62 (m, 2H), 7.65-7.55 (m, 2H), 7.49-7.42 (m, 1H), 7.33-7.20 (m, 2H), 4.83 (d, J=9.0 Hz, 1H), 4.39 (ddt, J=12.1, 6.3, 2.9 Hz, 1H), 3.88-3.70 (m, 2H), 2.96 (d, J=6.4 Hz, 2H), 1.24 (s, 9H).

C)

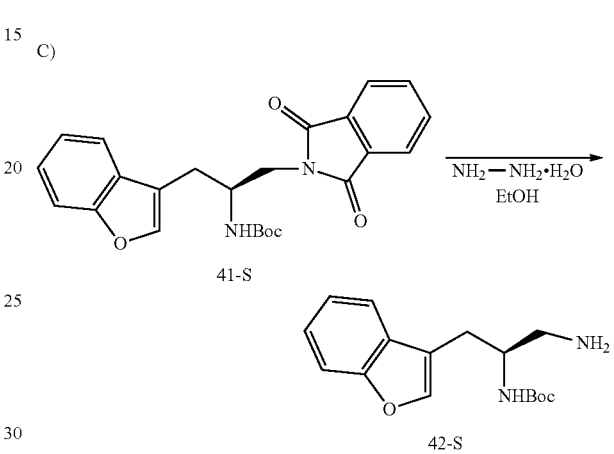

To a solution of compound 41-S (345 mg, 0.82 mmol) in ethanol (25 mL, 30 mL/mmol) was added hydrazine monohydrate (3.6 mL, 73.8 mmol). The reaction mixture was stirred at 80° C. in sealed tube for 2 h, concentrated under vacuum. Flash chromatography (CH$_2$Cl$_2$:CH$_3$OH, from 100:1 to 50:50) to afford compound 42-S (233 mg, 98%).

R$_f$=0.1 (CH$_2$Cl$_2$:CH$_3$OH, 8:2).

$^1$H NMR (400 MHz, CDCl$_3$): δ 7.62 (d, J=7.5 Hz, 1H), 7.49-7.42 (m, 2H), 7.33-7.18 (m, 2H), 4.85 (d, J=8.8 Hz, 1H), 3.91 (s, 1H), 2.91-2.76 (m, 3H), 2.67 (dd, J=13.1, 6.8 Hz, 1H), 1.25 (s, 9H).

D)

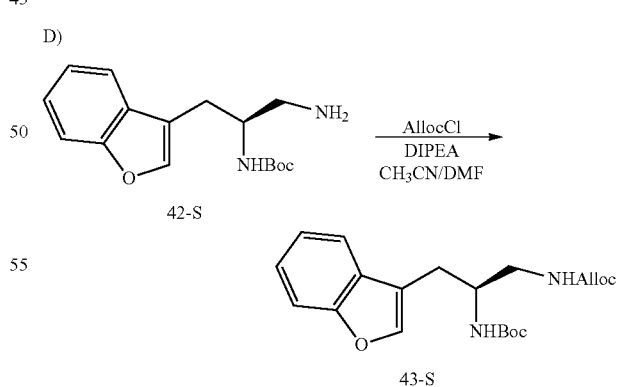

To a solution of compound 42-S (280 mg, 0.96 mmol) in CH$_3$CN (10 mL, 10 mL/mmol) and DMF (16 mL, 1 mL/mmol) was added N,N-diisopropylethylamine (0.14 mL, 0.77 mmol) and allyl chloroformate (1.02 mL, 9.64 mmol). The reaction was stirred at 23° C. for 2 h. The mixture was diluted with EtOAc and NH$_4$Cl was added and the mixture was extracted with EtOAc. The combined organic layers were dried over anhydrous Na₂SO₄, filtered, and concentrated under vacuum. The residue obtained was purified by flash chromatography (Hexane:EtOAc, from 100:1 to 1:100) to afford compound 43-S (445 mg, >100%).

R$_f$=0.5 (Hexane:EtOAc, 1:1).

¹H NMR (400 MHz, CDCl₃): δ 7.60 (d, J=7.6 Hz, 1H), 7.52-7.43 (m, 2H), 7.34-7.20 (m, 2H), 5.90 (ddt, J=16.4, 10.8, 5.6 Hz, 1H), 5.32-5.17 (m, 2H), 4.93-4.86 (m, 1H), 4.56 (d, J=5.6 Hz, 2H), 4.08-3.98 (m, 1H), 3.40-3.21 (m, 2H), 2.88 (m, 2H), 1.25 (s, 9H).

E)

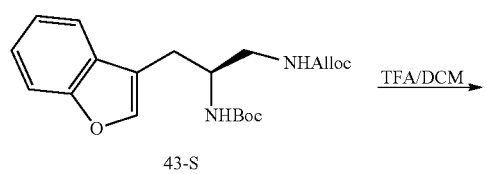

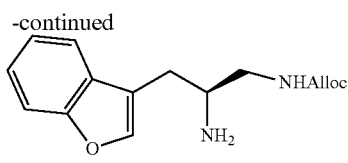

To a solution of compound 43-S (160 mg, 0.43 mmol) in CH₂Cl₂ (8 mL, 16.6 mL/mmol) was added trifluoroacetic acid (4 mL, 8.3 mL/mmol). The reaction mixture was stirred at 23° C. for 1.5 h, concentrated under vacuum. Flash chromatography (CH₂Cl₂:CH₃OH, from 100:1 to 50:50) to afford compound 44-S (175 mg, >100%).

R$_f$=0.2 (CH₂Cl₂:CH₃OH, 9:1).

¹H NMR (400 MHz, CD₃OD): δ 7.72 (s, 1H), 7.64 (dt, J=8.4, 0.9 Hz, 1H), 7.49 (dt, J=8.4, 0.9 Hz, 1H), 7.37-7.22 (m, 2H), 5.94 (ddt, J=16.3, 10.7, 5.5 Hz, 1H), 5.32 (dq, J=17.3, 1.7 Hz, 1H), 5.19 (dq, J=10.6, 1.5 Hz, 1H), 4.56 (dt, J=5.7, 1.5 Hz, 2H), 3.56 (qd, J=7.0, 4.4 Hz, 1H), 3.46-3.32 (m, 1H), 3.32-3.24 (m, 1H), 3.03 (dd, J=14.8, 6.9 Hz, 1H), 2.91 (ddd, J=14.8, 7.1, 0.9 Hz, 1H).

Example 24. Synthesis of allyl-N—[(R)-2-amino-3-(benzofuran-3-yl)propyl]carbamate (44-R)

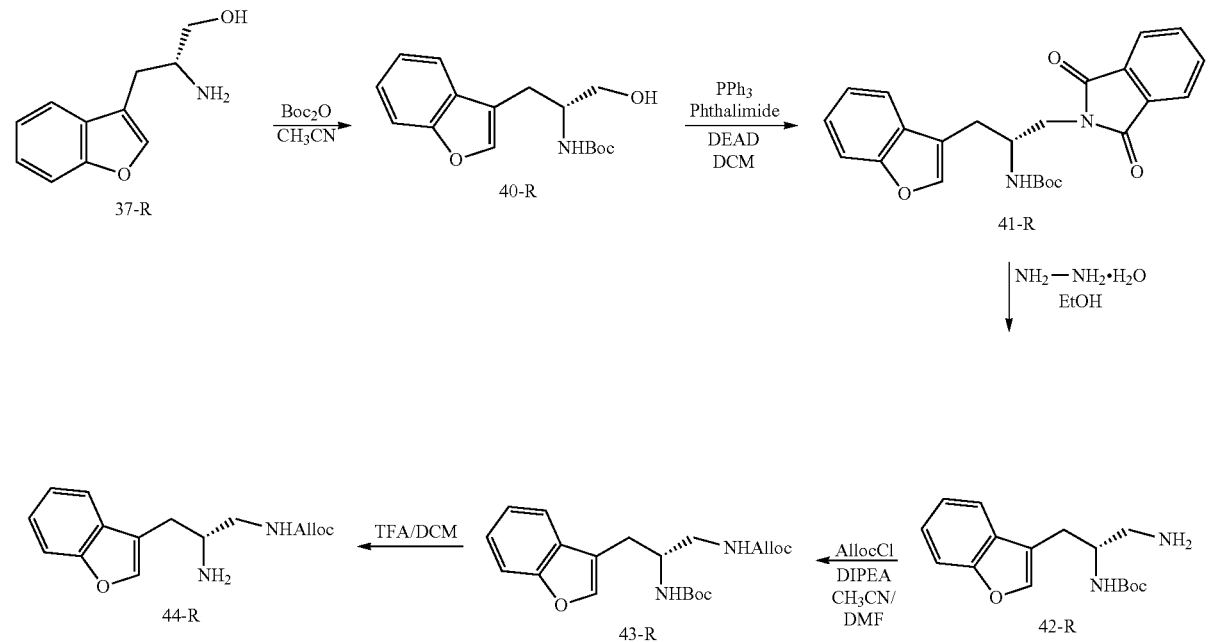

A)

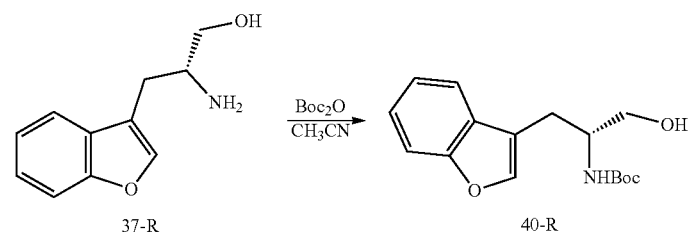

To a solution of compound 37-R (2.75 g, 14.4 mmol) in CH$_3$CN (58 mL, 4 mL/mmol) was added di-tert-butyl dicarbonate (6.27 g, 28.76 mmol). The reaction mixture was stirred at 23° C. for 2.5 h, concentrated under vacuum. Flash chromatography (CH$_2$Cl$_2$:CH$_3$OH, from 99:1 to 85:15) to afford compound 40-R (3.7 g, 88%).

R$_f$=0.6 (CH$_2$Cl$_2$:CH$_3$OH, 9:1).

$^1$H NMR (400 MHz, CDCl$_3$): δ 7.64 (d, J=7.6 Hz, 1H), 7.52-7.43 (m, 2H), 7.35-7.20 (m, 2H), 4.85 (d, J=8.2 Hz, 1H), 4.00 (bs, 1H), 3.69 (dd, J=11.0, 4.0 Hz, 1H), 3.62 (dd, J=10.9, 5.1 Hz, 1H), 2.94 (d, J=6.9 Hz, 2H), 1.42 (s, 9H).

B)

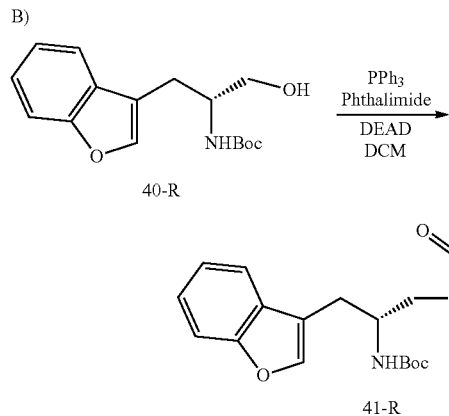

To a solution of compound 40-R (3.7 g, 12.7 mmol) in CH$_2$Cl$_2$ (76 mL, 6 mL/mmol) was added phthalimide (4.1 g, 28 mmol), triphenylphosphine (7.3 g, 28 mmol) and the mixture was cooled at 0° C. A solution of 40% of diethyl azodicarboxylate in CH$_2$Cl$_2$ (9.4 mL, 31.7 mmol) was added for 15 min. The reaction was stirred at 23° C. for 16 h, concentrated under vacuum. The residue obtained was purified by flash chromatography (CH$_2$Cl$_2$:CH$_3$OH, from 99:1 to 85:15) to afford compound 41-R (4.05 g, 76%).

R$_f$=0.8 (CH$_2$Cl$_2$:CH$_3$OH, 9:1).

$^1$H NMR (400 MHz, CDCl$_3$): δ 7.67-7.68 (m, 4H), 7.61 (d, J=7.5 Hz, 1H), 7.58 (s, 1H), 7.46 (d, J=7.5 Hz, 1H), 7.27 (dtd, J=17.2, 7.3, 1.4 Hz, 2H), 4.84 (d, J=9.0 Hz, 1H), 4.46-4.30 (m, 1H), 3.89-3.66 (m, 2H), 2.97 (d, J=6.4 Hz, 2H), 1.24 (s, 9H).

C)

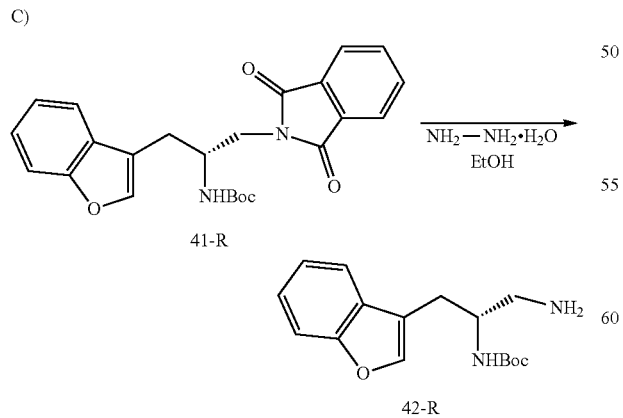

To a solution of compound 41-R (4.0 g, 9.5 mmol) in ethanol (285 mL, 30 mL/mmol) was added hydrazine monohydrate (41.5 mL, 856 mmol). The reaction mixture was stirred at 80° C. in sealed tube for 2 h, concentrated under vacuum. Flash chromatography (CH$_2$Cl$_2$:CH$_3$OH, from 100:1 to 50:50) to afford compound 42-R (2.2 g, 80%).

R$_f$=0.1 (CH$_2$Cl$_2$:CH$_3$OH, 8:2).

$^1$H NMR (400 MHz, CDCl$_3$): δ 7.60 (d, J=7.5 Hz, 1H), 7.45 (s, 1H), 7.44 (d, J=7.1 Hz, 1H), 7.25 (dtd, J=18.8, 7.3, 1.3 Hz, 2H), 4.94 (d, J=8.8 Hz, 1H), 3.98-3.78 (m, 1H), 2.90-2.77 (m, 2H), 2.65 (dd, J=13.1, 7.0 Hz, 1H), 1.40 (s, 9H).

D)

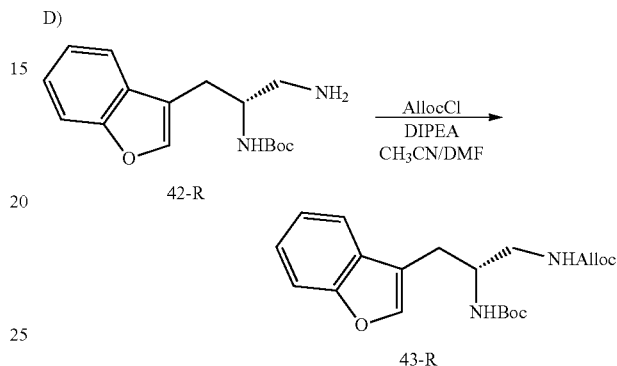

To a solution of compound 42-R (2.2 g, 7.6 mmol) in CH$_3$CN (76 mL, 10 mL/mmol) and DMF (7.6 mL, 1 mL/mmol) was added N,N-diisopropylethylamine (1.1 mL, 6.08 mmol) and allyl chloroformate (8.05 mL, 76 mmol). The reaction was stirred at 23° C. for 7 h. The mixture was diluted with EtOAc and NH$_4$Cl was added and the mixture was extracted with EtOAc. The combined organic layers were dried over anhydrous Na$_2$SO$_4$, filtered, and concentrated under vacuum. The residue obtained was purified by flash chromatography (Hexane:EtOAc, from 100:1 to 1:100) to afford compound 43-R (2.3 g, 81%).

R$_f$=0.7 (Hexane:EtOAc, 1:1).

$^1$H NMR (400 MHz, CDCl$_3$): δ 7.60 (d, J=7.5 Hz, 1H), 7.52-7.43 (m, 2H), 7.34-7.20 (m, 2H), 5.90 (ddt, J=17.3, 10.8, 5.6 Hz, 1H), 5.29 (d, J=17.2, 1H), 5.20 (d, J=10.4, 1H), 5.10 (t, J=6.2 Hz, 1H), 4.86 (d, J=8.4 Hz, 1H), 4.56 (d, J=5.4, 2H), 4.08-3.97 (m, 1H), 3.36 (dt, J=10.7, 4.7 Hz, 1H), 3.30-3.23 (m, 1H), 2.87 (td, J=14.8, 6.5 Hz, 2H), 1.41 (s, 9H).

E)

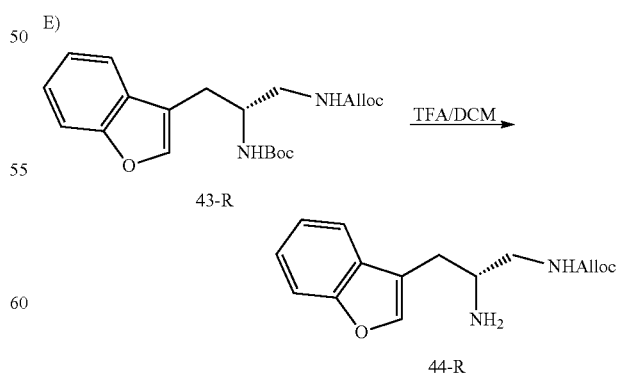

To a solution of compound 43-R (1.32 g, 3.52 mmol) in CH$_2$Cl$_2$ (60 mL, 16.6 mL/mmol) was added Trifluoroacetic acid (30 mL, 8.3 mL/mmol). The reaction mixture was stirred at 23° C. for 1.5 h, concentrated under vacuum. Flash chromatography (CH$_2$Cl$_2$:CH$_3$OH, from 100:1 to 50:50) to afford compound 44-R (0.90 g, 94%).

R$_f$=0.2 (CH$_2$Cl$_2$:CH$_3$OH, 9:1).

$^1$H NMR (400 MHz, CDCl$_3$): δ 7.75 (s, 1H), 7.69-7.61 (m, 1H), 7.54-7.46 (m, 1H), 7.39-7.24 (m, 2H), 5.95 (ddt, J=16.3, 10.8, 5.5 Hz, 1H), 5.32 (dd, J=17.3, 1.8 Hz, 1H), 5.24-5.16 (m, 1H), 4.57 (dt, J=5.7, 1.5 Hz, 2H), 3.68 (qd, J=7.1, 4.2 Hz, 1H), 3.48 (dd, J=14.8, 4.2 Hz, 1H), 3.42-3.30 (m, 1H), 3.14-2.95 (m, 2H).

Example 25

A)

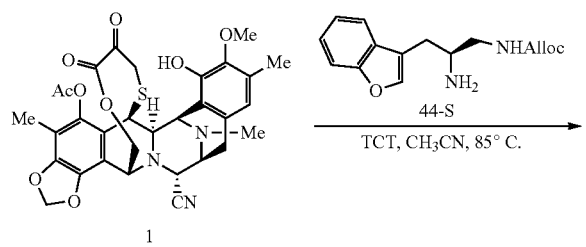

B)

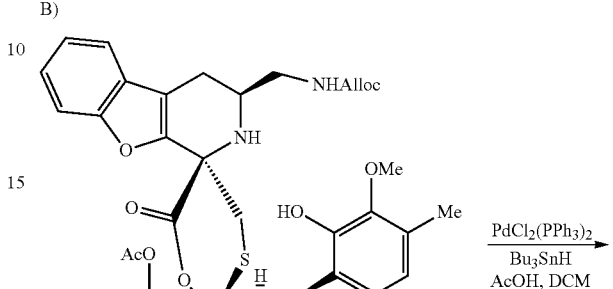

To a solution of compound 1 (750 mg, 1.2 mmol) in CH$_3$CN (120 mL, 0.01 M) was added compound 44-S (1370 mg, 6 mmol) and cyanuric chloride (TCT) (184 mg, 20%). The reaction mixture was stirred at 85° C. for 23 h and then aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, from 9:1 to 1:9) gives compound 45-S (755 mg, 72%).

R$_f$=0.36 (Hexane:EtOAc, 1:1).

$^1$H NMR (400 MHz, CDCl$_3$): δ 7.38-7.28 (m, 2H), 7.23-7.08 (m, 2H), 6.67 (s, 1H), 6.19 (d, J=1.4 Hz, 1H), 6.09-5.95 (m, 1H), 6.04 (d, J=1.4 Hz, 1H), 5.92 (s, 1H), 5.80 (s, 1H), 5.44-5.34 (m, 1H), 5.26 (dq, J=10.4, 1.3 Hz, 1H), 5.08 (dd, J=11.4, 1.1 Hz, 1H), 4.70-4.63 (m, 2H), 4.56 (s, 1H), 4.34 (s, 1H), 4.31-4.18 (m, 3H), 3.80 (s, 3H), 3.50-3.39 (m, 2H), 3.24-3.15 (m, 1H), 3.00 (dt, J=12.2, 6.0 Hz, 2H), 2.95 (d, J=5.2 Hz, 2H), 2.60 (dd, J=15.4, 4.5 Hz, 2H), 2.44 (dd, J=15.6, 5.2 Hz, 1H), 2.29 (s, 3H), 2.27 (s, 3H), 2.25-2.20 (m, 1H), 2.18 (s, 3H), 2.12 (s, 1H), 2.04 (s, 3H).

ESI-MS m/z: 878.2 (M+H)$^+$.

To a solution of compound 45-S (750 mg, 0.85 mmol) in CH$_2$Cl$_2$ (15.3 mL, 18 mL/mmol) was added bis(triphenylphosphine)palladium(II) dichloride (96 mg, 0.14 mmol) and acetic acid (0.5 mL, 8.5 mmol). Tributyltin hydride (1.4 mL, 5.1 mmol) was added at 0° C., and the reaction mixture was stirred at 0° C. for 30 minutes, and was concentrated under vacuum. Flash chromatography (Hexane:EtOAc, from 100:1 to 1:100 and CH$_2$Cl$_2$:CH$_3$OH, from 100:1 to 1:100) to afford compound 46-S (430 mg, 64%).

R$_f$=0.3 (CH$_2$Cl$_2$:CH$_3$OH, 1:1).

$^1$H NMR (400 MHz, CDCl$_3$): δ 7.37-7.29 (m, 2H), 7.22-7.11 (m, 2H), 6.57 (s, 1H), 6.21 (d, J=1.5 Hz, 1H), 6.06 (d, J=1.5 Hz, 1H), 5.07 (d, J=11.5 Hz, 1H), 4.57 (s, 1H), 4.37 (s, 1H), 4.29-4.23 (m, 2H), 4.14 (s, 1H), 3.79 (s, 3H), 3.50-3.47 (m, 2H), 3.38 (d, J=8.7 Hz, 1H), 2.95-2.71 (m, 4H), 2.68-2.52 (m, 2H), 2.51-2.38 (m, 1H), 2.35 (s, 3H), 2.33-2.26 (m, 1H), 2.29 (s, 3H), 2.17-2.08 (m, 1H), 2.10 (s, 3H), 2.04 (s, 3H).

ESI-MS m/z: 794.3 (M+H)$^+$.

C)

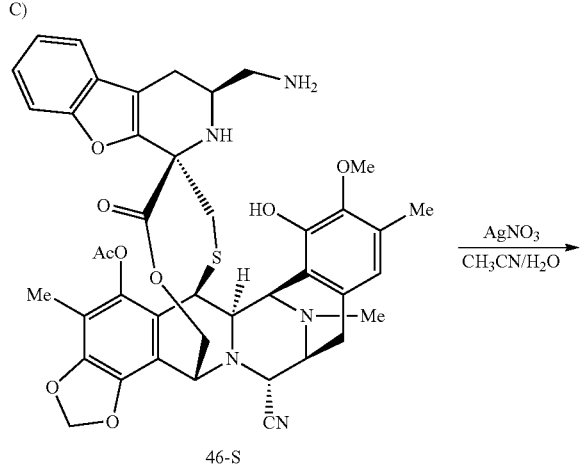

To a solution of compound 46-S (550 mg, 0.7 mmol) in CH$_3$CN:H$_2$O (1.39:1, 49 mL, 0.015 M) was added AgNO$_3$ (2.4 g, 14 mmol). After 16 h at 23° C., the reaction was quenched with a mixture 1:1 of saturated aqueous solutions of NaCl and NaHCO$_3$, stirred for 15 min, diluted with CH$_2$Cl$_2$, stirred for 5 min, and extracted with CH$_2$Cl$_2$. The combined organic layers were dried over anhydrous Na$_2$SO$_4$, filtered, and concentrated under vacuum. The residue obtained was purified by flash chromatography (CH$_2$Cl$_2$:CH$_3$OH, from 99:1 to 85:15) to give compound 47-S (53 mg, 10%).

R$_f$=0.1 (CH$_2$Cl$_2$:CH$_3$OH, 9:1).

$^1$H NMR (500 MHz, CDCl$_3$): δ 7.36 (d, 7.9 Hz, 1H), 7.33 (d, 7.4 Hz, 1H), 7.23 (t, J=7.4 Hz, 1H), 7.16 (t, J=7.4 Hz, 1H), 6.77 (s, 1H), 6.20 (s, 1H), 6.04 (s, 1H), 5.92 (s, 1H), 5.20 (d, J=11.1 Hz, 1H), 4.90 (s, 1H), 4.50 (s, 1H), 4.46-4.39 (m, 1H), 4.25 (d, J=11.1 Hz, 1H), 4.20 (s, 1H), 3.84 (s, 3H), 3.81 (d, J=4.2 Hz, 1H), 3.58 (s, 1H), 3.40-3.14 (m, 3H), 2.90 (t, J=13.0 Hz, 1H), 2.76 (m, 3H), 2.50 (s, 3H), 2.46-2.37 (m, 1H), 2.32-2.26 (m, 2H), 2.30 (s, 3H), 2.15 (s, 3H), 2.04 (s, 3H).

$^{13}$C NMR (126 MHz, CD$_3$OD): δ 170.5, 169.2, 154.6, 149.1, 148.7, 145.7, 143.5, 141.0, 140.9, 131.2, 129.6, 126.9, 124.4, 122.5, 121.4, 119.7, 118.7, 115.0, 112.7, 111.0, 110.7, 102.1, 91.2, 63.5, 61.2, 59.2, 58.5, 55.3, 54.7, 53.4, 52.7, 43.3, 42.5, 39.9, 36.9, 29.3, 24.1, 23.6, 19.1, 15.0, 8.2.

ESI-MS m/z: 767.2 (M–H$_2$O+H)$^+$.

(+)-HR-ESI-TOF-MS m/z: 767.2794 [M–H$_2$O+H]$^+$ (Calcd. for C$_{41}$H$_{43}$N$_4$O$_9$S 767.2745).

Example 26

A)

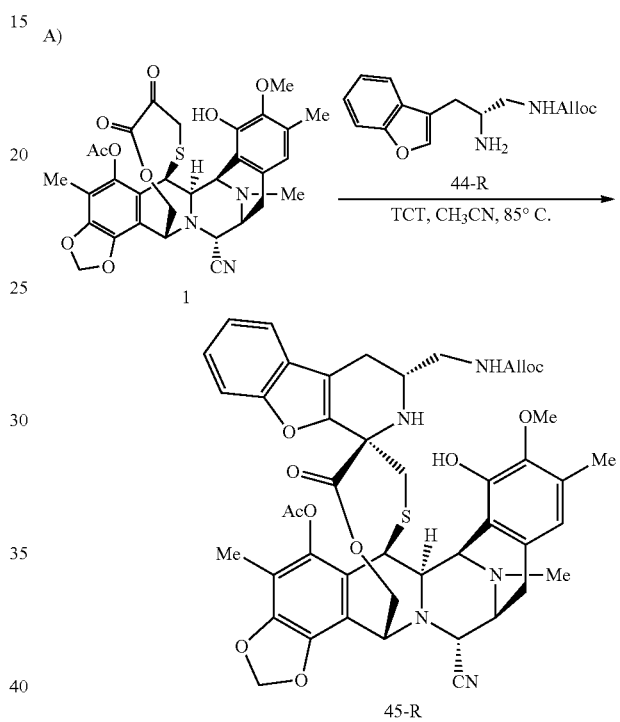

To a solution of compound 1 (621 mg, 1 mmol) in CH$_3$CN (100 mL, 0.01 M) was added compound 44-R (825 mg, 3 mmol) and cyanuric chloride (TCT) (248 mg, 40%). The reaction mixture was stirred at 85° C. for 66 h and then aqueous saturated solution of NaHCO$_3$ was added and the mixture was extracted with CH$_2$Cl$_2$. The combined organic layers were dried over anhydrous Na$_2$SO$_4$, filtered, and concentrated under vacuum. Flash chromatography (Hexane:EtOAc, from 9:1 to 1:9) gives compound 45-R (530 mg, 58%).

R$_f$=0.4 (Hexane:EtOAc, 1:1).

$^1$H NMR (400 MHz, CDCl$_3$): δ 7.42-7.28 (m, 2H), 7.23-7.08 (m, 2H), 6.60 (s, 1H), 6.20 (d, J=1.4 Hz, 1H), 6.04 (d, J=1.4 Hz, 1H), 6.01-5.92 (m, 1H), 5.77 (s, 1H), 5.44-5.20 (m, 2H), 5.09 (s, 1H), 5.04-4.96 (m, 1H), 4.71-4.55 (m, 2H), 4.34 (s, 1H), 4.30-4.18 (m, 3H), 3.79 (s, 3H), 3.53 (dd, J=10.2, 4.4 Hz, 1H), 3.46 (m, 2H), 3.50-3.40 (m, 1H), 3.03-2.87 (m, 2H), 2.67 (d, J=15.0 Hz, 1H), 2.47 (dd, J=15.6, 3.7 Hz, 1H), 2.40-2.32 (m, 2H), 2.30 (s, 3H), 2.29 (s, 3H), 2.19-2.12 (m, 2H), 2.16 (s, 3H), 2.09 (s, 3H).

ESI-MS m/z: 878.3 (M+H)$^+$.

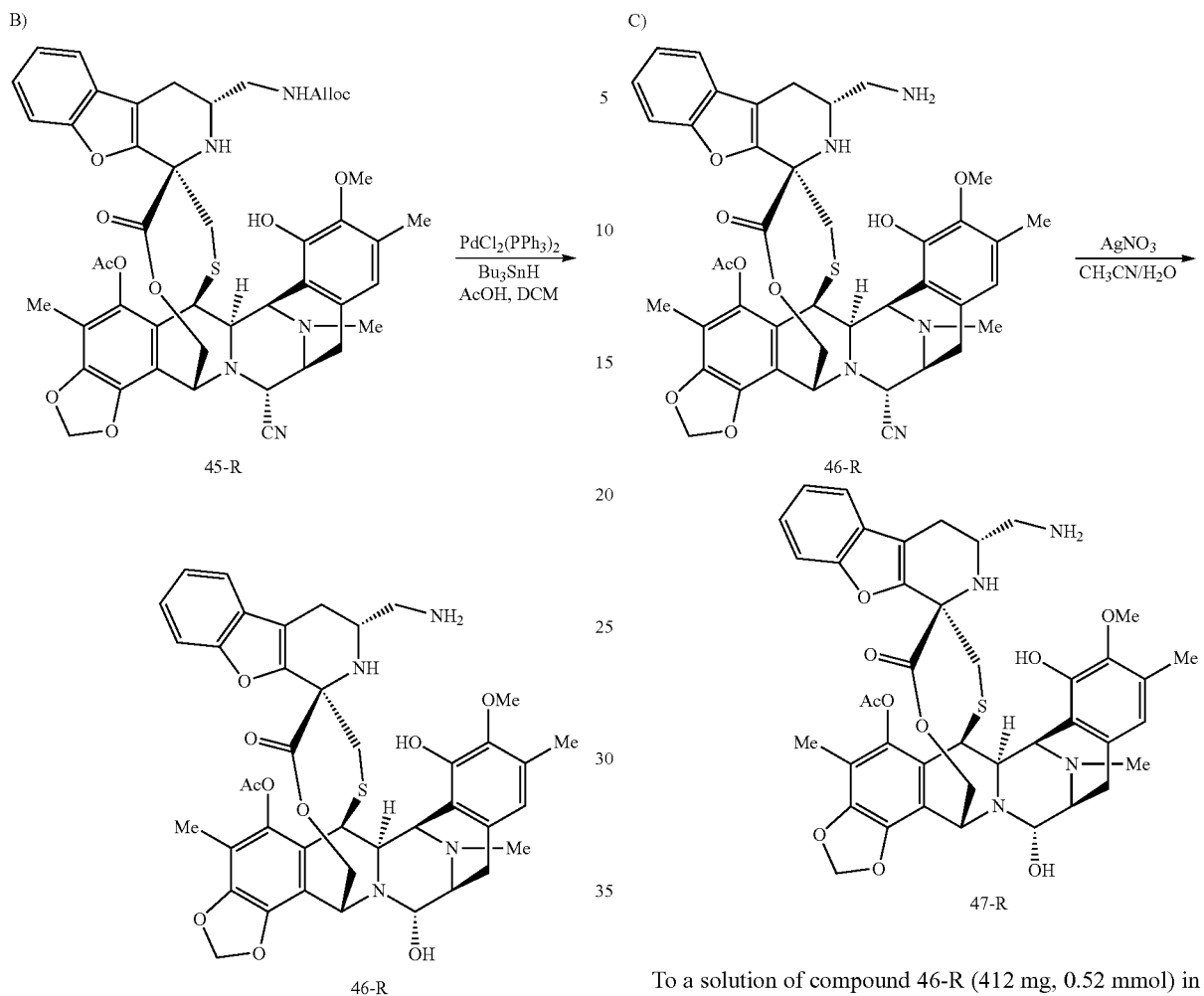

To a solution of compound 45-R (552 mg, 0.63 mmol) in $CH_2Cl_2$ (11.3 mL, 18 mL/mmol) was added bis(triphenylphosphine)palladium(II) dichloride (70.7 mg, 0.1 mmol) and acetic acid (0.36 mL, 6.3 mmol). Tributyltin hydride (1.02 mL, 3.8 mmol) was added at 0° C. and the reaction mixture was stirred at 0° C. for 0.5 h, and concentrated under vacuum The crude obtained was diluted with EtOAc, saturated aqueous solution of $NH_4Cl$ was added and the mixture was extracted with EtOAc. The combined organic layers were dried over anhydrous $Na_2SO_4$, filtered, and concentrated under vacuum. Flash chromatography (Hexane:EtOAc, from 100:1 to 1:100 and EtOAc:$CH_3OH$, from 100:1 to 1:100) to afford compound 46-R (423 mg, 85%).

$R_f$=0.3 ($CH_2Cl_2$:$CH_3OH$, 1:1).

$^1H$ NMR (400 MHz, $CDCl_3$): δ 7.45-7.28 (m, 2H), 7.23-7.08 (m, 2H), 6.56 (s, 1H), 6.19 (d, J=1.4 Hz, 1H), 6.05 (d, J=1.4 Hz, 1H), 4.98 (d, J=11.5 Hz, 1H), 4.59 (s, 1H), 4.34 (s, 1H), 4.27 (dd, J=5.1, 1.7 Hz, 1H), 4.22-4.16 (m, 2H), 3.80 (s, 3H), 3.49-3.39 (m, 2H), 3.31 (dq, J=9.8, 5.5, 4.5 Hz, 2H), 2.95 (s, 1H), 2.83 (d, J=5.6 Hz, 2H), 2.74-2.51 (m, 3H), 2.35 (s, 3H), 2.32-2.21 (m, 2H), 2.26 (s, 3H); 2.16 (s, 3H), 2.06 (s, 3H).

ESI-MS m/z: 794.3 (M+H)$^+$.

To a solution of compound 46-R (412 mg, 0.52 mmol) in $CH_3CN$:$H_2O$ (1.39:1, 36 mL, 0.015 M) was added $AgNO_3$ (1.76 g, 10.4 mmol). After 22 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give compound 47-R (175 mg, 43%).

$R_f$=0.1 ($CH_2Cl_2$:$CH_3OH$, 9:1).

$^1H$ NMR (500 MHz, $CDCl_3$): δ 7.34 (dd, J=11.1, 7.9 Hz, 2H), 7.22-7.07 (m, 2H), 6.57 (s, 1H), 6.17 (d, J=1.2 Hz, 1H), 6.01 (d, J=1.2 Hz, 1H), 5.11 (d, J=11.2 Hz, 1H), 4.84 (s, 1H), 4.53-4.47 (m, 2H), 4.21-4.07 (m, 2H), 3.80 (s, 3H), 3.56 (d, J=5.1 Hz, 1H), 3.43 (s, 1H), 3.24 (d, J=9.1 Hz, 1H), 2.98-2.78 (m, 4H), 2.72-2.58 (m, 2H), 2.38 (s, 3H), 2.35-2.27 (m, 2H), 2.28 (s, 3H), 2.14 (s, 3H), 2.08 (s, 3H).

$^{13}C$ NMR (101 MHz, $CD_3OD$): δ 170.6, 169.1, 155.0, 148.8, 145.6, 143.7, 141.1, 140.8, 130.9, 129.7, 126.9, 124.2, 122.4, 121.1, 119.6, 118.9, 118.7, 115.0, 113.2, 112.5, 111.0, 102.1, 91.3, 63.3, 60.4, 59.0, 58.4, 55.3, 54.6, 52.6, 51.1, 44.9, 42.4, 39.8, 38.7, 29.4, 24.0, 23.2, 19.1, 15.0, 8.3.

ESI-MS m/z: 767.2 (M–$H_2O$+H)$^+$.

(+)-HR-ESI-TOF-MS m/z: 767.2806 [M–$H_2O$+H]$^+$ (Calcd. for $C_{41}H_{43}N_4O_9S$ 767.2745).

Example 27. In Vitro Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

CELL LINES

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |
| PSN1 | CRM-CRL-3211 | human | pancreas | pancreas adenocarcinoma |
| PC-3 | CRL-1435 | human | prostate | prostate adenocarcinoma |
| 22Rv1 | CRL-2505 | human | prostate | prostate carcinoma |

Evaluation of Cytotoxic Activity Using the SBR and the MTT Colorimetric Assays A colorimetric assay, using sulforhodamine B (SRB) reaction has been adapted to provide a quantitative measurement of cell growth and viability (following the technique described by Skehan et al. *J. Natl. Cancer Inst.* 1990, 82, 1107-1112). Another colorimetric assay based on 3-(4,5-Dimethylthiazol-2-yl)-2,5-diphenyltetrazolium bromide (MTT) reduction to a purple formazan has been also used to assess the antiproliferative activity (following the technique described by Mosmann et al. *J. Immunol. Meth.* 1983, 65, 55-63).

These forms of assays employ 96-well cell culture microplates following the standards of the American National Standards Institute and the Society for Laboratory Automation and Screening (ANSI SLAS 1-2004 (R2012) Oct. 12, 2011. All the cell lines used in this study were obtained from the American Type Culture Collection (ATCC) and derive from different types of human cancer.

A549, HT29, MDA-MB-231 and PSN1 cells were maintained in Dulbecco's Modified Eagle Medium (DMEM) while PC-3 and 22Rv1 cells were maintained in Roswell Park Memorial Institute Medium (RPMI). All cell lines were supplemented with 10% Fetal Bovine Serum (FBS), 2 mM L-glutamine, 100 U/mL penicillin, and 100 U/mL streptomycin at 37° C., 5% $CO_2$ and 98% humidity. For the experiments, cells were harvested from subconfluent cultures using trypsinization and resuspended in fresh medium before counting and plating.

A549, HT29, MDA-MB-231 and PSN1 cells were seeded in 96 well microtiter plates, at 5000 cells per well in aliquots of 150 µL, and allowed to attach to the plate surface for 18 hours (overnight) in drug free medium. After that, one control (untreated) plate of each cell line was fixed (as described below) and used for time zero reference value. Culture plates were then treated with test compounds (50 µL aliquots of 4× stock solutions in complete culture medium plus 4% DMSO) using ten 2/5 serial dilutions (concentrations ranging from 10 to 0.003 µg/mL) and triplicate cultures (1% final concentration in DMSO). After 72 hours treatment, the antitumor effect was measured by using the SRB methodology: Briefly, cells were washed twice with PBS, fixed for 15 min in 1% glutaraldehyde solution at room temperature, rinsed twice in PBS, and stained in 0.4% SRB solution for 30 min at room temperature. Cells were then rinsed several times with 1% acetic acid solution and air-dried at room temperature. SRB was then extracted in 10 mM trizma base solution and the absorbance measured in an automated spectrophotometric plate reader at 490 nm.

An appropriate number of PC-3 and 22Rv1 cells, to reach a final cell density in the assay ranging from 5,000 to 15,000 cells per well depending on the cell line, were seeded in 96-well plates and allowed to stand in culture medium for 24 h at 37° C. under 5% CO2 and 98% humidity. Then, compounds or DMSO in culture medium were added to reach a final volume of 200 µL and the intended compound concentration in a range covering ten serial 2/5 dilutions starting from 0.1 µg/mL in 1% (v/v) DMSO. At this point a set of "time zero control plates" treated with 1% (v/v) DMSO were processed with MTT as described below. The rest of the plates were incubated during 72 h under the aforementioned environmental conditions. Afterwards 50 µL of a 1 mg/mL MTT solution in culture medium were added to the wells and incubated for 6-8 hours at 37° C. to allow formazan crystals generation. Culture medium was then removed and 100 µL of neat DMSO added to each well to dissolve the formazan product into a coloured solution whose absorbance at 540 nm was finally measured in a PolarStar Omega microplate multilabel reader (BMG Labtech, Ortenberg, Germany).

Effects on cell growth and survival were estimated by applying the NCI algorithm (Boyd M R and Paull K D. *Drug Dev. Res.* 1995, 34, 91-104). The values obtained in triplicate cultures were fitted by nonlinear regression to a four-parameters logistic curve by nonlinear regression analysis. Three reference parameters were calculated (according to the aforementioned NCI algorithm) by automatic interpolation of the curves obtained by such fitting: $GI_{50}$=compound concentration that produces 50% cell growth inhibition, as compared to control cultures; TGI=total cell growth inhibition (cytostatic effect), as compared to control cultures, and $LC_{50}$=compound concentration that produces 50% net cell killing cytotoxic effect).

Tables 1-7 illustrate data on the biological activity of compounds of the present invention together with biological activity of the reference compounds. Tables 8-9 provide data on the biological activity of several compounds of the invention compared to their analogues with a carboxylic acid group. Compounds A, B, E, F, ET-736, PM01183, 14-S, 15-S, 28-S, 28-R, 29-S, and 29-R, are not part of the present invention.

TABLE 1

Biological activity (Molar)

Compound

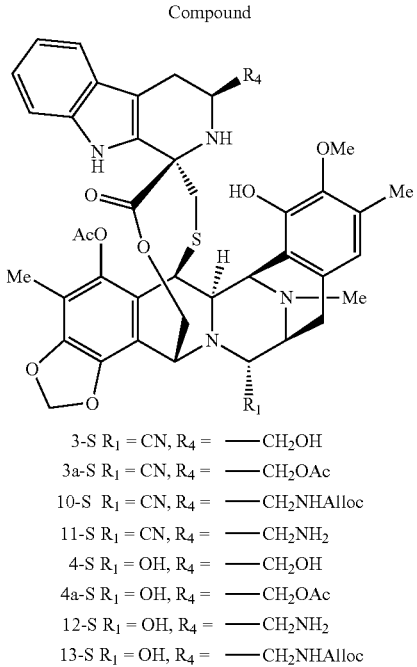

3-S R₁ = CN, R₄ = —CH₂OH
3a-S R₁ = CN, R₄ = —CH₂OAc
10-S R₁ = CN, R₄ = —CH₂NHAlloc
11-S R₁ = CN, R₄ = —CH₂NH₂
4-S R₁ = OH, R₄ = —CH₂OH
4a-S R₁ = OH, R₄ = —CH₂OAc
12-S R₁ = OH, R₄ = —CH₂NH₂
13-S R₁ = OH, R₄ = —CH₂NHAlloc Reference compound

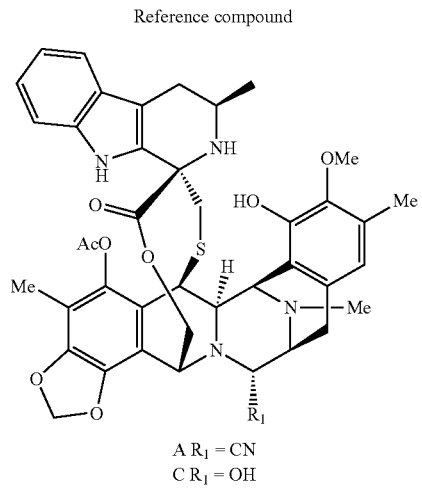

A R₁ = CN
C R₁ = OH

|   |   | A549 | HT29 | MDA-MB-231 | PSN1 | PC-3 | 22Rv1 |   | A549 | HT29 | MDA-MB-231 | PSN1 |
|---|---|---|---|---|---|---|---|---|---|---|---|---|
| $GI_{50}$ | 3-S | 4.03E−10 | 2.77E−10 | 4.91E−10 | 9.95E−10 |   |   | A | 8.36E−09 | 7.71E−09 | 7.07E−09 | 1.29E−08 |
| TGI |   | 6.17E−10 | >1.26E−07 | 5.29E−10 | 1.64E−09 |   |   |   | 8.87E−09 | 8.36E−09 | 9.38E−09 | 1.54E−08 |
| $LC_{50}$ |   | >1.26E−07 | >1.26E−07 | 6.17E−10 | >1.26E−07 |   |   |   | >1.29E−07 | >1.29E−07 | 1.41E−08 | 1.93E−08 |
| $GI_{50}$ | 3a-S | 3.11E−09 | 2.99E−09 | 2.87E−09 | 2.15E−09 |   |   |   |   |   |   |   |
| TGI |   | 3.23E−09 | 3.23E−09 | 3.59E−09 | 3.59E−09 |   |   |   |   |   |   |   |
| $LC_{50}$ |   | >1.20E−07 | >1.20E−07 | 4.90E−09 | 1.20E−08 |   |   |   |   |   |   |   |
| $GI_{50}$ | 10-S | 2.05E−08 | 1.14E−08 | 4.79E−09 | 7.64E−09 |   |   |   |   |   |   |   |
| TGI |   | 3.08E−08 | 1.25E−08 | 8.44E−09 | 1.25E−08 |   |   |   |   |   |   |   |
| $LC_{50}$ |   | 7.53E−08 | >1.14E−06 | 1.60E−08 | 2.39E−08 |   |   |   |   |   |   |   |
| $GI_{50}$ | 11-S | 8.45E−09 | 3.41E−09 | 2.27E−09 | 3.28E−09 |   |   |   |   |   |   |   |
| TGI |   | 2.65E−08 | >1.26E−07 | 3.41E−09 | 4.54E−09 |   |   |   |   |   |   |   |
| $LC_{50}$ |   | >1.26E−07 | >1.26E−07 | 6.43E−09 | 8.07E−09 |   |   |   |   |   |   |   |
| $GI_{50}$ | 4-S | 1.27E−09 | 1.27E−09 | 1.22E−09 | 1.78E−09 | 8.08E−10 | 3.58E−10 | C | 2.73E−08 | 2.08E−08 | 2.60E−08 | 3.64E−08 |
| TGI |   | 1.40E−09 | 1.40E−09 | 2.55E−09 | 2.29E−09 |   |   |   | 6.63E−08 | 2.34E−08 | 5.46E−08 | 4.42E−08 |
| $LC_{50}$ |   | >1.27E−07 | >1.27E−07 | 6.50E−09 | 3.44E−09 |   |   |   | >1.30E−07 | >1.30E−07 | >1.30E−07 | 6.50E−08 |
| $GI_{50}$ | 4a-S | 3.99E−09 | 3.14E−09 | 3.39E−09 | 3.02E−09 |   |   |   |   |   |   |   |
| TGI |   | 6.17E−09 | 3.39E−09 | 5.44E−09 | 3.27E−09 |   |   |   |   |   |   |   |
| $LC_{50}$ |   | >1.21E−07 | >1.21E−07 | 1.00E−08 | 3.51E−09 |   |   |   |   |   |   |   |
| $GI_{50}$ | 12-S | 2.04E−08 | 4.85E−09 | 5.23E−09 | 3.44E−09 |   |   |   |   |   |   |   |
| TGI |   | 5.61E−08 | 8.42E−09 | 8.42E−09 | 5.49E−09 |   |   |   |   |   |   |   |
| $LC_{50}$ |   | >1.28E−07 | >1.28E−07 | 1.53E−08 | 1.21E−08 |   |   |   |   |   |   |   |
| $GI_{50}$ | 13-S | 1.15E−08 | 1.15E−08 | 1.15E−08 | 1.96E−08 |   |   |   |   |   |   |   |
| TGI |   | 1.61E−08 | 1.27E−08 | 1.27E−08 | 2.88E−08 |   |   |   |   |   |   |   |
| $LC_{50}$ |   | 2.42E−08 | >1.15E−06 | 1.38E−08 | 4.61E−08 |   |   |   |   |   |   |   |

TABLE 2

Biological activity (Molar)

Compound

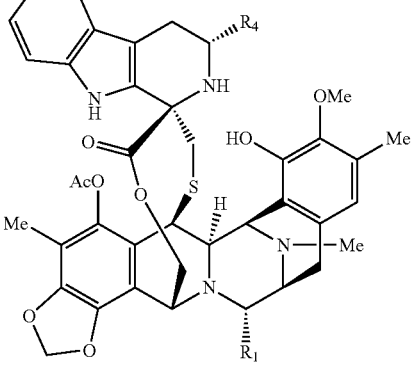

3-R $R_1 = CN$, $R_4 = $ —CH$_2$OH
10-R $R_1 = CN$, $R_4 = $ —CH$_2$NHAlloc
11-R $R_1 = CN$, $R_4 = $ —CH$_2$NH$_2$
4-R $R_1 = OH$, $R_4 = $ —CH$_2$OH
12-R $R_1 = OH$, $R_4 = $ —CH$_2$NH$_2$
13-R $R_1 = OH$, $R_4 = $ —CH$_2$NHAlloc Reference compound

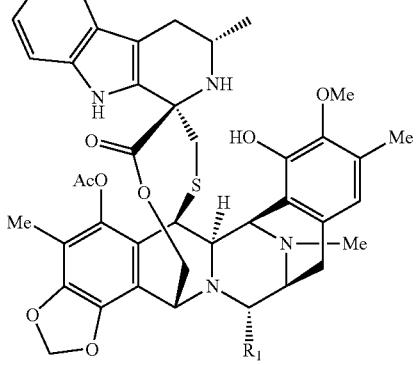

B $R_1 = CN$
D $R_1 = OH$

| | | A549 | HT29 | MDA-MB-231 | PSN1 | | A549 | HT29 | MDA-MB-231 | PSN1 |
|---|---|---|---|---|---|---|---|---|---|---|
| GI$_{50}$ | 3-R | 4.03E−10 | 2.77E−10 | 2.77E−10 | 3.90E−10 | B | 2.06E−08 | 8.48E−09 | 9.00E−09 | 1.93E−08 |
| TGI | | 5.79E−10 | >1.26E−07 | 5.04E−10 | 6.05E−10 | | 2.19E−08 | 9.13E−09 | 1.67E−08 | 2.06E−08 |
| LC$_{50}$ | | >1.26E−07 | >1.26E−07 | 1.25E−09 | >1.26E−07 | | >1.29E−07 | >1.29E−07 | 3.47E−08 | 2.31E−08 |
| GI$_{50}$ | 10-R | 3.76E−09 | 3.08E−09 | 2.85E−09 | 2.62E−09 | | | | | |
| TGI | | 5.93E−09 | >1.14E−07 | 4.33E−09 | 3.88E−09 | | | | | |
| LC$_{50}$ | | >1.14E−07 | >1.14E−07 | 7.18E−09 | 6.61E−09 | | | | | |
| GI$_{50}$ | 11-R | 1.77E−09 | 1.39E−09 | 1.01E−09 | 1.39E−09 | | | | | |
| TGI | | 4.54E−09 | >1.26E−07 | 1.51E−09 | 1.89E−09 | | | | | |
| LC$_{50}$ | | >1.26E−07 | >1.26E−07 | 2.65E−09 | >1.26E−07 | | | | | |
| GI$_{50}$ | 4-R | 1.27E−09 | 1.26E−09 | 1.27E−09 | 4.59E−10 | D | 1.25E−08 | 1.03E−08 | 9.88E−09 | 2.08E−08 |
| TGI | | 1.40E−09 | 1.40E−09 | 1.40E−09 | 8.54E−10 | | 2.86E−08 | 2.34E−08 | 1.95E−08 | 2.21E−08 |
| LC$_{50}$ | | >1.27E−07 | >1.27E−07 | 1.53E−09 | 2.55E−09 | | >1.30E−07 | >1.30E−07 | 5.33E−08 | 2.47E−08 |
| GI$_{50}$ | 12-R | 1.40E−09 | 5.74E−10 | 3.19E−10 | 4.98E−10 | | | | | |
| TGI | | 2.93E−09 | 1.10E−09 | 6.76E−10 | 1.22E−09 | | | | | |
| LC$_{50}$ | | 1.22E−08 | 2.93E−09 | 1.40E−09 | >1.28E−07 | | | | | |
| GI$_{50}$ | 13-R | 7.26E−09 | 6.91E−09 | 4.95E−09 | 2.88E−09 | | | | | |
| TGI | | 7.72E−09 | 7.60E−09 | 7.95E−09 | 3.11E−09 | | | | | |
| LC$_{50}$ | | >1.15E−07 | >1.15E−07 | 1.38E−08 | 3.46E−09 | | | | | |

TABLE 3

Biological activity (Molar)

Compound:
- 38-S R₁ = CN, R₄ = —CH₂OH
- 45-S R₁ = CN, R₄ = —CH₂NHAlloc
- 46-S R₁ = CN, R₄ = —CH₂NH₂
- 39-S R₁ = OH, R₄ = —CH₂OH
- 47-S R₁ = OH, R₄ = —CH₂NH₂

Reference compound:
- A R₁ = CN
- C R₁ = OH

|  |  | A549 | HT29 | MDA-MB-231 | PSN1 | PC-3 | 22Rv1 |  | A549 | HT29 | MDA-MB-231 | PSN1 |
| --- | --- | --- | --- | --- | --- | --- | --- | --- | --- | --- | --- | --- |
| GI$_{50}$ | 38-S | 8.05E−09 | 4.53E−09 | 2.52E−09 | 5.03E−09 |  |  | A | 8.36E−09 | 7.71E−09 | 7.07E−09 | 1.29E−08 |
| TGI |  | 8.55E−09 | 7.05E−09 | 4.28E−09 | 8.18E−09 |  |  |  | 8.87E−09 | 8.36E−09 | 9.38E−09 | 1.54E−08 |
| LC$_{50}$ |  | 9.44E−09 | >1.26E−07 | 7.80E−09 | 1.51E−08 |  |  |  | >1.29E−07 | >1.29E−07 | 1.41E−08 | 1.93E−08 |
| GI$_{50}$ | 45-S | 1.82E−08 | 1.82E−08 | 1.71E−08 | 1.94E−08 |  |  |  |  |  |  |  |
| TGI |  | 1.94E−08 | 1.94E−08 | 2.16E−08 | 2.62E−08 |  |  |  |  |  |  |  |
| LC$_{50}$ |  | 2.16E−08 | >1.14E−07 | 2.96E−08 | 3.64E−08 |  |  |  |  |  |  |  |
| GI$_{50}$ | 46-S | 8.19E−09 | 2.77E−09 | 3.65E−09 | 3.15E−09 |  |  |  |  |  |  |  |
| TGI |  | 2.14E−08 | 6.17E−09 | 6.80E−09 | 4.79E−09 |  |  |  |  |  |  |  |
| LC$_{50}$ |  | >1.26E−07 | >1.26E−07 | 1.26E−08 | 9.20E−09 |  |  |  |  |  |  |  |
| GI$_{50}$ | 39-S | 4.84E−09 | 3.94E−09 | 3.44E−09 | 8.02E−09 | 2.78E−09 | 4.81E−10 | C | 2.73E−08 | 2.08E−08 | 2.60E−08 | 3.64E−08 |
| TGI |  | 8.27E−09 | 6.74E−09 | 7.13E−09 | 1.02E−08 |  |  |  | 6.63E−08 | 2.34E−08 | 5.46E−08 | 4.42E−08 |
| LC$_{50}$ |  | 1.65E−08 | >1.27E−07 | 1.78E−08 | 1.27E−08 |  |  |  | >1.30E−07 | >1.30E−07 | >1.30E−07 | 6.50E−08 |
| GI$_{50}$ | 47-S | 1.40E−08 | 4.33E−09 | 6.24E−09 | 5.99E−09 |  |  |  |  |  |  |  |
| TGI |  | 2.80E−08 | 6.75E−09 | 9.68E−09 | 8.54E−09 |  |  |  |  |  |  |  |
| LC$_{50}$ |  | >1.27E−07 | >1.27E−07 | 1.66E−08 | 1.27E−08 |  |  |  |  |  |  |  |

TABLE 4

Biological activity (Molar)

Compound

38-R R₁ = CN, R₄ = —CH₂OH
45-R R₁ = CN, R₄ = —CH₂NHAlloc
46-R R₁ = CN, R₄ = —CH₂NH₂
39-R R₁ = OH, R₄ = —CH₂OH
47-R R₁ = OH, R₄ = —CH₂NH₂

Reference compound

B R₁ = CN
D R₁ = OH

|  |  | A549 | HT29 | MDA-MB-231 | PSN1 |  | A549 | HT29 | MDA-MB-231 | PSN1 |
| --- | --- | --- | --- | --- | --- | --- | --- | --- | --- | --- |
| GI$_{50}$ | 38-R | 6.54E−10 | 5.41E−10 | 4.53E−10 | 6.54E−10 | B | 2.06E−08 | 8.48E−09 | 9.00E−09 | 1.93E−08 |
| TGI |  | 1.04E−09 | 5.91E−10 | 8.43E−10 | 9.94E−10 |  | 2.19E−08 | 9.13E−09 | 1.67E−08 | 2.06E−08 |
| LC$_{50}$ |  | >1.26E−07 | >1.26E−07 | 2.01E−09 | 1.76E−09 |  | >1.29E−07 | >1.29E−07 | 3.47E−08 | 2.31E−08 |
| GI$_{50}$ | 45-R | 1.82E−08 | 1.25E−08 | 9.57E−09 | 1.06E−08 |  |  |  |  |  |
| TGI |  | 1.94E−08 | 2.28E−08 | 1.94E−08 | 1.94E−08 |  |  |  |  |  |
| LC$_{50}$ |  | 2.39E−08 | >1.14E−07 | 4.33E−08 | 3.76E−08 |  |  |  |  |  |
| GI$_{50}$ | 46-R | 1.51E−09 | 1.21E−09 | 1.23E−09 | 9.95E−10 |  |  |  |  |  |
| TGI |  | 2.77E−09 | 1.39E−09 | 1.39E−09 | 1.51E−09 |  |  |  |  |  |
| LC$_{50}$ |  | >1.26E−07 | >1.26E−07 | 1.51E−09 | 2.65E−09 |  |  |  |  |  |
| GI$_{50}$ | 39-R | 2.67E−10 | 2.93E−10 | 2.04E−10 | 3.65E−10 | D | 1.25E−08 | 1.03E−08 | 9.88E−09 | 2.08E−08 |
| TGI |  | 4.33E−10 | 6.24E−10 | 5.98E−10 | 5.73E−10 |  | 2.86E−08 | 2.34E−08 | 1.95E−08 | 2.21E−08 |
| LC$_{50}$ |  | >1.27E−07 | >1.27E−07 | 2.80E−09 | 1.06E−09 |  | >1.30E−07 | >1.30E−07 | 5.33E−08 | 2.47E−08 |
| GI$_{50}$ | 47-R | 2.04E−09 | 8.03E−10 | 5.99E−10 | 1.40E−09 |  |  |  |  |  |
| TGI |  | 3.82E−09 | 1.40E−09 | 1.17E−09 | 2.04E−09 |  |  |  |  |  |
| LC$_{50}$ |  | 1.40E−08 | >1.27E−07 | 2.55E−09 | 3.31E−09 |  |  |  |  |  |

TABLE 5

Biological activity (Molar)

Compound

MeO-substituted tetrahydro-β-carboline linked via ester to ecteinascidin-type pentacyclic core:

18-S R$_1$ = CN, R$_4$ = —CH$_2$OH
25-S R$_1$ = CN, R$_4$ = —CH$_2$NHAlloc
26-S R$_1$ = CN, R$_4$ = —CH$_2$NH$_2$
19-S R$_1$ = OH, R$_4$ = —CH$_2$OH
27-S R$_1$ = OH, R$_4$ = —CH$_2$NH$_2$ Reference Compound

E R$_1$ = CN
PM01183 R$_1$ = OH

|  |  | A549 | HT29 | MDA-MB-231 | PSN1 |  | A549 | HT29 | MDA-MB-231 | PSN1 |
|---|---|---|---|---|---|---|---|---|---|---|
| GI$_{50}$ | 18-S | 1.70E−09 | 1.21E−09 | 1.21E−09 | 9.59E−10 | E | 3.28E−09 | 3.15E−09 | 2.27E−09 | 2.77E−09 |
| TGI |  | 3.03E−09 | 1.34E−09 | 1.34E−09 | 1.34E−09 |  | 3.40E−09 | 3.40E−09 | 3.78E−09 | 4.53E−09 |
| LC$_{50}$ |  | >1.21E−07 | >1.21E−07 | 1.58E−09 | >1.21E−07 |  | 4.41E−09 | >1.26E−07 | 7.43E−09 | 8.94E−09 |
| GI$_{50}$ | 25-S | 7.17E−09 | 7.17E−09 | 5.84E−09 | 6.84E−09 |  |  |  |  |  |
| TGI |  | 7.61E−09 | 7.72E−09 | 9.04E−09 | 9.26E−09 |  |  |  |  |  |
| LC$_{50}$ |  | >1.10E−07 | >1.10E−07 | 1.54E−08 | 1.43E−08 |  |  |  |  |  |
| GI$_{50}$ | 26-S | 1.12E−08 | 2.79E−09 | 1.34E−09 | 3.04E−09 |  |  |  |  |  |
| TGI |  | 2.19E−08 | 3.16E−09 | 1.94E−09 | 3.28E−09 |  |  |  |  |  |
| LC$_{50}$ |  | >1.22E−07 | >1.22E−07 | 3.89E−09 | 3.52E−09 |  |  |  |  |  |
| GI$_{50}$ | 19-S | 3.07E−09 | 1.35E−09 | 1.96E−09 | 2.95E−09 | PM01183 | 3.31E−09 | 1.91E−09 | 2.29E−09 | 3.19E−09 |
| TGI |  | 3.31E−09 | 1.60E−09 | 3.31E−09 | 3.19E−09 |  | 3.57E−09 | 4.46E−09 | 3.95E−09 | 3.95E−09 |
| LC$_{50}$ |  | >1.23E−07 | >1.23E−07 | 1.10E−08 | >1.23E−07 |  | >1.27E−07 | >1.27E−07 | 1.02E−08 | 5.73E−09 |
| GI$_{50}$ | 27-S | 6.02E−09 | 1.23E−09 | 1.19E−09 | 1.97E−09 |  |  |  |  |  |
| TGI |  | 1.12E−08 | 1.35E−09 | 1.23E−09 | 2.83E−09 |  |  |  |  |  |
| LC$_{50}$ |  | >1.23E−07 | >1.23E−07 | 1.35E−09 | 4.55E−09 |  |  |  |  |  |

TABLE 6

Biological activity (Molar)

Compound

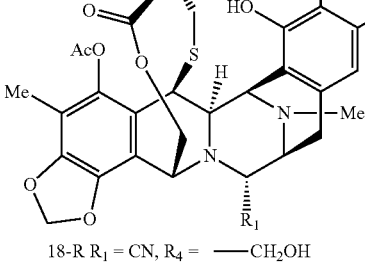

18-R $R_1$ = CN, $R_4$ = —CH$_2$OH
25-R $R_1$ = CN, $R_4$ = —CH$_2$NHAlloc
26-R $R_1$ = CN, $R_4$ = —CH$_2$NH$_2$
19-R $R_1$ = OH, $R_4$ = —CH$_2$OH
27-R $R_1$ = OH, $R_4$ = —CH$_2$NH$_2$ Reference Compound

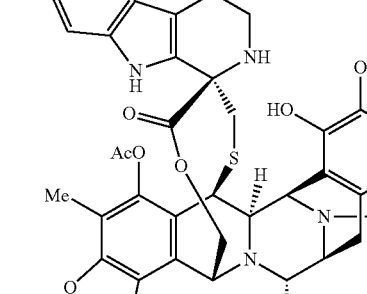

E $R_1$ = CN
PM01183 $R_1$ = OH

|  |  | A549 | HT29 | MDA-MB-231 | PSN1 |  | A549 | HT29 | MDA-MB-231 | PSN1 |
|---|---|---|---|---|---|---|---|---|---|---|
| GI$_{50}$ | 18-R | 1.21E−09 | 1.21E−09 | 1.21E−09 | 5.70E−10 | E | 3.28E−09 | 3.15E−09 | 2.27E−09 | 2.77E−09 |
| TGI |  | 1.34E−09 | 1.34E−09 | 1.34E−09 | 1.06E−09 |  | 3.40E−09 | 3.40E−09 | 3.78E−09 | 4.53E−09 |
| LC$_{50}$ |  | >1.21E−07 | >1.21E−07 | 1.46E−09 | >1.21E−07 |  | 4.41E−09 | >1.26E−07 | 7.43E−09 | 8.94E−09 |
| GI$_{50}$ | 25-R | 1.32E−09 | 1.54E−09 | 1.21E−09 | 1.21E−09 |  |  |  |  |  |
| TGI |  | 2.43E−09 | 2.76E−09 | 2.54E−09 | 2.32E−09 |  |  |  |  |  |
| LC$_{50}$ |  | 9.92E−09 | >1.10E−07 | 8.38E−09 | 6.73E−09 |  |  |  |  |  |
| GI$_{50}$ | 26-R | 1.94E−09 | 7.29E−10 | 1.17E−09 | 9.72E−10 |  |  |  |  |  |
| TGI |  | 3.40E−09 | 1.58E−09 | 1.22E−09 | 1.70E−09 |  |  |  |  |  |
| LC$_{50}$ |  | >1.22E−07 | >1.22E−07 | 1.46E−09 | 3.52E−09 |  |  |  |  |  |
| GI$_{50}$ | 19-R | 1.47E−09 | 1.72E−09 | 1.23E−09 | 1.23E−09 | PM01183 | 3.31E−09 | 1.91E−09 | 2.29E−09 | 3.19E−09 |
| TGI |  | 3.56E−09 | 1.72E−09 | 1.35E−09 | 1.35E−09 |  | 3.57E−09 | 4.46E−09 | 3.95E−09 | 3.95E−09 |
| LC$_{50}$ |  | >1.23E−07 | >1.23E−07 | >1.23E−07 | 1.47E−09 |  | >1.27E−07 | >1.27E−07 | 1.02E−08 | 5.73E−09 |
| GI$_{50}$ | 27-R | 2.09E−09 | 5.04E−10 | 3.07E−10 | 6.39E−10 |  |  |  |  |  |
| TGI |  | 3.93E−09 | 5.53E−10 | 5.41E−10 | 1.17E−09 |  |  |  |  |  |
| LC$_{50}$ |  | 1.01E−08 | >1.23E−07 | 8.60E−10 | 2.46E−09 |  |  |  |  |  |

TABLE 7

Biological activity (Molar)

Compound:
- 31 R₁ = CN, R₃ = H,
- 32 R₁ = OH, R₃ = H
- 34 R₁ = CN, R₃ = OMe
- 35 R₁ = OH, R₃ = OMe Reference compound:
- F R₁ = CN, R₃ = H
- ET-736 R₁ = OH, R₃ = H
- E R₁ = CN, R₃ = OMe
- PM01183 R₁ = OH, R₃ = OMe

|  |  | A549 | HT29 | MDA-MB-231 | PSN1 |  | A549 | HT29 | MDA-MB-231 | PSN1 |
| --- | --- | --- | --- | --- | --- | --- | --- | --- | --- | --- |
| GI$_{50}$ | 31 | 1.96E−08 | 1.05E−08 | 8.89E−09 | 6.80E−09 | F | 3.80E−08 | 2.09E−08 | 1.96E−08 | 3.27E−08 |
| TGI |  | 2.09E−08 | 1.57E−08 | 1.70E−08 | 1.57E−08 |  | 7.20E−08 | 2.36E−08 | 3.40E−08 | 6.02E−08 |
| LC$_{50}$ |  | 2.35E−08 | >1.31E−07 | 3.53E−08 | 4.31E−08 |  | >1.31E−07 | >1.31E−07 | 7.33E−08 | 1.07E−07 |
| GI$_{50}$ | 32 | 6.88E−09 | 6.88E−09 | 4.76E−09 | 6.09E−09 | ET-736 | 2.25E−08 | 2.12E−08 | 2.12E−08 | 3.97E−08 |
| TGI |  | >1.32E−08 | >1.32E−08 | 1.05E−08 | 8.34E−09 |  | 4.77E−08 | 2.25E−08 | 2.52E−08 | 5.96E−08 |
| LC$_{50}$ |  | >1.32E−08 | >1.32E−08 | >1.32E−08 | 1.20E−08 |  | >1.32E−07 | >1.32E−07 | 4.77E−08 | 1.02E−07 |
| GI$_{50}$ | 34 | 5.91E−08 | 5.41E−08 | 4.53E−08 | 5.41E−08 | E | 3.28E−09 | 3.15E−09 | 2.27E−09 | 2.77E−09 |
| TGI |  | 8.05E−08 | 8.55E−08 | 7.67E−08 | 5.91E−08 |  | 3.40E−09 | 3.40E−09 | 3.78E−09 | 4.53E−09 |
| LC$_{50}$ |  | >1.26E−07 | 1.25E−07 | 1.12E−07 | >1.26E−07 |  | 4.41E−09 | >1.26E−07 | 7.43E−09 | 8.94E−09 |
| GI$_{50}$ | 35 | 8.14E−09 | 7.89E−09 | 4.58E−09 | 6.24E−09 | PM01183 | 3.31E−09 | 1.91E−09 | 2.29E−09 | 3.19E−09 |
| TGI |  | 8.78E−09 | 8.65E−09 | 8.27E−09 | 9.03E−09 |  | 3.57E−09 | 4.46E−09 | 3.95E−09 | 3.95E−09 |
| LC$_{50}$ |  | >1.27E−07 | >1.27E−07 | 1.65E−08 | 1.40E−08 |  | >1.27E−07 | >1.27E−07 | 1.02E−08 | 5.73E−09 |

TABLE 8

Biological activity (Molar)

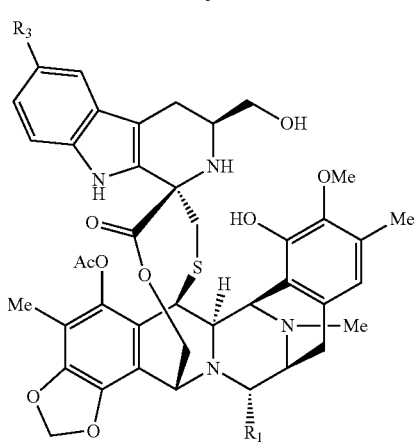

Compound

3-S $R_1$ = CN, $R_3$ = H
4-S $R_1$ = OH, $R_3$ = H
18-S $R_1$ = CN, $R_3$ = OMe
19-S $R_1$ = OH, $R_3$ = OMe

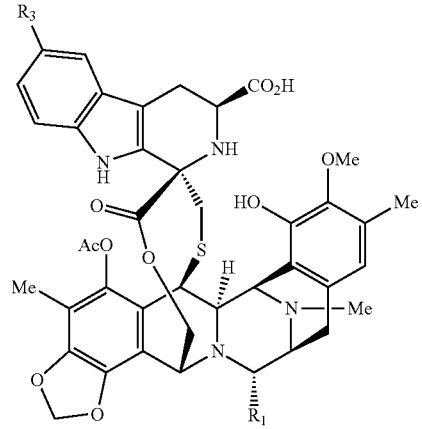

Reference compound

14-S $R_1$ = CN, $R_3$ = H
15-S $R_1$ = OH, $R_3$ = H
28-S $R_1$ = CN, $R_3$ = OMe
29-S $R_1$ = OH, $R_3$ = OMe

|   |   | A549 | HT29 | MDA-MB-231 | PSN1 |   | A549 | HT29 | MDA-MB-231 | PSN1 |
|---|---|---|---|---|---|---|---|---|---|---|
| $GI_{50}$ | 3-S | 4.03E−10 | 2.77E−10 | 4.91E−10 | 9.95E−10 | 14-S | >1.24E−07 | 1.21E−07 | 5.45E−08 | >1.24E−07 |
| TGI |  | 6.17E−10 | >1.26E−07 | 5.29E−10 | 1.64E−09 |  | >1.24E−07 | >1.24E−07 | 1.13E−07 | >1.24E−07 |
| $LC_{50}$ |  | >1.26E−07 | >1.26E−07 | 6.17E−10 | >1.26E−07 |  | >1.24E−07 | >1.24E−07 | >1.24E−07 | >1.24E−07 |
| $GI_{50}$ | 4-S | 1.27E−09 | 1.27E−09 | 1.22E−09 | 1.78E−09 | 15-S | >1.25E−06 | 3.00E−07 | 1.63E−07 | 2.38E−07 |
| TGI |  | 1.40E−09 | 1.40E−09 | 2.55E−09 | 2.29E−09 |  | >1.25E−06 | 5.13E−07 | 2.13E−07 | 4.63E−07 |
| $LC_{50}$ |  | >1.27E−07 | >1.27E−07 | 6.50E−09 | 3.44E−09 |  | >1.25E−06 | 9.14E−07 | 2.75E−07 | 8.39E−07 |
| $GI_{50}$ | 18-S | 1.70E−09 | 1.21E−09 | 1.21E−09 | 9.59E−10 | 28-S | 4.89E−07 | 2.51E−07 | 1.67E−07 | 2.51E−07 |
| TGI |  | 3.03E−09 | 1.34E−09 | 1.34E−09 | 1.34E−09 |  | >1.19E−06 | 3.46E−07 | 2.51E−07 | 3.94E−07 |
| $LC_{50}$ |  | >1.21E−07 | >1.21E−07 | 1.58E−09 | >1.21E−07 |  | >1.19E−06 | 6.33E−07 | 3.94E−07 | 6.92E−07 |
| $GI_{50}$ | 19-S | 3.07E−09 | 1.35E−09 | 1.96E−09 | 2.95E−09 | 29-S | 6.15E−07 | 3.62E−07 | 2.17E−07 | 3.86E−07 |
| TGI |  | 3.31E−09 | 1.60E−09 | 3.31E−09 | 3.19E−09 |  | >1.21E−06 | 5.31E−07 | 3.74E−07 | 5.07E−07 |
| $LC_{50}$ |  | >1.23E−07 | >1.23E−07 | 1.10E−08 | >1.23E−07 |  | >1.21E−06 | 8.32E−07 | 6.88E−07 | 6.88E−07 |

TABLE 9

Biological activity (Molar)

Compound: 18-R R$_1$ = CN; 19-R R$_1$ = OH (structure with MeO, OH, NH, OMe, HO, Me, AcO, S, N-Me, O, R$_1$)

Reference Compound: 28-R R$_1$ = CN; 29-R R$_1$ = OH (structure with MeO, CO$_2$H, NH, OMe, HO, Me, AcO, S, N-Me, O, R$_1$)

|  |  | A549 | HT29 | MDA-MB-231 | PSN1 |  | A549 | HT29 | MDA-MB-231 | PSN1 |
|---|---|---|---|---|---|---|---|---|---|---|
| GI$_{50}$ | 18-R | 1.21E−09 | 1.21E−09 | 1.21E−09 | 5.71E−10 | 28-R | 1.67E−07 | 3.10E−08 | 1.91E−08 | 2.15E−08 |
| TGI |  | 1.34E−09 | 1.34E−09 | 1.34E−09 | 1.06E−09 |  | 3.58E−07 | 3.34E−08 | 3.22E−08 | 3.58E−08 |
| LC$_{50}$ |  | >1.21E−07 | >1.21E−07 | 1.46E−09 | >1.21E−07 |  | >1.19E−06 | >1.19E−06 | 9.19E−08 | 6.68E−08 |
| GI$_{50}$ | 19-R | 1.47E−09 | 1.72E−09 | 1.23E−09 | 1.23E−09 | 29-R | 9.05E−08 | 3.02E−08 | 1.69E−08 | 3.02E−08 |
| TGI |  | 3.56E−09 | 1.72E−09 | 1.35E−09 | 1.35E−09 |  | 1.93E−07 | 3.26E−08 | 2.77E−08 | 3.14E−08 |
| LC$_{50}$ |  | >1.23E−07 | >1.23E−07 | >1.23E−07 | 1.47E−09 |  | >1.21E−06 | >1.21E−06 | 1.57E−07 | 3.50E−08 |

The compounds of the present invention are shown to have high potency in vitro, when compared against reference compounds. This demonstrates that the compounds according to the present invention exhibit high cytoxiticy towards cancer cells and are useful in the treatment of cancer.

Example 28. MTD and MTMD Determination

Female CD-1 or Athymic Nude-Fox1 nu/nu mice (Envigo) were utilized for all experiments. Animals (N=10/cage) were housed in individually ventilated cages (Sealsafe Plus®, Techniplast S.P.A.), on a 12-hour light-dark cycle at 21-23° C. and 40-60% humidity. Mice were allowed free access to irradiated standard rodent diet (Tecklad 2914C) and sterilized water. Animals were acclimated for five days prior to being individually tattoo-identified. Animal protocols were reviewed and approved according to the regional Institutional Animal Care and Use Committees.

Mice were randomly allocated into experimental groups and intravenously administered, once for the MTD (Maximum Tolerated Dose) determination or one administration a week during three consecutive weeks, for the MTMD (Maximum Tolerated Multiple Dose) determination study. The animals were administered with white formulation or with compound dissolved in the experimental formulation at different concentrations. The volume administered was always 10 mL/kg. Once administered, animals were monitored for clinical signs of systemic toxicity, changes in body weight and mortality up to 14 days after the administration.

MTD results are summarized in Table 10

TABLE 10

| Compound | Route/Schedule | Doses (mg/Kg) | MTD (mg/kg) |
|---|---|---|---|
| 4-S | iv/SD | 0.00, 0.25, 0.50, 1.00, 1.50, 2.00, 2.50, 5.00 | 1.0 |
| 4-R |  |  | 0.25 |
| 19-S |  |  | 0.5 |
| 19-R |  | 0.00, 0.10, 0.15, 0.25, 0.50, 1.00, 1.50, 2.00, 2.50, 5.00 | 0.15 |
| Comp C |  | 0.00, 0.25, 0.50, 1.00, 1.50, 2.00, 2.50, 3.00, 4.00, 5.00 | 3.0 |
| Comp D |  | 0.00, 0.25, 0.50, 1.00, 2.00, 4.00, 6.00, 8.00 | 0.5 |
| 32 |  | 0.00, 0.25, 0.50, 1.00, 1.50, 2.00, 2.50, 5.00 | 0.5 |

MTMD results are summarized in Table 11

TABLE 11

| Compound | Route/Schedule | Doses (mg/Kg) | MTMD (mg/kg) |
|---|---|---|---|
| 4-S | iv/Q7dx3 | 0.00, 0.50, 0.75, 1.00, 1.25 | 1.25 |
| 4-R |  | 0.00, 0.15, 0.20, 0.25, 0.30 | 0.30 |
| 12-S |  | 0.00, 0.10, 0.25, 0.50, 0.75, 1.00, 1.25, 1.50, 2.00, 2.50, 5.00 | 0.25 |
| 12-R |  | 0.00, 0.010, 0.025, 0.050, 0.075, 0.10, 0.25, 0.50, 0.75, 1.00, 1.25, 1.50, 2.00, 2.50, 5.00 | 0.05 |
| 19-S |  | 0.00, 0.10, 0.25, 0.50, 0.75 | 0.75 |
| 19-R |  | 0.00, 0.025, 0.075, 0.10, 0.15 | 0.15 |
| Comp C |  | 0.0, 1.0, 1.5, 2.0, 3.0, 4.0 | 3.0 |
| Comp D |  | 0.00, 0.10, 0.25, 0.50, 0.75 | 0.5 |
| 32 |  | 0.00, 0.10, 0.25, 0.50, 0.75 | 0.5 |

TABLE 11-continued

| Compound | Route/Schedule | Doses (mg/Kg) | MTMD (mg/kg) |
|---|---|---|---|
| 35 | | 0.00, 0.10, 0.25, 0.50, 0.75 | 0.25 |
| 39-S | | 0.00, 0.01, 0.025, 0.05, 0.075, 0.10, 0.25, 0.50, 0.75, 1.00, 1.25, 1.50, 2.00, 2.50, 5.00 | 1.25 |
| 47-R | | 0.00, 0.01, 0.025, 0.05, 0.075, 0.10, 0.25, 0.50, 0.75, 1.00, 1.25, 1.50, 2.00, 2.50, 5.00 | 0.1 |
| ET-736 | | 0.00, 0.10, 0.25, 0.50, 0.75 | 0.5 |
| PM01183 | | 0.00, 0.14, 0.18 | 0.18 | iv, intravenously
Q7dx3, three cumulated doses administered in a weekly basis.

Examples 29-40. In Vivo Xenografts

Female athymic nu/nu mice (Harlan Laboratories Models, S. L. Barcelona, Spain or Envigo, Spain) were utilized for all experiments. Animal were housed in individually ventilated cages Sealsafe® Plus, Techniplast S.P.A.), up to ten per cage on a 12-hour light-dark cycle at 21-23° C. and 40-60% humidity. Mice were allowed free access to irradiated standard rodent diet (Tecklad 2914C) and sterilized water. Animals were acclimated for at least 5 days prior to tumor implantation with a tumor cell suspension.

CELL LINES

| Name | N° ATCC | N° ECCC* | Species | Tissue | Characteristics |
|---|---|---|---|---|---|
| HT1080 | CCL-121 | — | human | connective | Fibrosarcoma |
| MDA-MB-231 | HTB-26 | — | human | breast | Breast adenocarcinoma |
| H460 | HTB-177 | — | human | lung, pleural effusion | NSCLC |
| A2780 | — | 93112519 | human | ovarian | Ovarian carcinoma |
| HGC27 | — | 94042256 | human | gastric | Gastric carcinoma |
| H526 | CRL-5811 | — | human | lung | SCLC |
| H82 | HTB-175 | — | human | lung | SCLC |
| PC3 | CLR-1435 | — | human | prostate; derived from metastatic site: bone | Prostatic adenocarcinoma |
| DU145 | HTB-81 | | human | prostate; derived from metastatic site: brain | Prostatic carcinoma |
| 22Rv1 | CRL-2505 | | human | prostate | Prostatic carcinoma |

*European Collection of Cell Cultures

HT1080 cells were maintained in vitro at 37° C. with 5% $CO_2$ in Minimum Essential Medium Eagle (MEME) (Sigma-Aldrich, Co). Each animal was orthotopically implanted into gastroecnemius muscle by an intramuscular injection using a 26 G needle and a 1 cc syringe at 4-6 weeks of age, with $10 \times 10^6$ HT1080 cells, suspended in serum free medium, without antibiotics.

MDA-MB-231 cells were maintained in vitro at 37° C. with 5% $CO_2$ in Dulbecco's Modified Eagle's Medium (Sigma-Aldrich, Co). Culture cells were passaged every 3 to 5 days upon reaching confluence. Each animal was subcutaneously implanted (on the right flank using 26 G needle and a 1 cc syringe) at 4-6 weeks of age with $7.5 \times 10^6$ MDA-MB-231 cells suspended in 0.05 mL of a solution consisting of 50% Matrigel® (Corning Incorporated Life Sciences) and 50% medium without serum or antibiotics.

H460 cells were maintained in vitro at 37° C. with 5% $CO_2$ in Dulbecco's Modified Eagle's Medium (Sigma-Aldrich, Co). Culture cells were passaged every 3 to 5 days upon reaching confluence. Each animal was subcutaneously implanted (on the right flank using 26 G needle and a 1 cc syringe) at 4-6 weeks of age with $5 \times 10^6$ H460 cells suspended in 0.05 mL of a solution consisting of 50% Matrigel® (Corning Incorporated Life Sciences) and 50% medium without serum or antibiotics.

A2780 cells were maintained in vitro at 37° C. with 5% $CO_2$ in RPMI-1640 (Sigma-Aldrich, Co). Culture cells were passaged every 3 to 5 days upon reaching confluence. Each animal was subcutaneously implanted (on the right flank using 26 G needle and a 1 cc syringe) at 4-6 weeks of age with $10 \times 10^6$ A2780 cells suspended in 0.05 mL of a solution consisting of 50% Matrigel® (Corning Incorporated Life Sciences) and 50% medium without serum or antibiotics.

HGC27 cells were maintained in vitro at 37° C. with 5% $CO_2$ in Iscove's Modified Dulbecco's Medium (Sigma Aldrich, Co). Culture cells were passage every 3 to 5 days on reaching confluence. Each animal was subcutaneously implanted (on the right flank using 26 G needle and a 1 cc syringe) at 4-6 weeks of age with $5 \times 10^6$ HGC-27 cells suspended in 0.05 mL of a solution consisting of 50% Matrigel® (Corning Incorporated Life Sciences), 50% medium without serum or antibiotics.

H526 cells were maintained in vitro at 37° C. with 5% $CO_2$ in RPMI-1640 Medium (Sigma-Aldrich, Co). H526 cells were grown as a suspension and maintained by addition of fresh medium, as the cell density increases, every 2 to 3 days. Every week, culture was reestablished by centrifugation of the suspension with subsequent resuspension in fresh medium at a concentration of $1 \times 10^5$ cell/mL. Each animal was subcutaneously implanted (on the right flank using 26 G needle and a 1 cc syringe) at 4-6 weeks of age with $5 \times 10^6$ H526 cells suspended in 0.05 mL of a solution consisting of 50% Matrigel® (Corning Incorporated Life Sciences) and 50% medium without serum or antibiotics.

H82 cells were maintained in vitro at 37° C. with 5% $CO_2$ in RPMI-1640 Medium (Sigma-Aldrich, Co). H82 cells were grown as a suspension and maintained by addition of fresh medium, as the cell density increases, every 2 to 3 days. Every week, culture was reestablished by centrifugation of the suspension with subsequent resuspension in fresh medium at a concentration of $1 \times 10^5$ cell/ml. Animals were subcutaneously implanted (on the right flank using 26 G needle and a 1 cc syringe) at 4-6 weeks of age with $5 \times 10^6$ H82 cells, suspended in 0.05 mL of a solution consisting of 50% Matrigel® (Corning Incorporated Life Sciences) and 50% medium without serum or antibiotics.

PC3 cells were maintained in vitro at 37° C. with 5% CO2 in RPMI-1640 Medium (Sigma-Aldrich, Co). Culture cells were passaged every 3 to 5 days upon reaching confluence. Each female athymic mice was subcutaneously implanted (on the right flank using a 26 G needle and a 1 cc syringe) at 4-6 weeks of age with $3 \times 10^6$ PC3 cells suspended in 0.05 mL of a solution consisting of 50% Matrigel® Matrix (Corning Incorporated Life Sciences) and 50% medium without serum or antibiotics. In this model, instead of male, female animals were used because PC-3 growth is not hormone dependant.

DU-145 cells were maintained in vitro at 37° C. with 5% CO2 in RPMI-1640 Medium (Sigma-Aldrich, Co). Culture cells were passaged every 3 to 5 days upon reaching confluence Each male athymic mice was subcutaneously implanted (on the right flank using a 26 G needle and a 1 cc syringe) at 4-6 weeks of age with 5×10⁶ DU-145 cells suspended in 0.05 mL of a solution consisting of 50% Matrigel® Matrix (Corning Incorporated Life Sciences) and 50% medium without serum or antibiotics.

22Rv1 cells were maintained in vitro at 37° C. with 5% $CO_2$ in RPMI-1640 Medium (Sigma-Aldrich, Co). Culture cells were passage every 3 to 5 days upon reaching confluence. Each male athymic mice was subcutaneously implanted (on the right flank using 26 G needle and a 1 cc syringe) at 4-6 weeks of age with 5×10⁶ 22 Rv1 cells suspended in 0.05 mL of a solution consisting of 50% Matrigel® Matrix (Corning Incorporated Life Sciences) and 50% medium without serum or antibiotics.

Treatment tolerability was assessed by monitoring body weight evolution, clinical signs of systemic toxicity, as well as evidences of local damage in the injection site.

In xenograft studies with HT1080 cell line:
Total diameter (tumor+leg) measurements were determined by using digital caliper (Fowler Sylvac, S235PAT). This total diameter and animal body weights were measured 2-3 times per week starting from the first day of treatment (day 0).
When total diameter reached a length of about 7.0-8.0 mm, mice were randomly allocated into the treatments and control groups (N=8-10/group) based on body weight and tumor measurements by using NewLab Oncology Software (version 2.25.06.00).
Comparison of the median total diameter (tumor+leg) in the treatment groups to the median total diameter (tumor+leg) in the control group was used for evaluation of the antitumoral efficacy.
Animals were euthanized when their total leg diameter reached ca. 18 mm.

In xenograft studies with other cell lines:
Tumor volume was calculated using the equation $(a \cdot b^2)/2$, where a: length (longest diameter) and b: width (shortest diameter) were measured in mm by using digital caliper (Fowler Sylvac, S235PAT). Tumor dimensions and body weights were recorded 2-3 times per week starting from the first day of treatment.
When tumors reached ca. 150-250 mm³, tumor bearing animals (N=8-10/group) were randomly allocated into the treatment groups, based on body weight and tumor measurements by using NewLab Oncology Software (version 2.25.06.00).
Comparison between median tumor volume of treated groups and control group was used for evaluation of the antitumoral efficacy.
Animals were euthanized when their tumors reached ca. 2000 mm³ and/or severe necrosis was seen.

Treatments producing >20% lethality and/or 20% net body weight loss were considered toxic.

Tables and figures summarize the data obtained from complete experimental groups, i.e. those groups keeping the initial number of animals, n=8-10. However, once the first animal is sacrificed due to a tumor length >18 mm or a tumor size >2000 mm³, the experimental group will be considered incomplete. Therefore, data generated subsequently to the sacrifice day and onwards will not be presented (i.e. neither in tables nor in the figures).

Example 29. In Vivo Studies to Determine the Effect of 4-S and 12-S in Several Xenograft Models 4-S, 12-S and compound C were provided in the form of freeze-dried vials of lyophilized product. Each vial was reconstituted with water for infusion to a concentration of 0.5 mg/mL. Further dilutions were made with 5% dextrose solution for injection to the dosing formulation concentration. The administered doses of 4-S, 12-S and compound C were 1.25 mg/kg, 0.25 mg/kg and 3.0 mg/kg, respectively.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 4-S, 12-S and Compound C, as well as placebo, were intravenously administered once per week for 3 consecutive weeks, on Days 0, 7 and 14, whenever it was possible.

Example 29a. In Vivo Studies to Determine the Effect of 4-S and 12-S in Human Fibrosarcoma Xenografts The aim of this study was to compare the antitumoral activity of 4-S and 12-S with the antitumoral activity of compound C by using a xenograft model of human sarcoma.

The tumor model used in this study was HT1080 cell line.

Table 12 reports the total diameter (tumor+leg) evaluation of HT1080 tumors in mice treated with placebo, compound C, 4-S, and 12-S. These results are also showed in FIG. 1.

TABLE 12

| | Total diameter (tumor + leg) (mm) | | | |
|---|---|---|---|---|
| Days | Control | Compound C | 4-S | 12-S |
| 0.0 | 7.5 | 7.5 | 7.5 | 7.5 |
| 2.0 | 9.4 | 8.8 | 7.7 | 8.2 |
| 5.0 | 11.4 | 9.0 | 8.3 | 8.6 |
| 7.0 | 12.1 | 9.6 | 8.8 | 9.5 |
| 9.0 | 13.2 | 10.2 | 8.4 | 10.0 |
| 12.0 | 14.5 | 10.2 | 8.4 | 11.2 |
| 14.0 | 15.2 | 11.2 | 9.6 | 11.7 |
| 16.0 | 15.9 | 12.4 | 10.0 | 12.7 |
| 19.0 | 18.0 | 13.3 | 10.4 | 13.5 |
| 21.0 | | 15.2 | 12.1 | 14.4 |
| 23.0 | | 18.0 | 12.7 | 16.5 |
| 27.0 | | | 13.5 | 15.2 |
| 30.0 | | | 15.6 | 16.4 |
| 33.0 | | | 18.0 | |

Example 29b. In Vivo Studies to Determine the Effect of 4-S and 12-S in Human Breast Xenografts The aim of this study was to compare the antitumoral activity of 4-S and 12-S with the antitumoral activity of compound C by using a xenograft model of human breast cancer.

The tumor model used in this study was MDA-MB-231 cell line.

Figure 2:
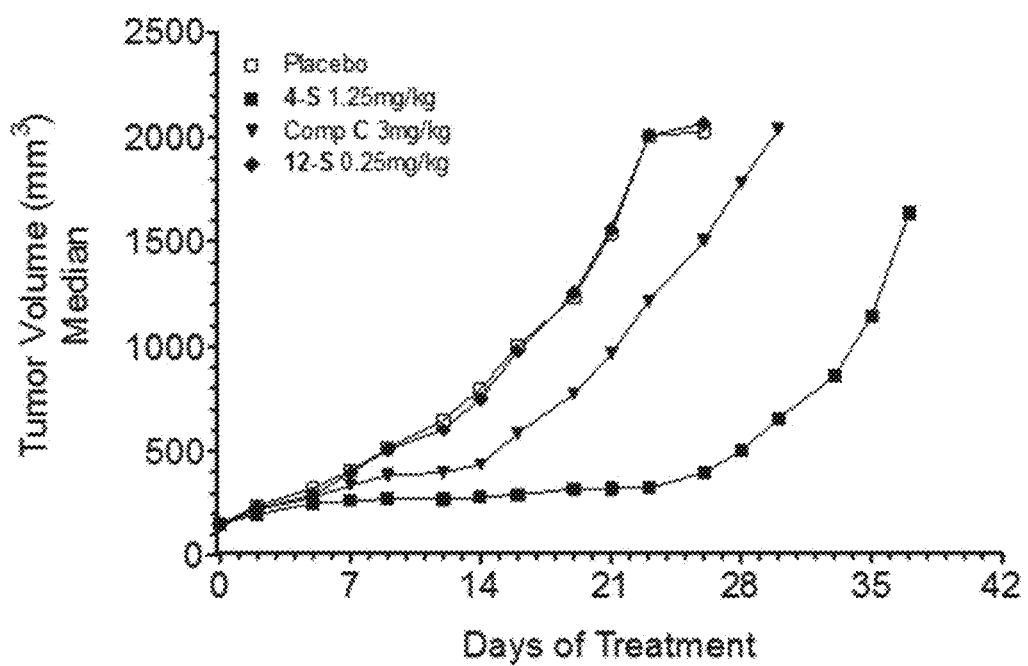
FIG. 2. Tumor volume evaluation of MDA-MB-231 tumors in mice treated with placebo, compound C, 4-S, and 12-S.

Table 13 reports the median tumor volume evaluation of MDA-MB-231 tumors in mice treated with placebo, compound C, 4-S, and 12-S. These results are also showed in FIG. 2.

TABLE 13

| | Median Tumor Volume (mm³) | | | |
|---|---|---|---|---|
| Days | Control | Compound C | 4-S | 12-S |
| 0.0 | 149.4 | 149.4 | 150.6 | 150.2 |
| 2.0 | 240.0 | 217.1 | 197.3 | 229.9 |
| 5.0 | 325.1 | 281.3 | 250.9 | 290.5 |

TABLE 13-continued

| | Median Tumor Volume (mm³) | | | |
|---|---|---|---|---|
| Days | Control | Compound C | 4-S | 12-S |
| 7.0 | 407.8 | 338.6 | 265.0 | 398.2 |
| 9.0 | 514.8 | 385.1 | 272.5 | 508.9 |
| 12.0 | 648.1 | 400.4 | 270.6 | 602.5 |
| 14.0 | 799.0 | 436.9 | 281.3 | 751.0 |
| 16.0 | 1002.5 | 585.7 | 293.6 | 977.7 |
| 19.0 | 1233.9 | 774.7 | 322.1 | 1252.6 |
| 21.0 | 1539.1 | 965.9 | 324.4 | 1560.7 |
| 23.0 | 2006.5 | 1215.2 | 326.6 | 2005.9 |
| 26.0 | 2027.7 | 1503.2 | 398.8 | 2066.2 |
| 28.0 | | 1785.3 | 501.8 | |
| 30.0 | | 2037.1 | 654.8 | |
| 33.0 | | | 856.7 | |
| 35.0 | | | 1147.1 | |
| 37.0 | | | 1635.9 | |

Example 29c. In Vivo Studies to Determine the Effect of 4-S and 12-S in Human Lung Tumor Xenografts The aim of this study was to compare the antitumoral activity of 4-S and 12-S with the antitumoral activity of compound C by using three different xenograft models of human lung cancer. These models correspond to non-small cell lung cancer (H-460 cell line) and to small cell lung cancer (H526 and H82 cell lines).

Figure 3:
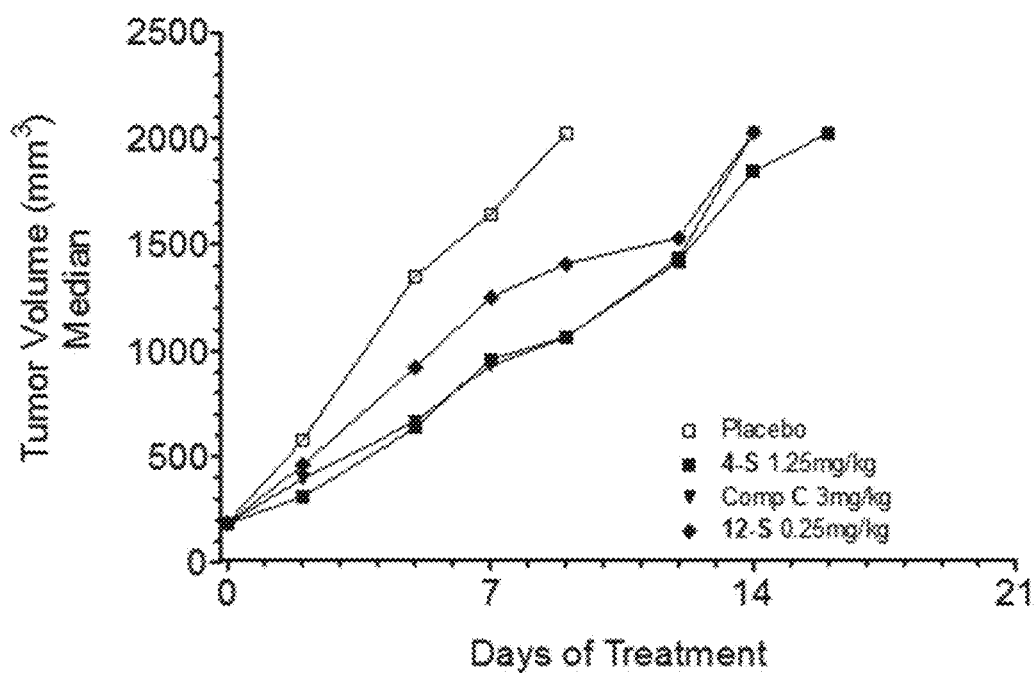
FIG. 3. Tumor volume evaluation of H460 tumors in mice treated with placebo, compound C, 4-S, and 12-S.

Table 14 reports the median tumor volume evaluation of H460 tumors in mice treated with placebo, compound C, 4-S, and 12-S. These results are also showed in FIG. 3.

TABLE 14

| | Median Tumor Volume (mm³) | | | |
|---|---|---|---|---|
| Days | Control | Compound C | 4-S | 12-S |
| 0.0 | 187.4 | 186.1 | 185.9 | 186.0 |
| 2.0 | 577.5 | 395.4 | 310.9 | 460.5 |
| 5.0 | 1352.0 | 665.9 | 634.6 | 922.4 |
| 7.0 | 1642.9 | 929.5 | 959.1 | 1252.1 |
| 9.0 | 2025.0 | 1063.7 | 1064.9 | 1409.4 |
| 12.0 | | 1436.5 | 1421.0 | 1531.7 |
| 14.0 | | 2025.0 | 1845.5 | 2025.0 |
| 16.0 | | 2025.0 | 2025.0 | |

Figure 4:
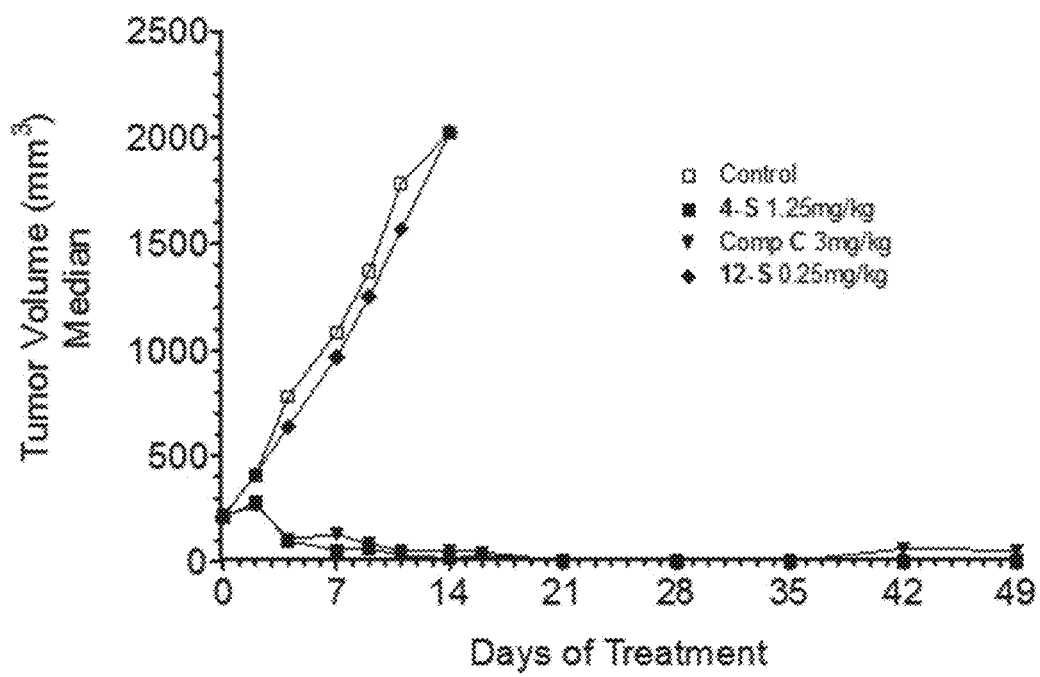
FIG. 4. Tumor volume evaluation of H526 tumors in mice treated with placebo, compound C, 4-S, and 12-S.

Table 15 reports the median tumor volume evaluation of H526 tumors in mice treated with placebo, compound C, 4-S and 12-S. These results are also showed in FIG. 4.

TABLE 15

| | Median Tumor Volume (mm³) | | | |
|---|---|---|---|---|
| Days | Control | Compound C | 4-S | 12-S |
| 0.0 | 217.2 | 217.9 | 211.8 | 212.7 |
| 2.0 | 410.7 | 262.4 | 279.0 | 412.7 |
| 4.0 | 778.5 | 108.3 | 98.8 | 637.9 |
| 7.0 | 1083.2 | 129.8 | 56.7 | 968.5 |
| 9.0 | 1371.0 | 85.9 | 62.5 | 1250.3 |
| 11.0 | 1782.0 | 52.3 | 32.0 | 1568.0 |
| 14.0 | 2025.0 | 54.1 | 18.0 | 2025.0 |
| 16.0 | | 47.3 | 32.0 | |
| 21.0 | | 4.0 | 4.0 | |
| 28.0 | | 4.0 | 4.0 | |
| 35.0 | | 4.0 | 4.0 | |
| 42.0 | | 62.5 | 4.0 | |
| 49.0 | | 53.5 | 4.0 | |

Figure 5:
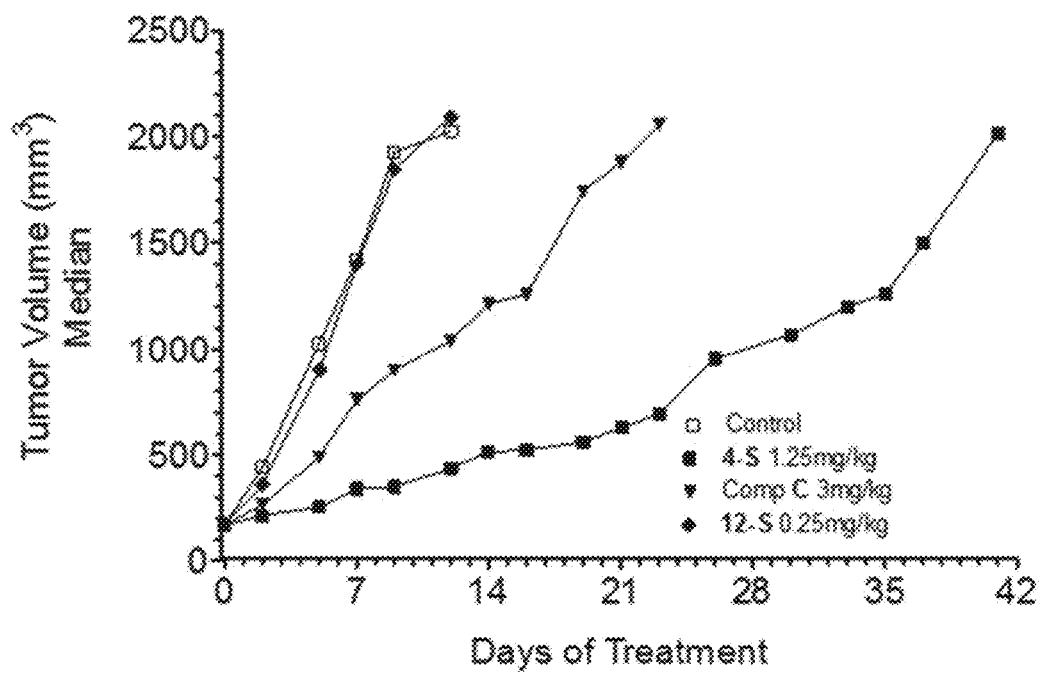
FIG. 5. Tumor volume evaluation of H82 tumors in mice treated with placebo, compound C, 4-S, and 12-S.

Table 16 reports the median tumor volume evaluation of H82 tumors in mice treated with placebo, compound C, 4-S and 12-S. These results are also showed in FIG. 5.

TABLE 16

| | Median Tumor Volume (mm³) | | | |
|---|---|---|---|---|
| Days | Control | Compound C | 4-S | 12-S |
| 0.0 | 171.6 | 170.5 | 168.3 | 174.0 |
| 2.0 | 439.4 | 265.3 | 215.2 | 360.1 |
| 5.0 | 1024.7 | 488.7 | 253.6 | 899.7 |
| 7.0 | 1422.0 | 760.0 | 341.4 | 1398.6 |
| 9.0 | 1923.8 | 899.5 | 349.4 | 1847.6 |
| 12.0 | 2025.0 | 1038.5 | 436.4 | 2089.7 |
| 14.0 | | 1213.4 | 516.0 | |
| 16.0 | | 1256.4 | 521.8 | |
| 19.0 | | 1741.5 | 560.9 | |
| 21.0 | | 1878.8 | 627.7 | |
| 23.0 | | 2057.0 | 690.9 | |
| 26.0 | | | 953.4 | |
| 28.0 | | | 847.1 | |
| 30.0 | | | 1067.5 | |
| 33.0 | | | 1200.6 | |
| 35.0 | | | 1257.7 | |
| 37.0 | | | 1497.7 | |
| 41.0 | | | 2014.2 | |

Example 29d. In Vivo Studies to Determine the Effect of 4-S and 12-S in Human Ovarian Tumor Xenografts The aim of this study was to compare the antitumoral activity of 4-S and 12-S with the antitumoral activity of compound C by using a xenograft model of human ovarian cancer.

The tumor model used in this study was A2780.

Figure 6:
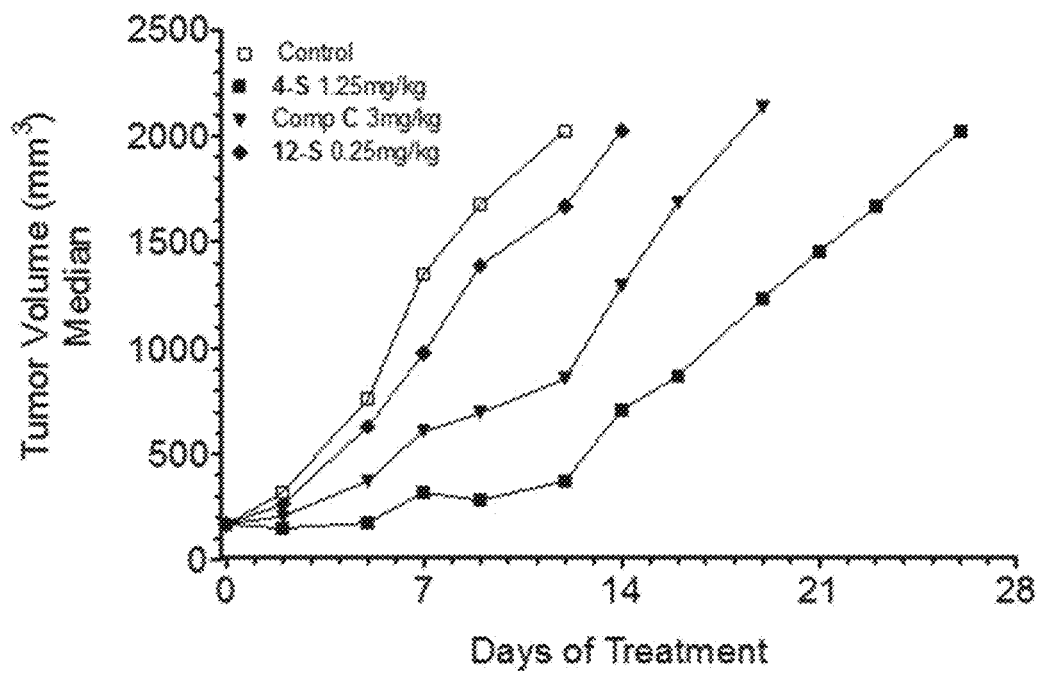
FIG. 6. Tumor volume evaluation of A2780 tumors in mice treated with placebo, compound C, 4-S, and 12-S.

Table 17 reports the volume evaluation of A2780 tumors in mice treated with placebo, compound C, 4-S, and 12-S. These results are also showed in FIG. 6.

TABLE 17

| | Median Tumor Volume (mm³) | | | |
|---|---|---|---|---|
| Days | Control | Compound C | 4-S | 12-S |
| 0.0 | 169.5 | 169.6 | 168.3 | 168.5 |
| 2.0 | 317.5 | 206.3 | 150.6 | 262.1 |
| 5.0 | 758.9 | 372.7 | 175.9 | 628.6 |
| 7.0 | 1351.9 | 607.6 | 317.7 | 976.3 |
| 9.0 | 1675.8 | 696.2 | 281.9 | 1387.5 |
| 12.0 | 2025.0 | 855.6 | 372.1 | 1666.0 |
| 14.0 | | 1293.9 | 709.2 | 2025.0 |
| 16.0 | | 1683.5 | 870.9 | |
| 19.0 | | 2137.5 | 1235.4 | |
| 21.0 | | | 1453.3 | |
| 23.0 | | | 1666.0 | |
| 26.0 | | | 2025.0 | |

Example 29e. In Vivo Studies to Determine the Effect of 4-S and 12-S in Human Gastric Tumor Xenografts The aim of this study was to compare the antitumoral activity of 4-S and 12-S with the antitumoral activity of Compound C by using a xenograft model of human gastric cancer.

The tumor model used in this study was HGC27.

Figure 7:
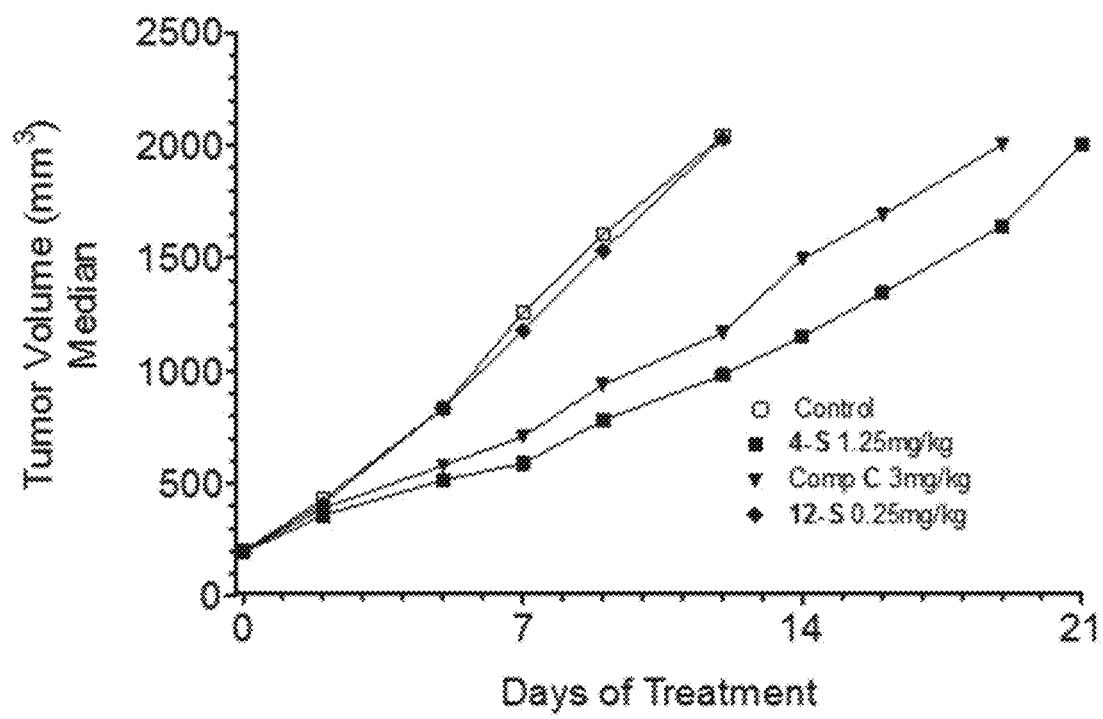
FIG. 7. Tumor volume evaluation of HGC-27 tumors in mice treated with placebo, compound C, 4-S, and 12-S.

Table 18 reports tumor volume growth of HGC27 tumors in mice treated with placebo, compound C, 4-S, and 12-S. These results are also showed in FIG. 7.

TABLE 18

| | Median Tumor Volume (mm³) | | | |
|---|---|---|---|---|
| Days | Control | Compound C | 4-S | 12-S |
| 0.0 | 200.7 | 195.0 | 194.8 | 196.6 |
| 2.0 | 429.0 | 391.0 | 358.6 | 411.9 |
| 5.0 | 835.5 | 578.6 | 515.3 | 834.1 |
| 7.0 | 1256.5 | 708.2 | 589.2 | 1176.6 |
| 9.0 | 1602.2 | 937.7 | 779.4 | 1531.6 |
| 12.0 | 2040.7 | 1169.5 | 980.8 | 2030.2 |
| 14.0 | | 1496.8 | 1153.3 | |
| 16.0 | | 1690.6 | 1346.2 | |
| 19.0 | | 2004.0 | 1643.4 | |
| 21.0 | | | 2004.7 | |

Example 30. In Vivo Studies to Determine the Effect of 4-R in Several Xenograft Models 4-R was provided in the form of freeze dried vials. 4-R cake was reconstituted with water for infusion to a concentration of 0.5 mg/mL. The 4-R stock solution was further diluted in 5% dextrose solution for injection to the dosing formulation concentration. The 4-R administered dose was 0.30 mg/kg.

Compound D was provided in the form of drug substance vials. Each vial was reconstituted first by total dissolution in DMSO and then adding Kolliphor ELP (BASF)/ethanol absolute (1:1, v/v) to a concentration of 0.8 mg/mL. Further dilutions were made with a lactate buffer solution (pH=4.0) to the dosing formulation concentration. The Compound D administered dose was 0.5 mg/kg.

PM01183 was provided in the form of vials of lyophilized product. Each vial was reconstituted with water for infusion to a concentration of 0.2 mg/mL. Further dilutions were made with 5% glucose or 0.9% sodium chloride solution for injection to the dosing formulation concentrations. The administered dose was 0.18 mg/kg.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 4-R, Compound D and PM01183, as well as placebo, were intravenously administered once per week for 3 consecutive weeks, on Days 0, 7 and 14, whenever it was possible.

Example 30a. In Vivo Studies to Determine the Effect of 4-R in Human Fibrosarcoma Xenografts The aim of this study was to compare the antitumoral activity of 4-R and Compound D with the antitumoral activity of PM01183 by using a xenograft model of human sarcoma.

The tumor model used in this study was HT1080 cell line.

Figure 8:
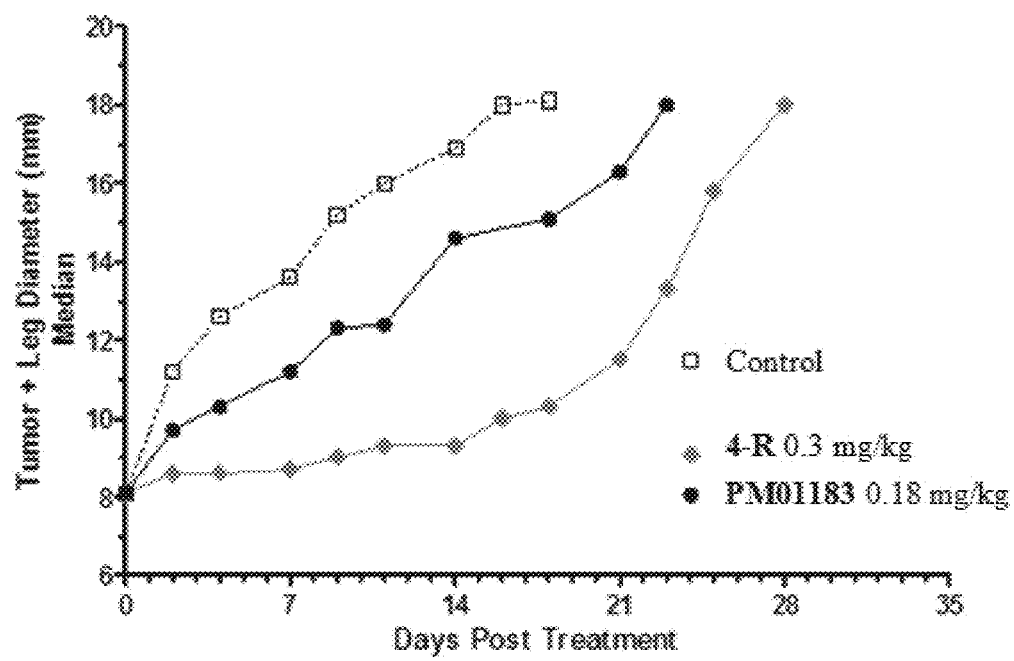
FIG. 8. Tumor total diameter evaluation of HT1080 tumors in mice treated with placebo, PM01183 and 4-R.

Table 19 reports the total diameter (tumor+leg) evaluation of HT1080 tumors in mice treated with placebo, PM01183 and 4-R. These results are also showed in FIG. 8.

TABLE 19

| | Total diameter (tumor + leg) (mm) | | |
|---|---|---|---|
| Days | Control | PM01183 | 4-R |
| 0 | 8.1 | 8.1 | 8.1 |
| 2 | 11.2 | 9.7 | 8.6 |
| 7 | 13.6 | 11.2 | 8.7 |

TABLE 19-continued

| | Total diameter (tumor + leg) (mm) | | |
|---|---|---|---|
| Days | Control | PM01183 | 4-R |
| 9 | 15.2 | 12.3 | 9.0 |
| 14 | 16.9 | 14.6 | 9.3 |
| 18 | 18.1 | 15.6 | 10.3 |
| 21 | | 15.1 | 11.5 |
| 23 | | 16.3 | 13.3 |
| 25 | | 18.0 | 15.8 |
| 28 | | | 18.0 |

Figure 9:
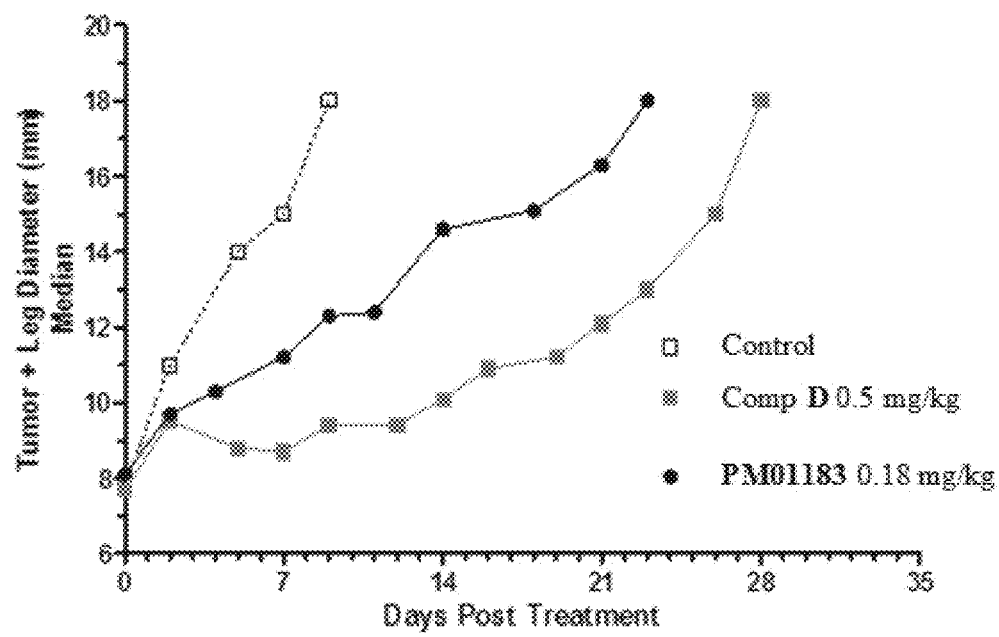
FIG. 9. Tumor total diameter evaluation of HT1080 tumors in mice treated with placebo, PM01183 and Compound D.

Table 20 reports the total diameter (tumor+leg) evaluation of HT1080 tumors in mice treated with placebo, PM01183 and Compound D. These results are also showed in FIG. 9.

TABLE 20

| | Total diameter (tumor + leg) (mm) | | |
|---|---|---|---|
| Days | Control | PM01183 | Compound D |
| 0 | 7.8 | 7.7 | 7.7 |
| 2 | 11.0 | 9.2 | 9.5 |
| 5 | 14.0 | 9.8 | 8.8 |
| 7 | 15.0 | 12.2 | 8.7 |
| 9 | 18.0 | 12.6 | 9.4 |
| 12 | | 13.1 | 9.4 |
| 14 | | 14.6 | 10.1 |
| 16 | | 14.5 | 10.9 |
| 19 | | 15.0 | 11.2 |
| 21 | | 18.0 | 12.1 |
| 23 | | | 13.0 |
| 26 | | | 15.0 |
| 28 | | | 18.0 |

Example 30b. In Vivo Studies to Determine the Effect of 4-R in Human Breast Xenografts The aim of this study was to compare the antitumoral activity of 4-R and Compound D with the antitumoral activity of PM01183 by using a xenograft model of human breast cancer.

The tumor model used in this study was MDA-MB-231 cell line.

Figure 10:
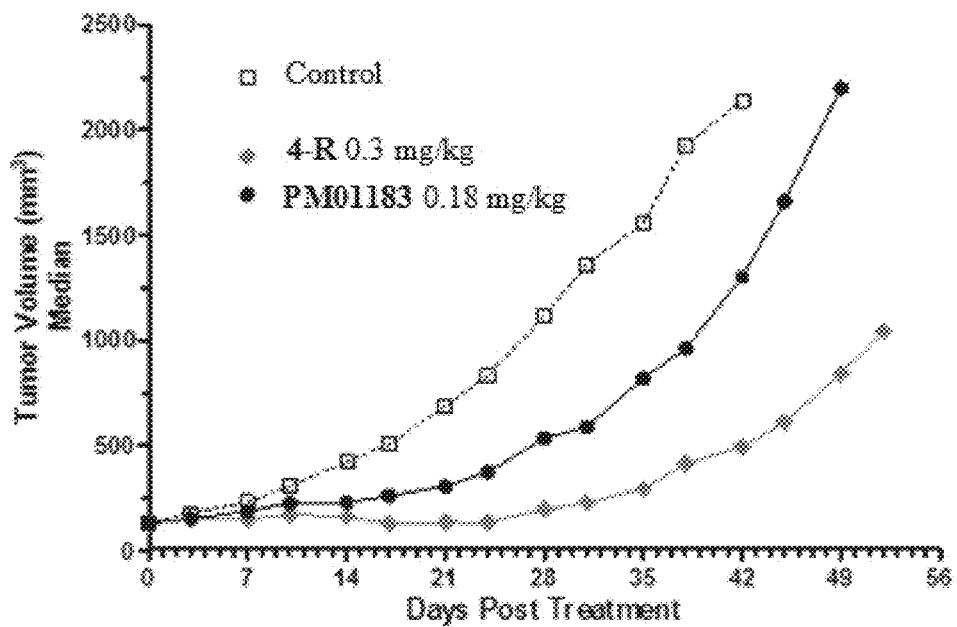
FIG. 10. Tumor volume evaluation of MDA-MB-231 tumors in mice treated with placebo, PM01183 and 4-R.

Table 21 reports the median tumor volume evaluation of MDA-MB-231 tumors in mice treated with placebo, PM01183 and 4-R. These results are also showed in FIG. 10.

TABLE 21

| | Median Tumor Volume (mm³) | | |
|---|---|---|---|
| Days | Control | PM01183 | 4-R |
| 0 | 130.6 | 129.3 | 129.3 |
| 7 | 230.7 | 189.0 | 151.9 |
| 14 | 422.2 | 230.1 | 164.1 |
| 21 | 687.7 | 305.9 | 136.8 |
| 28 | 1114.9 | 535.8 | 195.9 |
| 35 | 1555.3 | 819.7 | 294.2 |
| 42 | 2138.5 | 962.7 | 494.4 |
| 49 | | 1301.3 | 843.8 |
| 52 | | 2199.4 | 1042.5 |

Figure 11:
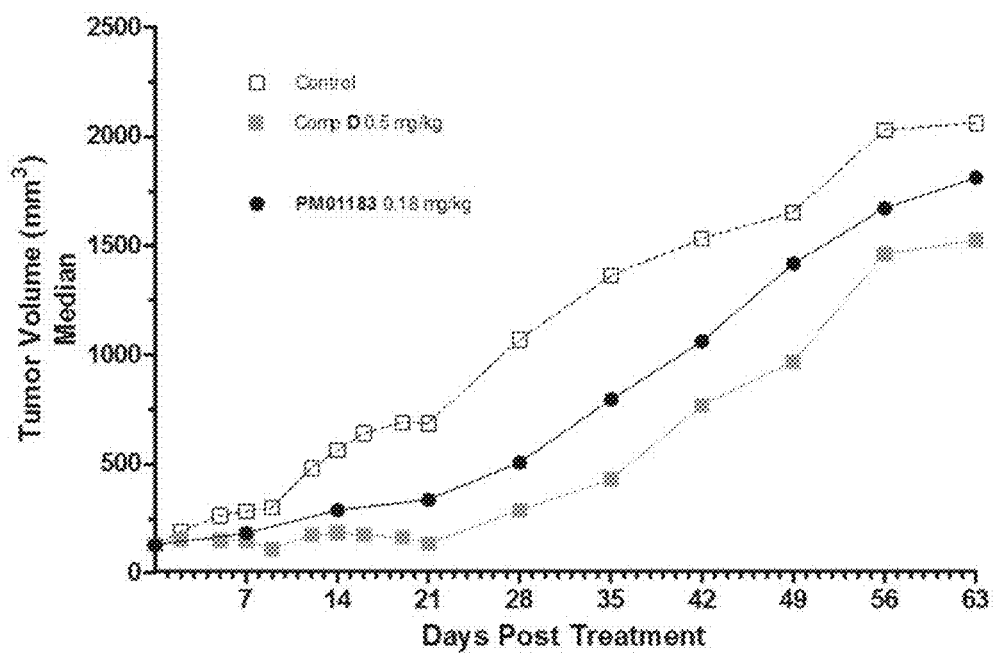
FIG. 11. Tumor volume evaluation of MDA-MB-231 tumors in mice treated with placebo, PM01183 and Compound D.

Table 22 reports the volume evaluation of MDA-MB-231 tumors in mice treated with placebo, PM01183 and Compound D. These results are also showed in FIG. 11.

TABLE 22

| | Median Tumor Volume (mm³) | | |
|---|---|---|---|
| Days | Control | PM01183 | Compound D |
| 0 | 129.2 | 129.6 | 129.5 |
| 7 | 284.0 | 185.9 | 147.9 |
| 14 | 564.3 | 290.8 | 186.4 |
| 21 | 686.0 | 337.9 | 136.5 |
| 28 | 1068.6 | 507.4 | 290.7 |
| 35 | 1359.4 | 796.1 | 431.7 |
| 42 | 1533.7 | 1062.5 | 770.1 |
| 49 | 1653.1 | 1416.3 | 970.0 |
| 56 | 2029.3 | 1673.3 | 1461.9 |
| 63 | 2060.8 | 1811.9 | 1526.4 |

Example 30c. In Vivo Studies to Determine the Effect of 4-R in Human Lung Tumor Xenografts The aim of this study was to compare the antitumoral activity of 4-R and Compound D with the antitumoral activity of PM01183 by using a xenograft model of human lung cancer.

The tumor model used in this study was H-460 cell line.

Figure 12:
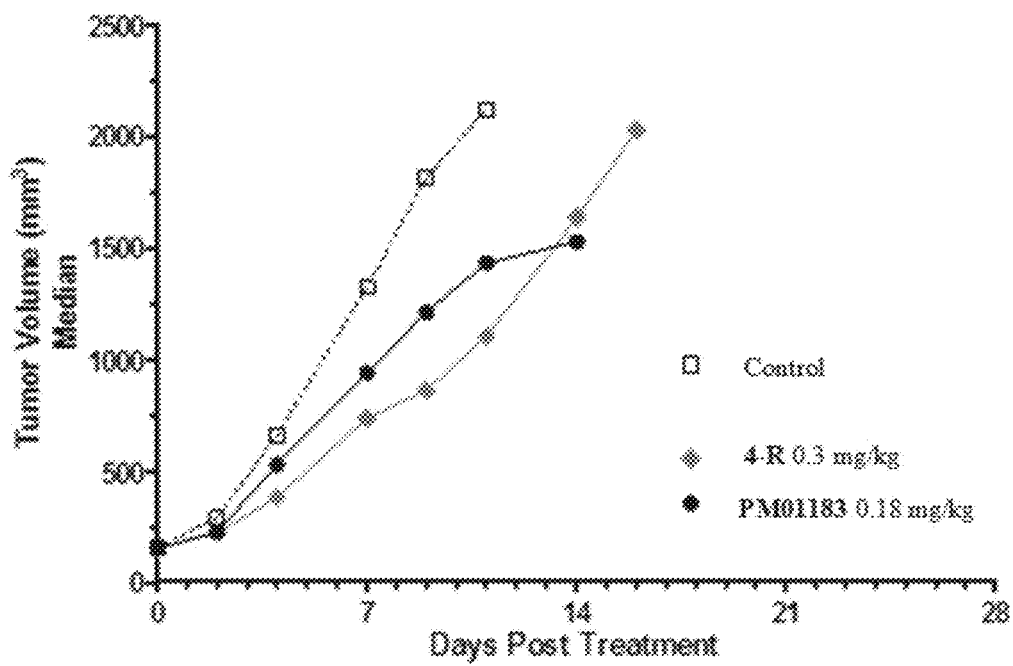
FIG. 12. Tumor volume evaluation of H460 tumors in mice treated with placebo, PM01183 and 4-R.

Table 23 reports the volume evaluation of H460 tumors in mice treated with placebo, PM01183 and 4-R. These results are also showed in FIG. 12.

TABLE 23

| | Median Tumor Volume (mm³) | | |
|---|---|---|---|
| Days | Control | PM01183 | 4-R |
| 0 | 156.2 | 156.7 | 155.5 |
| 2 | 290.9 | 227.3 | 223.3 |
| 7 | 1323.8 | 940.4 | 737.8 |
| 9 | 1816.9 | 1210.3 | 861.0 |
| 11 | 2120.9 | 1433.8 | 1102.9 |
| 14 | | 1529.5 | 1638.0 |
| 16 | | | 2028.6 |

Figure 13:
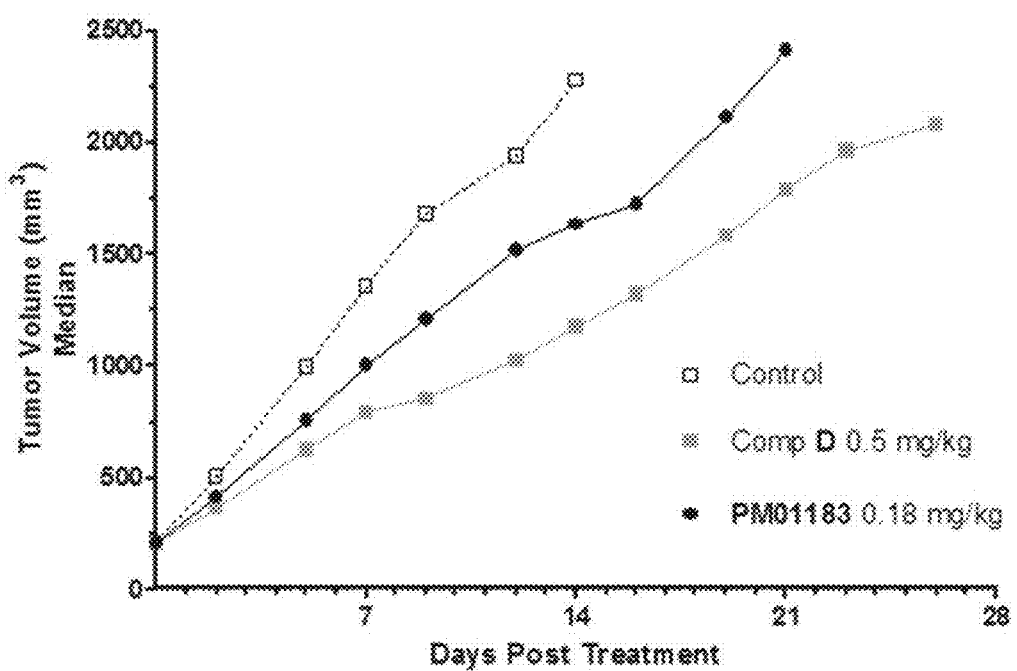
FIG. 13. Tumor volume evaluation of H460 tumors in mice treated with placebo, PM01183 and Compound D.

Table 24 reports the volume evaluation of H460 tumors in mice treated with placebo, PM01183 and Compound D. These results are also showed in FIG. 13.

TABLE 24

| | Median Tumor Volume (mm³) | | |
|---|---|---|---|
| Days | Control | PM01183 | Compound D |
| 0 | 205.2 | 204.5 | 203.4 |
| 2 | 508.0 | 418.1 | 367.3 |
| 7 | 1355.8 | 1004.0 | 792.0 |
| 9 | 1682.1 | 1211.3 | 854.6 |
| 12 | 1938.6 | 1515.4 | 1026.7 |
| 14 | 2275.9 | 1633.3 | 1175.8 |
| 16 | | 1723.9 | 1322.1 |
| 19 | | 2112.3 | 1581.1 |
| 21 | | 2409.4 | 1789.3 |
| 23 | | | 1966.5 |
| 26 | | | 2080.7 |

Example 30d. In Vivo Studies to Determine the Effect of 4-R in Human Ovarian Tumor Xenografts The aim of this study was to compare the antitumoral activity of 4-R and Compound D with the antitumoral activity of PM01183 by using a xenograft model of human ovarian cancer.

The tumor model used in this study was A2780.

Figure 14:
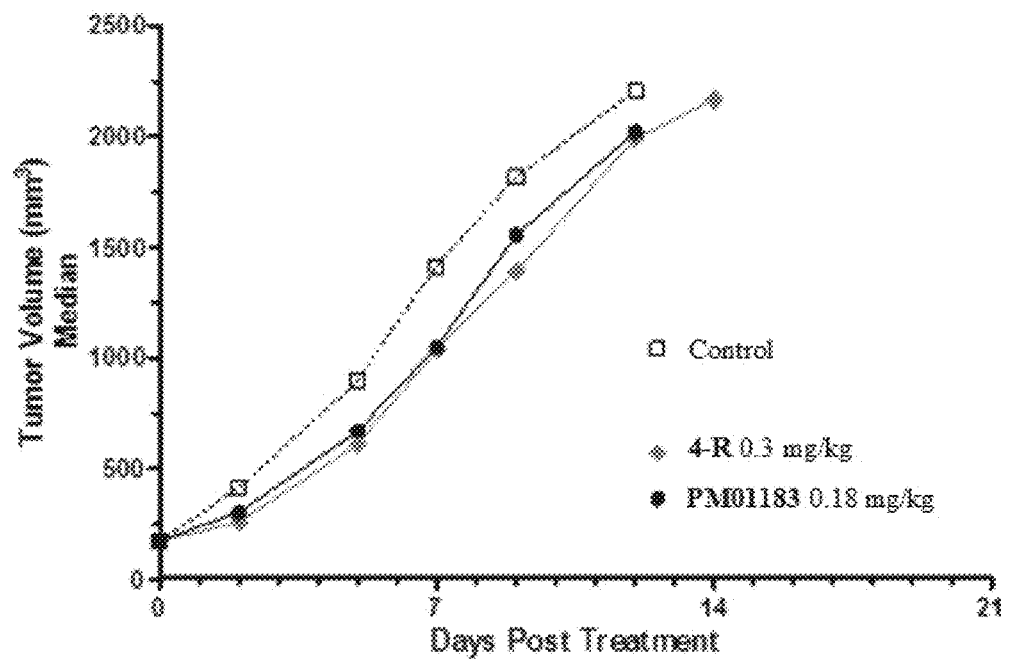
FIG. 14. Tumor volume evaluation of A2780 tumors in mice treated with placebo, PM01183 and 4-R.

Table 25 reports the volume evaluation of A2780 tumors in mice treated with placebo, PM01183 and 4-R. These results are also showed in FIG. 14.

TABLE 25

| | Median Tumor Volume (mm³) | | |
|---|---|---|---|
| Days | Control | PM01183 | 4-R |
| 0 | 172.8 | 175.5 | 175.2 |
| 5 | 896.6 | 671.2 | 611.4 |
| 7 | 1415.3 | 1048.9 | 1036.5 |
| 12 | 2205.3 | 2020.3 | 1992.0 |
| 14 | | | 2165.3 |

Figure 15:
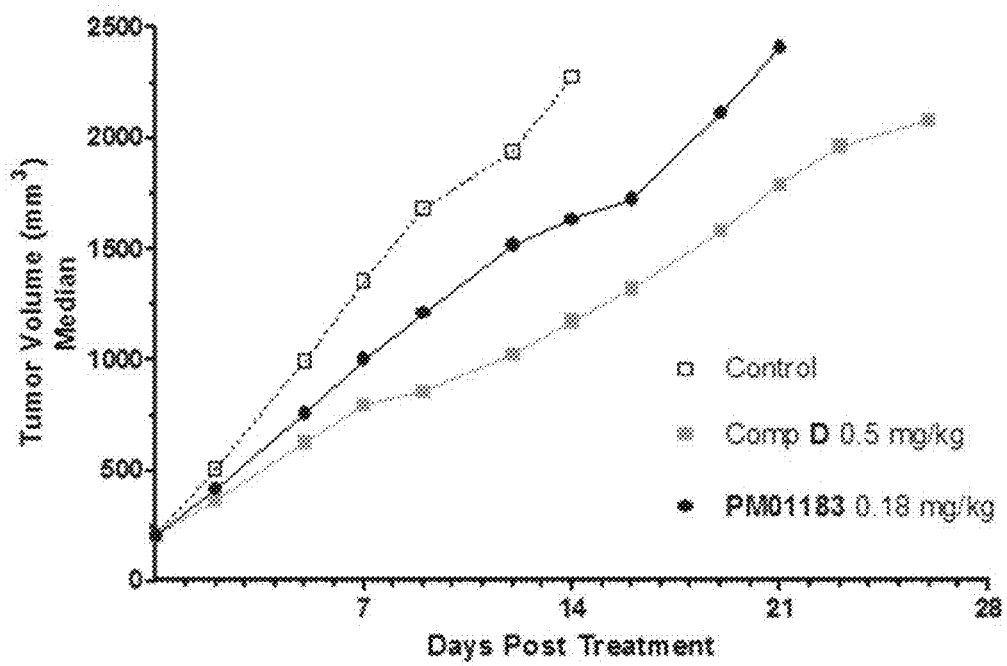
FIG. 15. Tumor volume evaluation of A2780 tumors in mice treated with placebo, PM01183 and Compound D.

Table 26 reports the volume evaluation of A2780 tumors in mice treated with placebo, PM01183 and Compound D. These results are also showed in FIG. 15.

TABLE 26

| | Median Tumor Volume (mm³) | | |
|---|---|---|---|
| Days | Control | PM01183 | Compound D |
| 0 | 189.4 | 191.2 | 190.1 |
| 3 | 588.5 | 454.5 | 319.6 |
| 5 | 1086.0 | 772.1 | 514.4 |
| 7 | 1428.6 | 1161.5 | 897.4 |
| 10 | 2077.1 | 1615.6 | 1239.8 |
| 12 | 2163.1 | 1703.0 | 1656.2 |
| 14 | | 2029.3 | 1951.7 |
| 17 | | | 2121.7 |
| 19 | | | 2068.6 |

Example 30e. In Vivo Studies to Determine the Effect of 4-R in Human Gastric Tumor Xenografts The aim of this study was to compare the antitumoral activity of 4-R and Compound D with the antitumoral activity of PM01183 by using a xenograft model of human gastric cancer.

The tumor model used in this study was HGC27.

Figure 16:
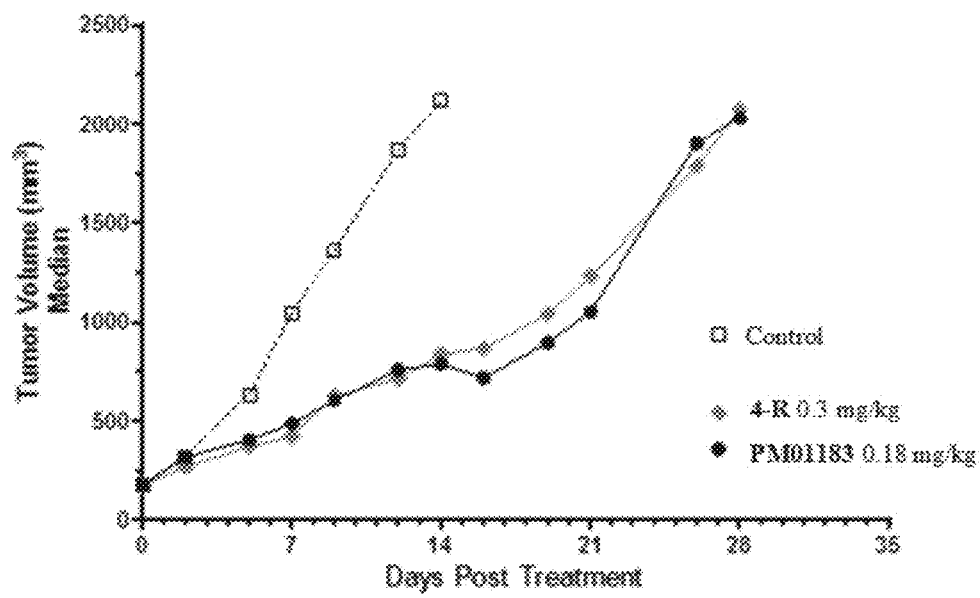
FIG. 16. Tumor volume evaluation of HGC-27 tumors in mice treated with placebo, PM01183 and 4-R.

Table 27 reports tumor volume growth of HGC27 tumors in mice treated with placebo, PM01183 and 4-R. These results are also showed in FIG. 16.

TABLE 27

| | Median Tumor Volume (mm³) | | |
|---|---|---|---|
| Days | Control | PM01183 | 4-R |
| 0 | 174.6 | 171.6 | 173.0 |
| 2 | 319.1 | 317.5 | 266.8 |
| 5 | 632.5 | 404.0 | 370.7 |
| 7 | 1046.0 | 485.7 | 418.5 |
| 9 | 1359.1 | 604.6 | 627.8 |
| 12 | 1863.8 | 760.8 | 713.5 |
| 14 | 2115.0 | 789.6 | 837.0 |
| 16 | | 719.5 | 867.1 |
| 19 | | 895.9 | 1040.2 |
| 21 | | 1051.3 | 1229.8 |
| 26 | | 1901.2 | 1784.5 |
| 28 | | 2028.9 | 2073.6 |

Figure 17:
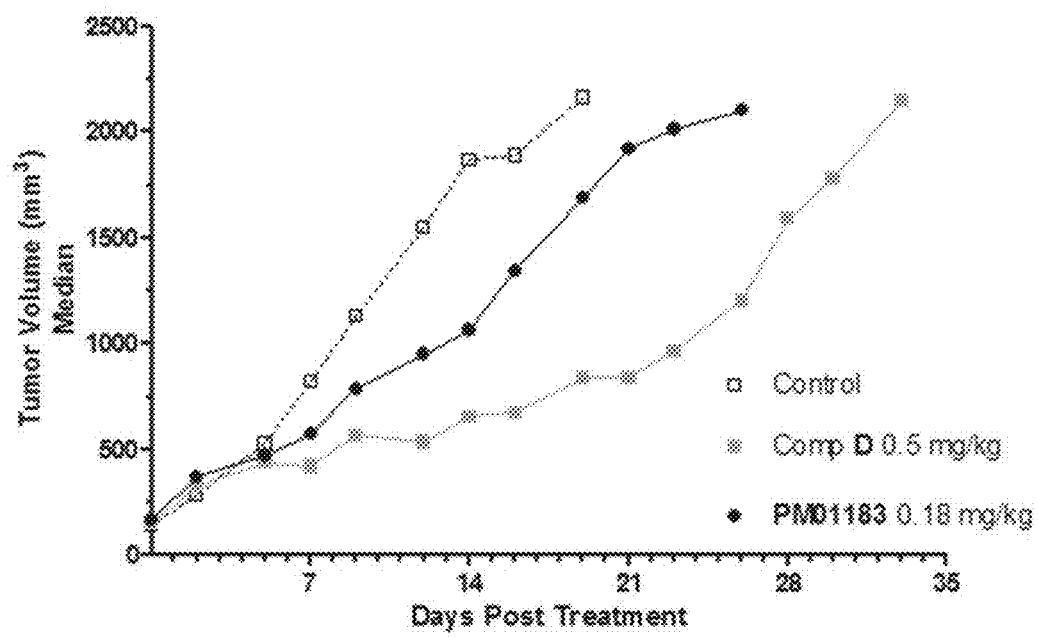
FIG. 17. Tumor volume evaluation of HGC-27 tumors in mice treated with placebo, PM01183 and Compound D.

Table 28 reports tumor volume growth of HGC27 tumors in mice treated with placebo, PM01183 and Compound D. These results are also showed in FIG. 17.

TABLE 28

| | Median Tumor Volume (mm³) | | |
|---|---|---|---|
| Days | Control | PM01183 | Compound D |
| 0 | 142.3 | 169.5 | 157.4 |
| 2 | 286.5 | 372.4 | 327.6 |
| 5 | 527.7 | 474.1 | 439.6 |
| 7 | 821.4 | 571.8 | 418.7 |
| 9 | 1130.9 | 787.9 | 567.9 |
| 12 | 1547.8 | 951.1 | 537.0 |
| 14 | 1868.5 | 1064.4 | 654.6 |
| 16 | 1887.0 | 1346.1 | 672.4 |
| 19 | 2162.3 | 1691.8 | 843.0 |
| 21 | | 1920.0 | 842.7 |
| 23 | | 2011.4 | 963.7 |
| 26 | | 2102.2 | 1203.3 |
| 28 | | | 1589.7 |
| 30 | | | 1777.6 |
| 33 | | | 2146.2 |

Example 31. In Vivo Studies to Determine the Effect of 12-R in Several Xenograft Models 12-R was provided in the form of freeze dries vials. 12-R cake was reconstituted with water for infusion to a concentration of 0.5 mg/mL. The 12-R stock solution was further diluted in 5% dextrose solution for injection to the dosing formulation concentration. The 12-R administered dose was 0.05 mg/kg.

Compound D was provided in the form of drug substance vials. Each vial was reconstituted first by total dissolution in DMSO and then adding Kolliphor ELP (BASF)/ethanol absolute (1:1, v/v) to a concentration of 0.8 mg/mL. Further dilutions were made with a lactate buffer solution (pH=4.0) to the dosing formulation concentration. The Compound D administered dose was 0.5 mg/kg.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 12-R, Compound D, as well as placebo, were intravenously administered once per week for 3 consecutive weeks, on Days 0, 7 and 14, whenever it was possible.

Example 31a. In Vivo Studies to Determine the Effect of 12-R in Human Fibrosarcoma Xenografts The aim of this study was to compare the antitumoral activity of 12-R with the antitumoral activity of Compound D by using a xenograft model of human sarcoma.

The tumor model used in this study was HT1080 cell line.

Figure 18:
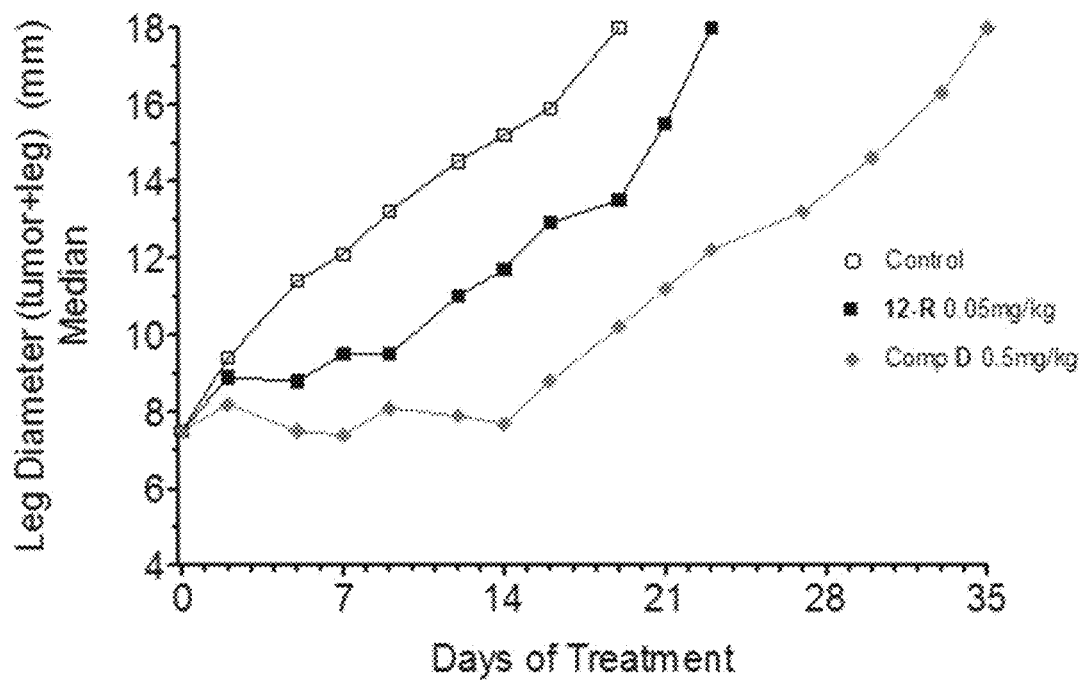
FIG. 18. Tumor total diameter evaluation of HT1080 tumors in mice treated with placebo, compound D and 12-R.

Table 29 reports the total diameter (tumor+leg) evaluation of HT1080 tumors in mice treated with placebo, Compound D and 12-R. These results are also showed in FIG. 18.

TABLE 29

| | Total diameter (tumor + leg) (mm) | | |
|---|---|---|---|
| Days | Control | Compound D | 12-R |
| 0.0 | 7.5 | 7.5 | 7.5 |
| 2.0 | 9.4 | 8.2 | 8.9 |
| 5.0 | 11.4 | 7.5 | 8.8 |
| 7.0 | 12.1 | 7.4 | 9.5 |
| 9.0 | 13.2 | 8.1 | 9.5 |
| 12.0 | 14.5 | 7.9 | 11.0 |
| 14.0 | 15.2 | 7.7 | 11.7 |
| 16.0 | 15.9 | 8.8 | 12.9 |
| 19.0 | 18.0 | 10.2 | 13.5 |
| 21.0 | | 11.2 | 15.5 |
| 23.0 | | 12.2 | 18.0 |
| 27.0 | | 13.2 | |
| 30.0 | | 14.6 | |
| 33.0 | | 16.3 | |
| 35.0 | | 18.0 | |

Example 31b. In Vivo Studies to Determine the Effect of 12-R in Human Breast Xenografts The aim of this study was to compare the antitumoral activity of 12-R with the antitumoral activity of Compound D by using a xenograft model of human breast cancer.

The tumor model used in this study was MDA-MB-231 cell line.

Figure 19:
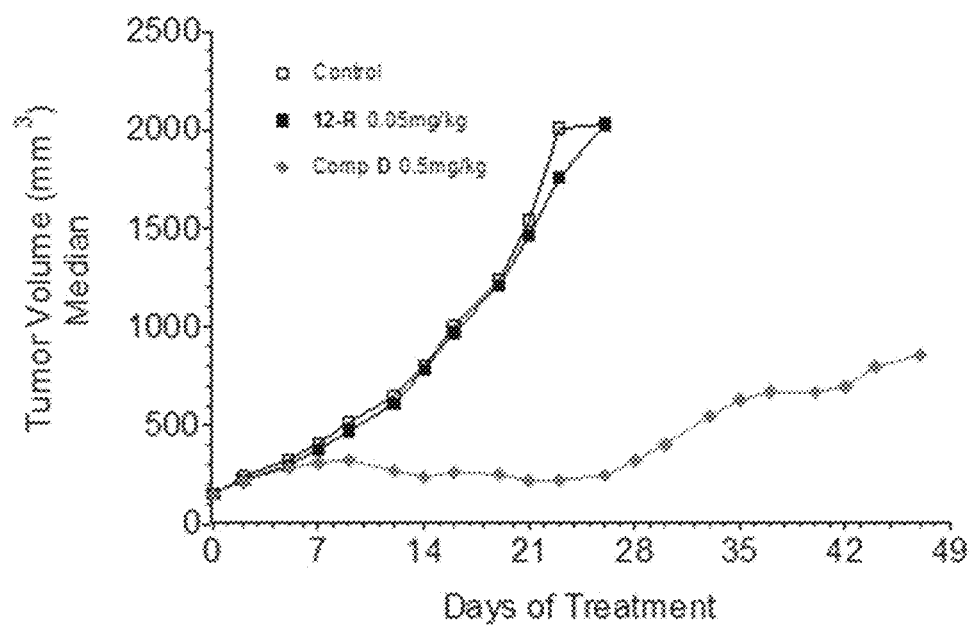
FIG. 19. Tumor volume evaluation of MDA-MB-231 tumors in mice treated with placebo, compound D and 12-R.

Table 30 reports the median tumor volume evaluation of MDA-MB-231 tumors in mice treated with placebo, Compound D and 12-R. These results are also showed in FIG. 19.

TABLE 30

| | Median Tumor Volume (mm³) | | |
|---|---|---|---|
| Days | Control | Compound D | 12-R |
| 0.0 | 149.4 | 149.6 | 149.8 |
| 2.0 | 240.0 | 217.2 | 223.0 |
| 5.0 | 325.1 | 284.5 | 296.1 |
| 7.0 | 407.8 | 310.0 | 378.3 |
| 9.0 | 514.8 | 325.5 | 472.7 |
| 12.0 | 648.1 | 268.4 | 609.9 |
| 14.0 | 799.0 | 237.7 | 782.5 |
| 16.0 | 1002.5 | 261.2 | 972.4 |
| 19.0 | 1233.9 | 251.3 | 1211.0 |
| 21.0 | 1539.1 | 219.9 | 1463.4 |
| 23.0 | 2006.5 | 221.8 | 1756.5 |
| 26.0 | 2027.7 | 245.5 | 2028.6 |
| 28.0 | | 320.3 | |
| 30.0 | | 401.6 | |
| 33.0 | | 545.8 | |
| 35.0 | | 629.2 | |
| 37.0 | | 670.7 | |
| 40.0 | | 669.9 | |
| 42.0 | | 696.3 | |
| 44.0 | | 798.1 | |
| 47.0 | | 857.7 | |

Example 31c. In Vivo Studies to Determine the Effect of 12-R in Human Lung Tumor Xenografts The aim of this study was to compare the antitumoral activity of 12-R with the antitumoral activity of Compound D by using three different xenograft models of human lung cancer. These models correspond to non-small cell lung cancer (H460 cell line and to small cell lung cancer (H526 and H82 cell lines).

Figure 20:
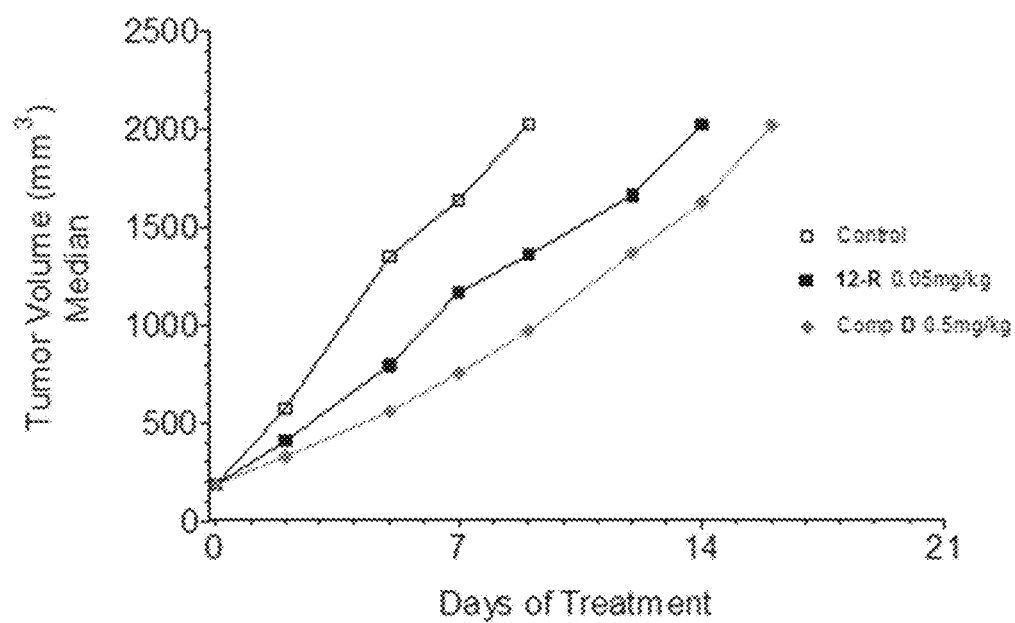
FIG. 20. Tumor volume evaluation of H460 tumors in mice treated with placebo, compound D and 12-R.

Table 31 reports the volume evaluation of H460 tumors in mice treated with placebo, Compound D and 12-R. These results are also showed in FIG. 20.

TABLE 31

| | Median Tumor Volume (mm³) | | |
|---|---|---|---|
| Days | Control | Compound D | 12-R |
| 0.0 | 187.4 | 187.2 | 187.0 |
| 2.0 | 577.5 | 329.7 | 410.7 |
| 5.0 | 1352.0 | 559.4 | 796.7 |
| 7.0 | 1642.9 | 756.5 | 1167.9 |
| 9.0 | 2025.0 | 971.9 | 1360.3 |
| 12.0 | | 1370.9 | 1666.0 |
| 14.0 | | 1626.8 | 2025.0 |
| 16.0 | | 2025.0 | |

Figure 21:
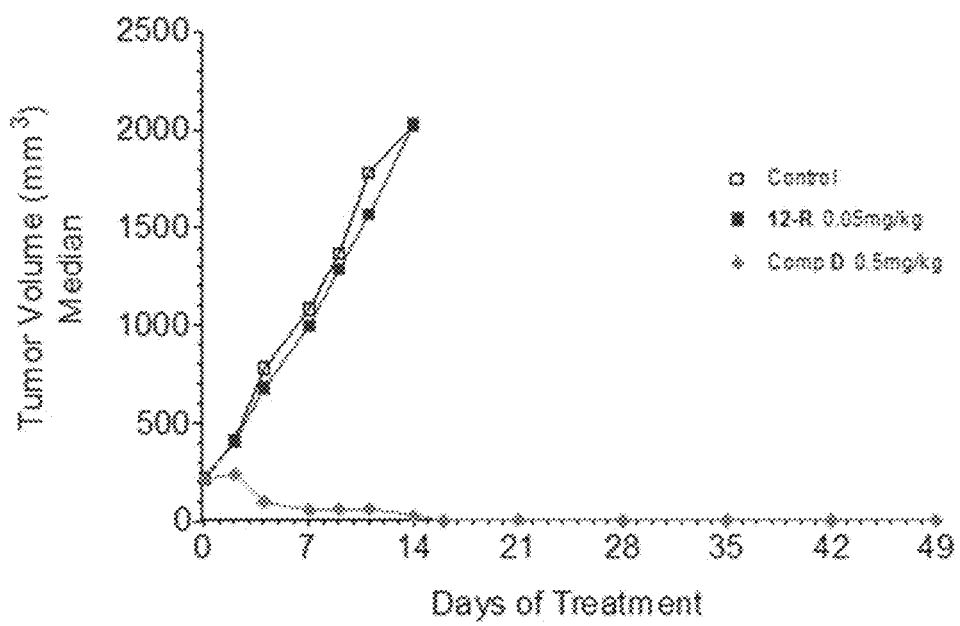
FIG. 21. Tumor volume evaluation of H526 tumors in mice treated with placebo, compound D and 12-R.

Table 32 reports the median tumor volume evaluation of H526 tumors in mice treated with placebo, compound D and 12-R. The results are also shown in FIG. 21.

TABLE 32

| | Median Tumor Volume (mm³) | | |
|---|---|---|---|
| Days | Control | Compound D | 12-R |
| 0.0 | 217.20 | 216.1 | 214.20 |
| 2.0 | 410.70 | 240.9 | 404.50 |
| 4.0 | 778.50 | 99.3 | 680.50 |
| 7.0 | 1083.20 | 56.7 | 995.20 |
| 9.0 | 1371.00 | 62.5 | 1290.50 |
| 11.0 | 1782.00 | 62.5 | 1568.00 |
| 14.0 | 2025.00 | 32.0 | 2025.00 |
| 16.0 | | 4.0 | |
| 21.0 | | 4.0 | |
| 28.0 | | 4.0 | |
| 35.0 | | 4.0 | |
| 42.0 | | 4.0 | |
| 49.0 | | 4.0 | |

Figure 22:
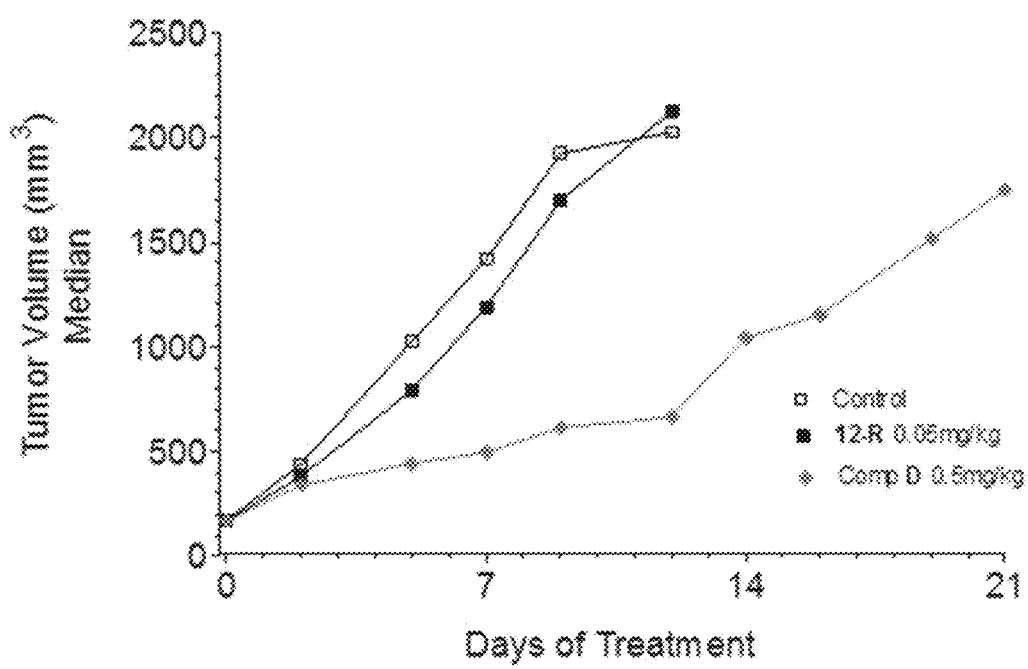
FIG. 22. Tumor volume evaluation of H82 tumors in mice treated with placebo, compound D and 12-R.

Table 33 reports the median tumor volume evaluation of H82 tumors in mice treated with placebo, compound D and 12-R. The results are also shown in FIG. 22.

TABLE 33

| | Median Tumor Volume (mm³) | | |
|---|---|---|---|
| Days | Control | Compound D | 12-R |
| 0.0 | 171.60 | 169.4 | 170.50 |
| 2.0 | 439.40 | 340.6 | 381.40 |
| 5.0 | 1024.70 | 443.3 | 793.20 |
| 7.0 | 1422.00 | 496.2 | 1187.20 |
| 9.0 | 1923.80 | 614.1 | 1699.30 |
| 12.0 | 2025.00 | 665.5 | 2125.60 |
| 14.0 | | 1041.6 | |
| 16.0 | | 1151.2 | |
| 19.0 | | 1516.7 | |
| 21.0 | | 1748.0 | |

Example 31d. In Vivo Studies to Determine the Effect of 12-R in Human Ovarian Tumor Xenografts The aim of this study was to compare the antitumoral activity of 12-R with the antitumoral activity of Compound D by using a xenograft model of human ovarian cancer.

The tumor model used in this study was A2780.

Figure 23:
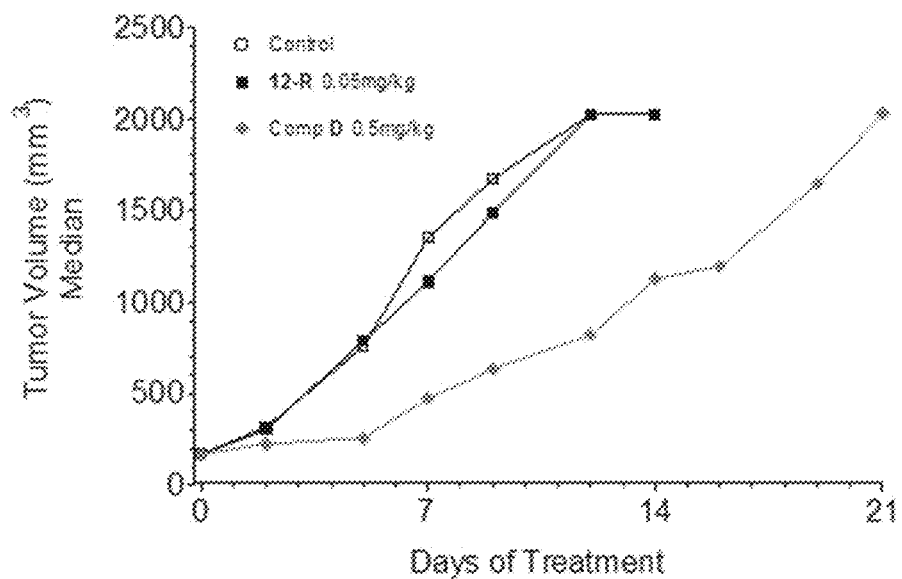
FIG. 23. Tumor volume evaluation of A2780 tumors in mice treated with placebo, compound D and 12-R.

Table 34 reports the volume evaluation of A2780 tumors in mice treated with placebo, Compound D and 12-R. These results are also showed in FIG. 23.

TABLE 34

| | Median Tumor Volume (mm³) | | |
|---|---|---|---|
| Days | Control | Compound D | 12-R |
| 0.0 | 169.5 | 168.8 | 169.6 |
| 2.0 | 317.5 | 225.7 | 302.8 |
| 5.0 | 758.9 | 256.6 | 786.5 |
| 7.0 | 1351.9 | 473.8 | 1113.5 |
| 9.0 | 1675.8 | 633.6 | 1490.6 |
| 12.0 | 2025.0 | 822.8 | 2025.00 |
| 14.0 | | 1129.3 | 2025.00 |
| 16.0 | | 1198.6 | |
| 19.0 | | 1649.6 | |
| 21.0 | | 2025.0 | |

Example 31e. In Vivo Studies to Determine the Effect of 12-R in Human Gastric Tumor Xenografts The aim of this study was to compare the antitumoral activity of 12-R with the antitumoral activity of Compound D by using a xenograft model of human gastric cancer.

The tumor model used in this study was HGC27.

Figure 24:
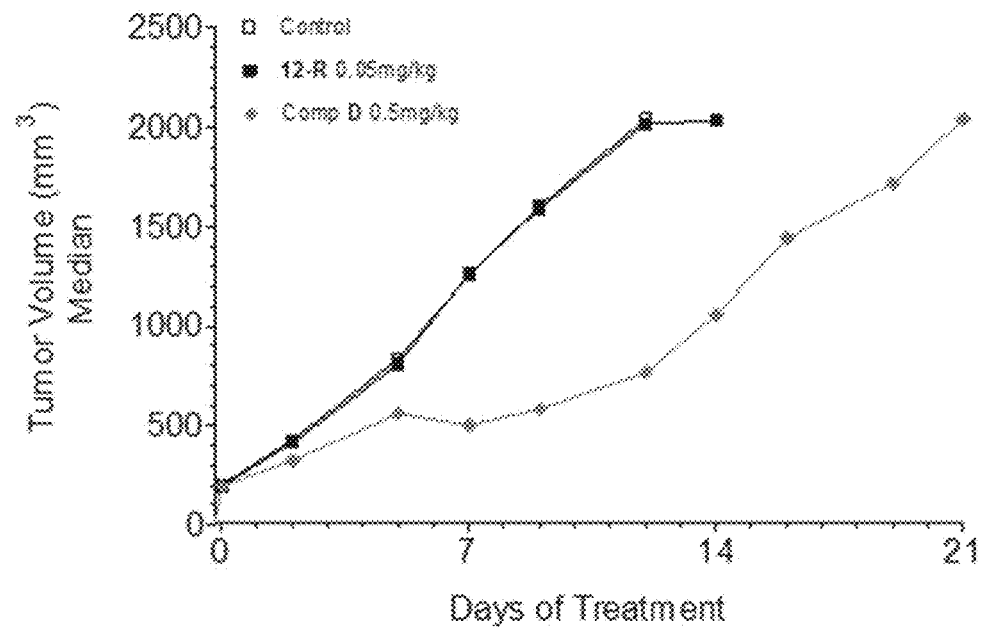
FIG. 24. Tumor volume evaluation of HGC-27 tumors in mice treated with placebo, compound D and 12-R.

Table 35 reports tumor volume growth of HGC27 tumors in mice treated with placebo, Compound D and 12-R. These results are also showed in FIG. 24.

TABLE 35

| | Median Tumor Volume (mm³) | | |
|---|---|---|---|
| Days | Control | Compound D | 12-R |
| 0.0 | 200.7 | 194.0 | 193.3 |
| 2.0 | 429.0 | 324.2 | 413.3 |
| 5.0 | 835.5 | 561.6 | 809.1 |
| 7.0 | 1256.5 | 504.2 | 1261.5 |
| 9.0 | 1602.2 | 584.2 | 1589.5 |
| 12.0 | 2040.7 | 767.7 | 2017.9 |
| 14.0 | | 1056.8 | 2034.9 |
| 16.0 | | 1440.2 | |
| 19.0 | | 1717.9 | |
| 21.0 | | 2043.4 | |

Example 32. In Vivo Studies to Determine the Effect of 19-S in Several Xenograft Models 19-S was provided in the form of freeze dried vials. 19-S cake was reconstituted with water for infusion to a concentration of 0.5 mg/mL. The 19-S stock solution was further diluted in 5% dextrose solution for injection to the dosing formulation concentration. The 19-S administered dose was 0.75 mg/kg.

PM01183 was provided in the form of vials of lyophilized product. Each vial was reconstituted with water for infusion to a concentration of 0.2 mg/mL. The PM01183 stock solution was further diluted in 5% glucose solution for injection to the dosing formulation concentrations. The administered dose was 0.18 mg/kg.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 19-S and PM01183, as well as placebo, were intravenously administered once per week for 3 consecutive weeks, on Days 0, 7 and 14, whenever it was possible.

Example 32a. In Vivo Studies to Determine the Effect of 19-S in Human Fibrosarcoma Xenografts The aim of this study was to compare the antitumoral activities of 19-S and PM01183 by using a xenograft model of human sarcoma.

The tumor model used in this study was HT1080 cell line.

Figure 25:
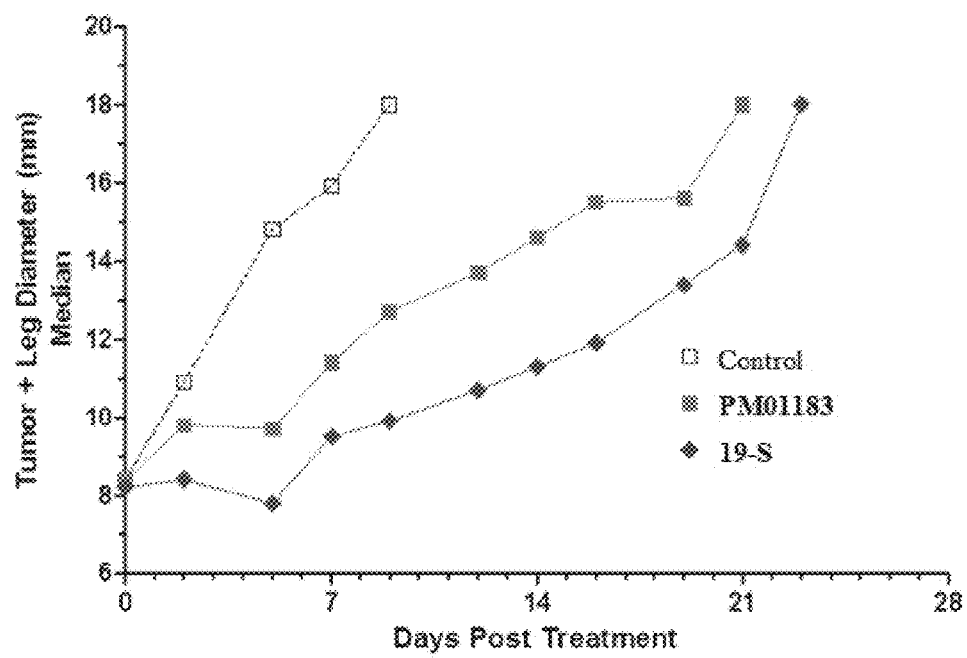
FIG. 25. Tumor total diameter evaluation of HT1080 tumors in mice treated with placebo, PM01183 and 19-S.

Table 36 reports the total diameter (tumor+leg) evaluation of HT1080 tumors in mice treated with placebo, PM01183 and 19-S. These results are also showed in FIG. 25.

TABLE 36

| | Total diameter (tumor + leg) (mm) | | |
|---|---|---|---|
| Days | Control | PM01183 | 19-S |
| 0 | 8.4 | 8.4 | 8.2 |
| 2 | 10.9 | 9.8 | 8.4 |
| 5 | 14.8 | 9.7 | 7.8 |
| 7 | 15.9 | 11.4 | 9.5 |
| 9 | 18.0 | 12.7 | 9.9 |
| 12 | | 13.7 | 10.7 |
| 14 | | 14.6 | 11.3 |
| 16 | | 15.5 | 11.9 |
| 19 | | 15.6 | 13.4 |
| 21 | | 18.0 | 14.4 |
| 23 | | | 18.0 |

Example 32b. In Vivo Studies to Determine the Effect of 19-S in Human Breast Adenocarcinoma Xenografts The aim of this study was to compare the antitumoral activities of 19-S and PM01183 by using a xenograft model of human breast cancer.

The tumor model used in this study was MDA-MB-231 cell line.

Figure 26:
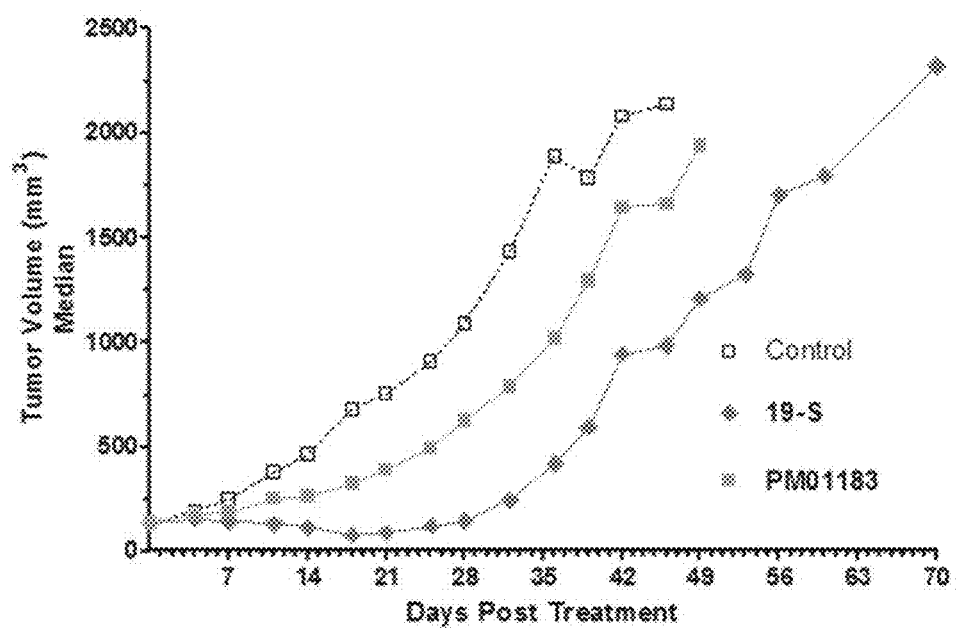
FIG. 26. Tumor volume evaluation of MDA-MB-231 tumors in mice treated with placebo, PM01183 and 19-S.

Table 37 reports the median tumor volume evaluation of MDA-MB-231 tumors in mice treated with placebo, PM01183 and 19-S. These results are also showed in FIG. 26.

TABLE 37

| | Median Tumor Volume (mm$^3$) | | |
|---|---|---|---|
| Days | Control | PM01183 | 19-S |
| 0 | 132.6 | 134.3 | 133.6 |
| 4 | 194.1 | 177.2 | 157.2 |
| 7 | 248.2 | 186.3 | 142.6 |
| 11 | 377.6 | 250.7 | 133.9 |
| 14 | 461.3 | 266.1 | 117.3 |
| 18 | 679.2 | 327.7 | 79.3 |
| 21 | 753.2 | 391.0 | 89.2 |
| 25 | 909.2 | 493.1 | 120.6 |
| 28 | 1090.7 | 627.3 | 144.4 |
| 32 | 1433.4 | 789.0 | 246.1 |
| 36 | 1887.5 | 1022.0 | 419.3 |
| 39 | 1785.2 | 1294.2 | 593.7 |
| 42 | 2081.5 | 1643.3 | 945.9 |
| 46 | 2137.5 | 1658.9 | 985.3 |
| 49 | | 1938.0 | 1211.5 |
| 53 | | | 1324.3 |
| 56 | | | 1703.9 |
| 60 | | | 1793.3 |
| 63 | | | 1603.0 |
| 70 | | | 2324.2 |

Example 32c. In Vivo Studies to Determine the Effect of 19-S in Human Lung Cancer Xenografts The aim of this study was to compare the antitumoral activities of 19-S and PM01183 by using a xenograft model of human lung cancer.

The tumor model used in this study was H-460 cell line.

Figure 27:
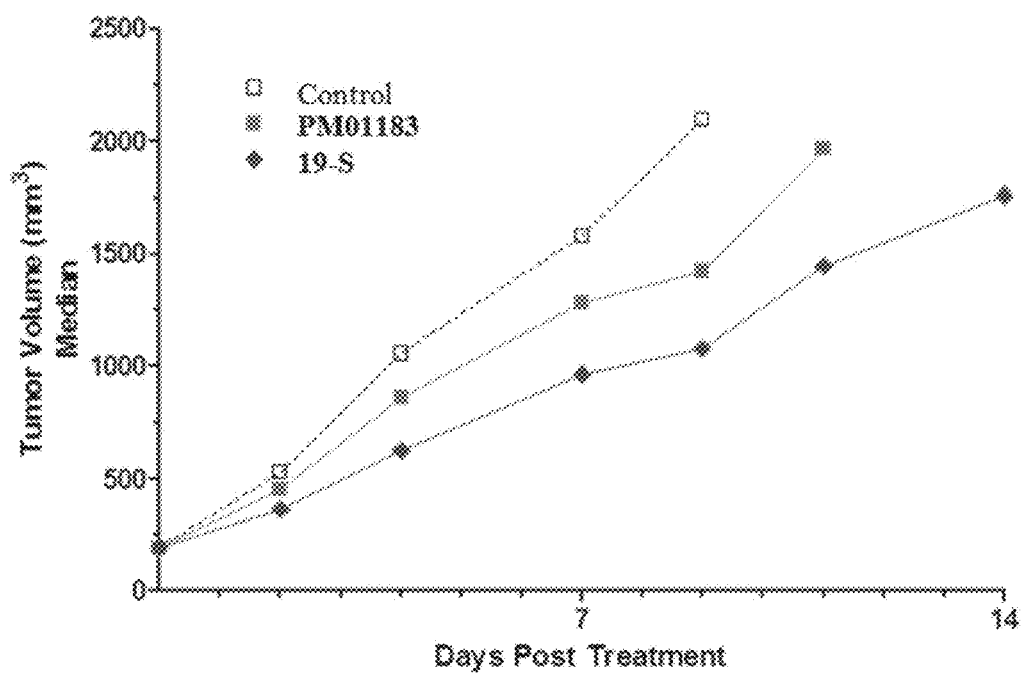
FIG. 27. Tumor volume evaluation of H460 tumors in mice treated with placebo, PM01183 and 19-S.

Table 38 reports the median tumor volume evaluation of H-460 tumors in mice treated with placebo, PM01183 and 19-S. These results are also showed in FIG. 27.

TABLE 38

| | Median Tumor Volume (mm$^3$) | | |
|---|---|---|---|
| Days | Control | PM01183 | 19-S |
| 0 | 197.0 | 196.3 | 196.9 |
| 2 | 529.5 | 457.0 | 364.0 |
| 4 | 1057.4 | 861.5 | 624.9 |
| 7 | 1582.5 | 1280.2 | 966.5 |
| 9 | 2094.8 | 1424.9 | 1078.2 |
| 11 | | 1969.9 | 1449.0 |
| 14 | | | 1761.5 |

Example 32d. In Vivo Studies to Determine the Effect of 19-S in Human Ovarian Tumor Xenografts The aim of this study was to compare the antitumoral activities of 19-S and PM01183 by using a xenograft model of human ovarian cancer.

The tumor model used in this study was A2780.

Figure 28:
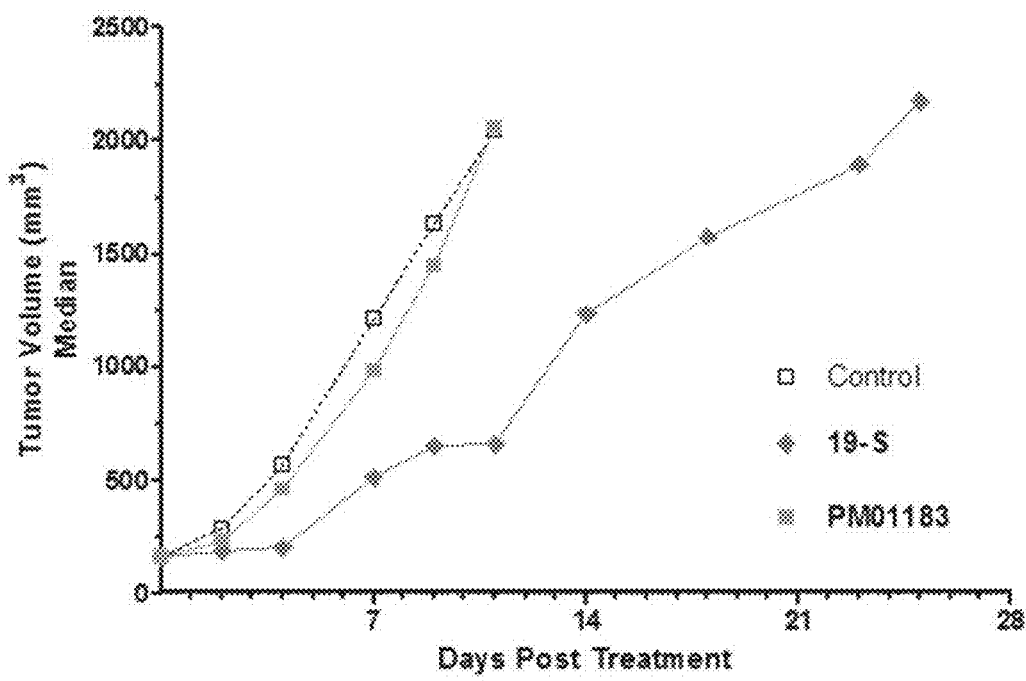
FIG. 28. Tumor volume evaluation of A2780 tumors in mice treated with placebo, PM01183 and 19-S.

Table 39 reports the median tumor volume evaluation of A2780 tumors in mice treated with placebo, PM01183 and 19-S. These results are also showed in FIG. 28.

TABLE 39

| | Median Tumor Volume (mm$^3$) | | |
|---|---|---|---|
| Days | Control | PM01183 | 19-S |
| 0 | 163.4 | 163.6 | 164.4 |
| 2 | 287.1 | 235.5 | 187.9 |
| 4 | 568.7 | 463.2 | 205.4 |
| 7 | 1211.3 | 986.3 | 513.6 |
| 9 | 1633.7 | 1451.4 | 650.6 |
| 11 | 2047.8 | 2062 | 659.8 |
| 14 | | | 1236.2 |
| 18 | | | 1575.9 |
| 23 | | | 1895.7 |
| 25 | | | 2177.0 |

Example 32e. In Vivo Studies to Determine the Effect of 19-S in Human Gastric Tumor Xenografts The aim of this study was to compare the antitumoral activities of 19-S and PM01183 by using a xenograft model of human gastric cancer.

The tumor model used in this study was HGC27.

Figure 29:
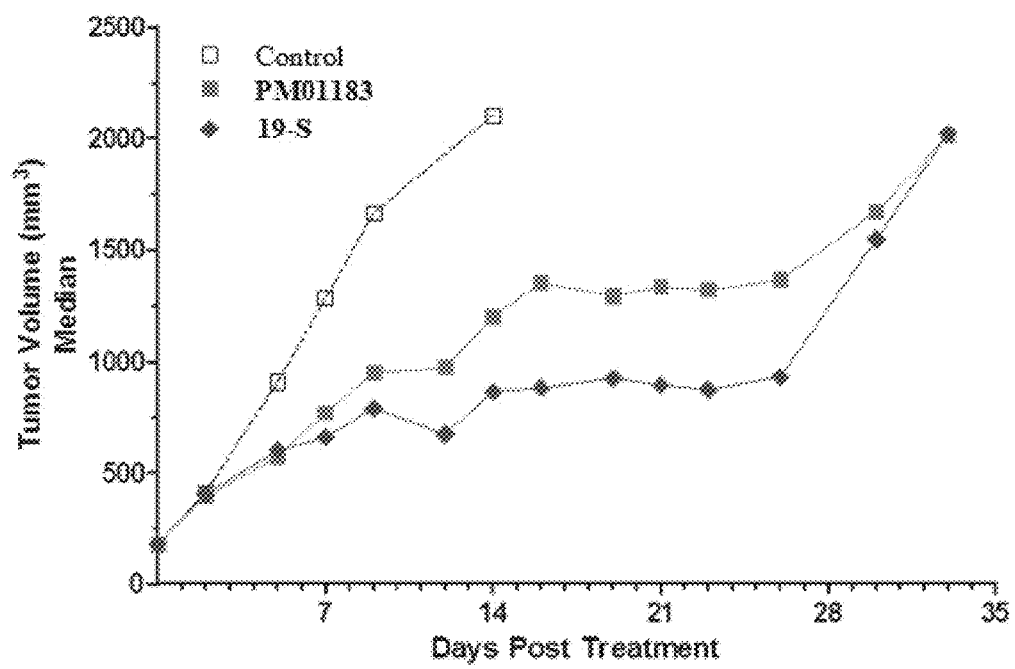
FIG. 29. Tumor volume evaluation of HGC27 tumors in mice treated with placebo, PM01183 and 19-S.

Table 40 reports the median tumor volume evaluation of HGC27 tumors in mice treated with placebo, PM01183 and 19-S. These results are also showed in FIG. 29.

TABLE 40

| | Median Tumor Volume (mm³) | | |
|---|---|---|---|
| Days | Control | PM01183 | 19-S |
| 0 | 178.3 | 177.6 | 181.5 |
| 2 | 409 | 395.6 | 404.6 |
| 5 | 907.4 | 572.4 | 600.3 |
| 7 | 1283.6 | 766.6 | 660.3 |
| 9 | 1664 | 950.7 | 787.5 |
| 14 | 2102.8 | 1199.4 | 864.4 |
| 16 | | 1353.1 | 882.4 |
| 19 | | 1294.3 | 925.2 |
| 21 | | 1335.1 | 893.6 |
| 23 | | 1320.3 | 874.4 |
| 26 | | 1364.5 | 932.1 |
| 30 | | 1671.9 | 1547.8 |
| 33 | | 2009.2 | 2020.4 |

Example 33. In Vivo Studies to Determine the Effect of 19-R in Several Xenograft Models 19-R was provided in the form of freeze dried vials. 19-R cake was reconstituted with water for infusion to a concentration of 0.5 mg/mL. The 19-R stock solution was further diluted in 5% dextrose solution for injection to the dosing formulation concentration. The 19-R administered dose was 0.15 mg/kg.

PM01183 was provided in the form of vials of lyophilized product. Each vial was reconstituted with water for infusion to a concentration of 0.2 mg/mL. The PM01183 stock solution was further diluted in 5% glucose solution for injection to the dosing formulation concentrations. The administered dose was 0.18 mg/kg.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 19-R and PM01183, as well as placebo, were intravenously administered once per week for 3 consecutive weeks, on Days 0, 7 and 14, whenever it was possible.

Example 33a. In Vivo Studies to Determine the Effect of 19-R in Human Fibrosarcoma Xenografts The aim of this study was to compare the antitumoral activity of 19-R with the antitumoral activity of PM01183 by using a xenograft model of human sarcoma.

The tumor model used in this study was HT1080 cell line.

Figure 30:
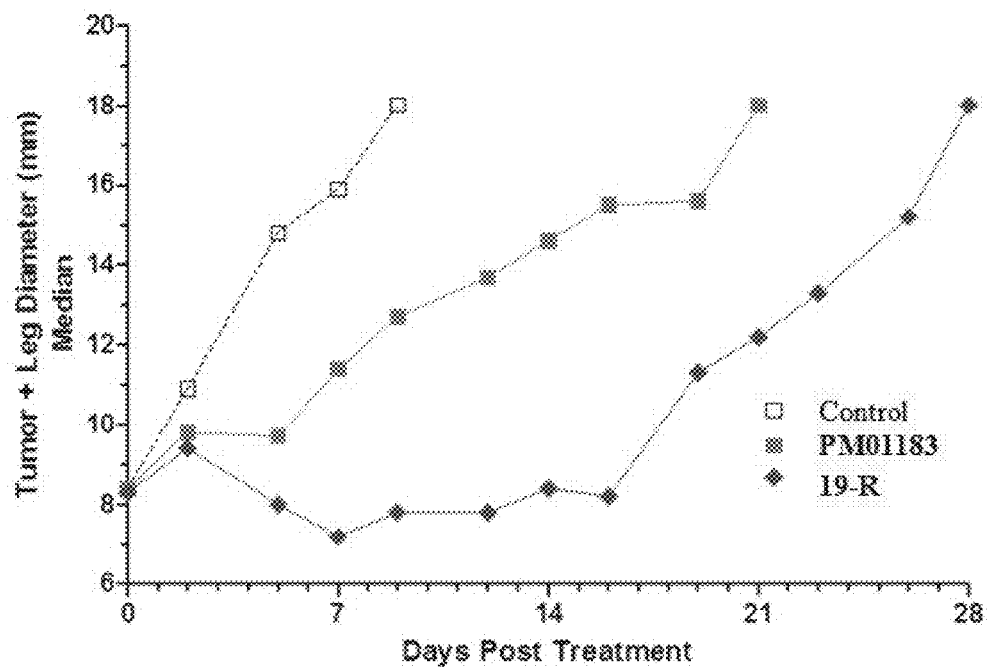
FIG. 30. Tumor total diameter evaluation of HT1080 tumors in mice treated with placebo, PM01183 and 19-R.

Table 41 reports the total diameter (tumor+leg) evaluation of HT-1080 tumors in mice treated with placebo, PM01183 and 19-R. These results are also showed in FIG. 30.

TABLE 41

| | Total diameter (tumor + leg) (mm) | | |
|---|---|---|---|
| Days | Control | PM01183 | 19-R |
| 0 | 8.4 | 8.4 | 8.3 |
| 2 | 10.9 | 9.8 | 9.4 |
| 5 | 14.8 | 9.7 | 8.0 |
| 7 | 15.9 | 11.4 | 7.2 |
| 9 | 18.0 | 12.7 | 7.8 |
| 12 | | 13.7 | 7.8 |
| 14 | | 14.6 | 8.4 |
| 16 | | 15.5 | 8.2 |
| 19 | | 15.6 | 11.3 |
| 21 | | 18.0 | 12.2 |

TABLE 41-continued

| | Total diameter (tumor + leg) (mm) | | |
|---|---|---|---|
| Days | Control | PM01183 | 19-R |
| 23 | | | 13.3 |
| 26 | | | 15.2 |
| 28 | | | 18.0 |

Example 33b. In Vivo Studies to Determine the Effect of 19-R in Human Breast Adenocarcinoma Xenografts The aim of this study was to compare the antitumoral activity of 19-R with the antitumoral activity of PM01183 by using a xenograft model of human breast cancer.

The tumor model used in this study was MDA-MB-231 cell line.

Figure 31:
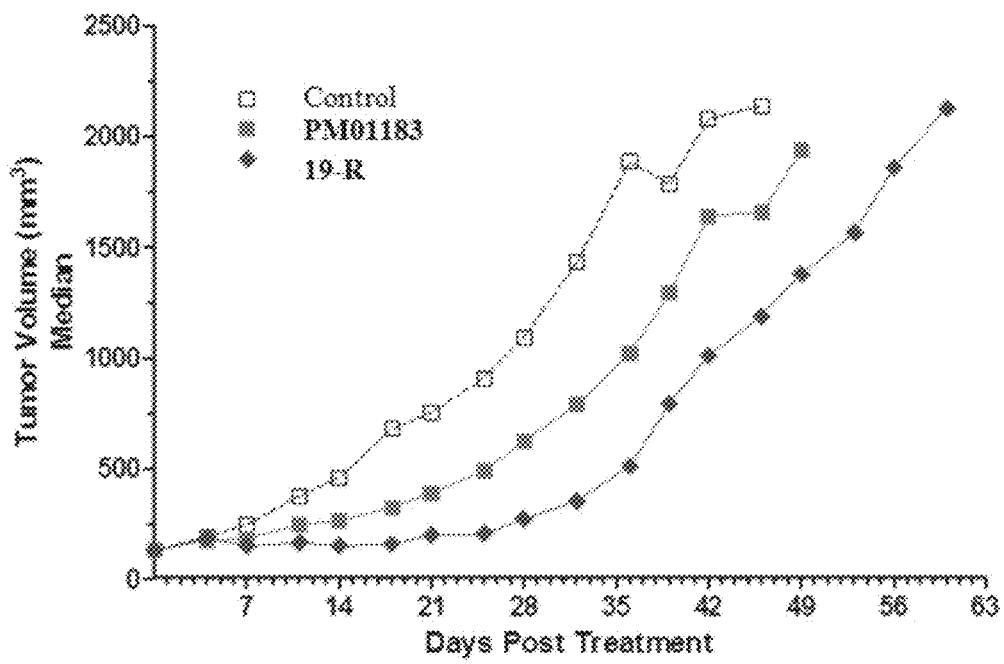
FIG. 31. Tumor volume evaluation of MDA-MB-231 tumors in mice treated with placebo, PM01183 and 19-R.

Table 42 reports the median tumor volume evaluation of MDA-MB-231 tumors in mice treated with placebo, PM01183 and 19-R. These results are also showed in FIG. 31.

TABLE 42

| | Median Tumor Volume (mm³) | | |
|---|---|---|---|
| Days | Control | PM01183 | 19-R |
| 0 | 132.6 | 134.3 | 132.5 |
| 4 | 194.1 | 177.2 | 189.3 |
| 7 | 248.2 | 186.3 | 151.9 |
| 11 | 377.6 | 250.7 | 167.5 |
| 14 | 461.3 | 266.1 | 152.6 |
| 18 | 679.2 | 327.7 | 162.2 |
| 21 | 753.2 | 391.0 | 201.2 |
| 25 | 909.2 | 493.1 | 208.5 |
| 28 | 1090.7 | 627.3 | 274.8 |
| 32 | 1433.4 | 789.0 | 355.8 |
| 36 | 1887.5 | 1022.0 | 513.8 |
| 39 | 1785.2 | 1294.2 | 793.7 |
| 42 | 2081.5 | 1643.3 | 1012.2 |
| 46 | 2137.5 | 1658.9 | 1188.5 |
| 49 | | 1938.0 | 1380.7 |
| 53 | | | 1568.0 |
| 56 | | | 1862.6 |
| 60 | | | 2129.4 |

Example 33c. In Vivo Studies to Determine the Effect of 19-R in Human Lung Tumor Xenografts The aim of this study was to compare the antitumoral activity of 19-R with the antitumoral activity of PM01183 by using a xenograft model of human lung cancer.

The tumor model used in this study was H-460 cell line.

Figure 32:
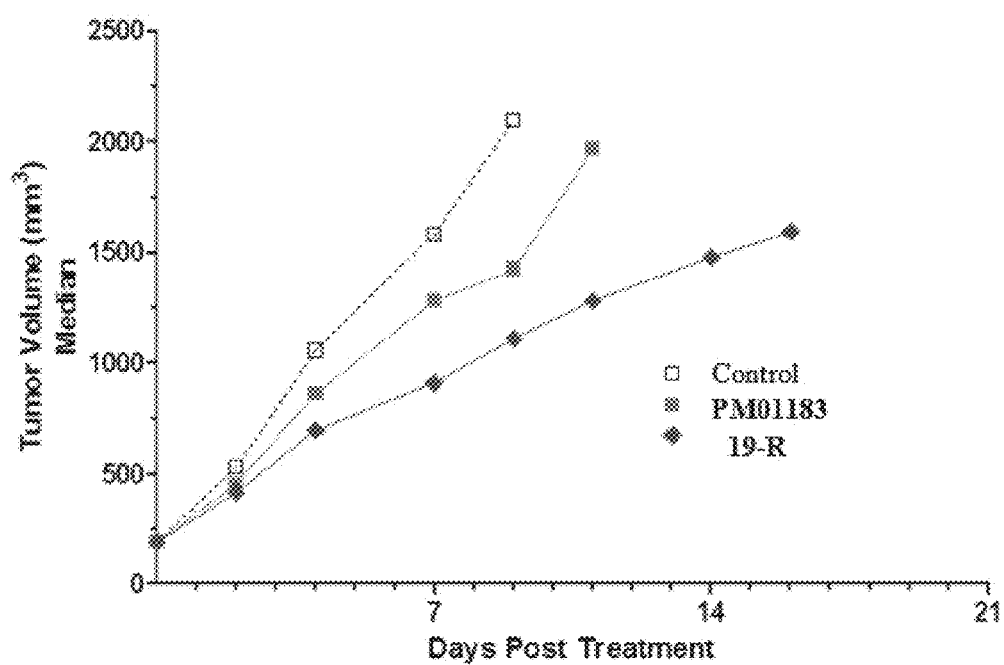
FIG. 32. Tumor volume evaluation of H460 tumors in mice treated with placebo, PM01183 and 19-R.

Table 43 reports the median tumor volume evaluation of H460 tumors in mice treated with placebo, PM01183 and 19-R. These results are also showed in FIG. 32.

TABLE 43

| | Median Tumor Volume (mm³) | | |
|---|---|---|---|
| Days | Control | PM01183 | 19-R |
| 0 | 197.0 | 196.3 | 196.8 |
| 2 | 529.5 | 457.0 | 418.7 |
| 4 | 1057.4 | 861.5 | 697.2 |
| 7 | 1582.5 | 1280.2 | 911.7 |
| 9 | 2094.8 | 1424.9 | 1111.5 |

TABLE 43-continued

| | Median Tumor Volume (mm³) | | |
|---|---|---|---|
| Days | Control | PM01183 | 19-R |
| 11 | 1969.9 | 1281.3 | |
| 14 | | 1478.7 | |
| 16 | | 1594.0 | |

Example 33d. In Vivo Studies to Determine the Effect of 19-R in Human Ovarian Tumor Xenografts The aim of this study was to compare the antitumoral activity of 19-R with the antitumoral activity of PM01183 by using a xenograft model of human ovarian cancer.

The tumor model used in this study was A2780.

Figure 33:
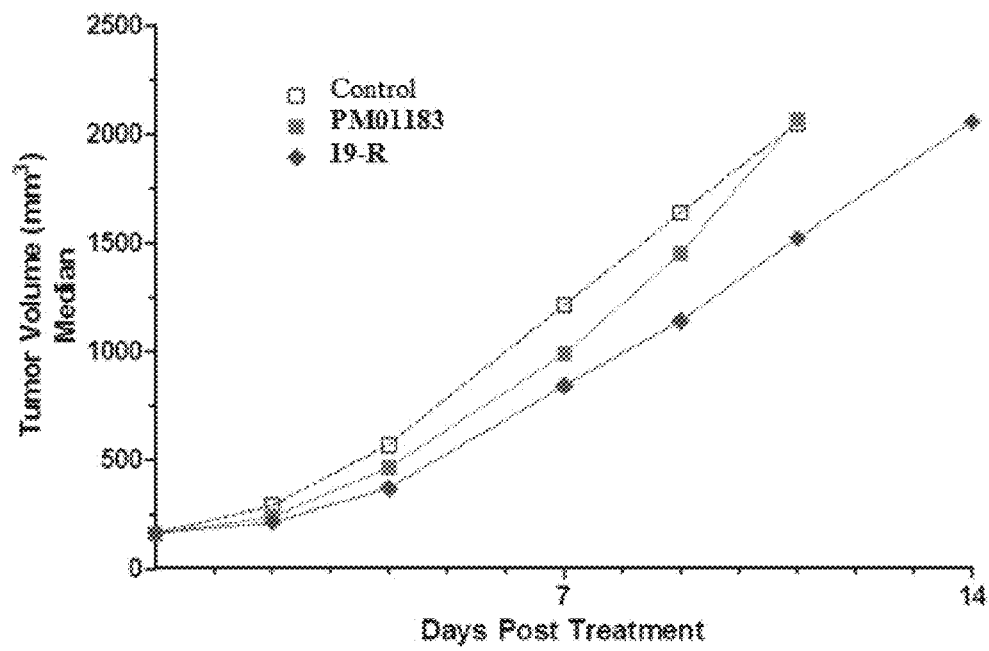
FIG. 33. Tumor volume evaluation of A2780 tumors in mice treated with placebo, PM01183 and 19-R.

Table 44 reports the median tumor volume evaluation of A2780 tumors in mice treated with placebo, PM01183 and 19-R. These results are also showed in FIG. 33.

TABLE 44

| | Median Tumor Volume (mm³) | | |
|---|---|---|---|
| Days | Control | PM01183 | 19-R |
| 0 | 163.4 | 163.6 | 162.8 |
| 2 | 287.1 | 236.5 | 212.9 |
| 4 | 568.7 | 463.2 | 368.5 |
| 7 | 1211.3 | 986.3 | 841.3 |
| 9 | 1633.7 | 1451.4 | 1138.9 |
| 11 | 2047.8 | 2062.0 | 1519.9 |
| 14 | | | 2056.0 |

Example 33e. In Vivo Studies to Determine the Effect of 19-R in Human Gastric Tumor Xenografts The aim of this study was to compare the antitumoral activity of 19-R with the antitumoral activity of PM01183 by using a xenograft model of human gastric cancer.

The tumor model used in this study was HGC27.

Figure 34:
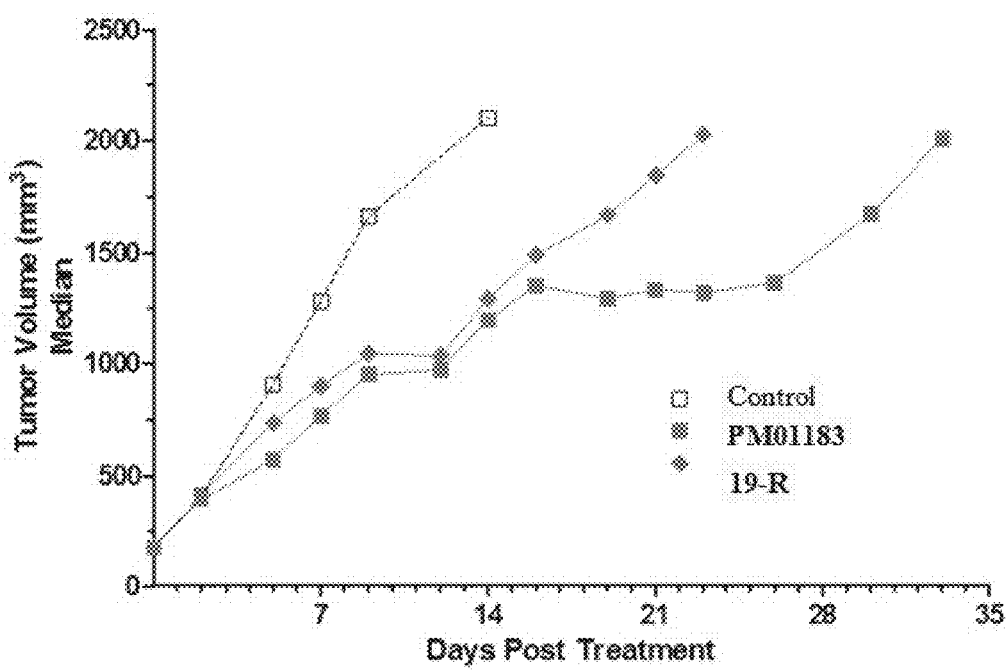
FIG. 34. Tumor volume evaluation of HGC-27 tumors in mice treated with placebo, PM01183 and 19-R.

Table 45 reports the median tumor volume evaluation of HGC-27 tumors in mice treated with placebo, PM01183 and 19-R. These results are also showed in FIG. 34.

TABLE 45

| | Median Tumor Volume (mm³) | | |
|---|---|---|---|
| Days | Control | PM01183 | 19-R |
| 0 | 178.3 | 177.6 | 182.0 |
| 2 | 409.0 | 395.6 | 414.9 |
| 5 | 907.4 | 572.4 | 735.0 |
| 7 | 1283.6 | 766.6 | 901.2 |
| 9 | 1664.0 | 950.7 | 1048.1 |
| 14 | 2102.8 | 1199.4 | 1293.9 |
| 16 | | 1353.1 | 1488.8 |
| 19 | | 1294.3 | 1668.3 |
| 21 | | 1335.1 | 1845.0 |
| 23 | | 1320.3 | 2025.0 |
| 26 | | 1364.5 | |
| 30 | | 1671.9 | |
| 33 | | 2009.2 | |

Example 34. In Vivo Studies to Determine the Effect of 39-S in Several Xenograft Models Compound 39-S and C were provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. The administered doses of 39-S and C were 1.25 and 3 mg/Kg, respectively.

Placebo was provided in the forms of vials of lyophilised product. Each vial (sucrose 200 mg+potassium dihydrogen phosphate 13.6 mg+phosphoric acid q.s. pH 3.8-4.5) was reconstituted with sterile water for injection (2 mL). Further dilutions were made with 5% dextrose solution for injection.

In these experiments, 39-S and compound C, as well as placebo, were intravenously administered on a weekly schedule at a volume of 10 mL/Kg.

Example 34a. In Vivo Studies to Determine the Effect of 39-S in Human Fibrosarcoma Xenografts The aim of this study was to evaluate the antitumoral activity of compound 39-S by comparison with the antitumoral activity of compound C by using a xenograft model of human sarcoma.

The tumor model used in this study was HT1080 cell line.

Figure 35:
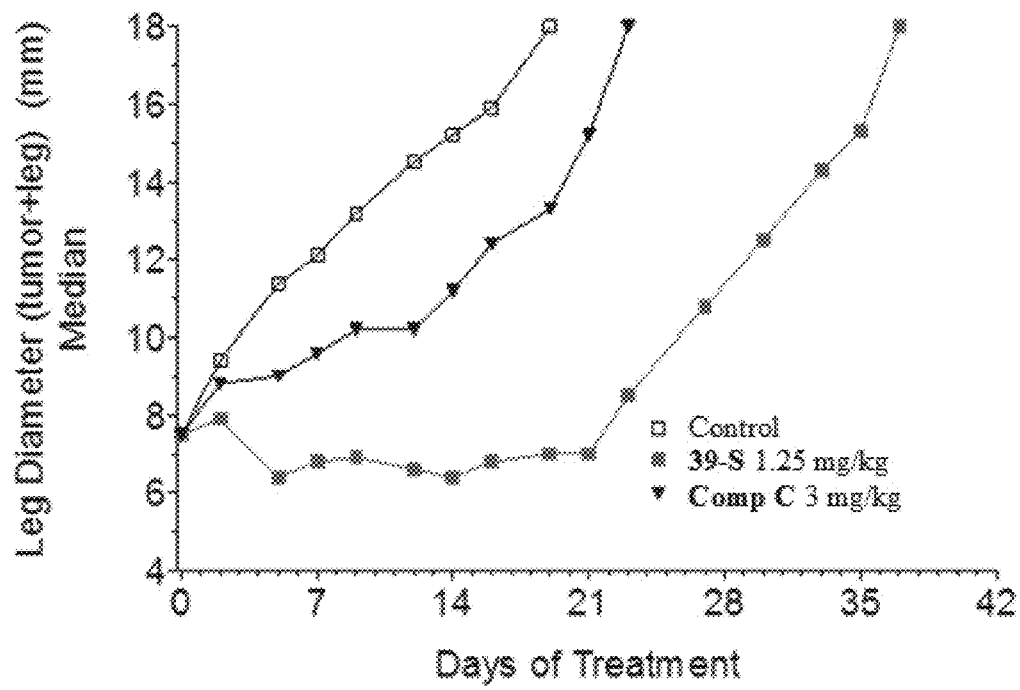
FIG. 35. Tumor total diameter evaluation of HT1080 tumors in mice treated with placebo, compound C and 39-S.

Table 46 reports the total diameter (tumor+leg) evaluation of HT1080 tumors in mice treated with placebo, compound C and 39-S. These results are also showed in FIG. 35.

TABLE 46

| | Total diameter (tumor + leg) (mm) | | |
|---|---|---|---|
| Days | Control | 39-S | Compound C |
| 0 | 7.5 | 7.5 | 7.5 |
| 2 | 9.4 | 7.9 | 8.8 |
| 5 | 11.4 | 6.4 | 9.0 |
| 7 | 12.1 | 6.8 | 9.6 |
| 9 | 13.2 | 6.9 | 10.2 |
| 12 | 14.5 | 6.6 | 10.2 |
| 14 | 15.2 | 6.4 | 11.2 |
| 16 | 15.9 | 6.8 | 12.4 |
| 19 | 18.0 | 7.0 | 13.3 |
| 21 | | 7.0 | 15.2 |
| 23 | | 8.5 | 18.0 |
| 27 | | 10.8 | |
| 30 | | 12.5 | |
| 33 | | 14.3 | |
| 35 | | 15.3 | |
| 37 | | 18.0 | |

Example 34b. In Vivo Studies to Determine the Effect of 39-S in Human Breast Adenocarcinoma Xenografts The aim of this study was to compare the antitumoral activities of 39-S and compound C by using a xenograft model of human breast cancer.

The tumor model used in this study was MDA-MB-231 cell line.

Figure 36:
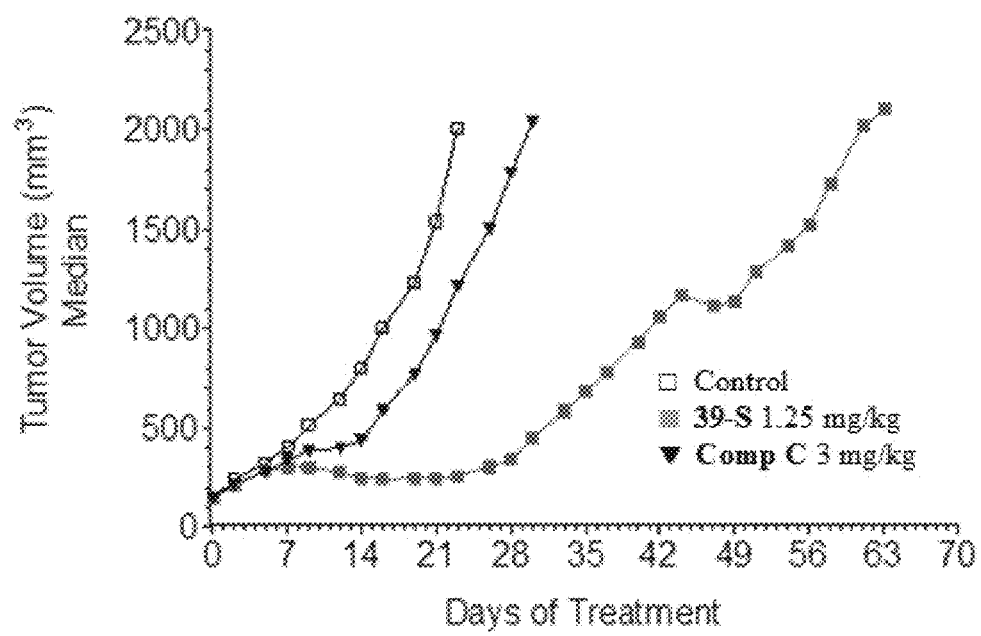
FIG. 36. Tumor volume evaluation of MDA-MB-231 tumors in mice treated with placebo, compound C and 39-S.

Table 47 reports the median tumor volume evaluation of MDA-MB-231 tumors in mice treated with placebo, compound C and 39-S. These results are also showed in FIG. 36.

TABLE 47

| | Median Tumor Volume (mm³) | | |
|---|---|---|---|
| Days | Control | 39-S | Compound C |
| 0 | 149.4 | 151.0 | 149.4 |
| 2 | 240.0 | 209.3 | 217.1 |

TABLE 47-continued

Median Tumor Volume (mm³)

| Days | Control | 39-S | Compound C |
|---|---|---|---|
| 5 | 325.1 | 290.9 | 281.3 |
| 7 | 407.8 | 301.8 | 338.6 |
| 9 | 514.8 | 300.8 | 385.1 |
| 12 | 648.1 | 278.7 | 400.4 |
| 14 | 799.0 | 249.7 | 436.9 |
| 16 | 1002.5 | 243.6 | 585.7 |
| 19 | 1233.9 | 248.3 | 774.7 |
| 21 | 1539.1 | 250.0 | 965.9 |
| 23 | 2006.5 | 260.3 | 1215.2 |
| 26 | 2027.7 | 304.9 | 1503.2 |
| 28 | | 337.1 | 1785.3 |
| 30 | | 451.3 | 2037.1 |
| 33 | | 584.1 | |
| 35 | | 683.4 | |
| 37 | | 784.7 | |
| 40 | | 937.4 | |
| 42 | | 1060.5 | |
| 44 | | 1170.5 | |
| 47 | | 1112.9 | |
| 49 | | 1138.6 | |
| 51 | | 1283.2 | |
| 54 | | 1415.1 | |
| 56 | | 1518.7 | |
| 58 | | 1728.5 | |
| 61 | | 2017.9 | |

Example 34c. In Vivo Studies to Determine the Effect of 39-S in Human Lung Cancer Xenografts The aim of this study was to compare the antitumoral activity of 39-S with the antitumoral activity of compound C by using three different xenograft models of human lung cancer. These models correspond to non-small cell lung cancer (H-460 cell line) and to small cell lung cancer (H526 and H82 cell lines).

Figure 37:
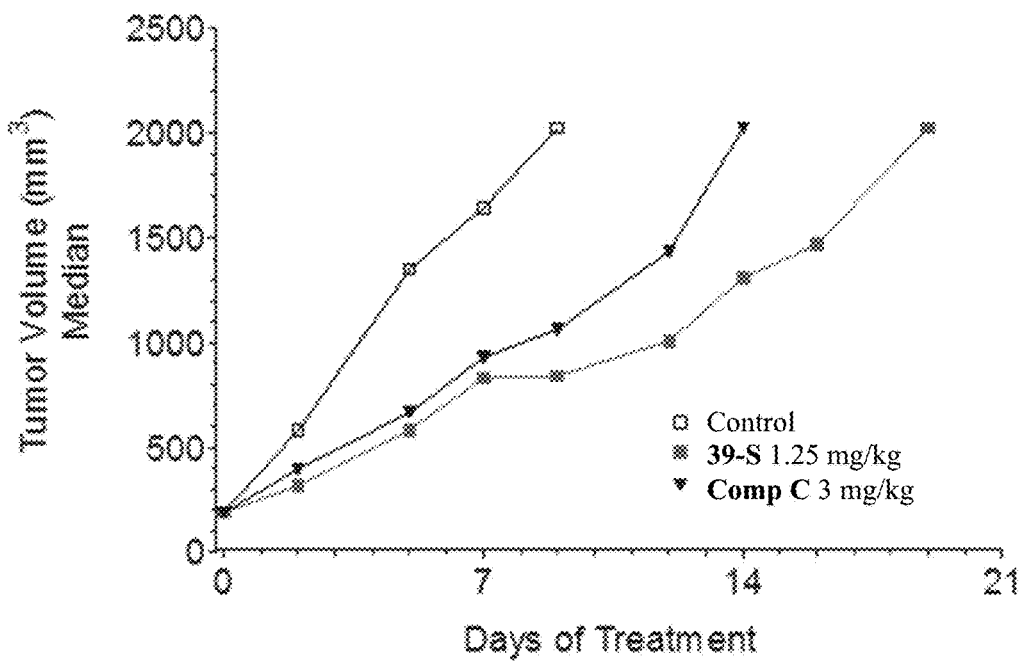
FIG. 37. Tumor volume evaluation of H460 tumors in mice treated with placebo, compound C and 39-S.

Table 48 reports the median tumor volume evaluation of H460 tumors in mice treated with placebo, compound C and 39-S. These results are also showed in FIG. 37.

TABLE 48

Median Tumor Volume (mm³)

| Days | Control | 39-S | Compound C |
|---|---|---|---|
| 0 | 187.4 | 187.8 | 186.1 |
| 2 | 577.5 | 314.4 | 395.4 |
| 5 | 1352.0 | 584.1 | 665.9 |
| 7 | 1642.9 | 831.2 | 929.5 |
| 9 | 2025.0 | 841.0 | 1063.7 |
| 12 | | 1008.0 | 1436.5 |
| 14 | | 1309.8 | 2025.0 |
| 16 | | 1470.0 | 2025.0 |
| 19 | | 2025.0 | |

Figure 38:
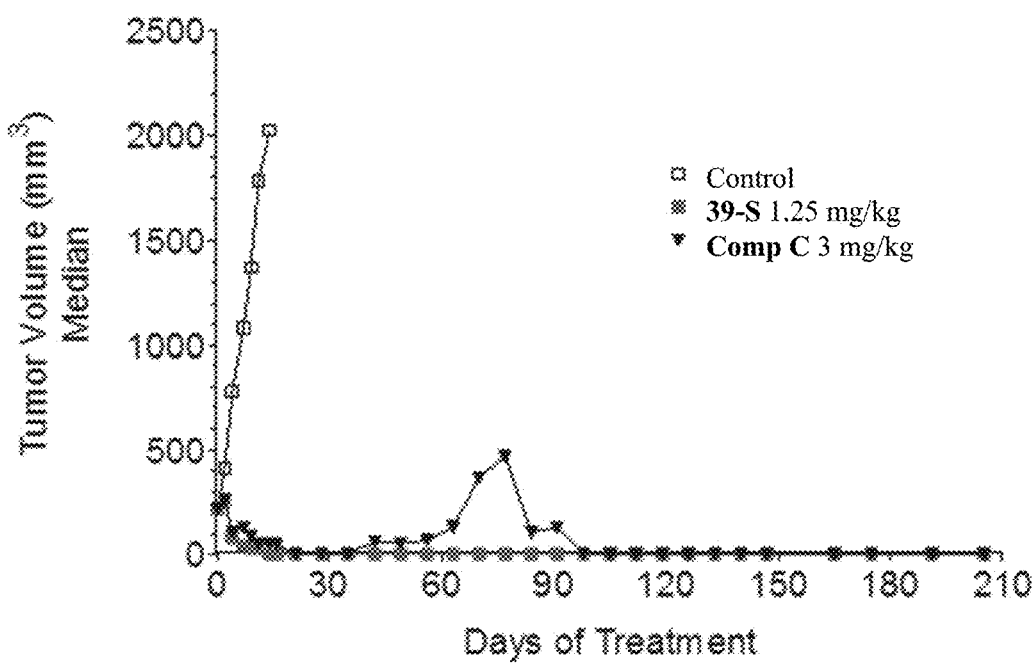
FIG. 38. Tumor volume evaluation of H526 tumors in mice treated with placebo, compound C and 39-S.

Table 49 reports the median tumor volume evaluation of H526 tumors in mice treated with placebo, compound C and 39-S. These results are also showed in FIG. 38.

TABLE 49

Median Tumor Volume (mm³)

| Days | Control | 39-S | Compound C |
|---|---|---|---|
| 0 | 217.2 | 214.5 | 217.9 |
| 2 | 410.7 | 260.3 | 262.4 |
| 4 | 778.5 | 80.0 | 108.3 |

TABLE 49-continued

Median Tumor Volume (mm³)

| Days | Control | 39-S | Compound C |
|---|---|---|---|
| 7 | 1083.2 | 46.2 | 129.8 |
| 9 | 1371.0 | 32.0 | 85.9 |
| 11 | 1782.0 | 32.0 | 52.3 |
| 14 | 2025.0 | 4.0 | 54.1 |
| 16 | | 4.0 | 47.3 |
| 21 | | 4.0 | 4.0 |
| 28 | | 4.0 | 4.0 |
| 35 | | 4.0 | 4.0 |
| 42 | | 4.0 | 62.5 |
| 49 | | 4.0 | 53.5 |
| 56 | | 4.0 | 70.0 |
| 63 | | 4.0 | 132.3 |
| 70 | | 4.0 | 368.5 |
| 77 | | 4.0 | 465.8 |
| 84 | | 4.0 | 107.4 |
| 91 | | 4.0 | 130.0 |
| 98 | | 4.0 | 4.0 |
| 105 | | 4.0 | 4.0 |
| 112 | | 4.0 | 4.0 |
| 119 | | 4.0 | 4.0 |
| 126 | | 4.0 | 4.0 |
| 133 | | 4.0 | 4.0 |
| 140 | | 4.0 | 4.0 |
| 147 | | 4.0 | 4.0 |
| 165 | | 4.0 | 4.0 |
| 175 | | 4.0 | 4.0 |
| 191 | | 4.0 | 4.0 |
| 205 | | 4.0 | 4.0 |

Figure 39:
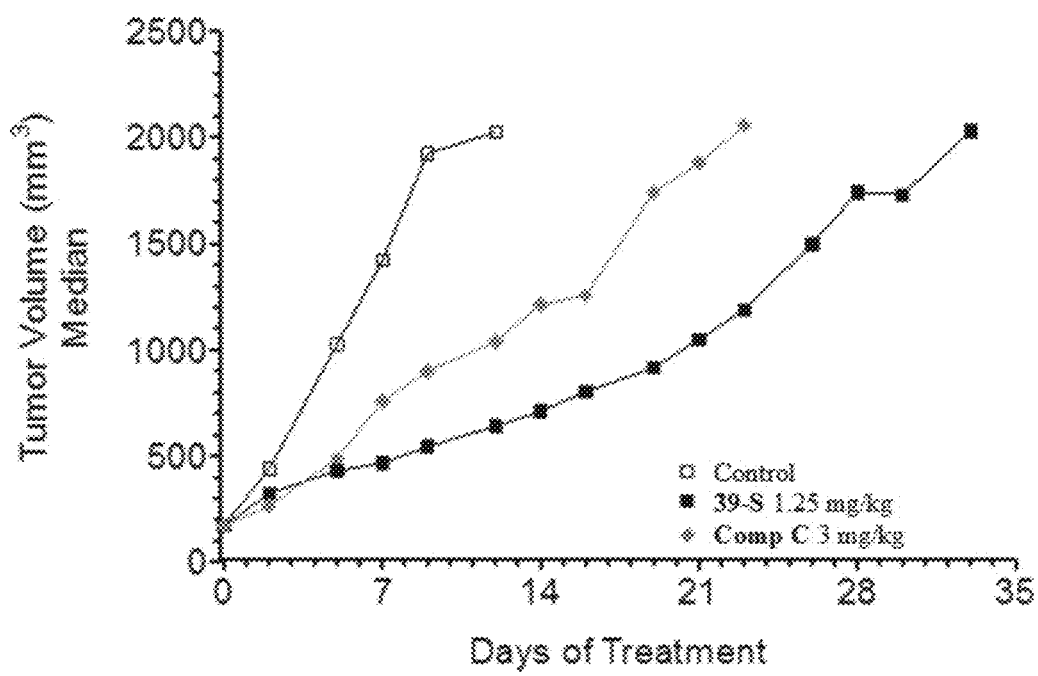
FIG. 39. Tumor volume evaluation of H82 tumors in mice treated with placebo, compound C and 39-S.

Table 50 reports the median tumor volume evaluation of H82 tumors in mice treated with placebo, compound C and 39-S. These results are also showed in FIG. 39.

TABLE 50

Median Tumor Volume (mm³)

| Days | Control | 39-S | Compound C |
|---|---|---|---|
| 0 | 171.6 | 170.3 | 170.5 |
| 2 | 439.4 | 325.2 | 265.3 |
| 5 | 1024.7 | 430.8 | 488.7 |
| 7 | 1422.0 | 466.2 | 760.0 |
| 9 | 1923.8 | 544.3 | 899.5 |
| 12 | 2025.0 | 640.3 | 1038.5 |
| 14 | | 711.2 | 1213.4 |
| 16 | | 802.7 | 1256.4 |
| 19 | | 916.0 | 1741.5 |
| 21 | | 1047.2 | 1878.8 |
| 23 | | 1189.1 | 2057.0 |
| 26 | | 1497.2 | |
| 28 | | 1741.8 | |
| 30 | | 1731.7 | |
| 33 | | 2029.4 | |

Example 34d. In Vivo Studies to Determine the Effect of 39-S in Human Ovarian Tumor Xenografts The aim of this study was to compare the antitumoral activity of 39-S with the antitumoral activity of compound C by using a xenograft model of human ovarian cancer.

The tumor model used in this study was A2780.

Figure 40:
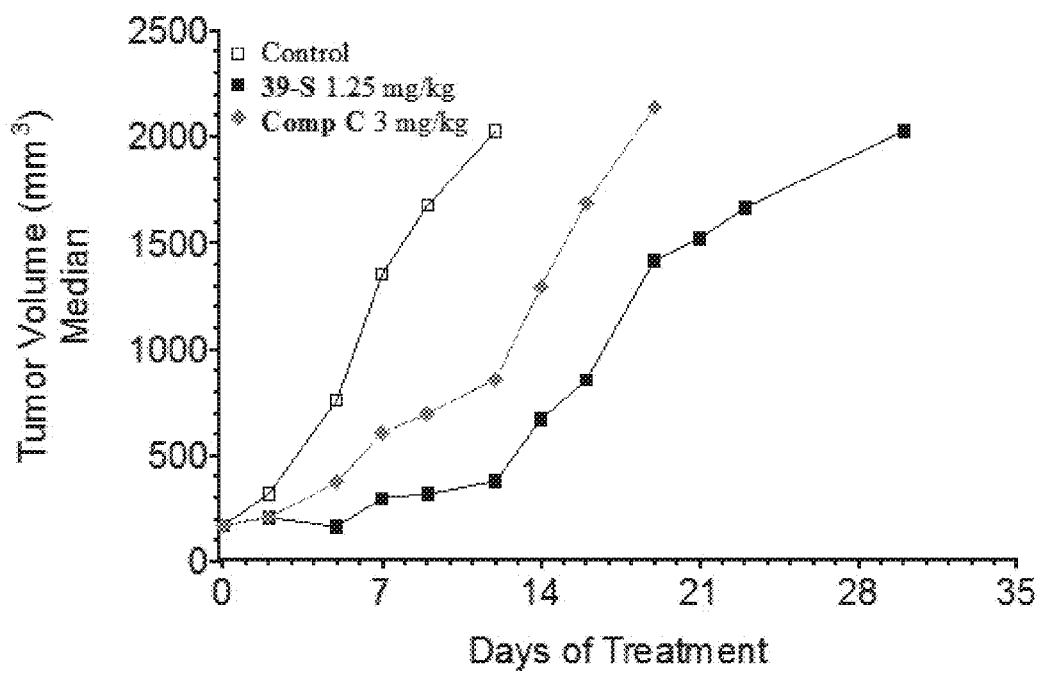
FIG. 40. Tumor volume evaluation of A2780 tumors in mice treated with placebo, compound C and 39-S.

Table 51 reports the volume evaluation of A2780 tumors in mice treated with placebo, compound C and 39-S. These results are also showed in FIG. 40.

TABLE 51

| Day | Median Tumor Volume (mm³) | | |
|---|---|---|---|
| | Control | 39-S | Compound C |
| 0 | 169.5 | 170.5 | 169.6 |
| 2 | 317.5 | 206.5 | 206.3 |
| 5 | 758.9 | 163.4 | 372.7 |
| 7 | 1351.9 | 298.6 | 607.6 |
| 9 | 1675.8 | 317.4 | 696.2 |
| 12 | 2025.0 | 378.2 | 855.6 |
| 14 | | 668.5 | 1293.9 |
| 16 | | 853.5 | 1683.5 |
| 19 | | 1415.5 | 2137.5 |
| 21 | | 1519.2 | |
| 23 | | 1666.0 | |
| 30 | | 2025.0 | |

Example 34e. In Vivo Studies to Determine the Effect of 39-S in Human Gastric Tumor Xenografts The aim of this study was to compare the antitumoral activity of 39-S with the antitumoral activity of compound C by using a xenograft model of human gastric cancer.

The tumor model used in this study was HGC27.

Figure 41:
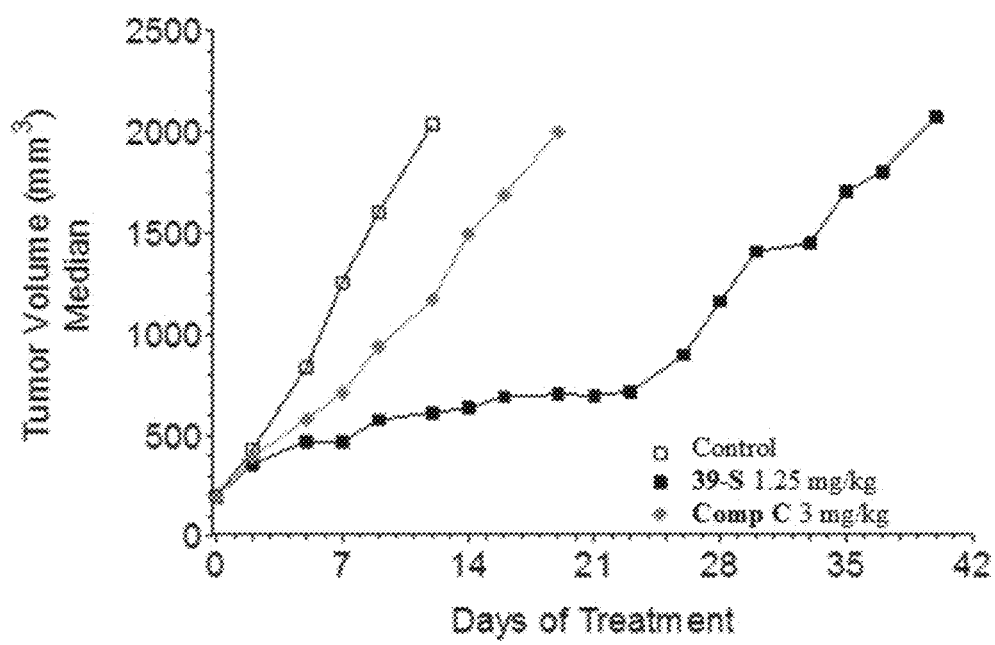
FIG. 41. Tumor volume evaluation of HGC27 tumors in mice treated with placebo, compound C and 39-S.

Table 52 reports tumor volume growth of HGC27 tumors in mice treated with placebo, compound C, and 39-S. These results are also showed in FIG. 41.

TABLE 52

| Days | Median Tumor Volume (mm³) | | |
|---|---|---|---|
| | Control | 39-S | Compound C |
| 0 | 200.7 | 195.6 | 195.0 |
| 2 | 429.0 | 356.3 | 391.0 |
| 5 | 835.5 | 469.7 | 578.6 |
| 7 | 1256.5 | 467.8 | 708.2 |
| 9 | 1602.2 | 575.2 | 937.7 |
| 12 | 2040.7 | 611.1 | 1169.5 |
| 14 | | 637.3 | 1496.8 |
| 16 | | 690.4 | 1690.6 |
| 19 | | 701.8 | 2004.0 |
| 21 | | 697.4 | 1741.4 |
| 23 | | 715.5 | 2056.4 |
| 26 | | 898.1 | |
| 28 | | 1163.4 | |
| 30 | | 1409.3 | |
| 33 | | 1450.5 | |
| 35 | | 1708.5 | |
| 37 | | 1804.4 | |
| 40 | | 2075.2 | |

Example 35. In Vivo Studies to Determine the Effect of 47-R in Several Xenograft Models Compound 47-R was provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. 47-R administered dose was 0.1 mg/Kg.

Compound D was provided in the form of powder drug substance. Each vial was reconstituted first by total dissolution in DMSO (Fisher) and then adding Kolliphor ELP (Basf)/ethanol absolute (Merk) (1:1, v/v) to a concentration of 0.8 mg/mL. Further dilutions were made with a lactate buffer solution (pH=4.0) to the dosing formulation concentration. Compound D administered dose was 0.5 mg/Kg.

Placebo was provided in the form of vials of lyophilised product. Each vial (sucrose 200 mg+potassium dihydrogen phosphate 13.6 mg+phosphoric acid q.s. pH 3.8-4.5) was reconstituted with sterile water for injection (2 mL). Further dilutions were made with 5% dextrose solution for injection.

In these experiments, 47-R and compound D, as well as placebo, were intravenously administered on a weekly schedule at a volume of 10 mL/Kg.

Example 35a. In Vivo Studies to Determine the Effect of 47-R in Human Fibrosarcoma Xenografts The aim of this study was to evaluate the antitumoral activity of compound 47-R by comparison with the antitumoral activity of compound D by using a xenograft model of human sarcoma.

The tumor model used in this study was HT1080 cell line.

Figure 42:
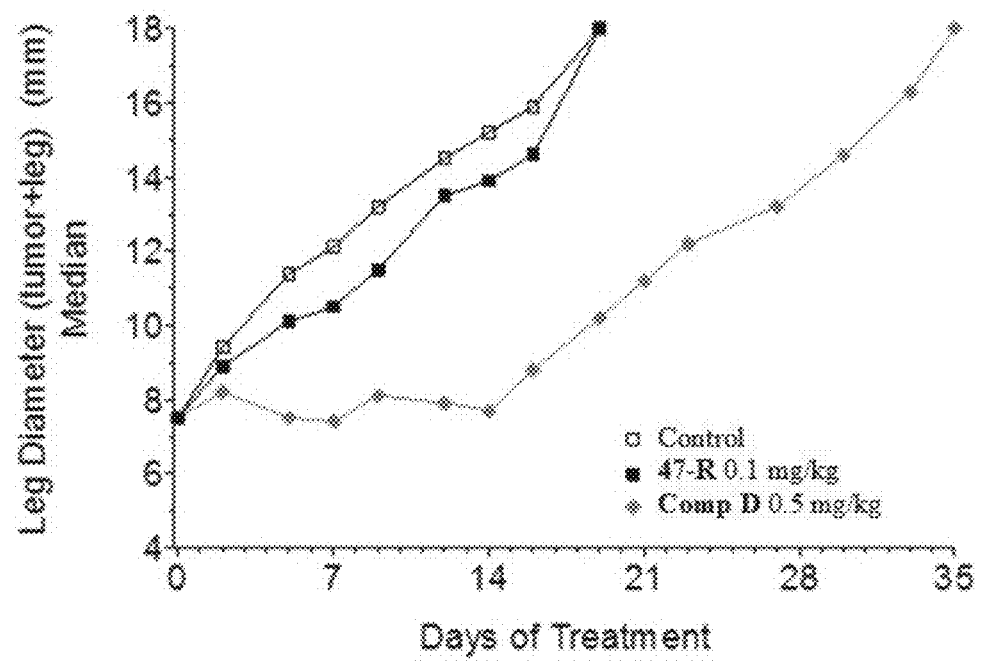
FIG. 42. Tumor total diameter evaluation of HT1080 tumors in mice treated with placebo, compound D and 47-R.

Table 53 reports the total diameter (tumor+leg) evaluation of HT1080 tumors in mice treated with placebo, compound D and 47-R. These results are also showed in FIG. 42.

TABLE 53

| Days | Total diameter (tumor + leg) (mm) | | |
|---|---|---|---|
| | Control | 47-R | Compound D |
| 0 | 7.5 | 7.5 | 7.5 |
| 2 | 9.4 | 8.9 | 8.2 |
| 5 | 11.4 | 10.1 | 7.5 |
| 7 | 12.1 | 10.5 | 7.4 |
| 9 | 13.2 | 11.5 | 8.1 |
| 12 | 14.5 | 13.5 | 7.9 |
| 14 | 15.2 | 13.9 | 7.7 |
| 16 | 15.9 | 14.6 | 8.8 |
| 19 | 18.0 | 18.0 | 10.2 |
| 21 | | | 11.2 |
| 23 | | | 12.2 |
| 27 | | | 13.2 |
| 30 | | | 14.6 |
| 33 | | | 16.3 |
| 35 | | | 18.0 |

Example 35b. In Vivo Studies to Determine the Effect of 47-R in Human Breast Adenocarcinoma Xenografts The aim of this study was to compare the antitumoral activities of 47-R and compound D by using a xenograft model of human breast cancer.

The tumor model used in this study was MDA-MB-231 cell line.

Figure 43:
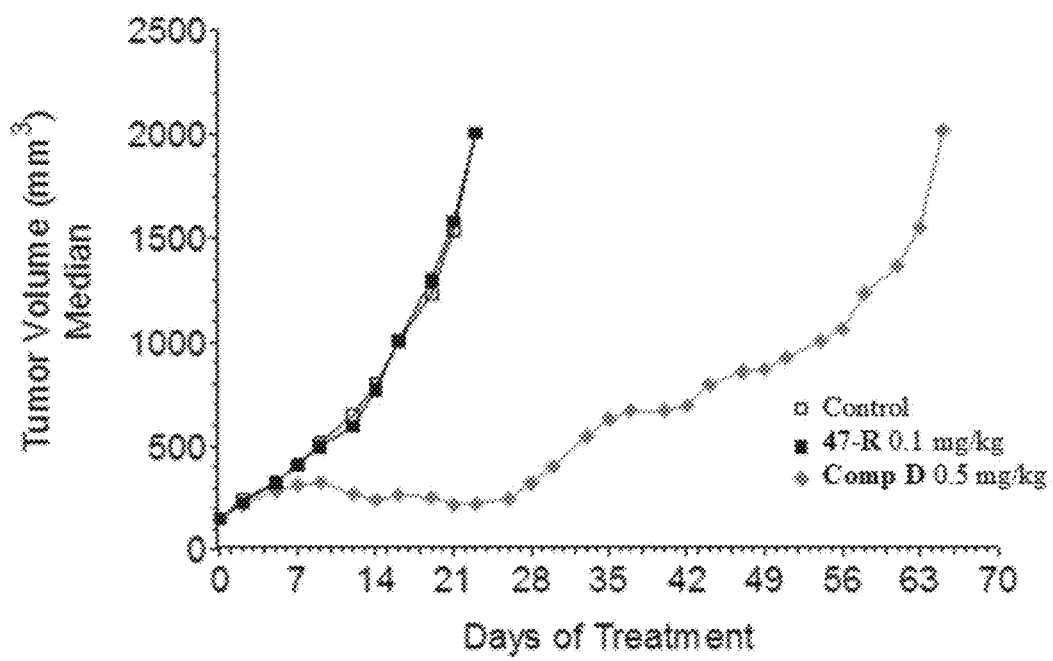
FIG. 43. Tumor volume evaluation of MDA-MB-231 tumors in mice treated with placebo, compound D and 47-R.

Table 54 reports the median tumor volume evaluation of MDA-MB-231 tumors in mice treated with placebo, compound D and 47-R. These results are also showed in FIG. 43.

TABLE 54

| Days | Median Tumor Volume (mm³) | | |
|---|---|---|---|
| | Control | 47-R | Compound D |
| 0 | 149.4 | 150.5 | 149.6 |
| 2 | 240.0 | 225.3 | 217.2 |
| 5 | 325.1 | 323.2 | 284.5 |
| 7 | 407.8 | 405.0 | 310.0 |
| 9 | 514.8 | 495.9 | 325.5 |
| 12 | 648.1 | 594.1 | 268.4 |
| 14 | 799.0 | 769.5 | 237.7 |
| 16 | 1002.5 | 1009.5 | 261.2 |
| 19 | 1233.9 | 1298.0 | 251.3 |

TABLE 54-continued

| | Median Tumor Volume (mm³) | | |
|---|---|---|---|
| Days | Control | 47-R | Compound D |
| 21 | 1539.1 | 1580.7 | 219.9 |
| 23 | 2006.5 | 2006.5 | 221.8 |
| 26 | 2027.7 | 2032.1 | 245.5 |
| 28 | | | 320.3 |
| 30 | | | 401.6 |
| 33 | | | 545.8 |
| 35 | | | 629.2 |
| 37 | | | 670.7 |
| 40 | | | 669.9 |
| 42 | | | 696.3 |
| 44 | | | 798.1 |
| 47 | | | 857.7 |
| 49 | | | 870.7 |
| 51 | | | 925.8 |
| 54 | | | 1005.4 |
| 56 | | | 1064.2 |
| 58 | | | 1235.6 |
| 61 | | | 1367.8 |
| 63 | | | 1553.7 |
| 65 | | | 2017.9 |

Example 35c. In Vivo Studies to Determine the Effect of 47-R in Human Lung Cancer Xenografts The aim of this study was to compare the antitumoral activity of 47-R with the antitumoral activity of compound D by using three different xenograft models of human lung cancer. These models correspond to non-small cell lung cancer (H-460 cell line) and to small cell lung cancer (H526 and H82 cell lines).

Figure 44:
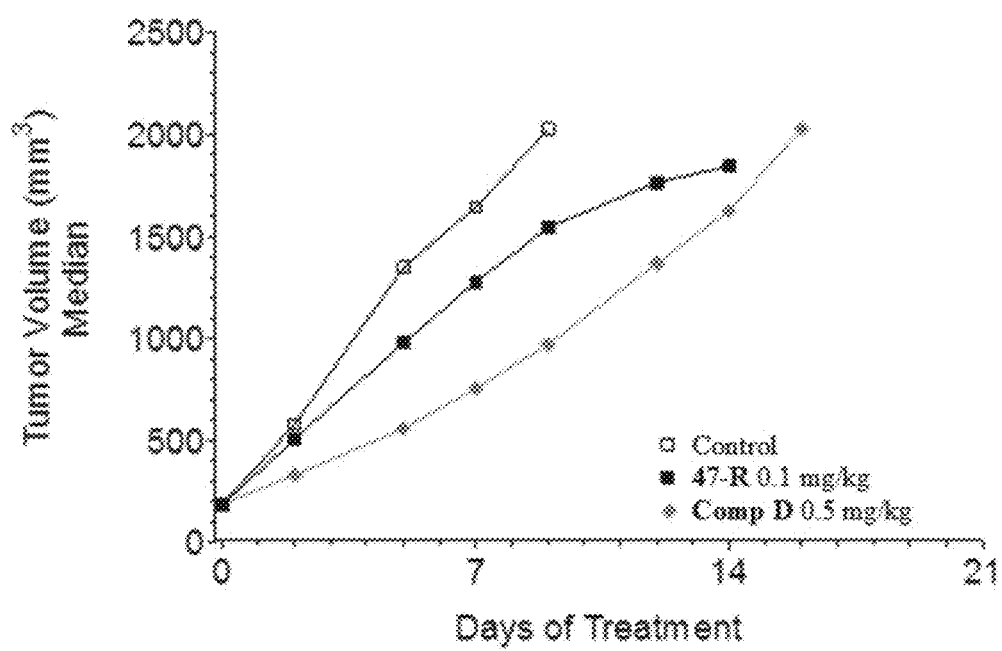
FIG. 44. Tumor volume evaluation of H460 tumors in mice treated with placebo, compound D and 47-R.

Table 55 reports the median tumor volume evaluation of H460 tumors in mice treated with placebo, compound D and 47-R. These results are also showed in FIG. 44.

TABLE 55

| | Median Tumor Volume (mm³) | | |
|---|---|---|---|
| Days | Control | 47-R | Compound D |
| 0 | 187.4 | 185.8 | 187.2 |
| 2 | 577.5 | 508.1 | 329.7 |
| 5 | 1352.0 | 979.3 | 559.4 |
| 7 | 1642.9 | 1280.0 | 756.5 |
| 9 | 2025.0 | 1543.1 | 971.9 |
| 12 | | 1764.0 | 1370.9 |
| 14 | | 1845.5 | 1626.8 |
| 16 | | | 2025.0 |

Figure 45:
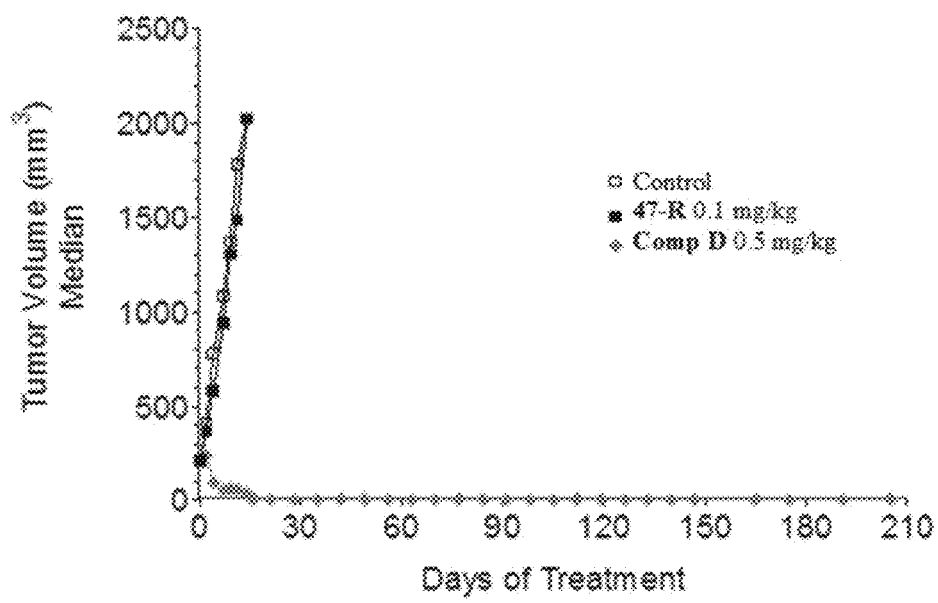
FIG. 45. Tumor volume evaluation of H526 tumors in mice treated with placebo, compound D and 47-R.

Table 56 reports the median tumor volume evaluation of H526 tumors in mice treated with placebo, compound D and 47-R. These results are also showed in FIG. 45.

TABLE 56

| | Median Tumor Volume (mm³) | | |
|---|---|---|---|
| Days | Control | 47-R | Compound D |
| 0 | 217.2 | 211.5 | 216.1 |
| 2 | 410.7 | 367.9 | 240.9 |
| 4 | 778.5 | 583.7 | 99.3 |
| 7 | 1083.2 | 941.7 | 56.7 |
| 9 | 1371.0 | 1305.2 | 62.5 |
| 11 | 1782.0 | 1484.7 | 62.5 |
| 14 | 2025.0 | 2025.0 | 32.0 |
| 16 | | | 4.0 |
| 21 | | | 4.0 |

TABLE 56-continued

| | Median Tumor Volume (mm³) | | |
|---|---|---|---|
| Days | Control | 47-R | Compound D |
| 28 | | | 4.0 |
| 35 | | | 4.0 |
| 42 | | | 4.0 |
| 49 | | | 4.0 |
| 56 | | | 4.0 |
| 63 | | | 4.0 |
| 70 | | | 4.0 |
| 77 | | | 4.0 |
| 84 | | | 4.0 |
| 91 | | | 4.0 |
| 98 | | | 4.0 |
| 105 | | | 4.0 |
| 112 | | | 4.0 |
| 119 | | | 4.0 |
| 126 | | | 4.0 |
| 133 | | | 4.0 |
| 140 | | | 4.0 |
| 147 | | | 4.0 |
| 165 | | | 4.0 |
| 175 | | | 4.0 |
| 191 | | | 4.0 |
| 205 | | | 4.0 |

Figure 46:
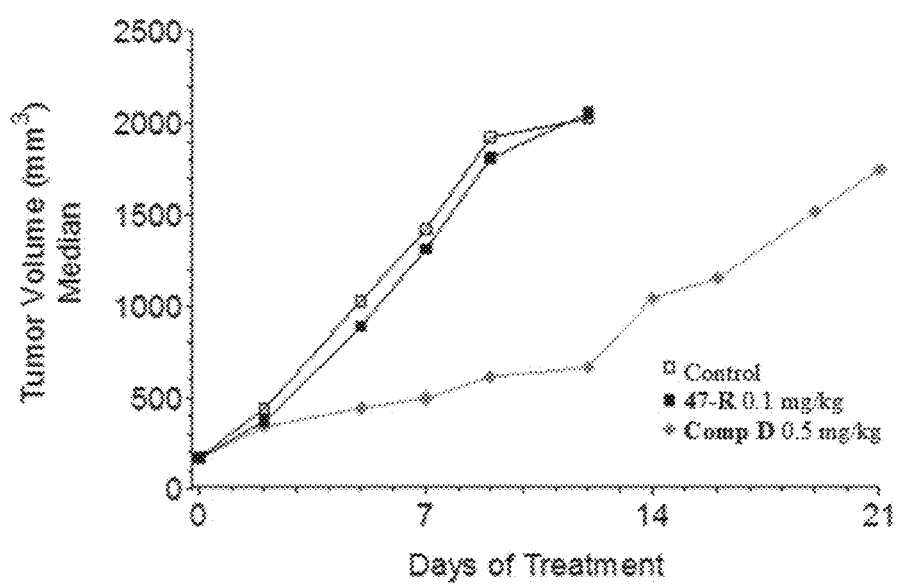
FIG. 46. Tumor volume evaluation of H82 tumors in mice treated with placebo, compound D and 47-R.

Table 57 reports the median tumor volume evaluation of H82 tumors in mice treated with placebo, compound D and 47-R. These results are also showed in FIG. 46.

TABLE 57

| | Median Tumor Volume (mm³) | | |
|---|---|---|---|
| Days | Control | 47-R | Compound D |
| 0 | 171.6 | 169.0 | 169.4 |
| 2 | 439.4 | 371.6 | 340.6 |
| 5 | 1024.7 | 888.8 | 443.3 |
| 7 | 1422.0 | 1314.2 | 496.2 |
| 9 | 1923.8 | 1811.0 | 614.1 |
| 12 | 2025.0 | 2055.4 | 665.5 |
| 14 | | | 1041.6 |
| 16 | | | 1151.2 |
| 19 | | | 1516.7 |
| 21 | | | 1748.0 |

Example 35d. In Vivo Studies to Determine the Effect of 47-R in Human Ovarian Tumor Xenografts The aim of this study was to compare the antitumoral activity of 47-R with the antitumoral activity of compound D by using a xenograft model of human ovarian cancer.

The tumor model used in this study was A2780.

Figure 47:
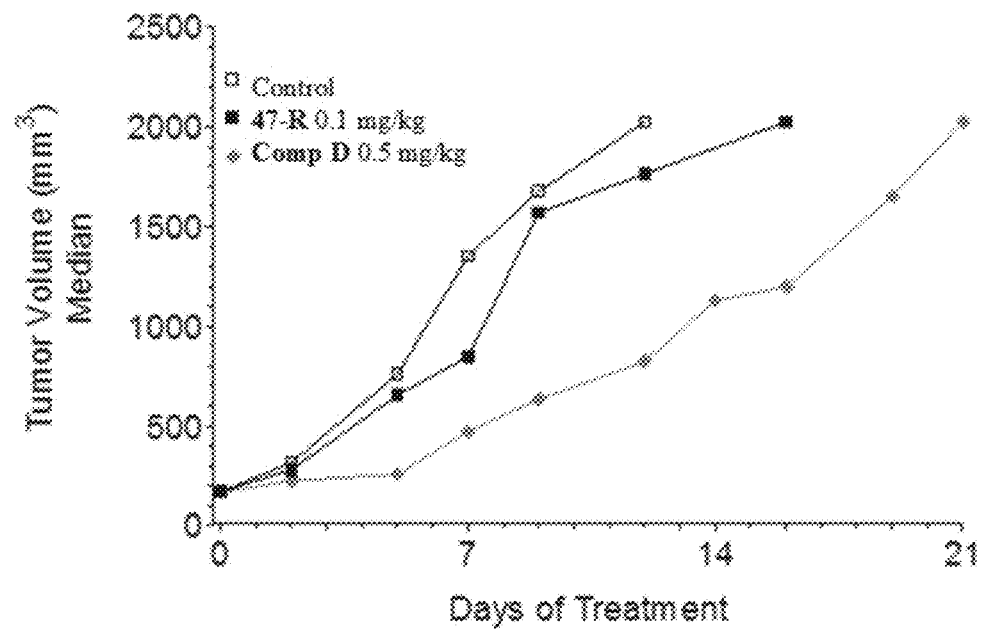
FIG. 47. Tumor volume evaluation of A2780 tumors in mice treated with placebo, compound D and 47-R.

Table 58 reports the volume evaluation of A2780 tumors in mice treated with placebo, compound D and 47-R. These results are also showed in FIG. 47.

TABLE 58

| | Median Tumor Volume (mm³) | | |
|---|---|---|---|
| Days | Control | 47-R | Compound D |
| 0 | 169.5 | 170.6 | 168.8 |
| 2 | 317.5 | 280.5 | 225.7 |
| 5 | 758.9 | 653.9 | 256.6 |
| 7 | 1351.9 | 848.7 | 473.8 |
| 9 | 1675.8 | 1569.1 | 633.6 |
| 12 | 2025.0 | 1764.0 | 822.8 |
| 14 | | 1666.0 | 1129.3 |

TABLE 58-continued

| | Median Tumor Volume (mm³) | | |
|---|---|---|---|
| Days | Control | 47-R | Compound D |
| 16 | | 2025.0 | 1198.6 |
| 19 | | | 1649.6 |
| 21 | | | 2025.0 |

Example 35e. In Vivo Studies to Determine the Effect of 47-R in Human Gastric Tumor Xenografts The aim of this study was to compare the antitumoral activity of 47-R with the antitumoral activity of compound D by using a xenograft model of human gastric cancer.

The tumor model used in this study was HGC27.

Figure 48:
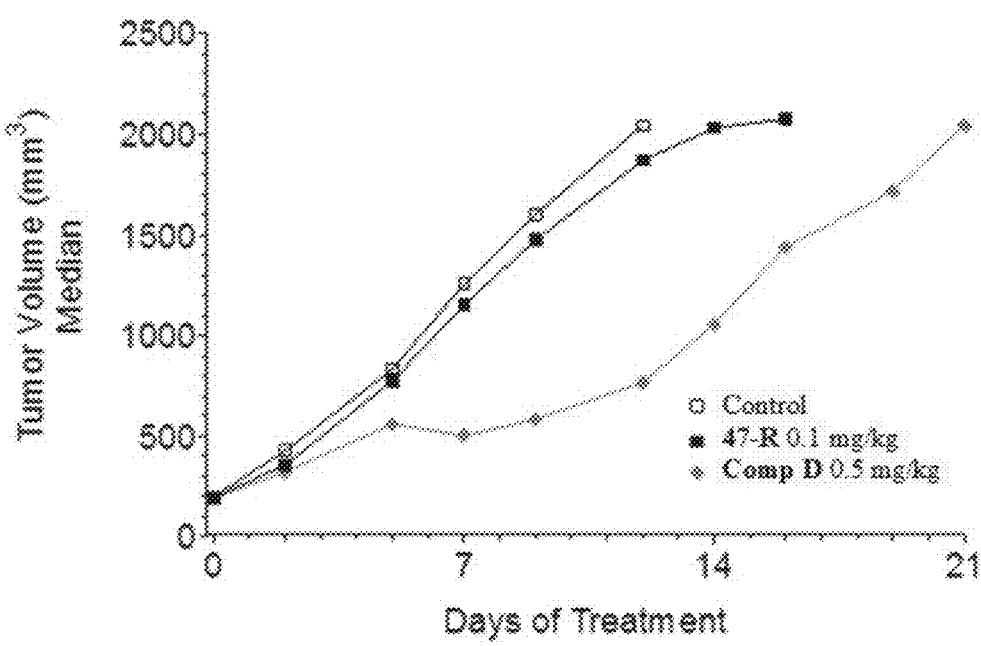
FIG. 48. Tumor volume evaluation of HGC27 tumors in mice treated with placebo, compound D and 47-R.

Table 59 reports tumor volume growth of HGC27 tumors in mice treated with placebo, compound D, and 47-R. These results are also showed in FIG. 48.

TABLE 59

| | Median Tumor Volume (mm³) | | |
|---|---|---|---|
| Days | Control | 47-R | Compound D |
| 0 | 200.7 | 194.0 | 194.0 |
| 2 | 429.0 | 359.4 | 324.2 |
| 5 | 835.5 | 774.8 | 561.6 |
| 7 | 1256.5 | 1155.4 | 504.2 |
| 9 | 1602.2 | 1474.7 | 584.2 |
| 12 | 2040.7 | 1870.2 | 767.7 |
| 14 | | 2031.3 | 1056.8 |
| 16 | | 2075.2 | 1440.2 |
| 19 | | | 1717.9 |
| 21 | | | 2043.4 |

Example 36. In Vivo Studies to Determine the Effect of 32 in Several Xenograft Models Compounds 32 and ET-736 were provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. The administered dose of 32 and ET-736 was 0.5 mg/Kg.

Placebo was provided in the form of lyophilised product. Each vial (sucrose 200 mg+potassium dihydrogen phosphate 13.6 mg+phosphoric acid q.s. pH 3.8-4.5) was reconstituted with sterile water for injection (2 mL). Further dilutions were made with 5% dextrose solution for injection.

In these experiments, 32 and ET-736, as well as placebo, were intravenously administered on a weekly schedule at a volume of 10 mL/Kg.

Example 36a. In Vivo Studies to Determine the Effect of 32 in Human Fibrosarcoma Xenografts The aim of this study was to evaluate the antitumoral activity of compound 32 by comparison with the antitumoral activity of ET-736 by using a xenograft model of human sarcoma.

The tumor model used in this study was HT-1080 cell line.

Figure 49:
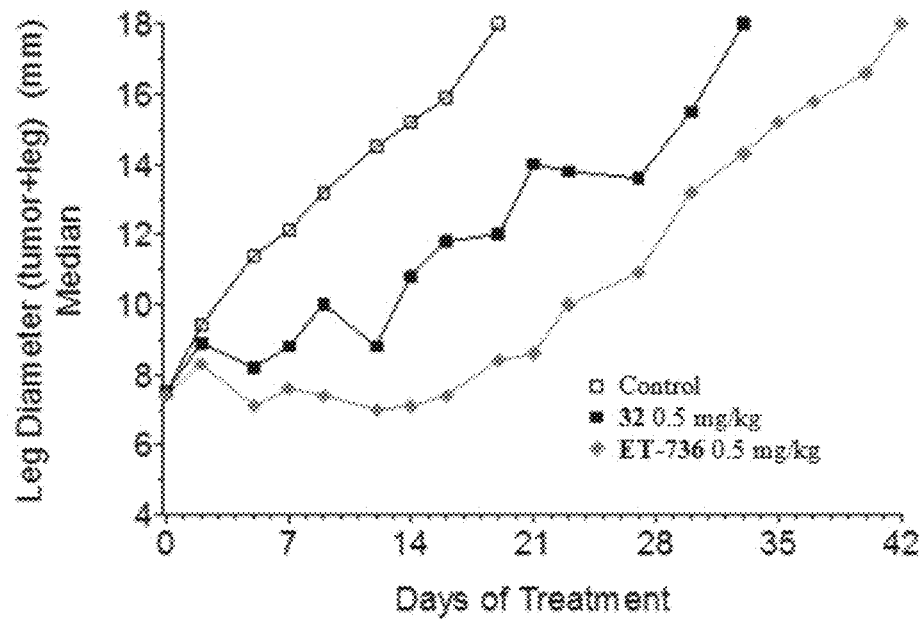
FIG. 49. Tumor total diameter evaluation of HT1080 tumors in mice treated with placebo, ET-736 and 32.

Table 60 reports the total diameter (tumor+leg) evaluation of HT1080 tumors in mice treated with placebo, ET-736 and 32. These results are also showed in FIG. 49.

TABLE 60

| | Total diameter (tumor + leg) (mm) | | |
|---|---|---|---|
| Days | Control | 32 | ET-736 |
| 0 | 7.5 | 7.5 | 7.4 |
| 2 | 9.4 | 8.9 | 8.3 |
| 5 | 11.4 | 8.2 | 7.1 |
| 7 | 12.1 | 8.8 | 7.6 |
| 9 | 13.2 | 10.0 | 7.4 |
| 12 | 14.5 | 8.8 | 7.0 |
| 14 | 15.2 | 10.8 | 7.1 |
| 16 | 15.9 | 11.8 | 7.4 |
| 19 | 18.0 | 12.0 | 8.4 |
| 21 | | 14.0 | 8.6 |
| 23 | | 13.8 | 10.0 |
| 27 | | 13.6 | 10.9 |
| 30 | | 15.5 | 13.2 |
| 33 | | 18.0 | 14.3 |
| 35 | | | 15.2 |
| 37 | | | 15.8 |
| 40 | | | 16.6 |
| 42 | | | 18.0 |

Example 36b. In Vivo Studies to Determine the Effect of 32 in Human Breast Adenocarcinoma Xenografts The aim of this study was to compare the antitumoral activities of 32 and ET-736 by using a xenograft model of human breast cancer.

The tumor model used in this study was MDA-MB-231 cell line.

Figure 50:
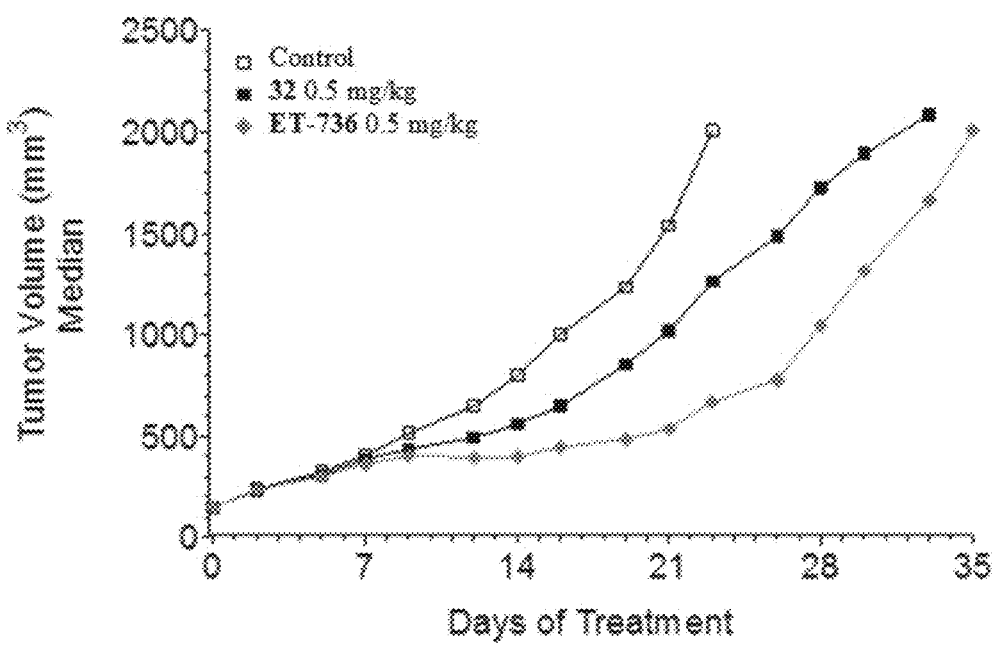
FIG. 50. Tumor volume evaluation of MDA-MB-231 tumors in mice treated with placebo, ET-736 and 32.

Table 61 reports the median tumor volume evaluation of MDA-MB-231 tumors in mice treated with placebo, ET-736 and 32. These results are also showed in FIG. 50.

TABLE 61

| | Median Tumor Volume (mm³) | | |
|---|---|---|---|
| Days | Control | 32 | ET-736 |
| 0 | 149.4 | 150.2 | 150.0 |
| 2 | 240.0 | 233.6 | 237.7 |
| 5 | 325.1 | 310.6 | 302.1 |
| 7 | 407.8 | 386.1 | 364.9 |
| 9 | 514.8 | 437.5 | 404.6 |
| 12 | 648.1 | 493.4 | 395.4 |
| 14 | 799.0 | 560.3 | 398.3 |
| 16 | 1002.5 | 649.5 | 447.2 |
| 19 | 1233.9 | 853.0 | 485.0 |
| 21 | 1539.1 | 1017.5 | 536.3 |
| 23 | 2006.5 | 1263.2 | 669.8 |
| 26 | 2027.7 | 1487.7 | 778.9 |
| 28 | | 1726.6 | 1046.1 |
| 30 | | 1892.6 | 1315.9 |
| 33 | | 2082.8 | 1664.9 |
| 35 | | | 2007.7 |

Example 36c. In Vivo Studies to Determine the Effect of 32 in Human Lung Cancer Xenografts The aim of this study was to compare the antitumoral activities of 32 and ET-736 by using three different xenograft models of human lung cancer. These models correspond to non-small cell lung cancer (H-460 cell line) and to small cell lung cancer (H526 and H82 cell lines).

Figure 51:
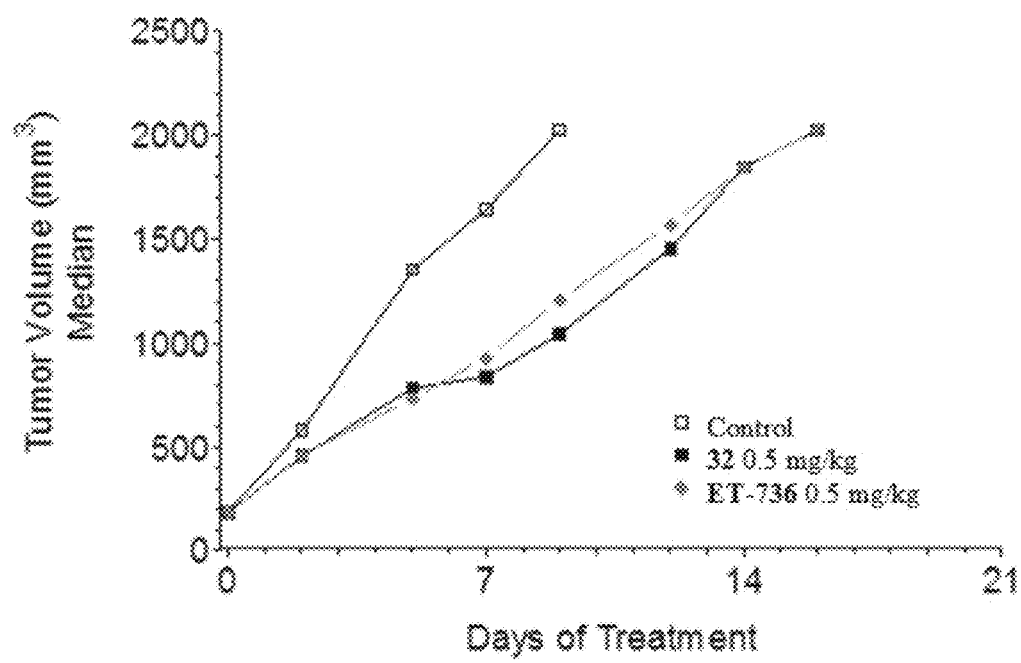
FIG. 51. Tumor volume evaluation of H460 tumors in mice treated with placebo, ET-736 and 32.

Table 62 reports the median tumor volume evaluation of H460 tumors in mice treated with placebo, ET-736 and 32. These results are also showed in FIG. 51.

TABLE 62

| Days | Median Tumor Volume (mm³) | | |
|---|---|---|---|
| | Control | 32 | ET-736 |
| 0 | 187.4 | 183.9 | 185.8 |
| 2 | 577.5 | 455.2 | 457.8 |
| 5 | 1352.0 | 784.8 | 732.8 |
| 7 | 1642.9 | 837.4 | 930.1 |
| 9 | 2025.0 | 1044.3 | 1207.2 |
| 12 | 2025.0 | 1452.4 | 1568.0 |
| 14 | | 1845.5 | 1845.5 |
| 16 | | 2025.0 | 2025.0 |

Figure 52:
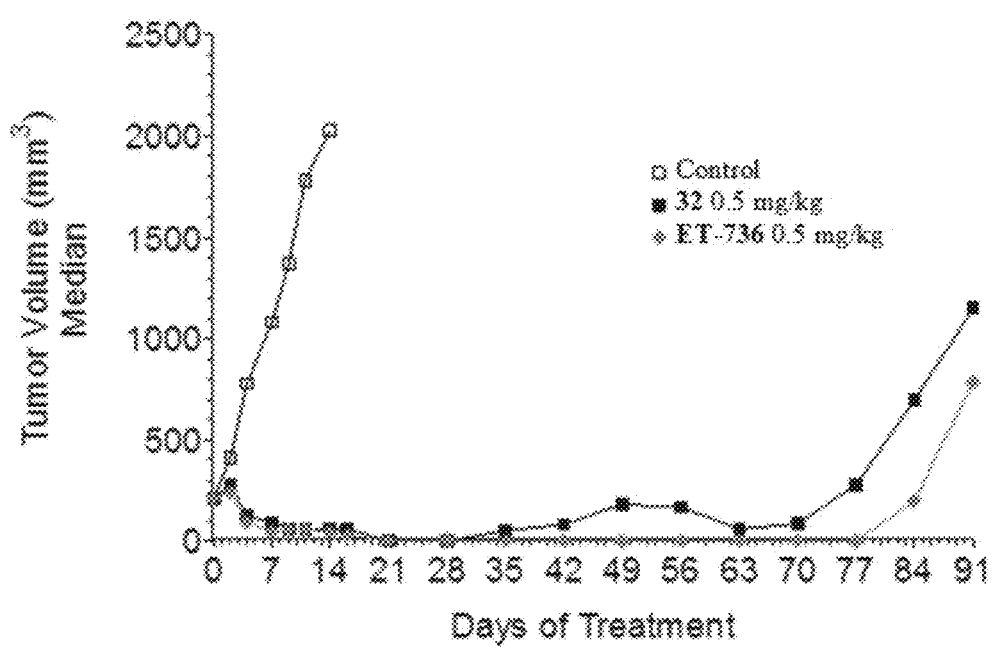
FIG. 52. Tumor volume evaluation of H526 tumors in mice treated with placebo, ET-736 and 32.

Table 63 reports the median tumor volume evaluation of H526 tumors in mice treated with placebo, ET-736 and 32. These results are also showed in FIG. 52.

TABLE 63

| Days | Median Tumor Volume (mm³) | | |
|---|---|---|---|
| | Control | 32 | ET-736 |
| 0 | 217.2 | 212.1 | 213.5 |
| 2 | 410.7 | 277.3 | 240.5 |
| 4 | 778.5 | 127.0 | 97.2 |
| 7 | 1083.2 | 95.0 | 48.8 |
| 9 | 1371.0 | 63.1 | 62.5 |
| 11 | 1782.0 | 62.5 | 62.5 |
| 14 | 2025.0 | 62.5 | 47.3 |
| 16 | | 62.5 | 32.0 |
| 21 | | 4.0 | 4.0 |
| 28 | | 4.0 | 4.0 |
| 35 | | 55.3 | 4.0 |
| 42 | | 85.3 | 4.0 |
| 49 | | 185.6 | 4.0 |
| 56 | | 169.1 | 4.0 |
| 63 | | 62.5 | 4.0 |
| 70 | | 88.9 | 4.0 |
| 77 | | 280.6 | 4.0 |
| 84 | | 694.2 | 199.8 |
| 91 | | 1150.9 | 786.5 |

Figure 53:
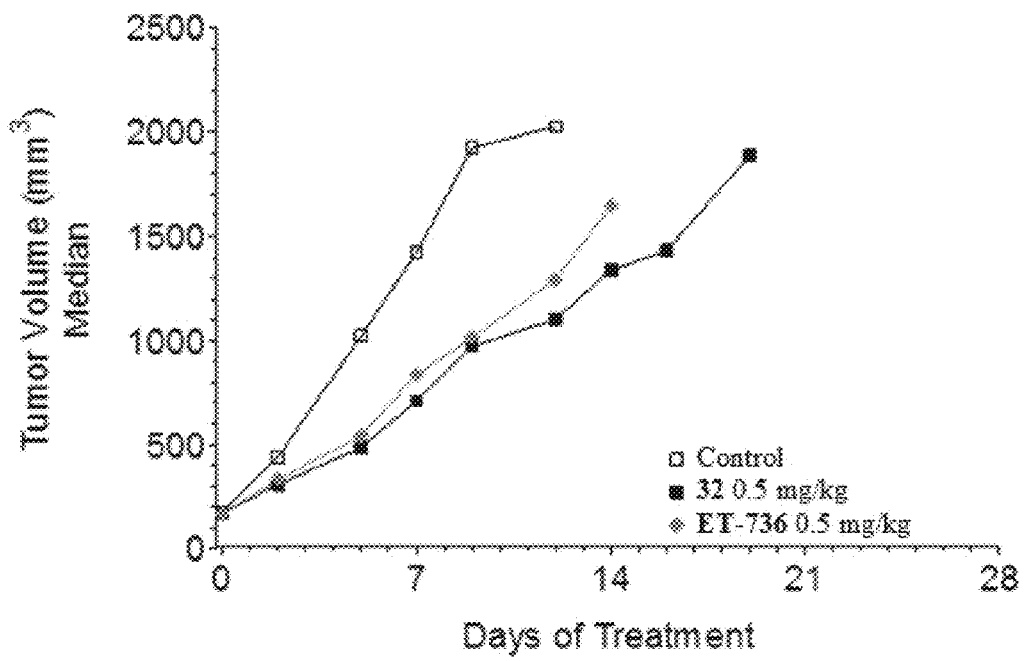
FIG. 53. Tumor volume evaluation of H82 tumors in mice treated with placebo, ET-736 and 32.

Table 64 reports the median tumor volume evaluation of H82 tumors in mice treated with placebo, ET-736 and 32. These results are also showed in FIG. 53.

TABLE 64

| Days | Median Tumor Volume (mm³) | | |
|---|---|---|---|
| | Control | 32 | ET-736 |
| 0 | 171.6 | 171.6 | 170.0 |
| 2 | 439.4 | 309.4 | 334.4 |
| 5 | 1024.7 | 485.0 | 539.4 |
| 7 | 1422.0 | 708.4 | 836.4 |
| 9 | 1923.8 | 972.6 | 1013.1 |
| 12 | 2025.0 | 1101.6 | 1290.9 |
| 14 | | 1339.6 | 1648.0 |
| 16 | | 1430.3 | |
| 19 | | 1885.7 | |

Example 36d. In Vivo Studies to Determine the Effect of 32 in Human Ovarian Tumor Xenografts The aim of this study was to compare the antitumoral activities of 32 and ET-736 by using a xenograft model of human ovarian cancer.

The tumor model used in this study was A2780.

Figure 54:
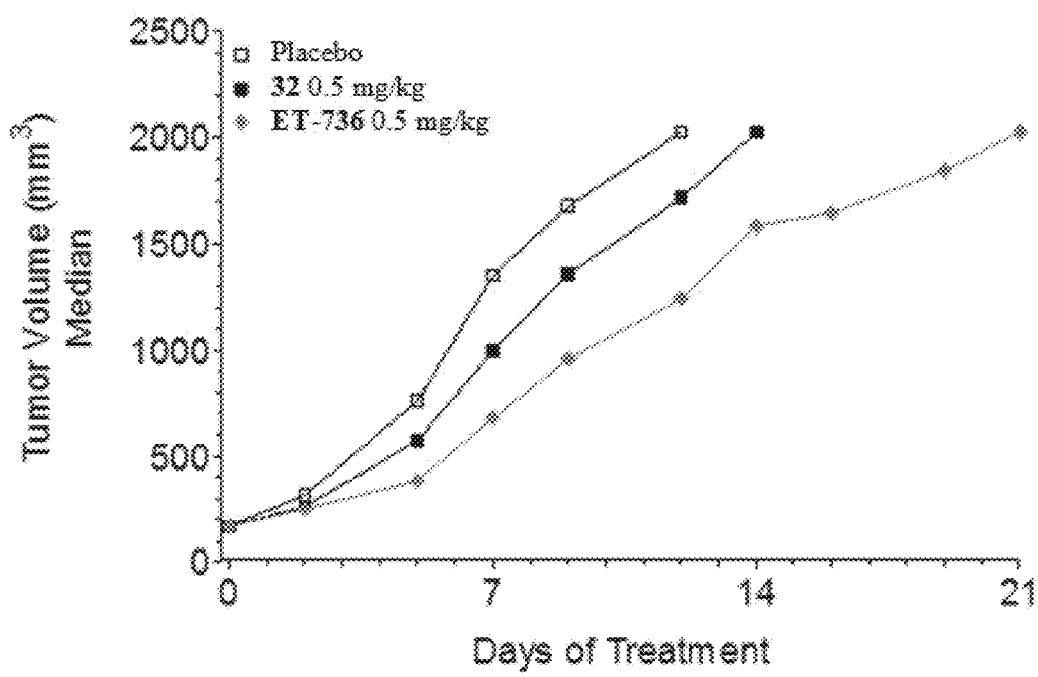
FIG. 54. Tumor volume evaluation of A2780 tumors in mice treated with placebo, ET-736 and 32.

Table 65 reports the volume evaluation of A2780 tumors in mice treated with placebo, ET-736 and 32. These results are also showed in FIG. 54.

TABLE 65

| Days | Median Tumor Volume (mm³) | | |
|---|---|---|---|
| | Control | 32 | ET-736 |
| 0 | 169.5 | 168.6 | 168.8 |
| 2 | 317.5 | 262.9 | 251.2 |
| 5 | 758.9 | 572.7 | 382.6 |
| 7 | 1351.9 | 997.5 | 676.1 |
| 9 | 1675.8 | 1359.9 | 959.4 |
| 12 | 2025.0 | 1715.0 | 1241.5 |
| 14 | | 2025.0 | 1582.7 |
| 16 | | 2025.0 | 1646.4 |
| 19 | | | 1845.5 |
| 21 | | | 2025.0 |

Example 36e. In Vivo Studies to Determine the Effect of 32 in Human Gastric Tumor Xenografts The aim of this study was to compare the antitumoral activities of 32 and ET-736 by using a xenograft model of human gastric cancer.

The tumor model used in this study was HGC27.

Figure 55:
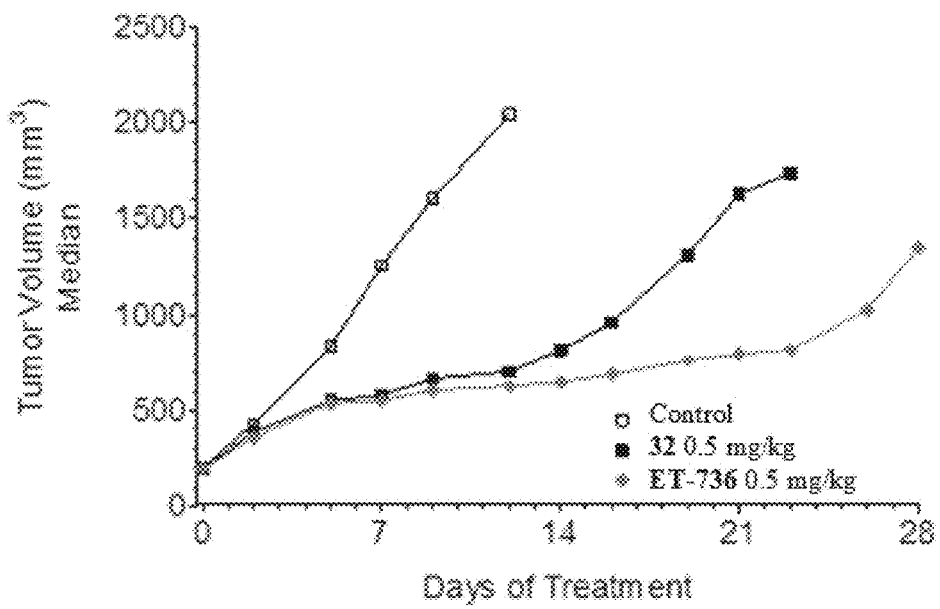
FIG. 55. Tumor volume evaluation of HGC27 tumors in mice treated with placebo, ET-736 and 32.

Table 66 reports tumor volume growth of HGC27 tumors in mice treated with placebo, ET-736 and 32. These results are also showed in FIG. 55.

TABLE 66

| Days | Median Tumor Volume (mm³) | | |
|---|---|---|---|
| | Control | 32 | ET-736 |
| 0 | 200.7 | 194.8 | 195.9 |
| 2 | 429.0 | 386.3 | 359.2 |
| 5 | 835.5 | 551.3 | 537.6 |
| 7 | 1256.5 | 579.2 | 553.5 |
| 9 | 1602.2 | 665.8 | 604.7 |
| 12 | 2040.7 | 701.1 | 627.4 |
| 14 | | 814.5 | 648.0 |
| 16 | | 959.9 | 687.6 |
| 19 | | 1312.4 | 760.0 |
| 21 | | 1626.8 | 792.4 |
| 23 | | 1737.3 | 818.9 |
| 26 | | | 1026.1 |
| 28 | | | 1354.9 |

Example 37. In Vivo Studies to Determine the Effect of 35 in Several Xenograft Models Compound 35 was provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. The administered dose of 35 was 0.25 mg/Kg.

PM01183 was provided in the form of vials of lyophilized product. Each vial was reconstituted with sterile water for injection to a concentration of 0.5 mg/mL. Further dilutions were made with 5% glucose or 0.9% sodium chloride solution for injection to the dosing formulation concentration. The administered dose of PM01183 was 0.18 mg/Kg.

Placebo was provided in the form of vials of lyophilised product each vial (sucrose 200 mg+potassium dihydrogen phosphate 13.6 mg+phosphoric acid q.s. pH 3.8-4.5) was reconstituted with sterile water for injection (2 mL). Further dilutions were made with 5% dextrose solution for injection.

In this experiment, compound 35 and PM01183, as well as placebo were intravenously administered on a weekly schedule at a volume of 10 mL/Kg.

Example 37a. In Vivo Studies to Determine the Effect of 35 in Human Fibrosarcoma Xenografts The aim of this study was to evaluate the antitumoral activities of compound 35 and PM01183 by using a xenograft model of human sarcoma.

The tumor model used in this study was HT-1080 cell line.

Figure 56:
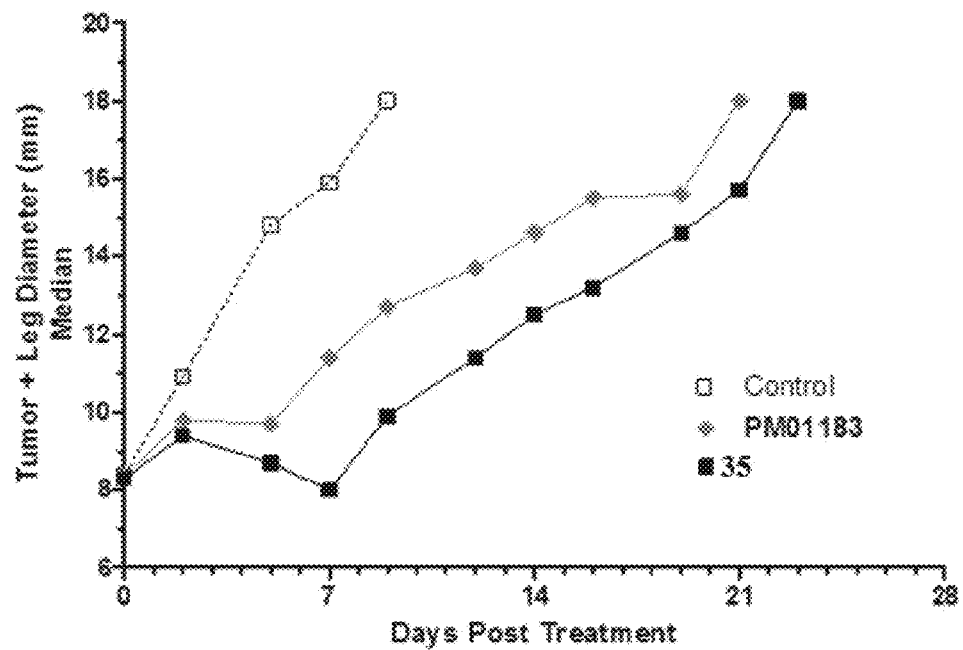
FIG. 56. Tumor total diameter evaluation of HT1080 tumors in mice treated with placebo, PM01183 and 35.

Table 67 reports the total diameter (tumor+leg) evaluation of HT1080 tumors in mice treated with placebo, PM01183 and 35. These results are also showed in FIG. 56.

TABLE 67

| | Total diameter (tumor + leg) (mm) | | |
|---|---|---|---|
| Days | Control | PM01183 | 35 |
| 0 | 8.4 | 8.4 | 8.3 |
| 2 | 10.9 | 9.8 | 9.4 |
| 5 | 14.8 | 9.7 | 8.7 |
| 7 | 15.9 | 11.4 | 8.0 |
| 9 | 18.0 | 12.7 | 9.9 |
| 12 | | 13.7 | 11.4 |
| 14 | | 14.6 | 12.5 |
| 16 | | 15.5 | 13.2 |
| 19 | | 15.6 | 14.6 |
| 21 | | 18.0 | 15.7 |
| 23 | | | 18.0 |

Example 37b. In Vivo Studies to Determine the Effect of 35 in Human Breast Adenocarcinoma Xenografts The aim of this study was to compare the antitumoral activities of 35 and PM01183 by using a xenograft model of human breast cancer.

The tumor model used in this study was MDA-MB-231 cell line.

Figure 57:
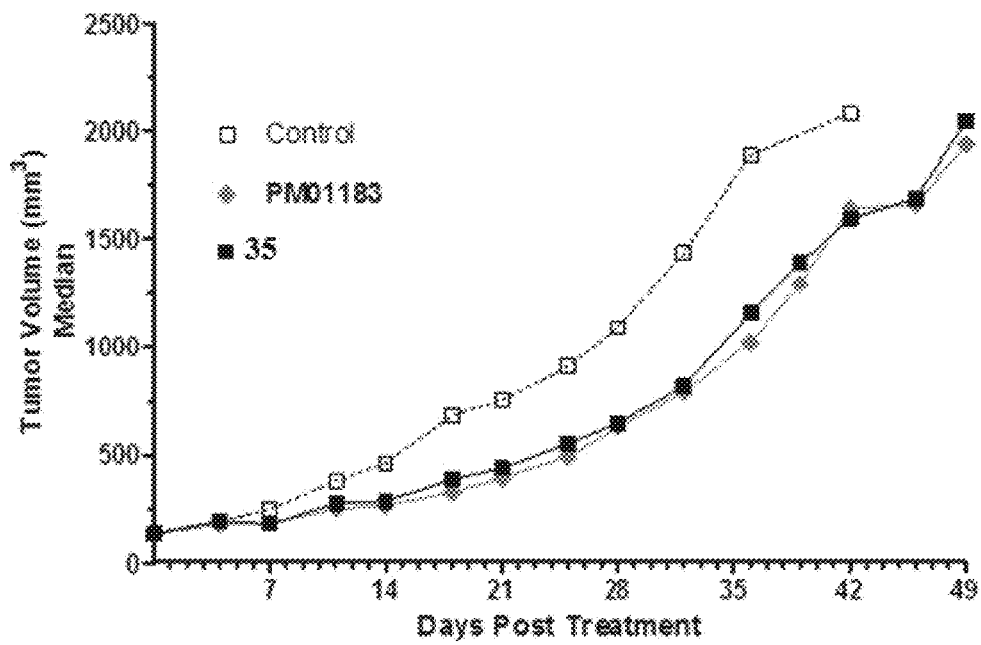
FIG. 57. Tumor volume evaluation of MDA-MB-231 tumors in mice treated with placebo, PM01183 and 35.

Table 68 reports the median tumor volume evaluation of MDA-MB-231 tumors in mice treated with placebo, PM01183 and 35. These results are also showed in FIG. 57.

TABLE 68

| | Median Tumor Volume (mm$^3$) | | |
|---|---|---|---|
| Days | Control | 35 | PM01183 |
| 0 | 132.6 | 132.7 | 134.3 |
| 4 | 194.1 | 193.6 | 177.2 |
| 7 | 248.2 | 179.1 | 186.3 |
| 11 | 377.6 | 276.7 | 250.7 |
| 14 | 461.3 | 286.0 | 266.1 |
| 18 | 679.2 | 384.5 | 327.7 |
| 21 | 753.2 | 436.8 | 391.0 |
| 25 | 909.2 | 554.3 | 493.1 |
| 28 | 1090.7 | 647.0 | 627.3 |
| 32 | 1433.4 | 817.5 | 789.0 |
| 36 | 1887.5 | 1156.7 | 1022.0 |
| 39 | 1785.2 | 1387.6 | 1294.2 |
| 42 | 2081.5 | 1595.3 | 1643.3 |
| 46 | 2137.5 | 1689.9 | 1658.9 |
| 49 | | 2044.2 | 1938.0 |

Example 37c. In Vivo Studies to Determine the Effect of 35 in Human Lung Cancer Xenografts The aim of this study was to compare the antitumoral activities of 35 and PM01183 by using a xenograft model of human lung cancer.

The tumor model used in this study was H460 cell line.

Figure 58:
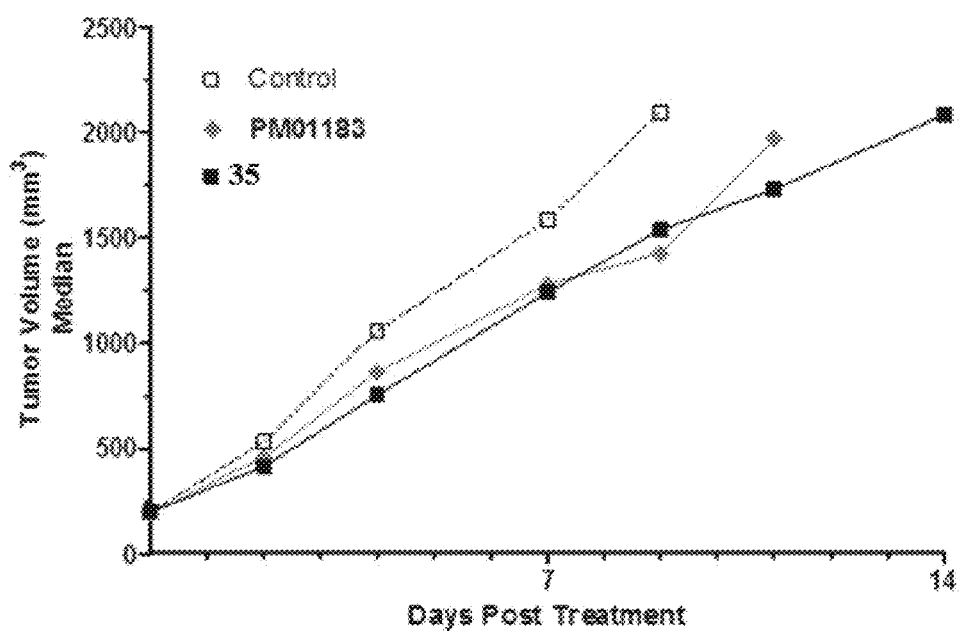
FIG. 58. Tumor volume evaluation of H460 tumors in mice treated with placebo, PM01183 and 35.

Table 69 reports the median tumor volume evaluation of H460 tumors in mice treated with placebo, PM01183 and 35. These results are also showed in FIG. 58.

TABLE 69

| | Median Tumor Volume (mm$^3$) | | |
|---|---|---|---|
| Days | Control | PM01183 | 35 |
| 0 | 197.0 | 196.3 | 197.2 |
| 2 | 529.5 | 457.0 | 415.3 |
| 4 | 1057.4 | 861.5 | 750.8 |
| 7 | 1582.5 | 1280.2 | 1242.3 |
| 9 | 2094.8 | 1424.9 | 1536.3 |
| 11 | | 1969.9 | 1728.7 |
| 14 | | | 2080.9 |

Example 37d. In Vivo Studies to Determine the Effect of 35 in Human Ovarian Tumor Xenografts The aim of this study was to compare the antitumoral activities of 35 and PM01183 by using a xenograft model of human ovarian cancer.

The tumor model used in this study was A2780.

Figure 59:
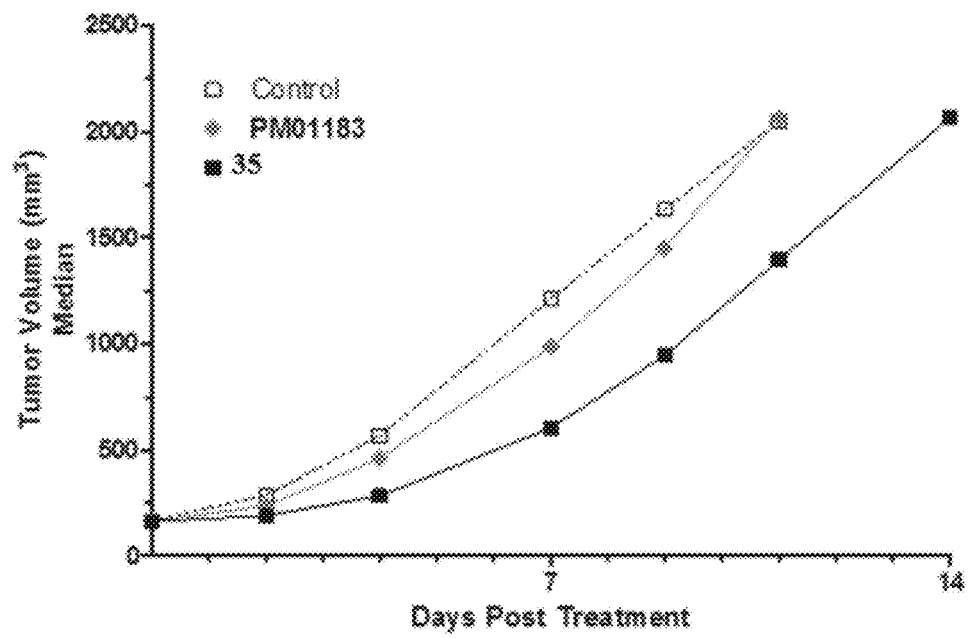
FIG. 59. Tumor volume evaluation of A2780 tumors in mice treated with placebo, PM01183 and 35.

Table 70 reports the volume evaluation of A2780 tumors in mice treated with placebo, PM01183 and 35. These results are also showed in FIG. 59.

TABLE 70

| | Median Tumor Volume (mm$^3$) | | |
|---|---|---|---|
| Days | Control | PM01183 | 35 |
| 0 | 163.4 | 163.6 | 163.6 |
| 2 | 287.1 | 236.5 | 189.9 |
| 4 | 568.7 | 463.2 | 284.3 |
| 7 | 1211.3 | 986.3 | 606.4 |
| 9 | 1633.7 | 1451.4 | 946.9 |
| 11 | 2047.8 | 2062.0 | 1394.2 |
| 14 | | | 2067.7 |

Example 37e. In Vivo Studies to Determine the Effect of 35 in Human Gastric Tumor Xenografts The aim of this study was to compare the antitumoral activities of 35 and PM01183 by using a xenograft model of human gastric cancer.

The tumor model used in this study was HGC27.

Figure 60:
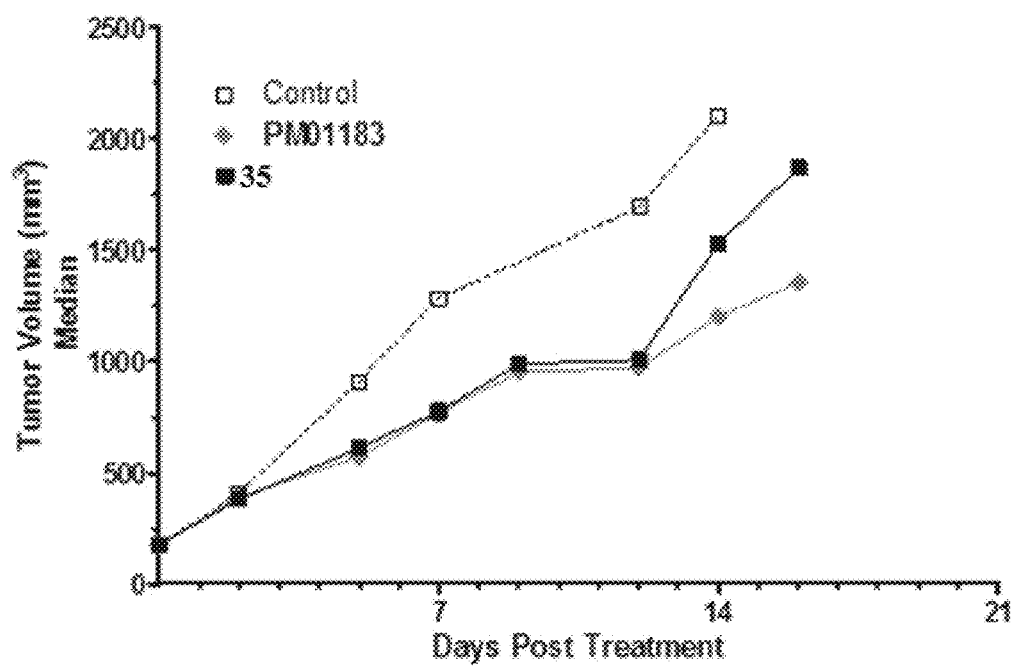
FIG. 60. Tumor volume evaluation of HGC27 tumors in mice treated with placebo, PM01183 and 35.

Table 71 reports volume growth of HGC27 tumors in mice treated with placebo, PM01183 and 35. These results are also showed in FIG. 60.

TABLE 71

| | Median Tumor Volume (mm$^3$) | | |
|---|---|---|---|
| Days | Control | 35 | PM01183 |
| 0 | 178.3 | 182.3 | 177.6 |
| 2 | 409.0 | 382.2 | 395.6 |

TABLE 71-continued

| | Median Tumor Volume (mm³) | | |
|---|---|---|---|
| Days | Control | 35 | PM01183 |
| 5 | 907.4 | 610.8 | 572.4 |
| 7 | 1283.6 | 775.5 | 766.6 |
| 9 | 1664.0 | 988.0 | 950.7 |
| 12 | 1692.4 | 1005.6 | 972.0 |
| 14 | 2102.8 | 1531.7 | 1199.4 |
| 16 | | 1866.3 | 1353.1 |

Example 38. In Vivo Studies to Determine the Effect of 12-S and 12-R in Human Prostate Xenografts 12-S and 12-R were provided in the form of freeze-dried vials of lyophilized product. Each vial was reconstituted with water for infusion to a concentration of 0.5 mg/mL. Further dilutions were made with 5% dextrose solution for injection to the dosing formulation concentration. The administered doses of 12-S and 12-R were 0.25 mg/kg and 0.05 mg/kg respectively.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 12-S and 12-R, as well as placebo, were intravenously administered once per week for 3 consecutive weeks, on Days 0, 7 and 14, whenever it was possible.

The aim of this study was to compare the antitumoral activity of 12-S and 12-R by using a xenograft model of human prostate cancer.

The tumor model used in this study was PC-3 cell line.

Figure 61:
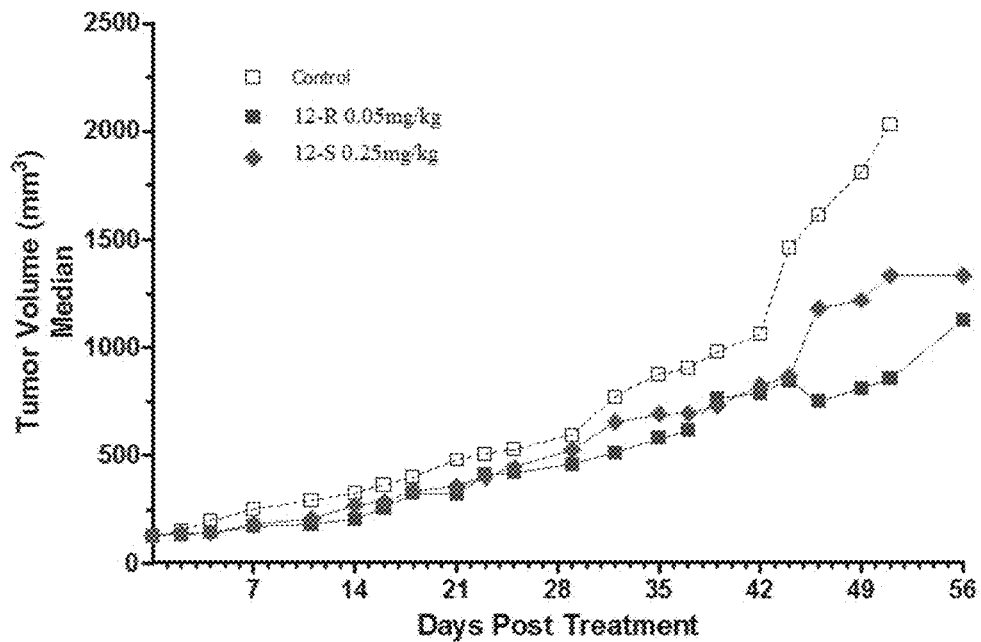
FIG. 61. Tumor volume evaluation of PC-3 tumors in mice treated with placebo, 12-S and 12-R.

Table 72 reports the median tumor volume evaluation of PC-3 tumors in mice treated with placebo, 12-S and 12-R. These results are also showed in FIG. 61.

TABLE 72

| | Median Tumor Volume (mm³) | | |
|---|---|---|---|
| Days | Control | 12-R | 12-S |
| 0 | 128.0 | 129.0 | 128.0 |
| 2 | 149.6 | 136.2 | 141.5 |
| 4 | 197.0 | 144.2 | 143.7 |
| 7 | 250.9 | 172.2 | 183.9 |
| 11 | 291.6 | 183.6 | 208.1 |
| 14 | 326.5 | 205.2 | 270.7 |
| 16 | 361.9 | 256.0 | 286.3 |
| 18 | 397.0 | 325.7 | 336.1 |
| 21 | 476.9 | 322.2 | 357.1 |
| 23 | 506.1 | 407.8 | 400.8 |
| 25 | 526.7 | 419.9 | 443.6 |
| 29 | 593.6 | 459.1 | 523.4 |
| 32 | 769.5 | 512.1 | 652.6 |
| 35 | 875.3 | 579.2 | 689.7 |
| 37 | 900.0 | 613.8 | 692.2 |
| 39 | 977.8 | 764.1 | 726.9 |
| 42 | 1061.5 | 785.0 | 823.7 |
| 44 | 1463.4 | 845.5 | 864.2 |
| 46 | 1612.8 | 748.0 | 1182.8 |
| 49 | 1809.2 | 808.7 | 1219.2 |
| 51 | 2030.9 | 855.8 | 1331.9 |
| 56 | | 1125.2 | 1335.2 |

Example 39. In Vivo Studies to Determine the Effect of 4-S in Human Prostate Xenografts The aim of this study was to compare the antitumoral activity of 4-S by using three different xenograft models of human prostate cancer. These models correspond to PC-3, DU-145 and 22Rv1 cell lines.

Compound 4-S was provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. The administered dose of 4-S varied depending on the study, being 1.25 mg/Kg when the tumor model was PC-3, 1.00 mg/Kg when the tumor model was DU-145 and 0.75 mg/Kg when the tumor model was 22Rv1, respectively.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 4-S, as well as placebo were intravenously administered once per week for 3 consecutive weeks, on Days 0, 7 and 14, whenever it was possible.

Figure 62:
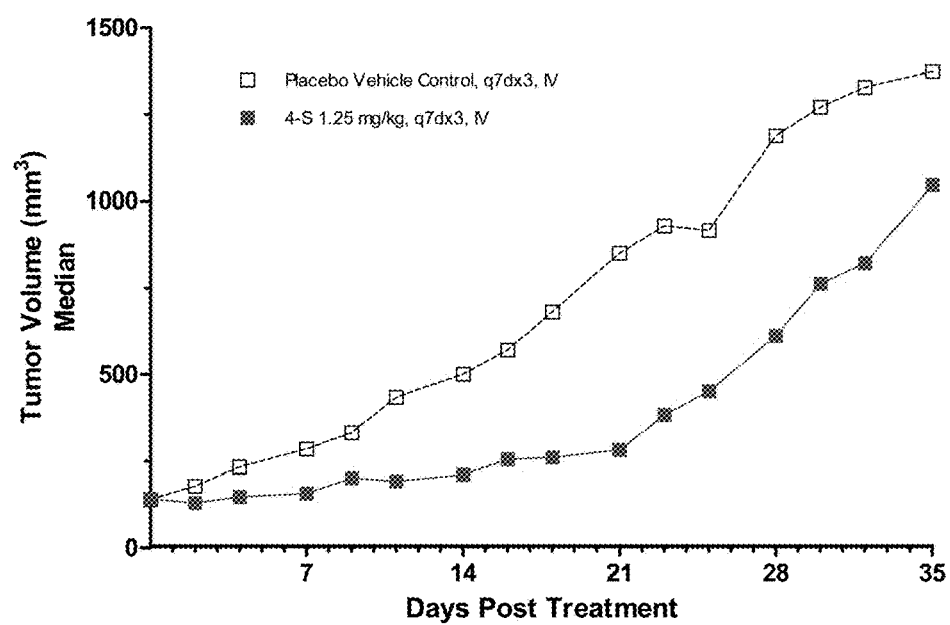
FIG. 62. Tumor volume evaluation of PC-3 tumors in mice treated with placebo and 4-S.

Table 73 reports the median tumor volume evaluation of PC-3 tumors in mice treated with placebo and 4-S. These results are also showed in FIG. 62.

TABLE 73

| | Median Tumor Volume (mm³) | |
|---|---|---|
| Days | Control | 4-S |
| 0 | 140.5 | 141.3 |
| 2 | 178.6 | 130.7 |
| 4 | 233.1 | 147.6 |
| 7 | 284.6 | 157.7 |
| 9 | 331.7 | 200.9 |
| 11 | 433.7 | 192.8 |
| 14 | 500.4 | 210.8 |
| 16 | 570.8 | 255.5 |
| 18 | 680.3 | 261.1 |
| 21 | 850.1 | 282.4 |
| 23 | 928.5 | 382.2 |
| 25 | 915.7 | 451.6 |
| 28 | 1187.5 | 611.1 |
| 30 | 1270.1 | 762.3 |
| 32 | 1327.1 | 821.6 |
| 35 | 1373.6 | 1045.6 |

Figure 63:
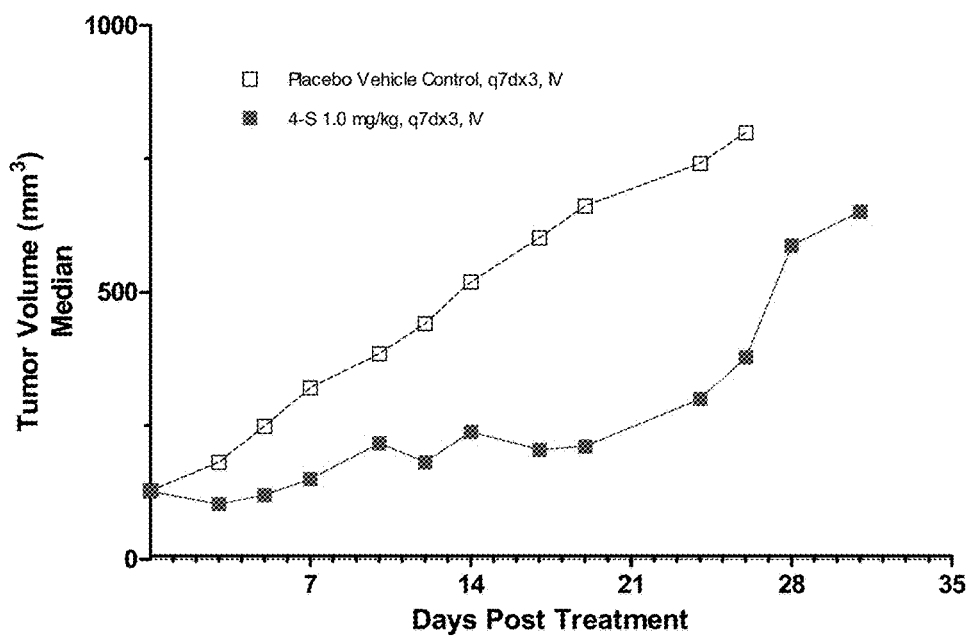
FIG. 63. Tumor volume evaluation of DU-145 tumors in mice treated with placebo and 4-S.

Table 74 reports the median tumor volume evaluation of DU-145 tumors in mice treated with placebo and 4-S. These results are also showed in FIG. 63.

TABLE 74

| | Median Tumor Volume (mm³) | |
|---|---|---|
| Days | Control | 4-S |
| 0 | 127.4 | 126.2 |
| 3 | 180.9 | 102.4 |
| 5 | 248.8 | 119.5 |
| 7 | 320.4 | 149.5 |
| 10 | 384.6 | 216.8 |
| 12 | 441.0 | 181.4 |
| 14 | 519.6 | 237.7 |
| 17 | 601.0 | 204.4 |
| 19 | 660.8 | 210.9 |
| 24 | 740.7 | 300.0 |
| 26 | 798.6 | 378.4 |

TABLE 74-continued

| | Median Tumor Volume (mm³) | |
|---|---|---|
| Days | Control | 4-S |
| 28 | | 587.0 |
| 31 | | 650.3 |

Figure 64:
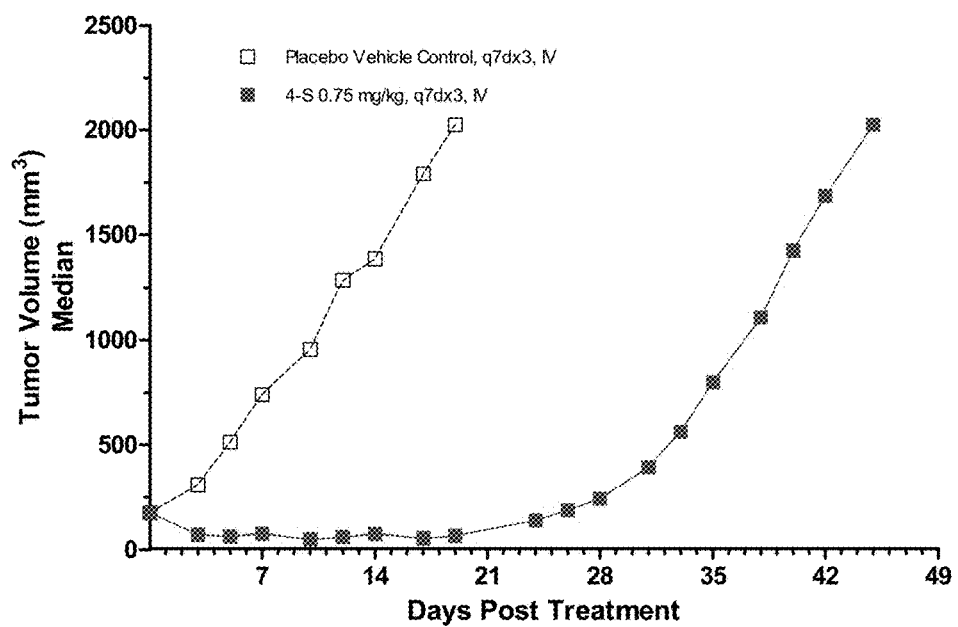
FIG. 64. Tumor volume evaluation of 22Rv1 tumors in mice treated with placebo and 4-S.

Table 75 reports the median tumor volume evaluation of 22Rv1 tumors in mice treated with placebo and 4-S. These results are also showed in FIG. 64.

TABLE 75

| | Median Tumor Volume (mm³) | |
|---|---|---|
| Days | Control | 4-S |
| 0 | 174.6 | 173.6 |
| 3 | 307.2 | 70.3 |
| 5 | 511.5 | 63.1 |
| 7 | 739.1 | 76.7 |
| 10 | 955.2 | 49.1 |
| 12 | 1286.1 | 59.8 |
| 14 | 1385.8 | 74.9 |
| 17 | 1791.1 | 55.1 |
| 19 | 2025.0 | 64.9 |
| 24 | | 138.4 |
| 26 | | 186.9 |
| 28 | | 242.0 |
| 31 | | 392.5 |
| 33 | | 561.8 |
| 35 | | 799.3 |
| 38 | | 1107.0 |
| 40 | | 1426.4 |
| 42 | | 1685.5 |
| 45 | | 2025.0 |

Example 40. In Vivo Studies to Determine the Effect of 39-S in Human Prostate Xenografts The aim of this study was to compare the antitumoral activity of 39-S by using three different xenograft models of human prostate cancer. These models correspond to PC-3, DU-145 and 22Rv1 cell lines.

Compound 39-S was provided in the form of freeze-dried vials of lyophilized product. Each vial was reconstituted with sterile water for injection to a concentration of 0.5 mg/mL. Further dilutions were made with 5% dextrose solution for injection to the dosing formulation concentration. The administered dose of 39-S varied depending on the study, being 1.25 mg/Kg when the tumor model was PC-3, 1.00 mg/Kg when the tumor model was DU-145 and 0.75 mg/Kg when the tumor model was 22Rv1, respectively.

Placebo was provided in the form of lyophilised cake containing 100 mg Sucrose+Potassium dihydrogen phosphate 6.8 mg+Phosphoric acid q.s. pH 3.8-4.5 which was reconstituted with water for infusion.

In these experiments, 39-S, as well as placebo, were intravenously administered once per week for 3 consecutive weeks, on Days 0, 7 and 14, whenever it was possible.

Figure 65:
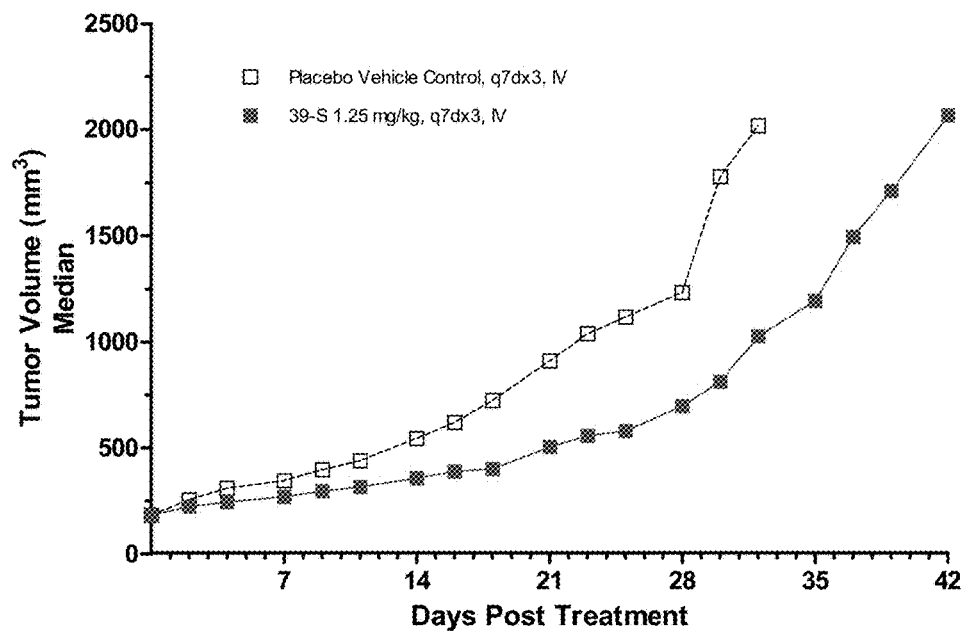
FIG. 65. Tumor volume evaluation of PC-3 tumors in mice treated with placebo and 39-S.

Table 76 reports the median tumor volume evaluation of PC-3 tumors in mice treated with placebo and 39-S. These results are also showed in FIG. 65.

TABLE 76

| | Median Tumor Volume (mm³) | |
|---|---|---|
| Days | Control | 39-S |
| 0 | 181.9 | 182.3 |
| 2 | 254.8 | 222.6 |
| 4 | 308.7 | 244.0 |
| 7 | 344.5 | 269.3 |
| 9 | 396.8 | 295.8 |
| 11 | 439.2 | 315.0 |
| 14 | 542.7 | 356.9 |
| 16 | 619.0 | 388.0 |
| 18 | 721.3 | 400.1 |
| 21 | 908.1 | 503.3 |
| 23 | 1039.1 | 556.0 |
| 25 | 1117.0 | 579.6 |
| 28 | 1232.3 | 694.9 |
| 30 | 1778.6 | 811.1 |
| 32 | 2018.1 | 1027.1 |
| 35 | | 1194.3 |
| 37 | | 1495.0 |
| 39 | | 1710.7 |
| 42 | | 2066.2 |

Figure 66:
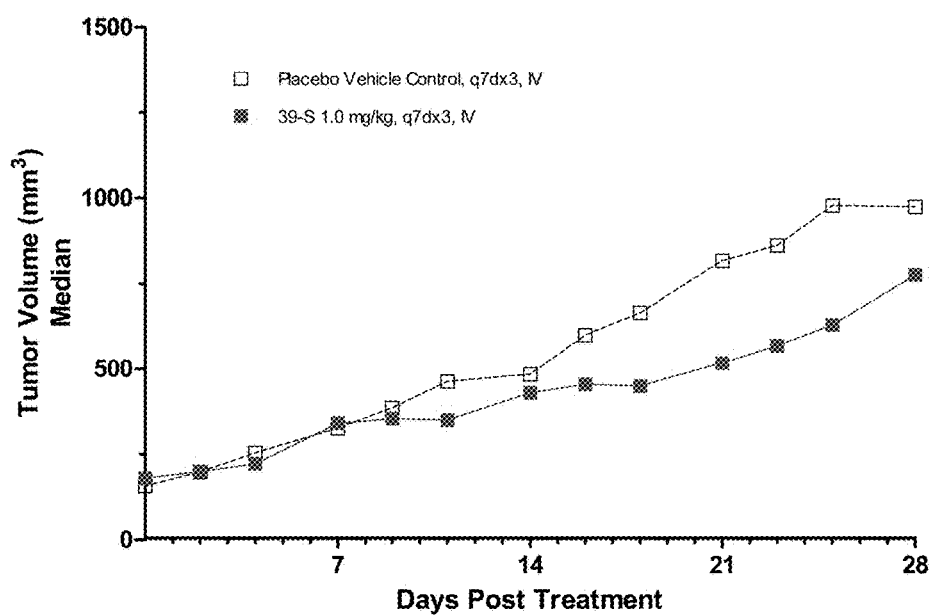
FIG. 66. Tumor volume evaluation of DU-145 tumors in mice treated with placebo and 39-S.

Table 77 reports the median tumor volume evaluation of DU-145 tumors in mice treated with placebo and 39-S. These results are also showed in FIG. 66.

TABLE 77

| | Median Tumor Volume (mm³) | |
|---|---|---|
| Days | Control | 39-S |
| 0 | 156.8 | 179.9 |
| 2 | 198.3 | 199.9 |
| 4 | 253.9 | 222.2 |
| 7 | 325.8 | 340.5 |
| 9 | 385.1 | 354.1 |
| 11 | 462.2 | 349.7 |
| 14 | 483.8 | 429.1 |
| 16 | 599.0 | 454.8 |
| 18 | 664.0 | 449.7 |
| 21 | 816.9 | 517.5 |
| 23 | 861.3 | 568.5 |
| 25 | 977.9 | 629.4 |
| 28 | 973.6 | 775.7 |

Figure 67:
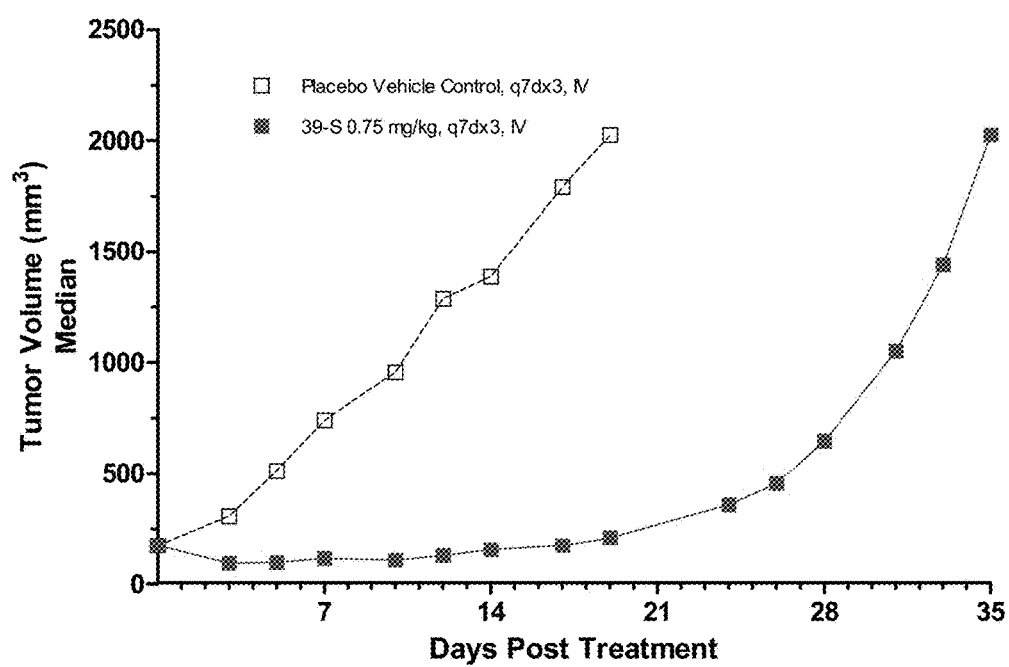
FIG. 67. Tumor volume evaluation of 22Rv1 tumors in mice treated with placebo and 39-S.

Table 78 reports the median tumor volume evaluation of 22Rv1 tumors in mice treated with placebo and 39-S. These results are also showed in FIG. 67.

TABLE 78

| | Median Tumor Volume (mm³) | |
|---|---|---|
| Days | Control | 39-S |
| 0 | 174.6 | 173.5 |
| 3 | 307.2 | 93.0 |
| 5 | 511.5 | 96.8 |
| 7 | 739.1 | 115.2 |
| 10 | 955.2 | 108.2 |
| 12 | 1286.1 | 128.4 |
| 14 | 1385.8 | 155.6 |
| 17 | 1791.1 | 173.4 |
| 19 | 2025.0 | 210.2 |
| 24 | | 358.8 |
| 26 | | 456.5 |
| 28 | | 645.2 |
| 31 | | 1049.5 |
| 33 | | 1439.4 |
| 35 | | 2025.0 |

Clauses

1. A compound of formula I, or a pharmaceutically acceptable salt or ester thereof:

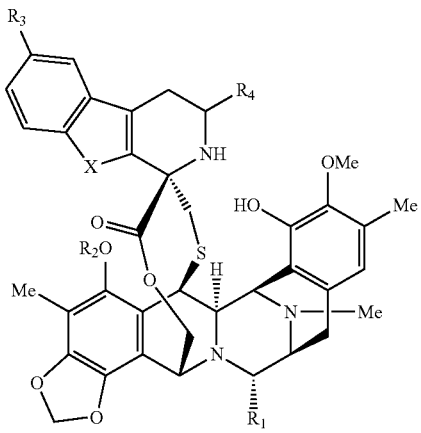

I wherein:
X is —NH— or —O—;
$R_1$ is —OH or —CN;
$R_2$ is a —C(=O)$R^a$ group;
$R_3$ is hydrogen or a —O$R^b$ group;
$R_4$ is selected from hydrogen, —CH$_2$OH, —CH$_2$O—(C=O)$R^c$, —CH$_2$NH$_2$ and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

2. The compound according to clause 1 of formula IA or a pharmaceutically acceptable salt or ester thereof:

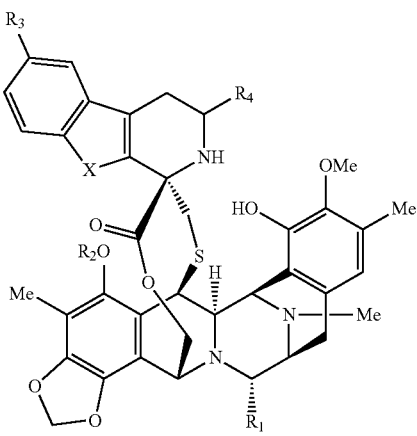

IA wherein:
X is —NH— or —O—;
$R_1$ is —OH or —CN;
$R_2$ is a —C(=O)$R^a$ group;
$R_3$ is hydrogen;
$R_4$ is selected from hydrogen, —CH$_2$OH, —CH$_2$O—(C=O)$R^c$, —CH$_2$NH$_2$ and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

3. The compound according to clause 1 of formula IB or a pharmaceutically acceptable salt or ester thereof:

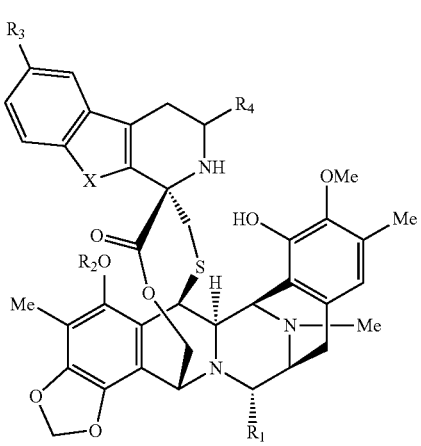

IB wherein:
X is —NH— or —O—;
$R_1$ is —OH or —CN;
$R_2$ is a —C(=O)$R^a$ group;
$R_3$ is a —O$R^b$ group;
$R_4$ is selected from hydrogen, —CH$_2$OH, —CH$_2$O—(C=O)$R^c$, —CH$_2$NH$_2$ and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

4. The compound according to clause 1 selected from formula Ia or Ib, or a pharmaceutically acceptable salt or ester thereof:

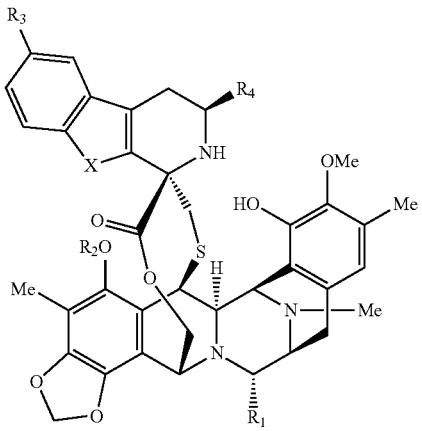

Ia

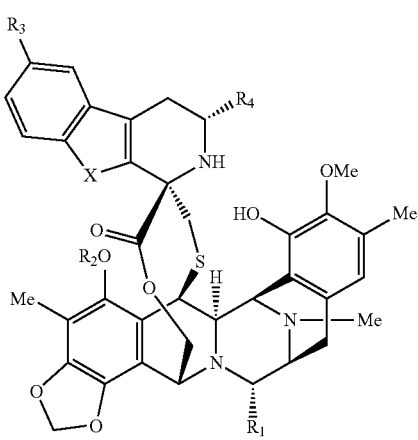

Ib wherein:

X is —NH— or —O—;

$R_1$ is —OH or —CN;

$R_2$ is a —C(=O)$R^a$ group;

$R_3$ is hydrogen or a —O$R^b$ group;

$R_4$ is selected from —CH$_2$OH, —CH$_2$OC(=O)$R^c$, —CH$_2$NH$_2$, and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino.

5. The compound according to clause 2 selected from formula IAa or IAb, or a pharmaceutically acceptable salt or ester thereof:

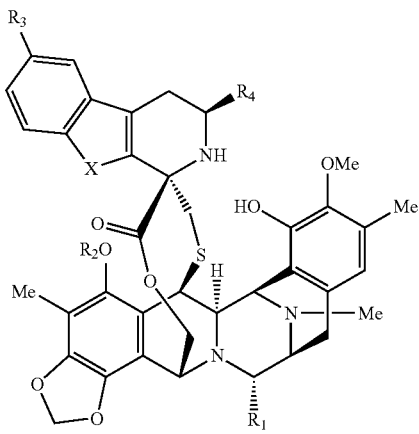

IAa

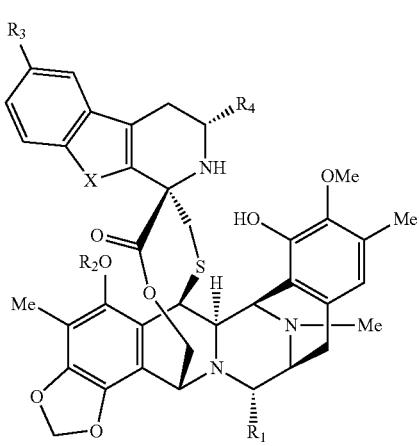

IAb wherein:

X is —NH— or —O—;

$R_1$ is —OH or —CN;

$R_2$ is a —C(=O)$R^a$ group;

$R_3$ is hydrogen;

$R_4$ is selected from —CH$_2$OH, —CH$_2$OC(=O)$R^c$, —CH$_2$NH$_2$, and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino.

6. The compound according to clause 3 selected from formula IBa or IBb, or a pharmaceutically acceptable salt or ester thereof:

IBa

[Structure of IBa]

IBb

[Structure of IBb]

wherein:
X is —NH— or —O—;
$R_1$ is —OH or —CN;
$R_2$ is a —C(=O)$R^a$ group;
$R_3$ is a —O$R^b$ group;
$R_4$ is selected from —CH$_2$OH, —CH$_2$OC(=O)$R^c$, —CH$_2$NH$_2$, and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino.

7. The compound according to any preceding clause wherein X is —NH—.

8. The compound according to any preceding clause wherein X is —O—.

9. The compound according to any preceding clause wherein $R_4$ is selected from —CH$_2$OH, —CH$_2$O(C=O)$R^c$, —CH$_2$NH$_2$, and —CH$_2$NHProt$^{NH}$ wherein $R^c$ is substituted or unsubstituted $C_1$-$C_6$ alkyl.

10. The compound according to clause 9, wherein $R^c$ is methyl.

11. The compound according to clause 9, wherein $R_4$ is —CH$_2$OH.

12. The compound according to clause 9, wherein $R_4$ is —CH$_2$NH$_2$.

13. The compound according to clause 1 of formula Ic or a pharmaceutically acceptable salt or ester thereof Ic

[Structure of Ic]

wherein:
$R_1$ is —OH or —CN;
$R_2$ is a —C(=O)$R^a$ group;
$R_3$ is hydrogen or a —O$R^b$ group;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

14. The compound according to clause 2 of formula IAc or a pharmaceutically acceptable salt or ester thereof IAc

[Structure of IAc]

wherein:
$R_1$ is —OH or —CN;
$R_2$ is a —C(=O)R' group;
$R_3$ is hydrogen;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

15. The compound according to clause 3 of formula IBc or a pharmaceutically acceptable salt or ester thereof

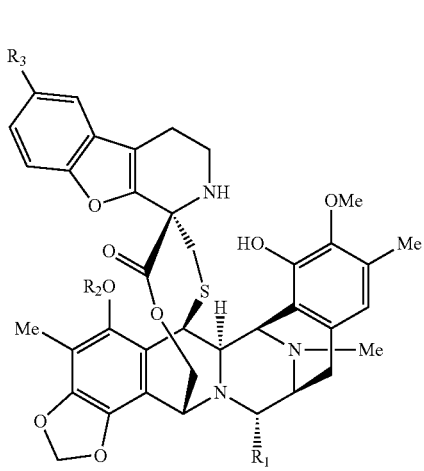

IBc wherein:

$R_1$ is —OH or —CN;

$R_2$ is a —C(=O)$R^a$ group;

$R_3$ is a —O$R^b$ group;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

16. The compound according to any preceding clause wherein $R_1$ is —OH.

17. The compound according to any preceding clause wherein $R_2$ is a —C(=O)$R^a$ group where $R^a$ is substituted or unsubstituted $C_1$-$C_6$ alkyl.

18. The compound according to clause 17 wherein $R_2$ is acetyl.

19. The compound according to clause 1 wherein $R_3$ is hydrogen or —O$R^b$ wherein $R^b$ is substituted or unsubstituted $C_1$-$C_6$ alkyl.

20. The compound according to clause 19 wherein $R_3$ is selected from hydrogen and methoxy.

21. The compound according to clause 20 wherein $R_3$ is hydrogen.

22. The compound according to clause 20 wherein $R_3$ is methoxy.

23. The compound according to any one of clauses 1, 2, 4, 5, 13 or 14 wherein $R_3$ is hydrogen.

24. The compound according to any one of clauses 1, 3, 4, 6, 13 or 15 wherein $R_3$ is —O$R^b$ wherein $R^b$ is substituted or unsubstituted $C_1$-$C_6$ alkyl.

25. The compound according to clause 24 wherein $R_3$ is methoxy.

26. The compound according to clause 1 of formula:

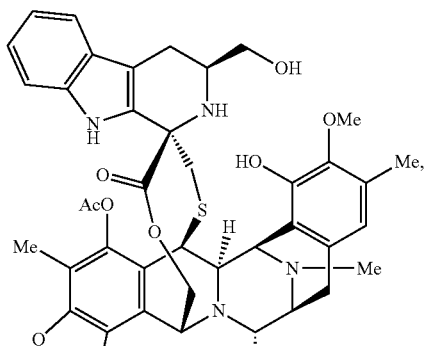

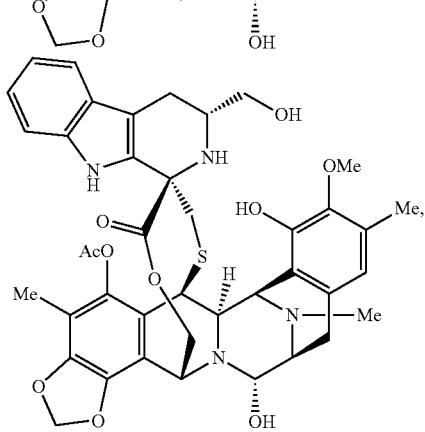

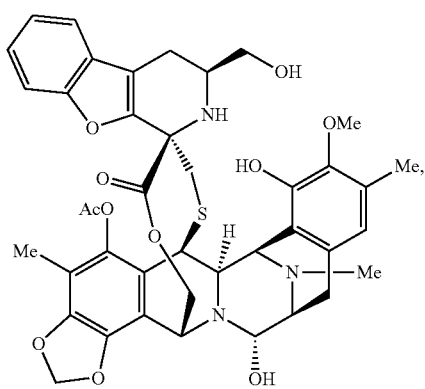

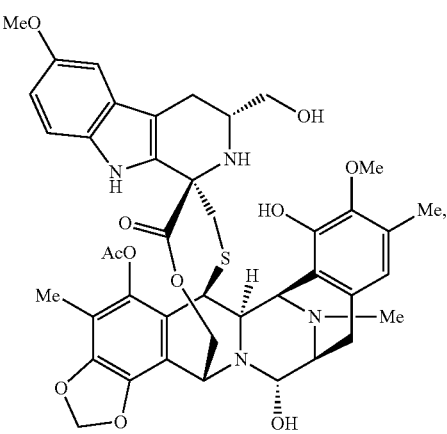 [SMILES: COc1ccc2oc3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

-continued
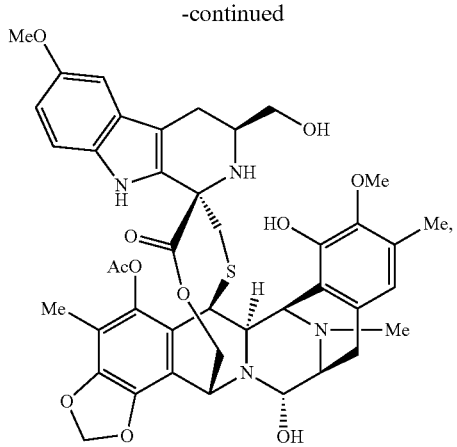
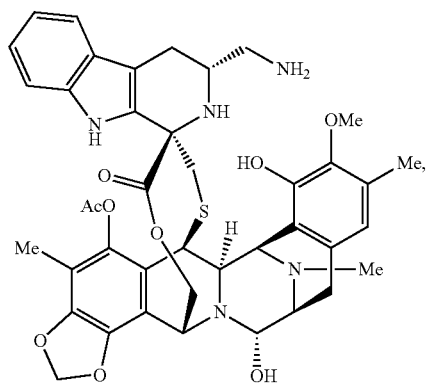
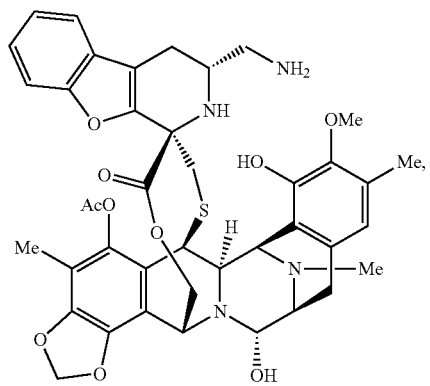
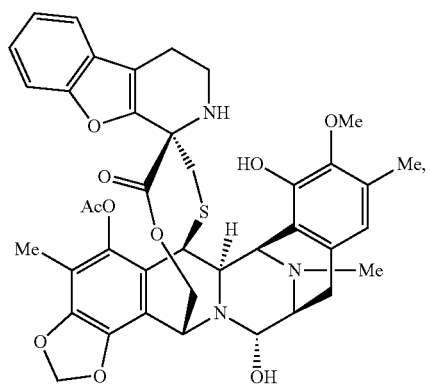
-continued
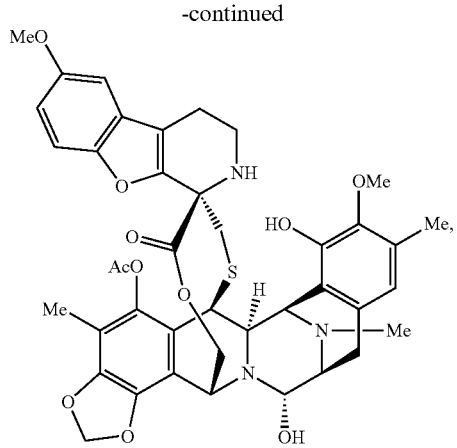
or a pharmaceutically acceptable salt or ester thereof.
27. The compound according to clause 1 of formula:
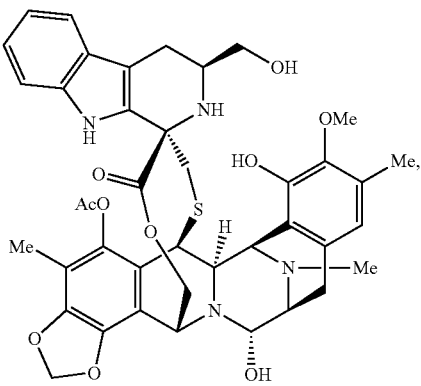
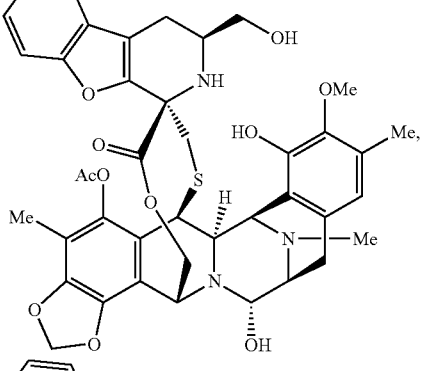
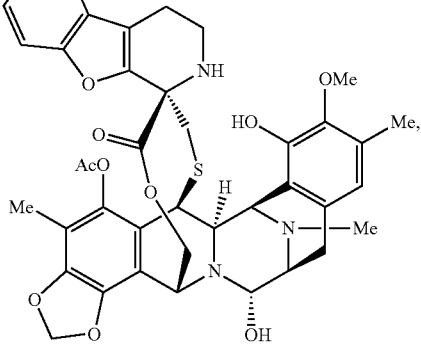

-continued
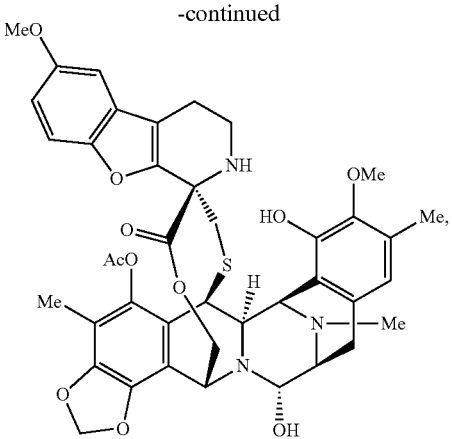
or a pharmaceutically acceptable salt or ester thereof.
28. The compound according to clause 1 of formula:
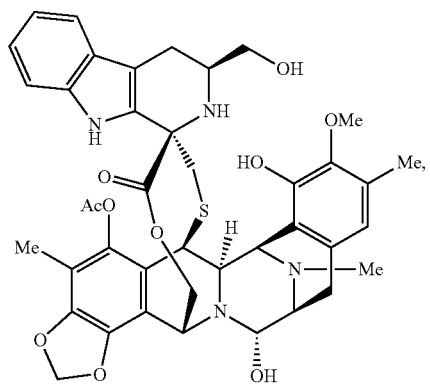
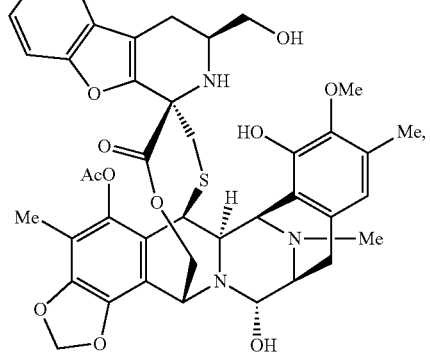
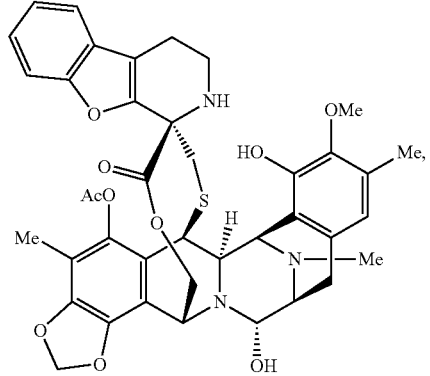
or a pharmaceutically acceptable salt or ester thereof.
29. The compound according to clause 2 of formula:
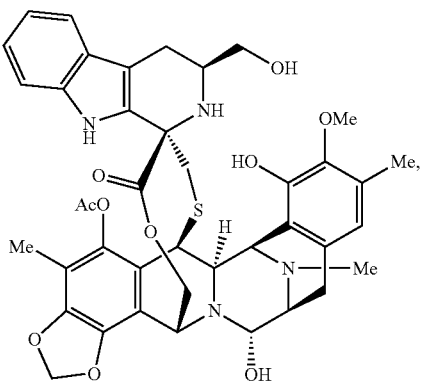
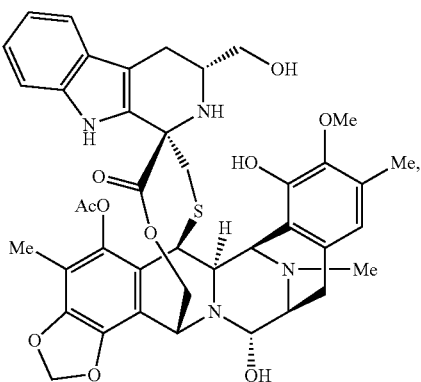
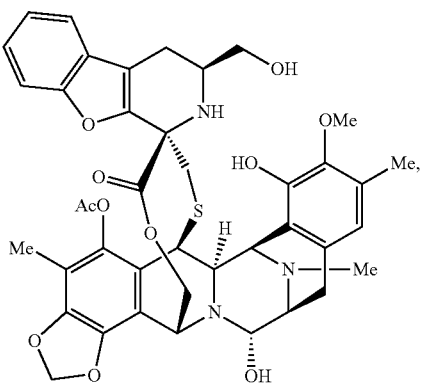
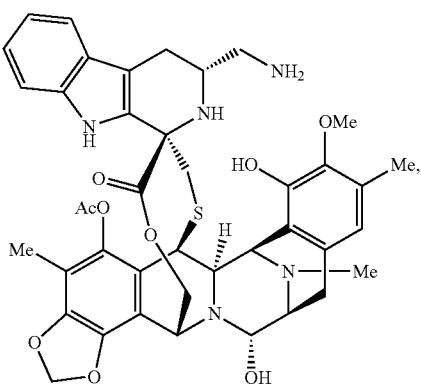

219
-continued
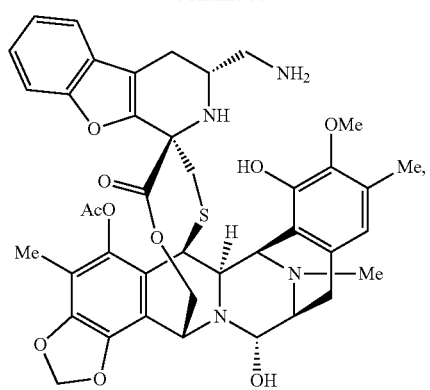
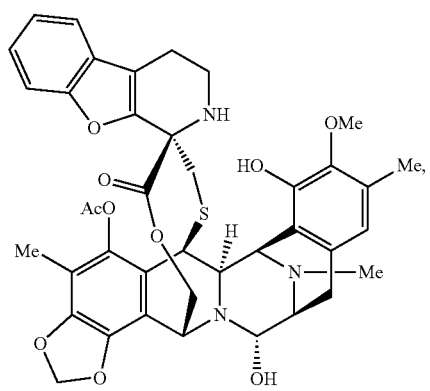
or a pharmaceutically acceptable salt or ester thereof.
30. The compound according to clause 2 of formula:
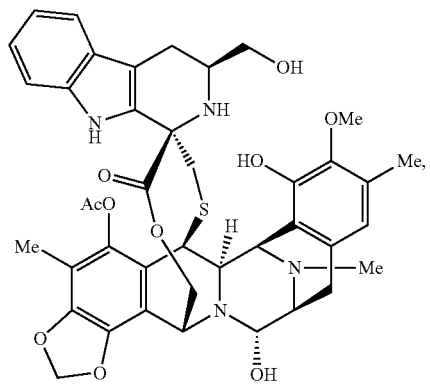
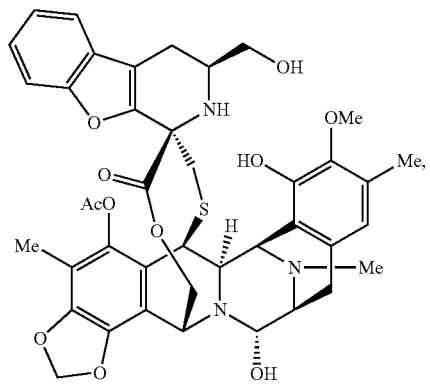
220
-continued
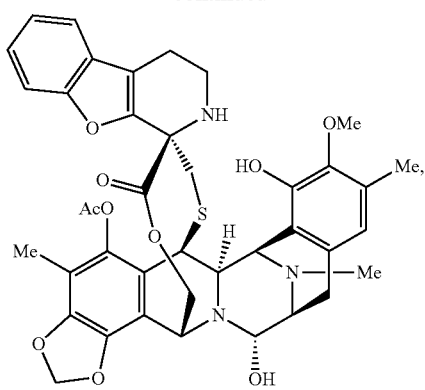
a pharmaceutically acceptable salt or ester thereof.
31. The compound according to clause 3 of formula:
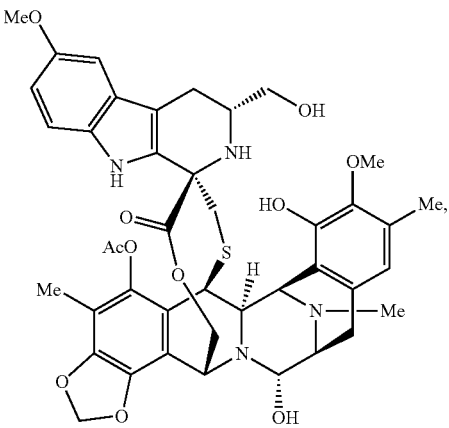
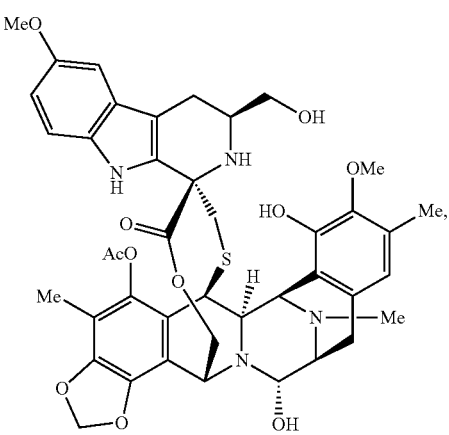

221
-continued

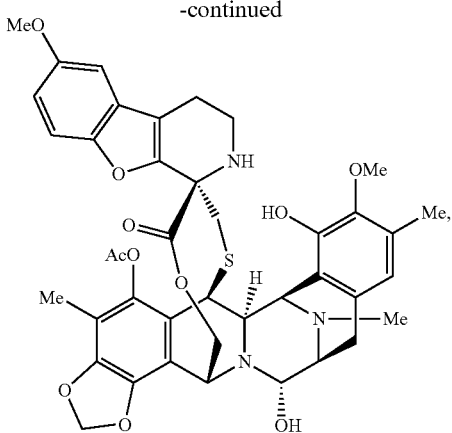

or a pharmaceutically acceptable salt or ester thereof.

32. The compound according to clause 3 of formula:

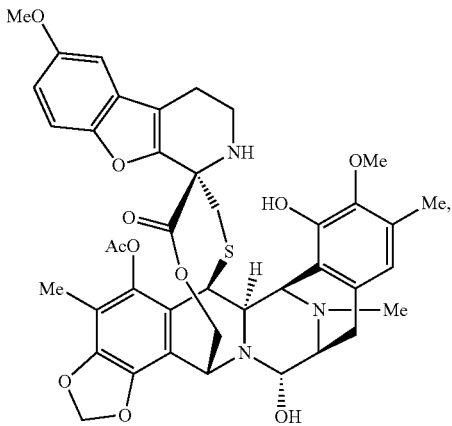 [SMILES: COc1ccc2oc3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

or a pharmaceutically acceptable salt or ester thereof.

33. A pharmaceutical composition comprising a compound according to any one of clauses 1 to 32 or a pharmaceutically acceptable salt or ester thereof and a pharmaceutically acceptable carrier.

34. A compound according to any one of clauses 1 to 32, or a pharmaceutically acceptable salt or ester thereof, or a composition according to clause 33, for use as a medicament.

35. A compound according to any one of clauses 1 to 32, or a pharmaceutically acceptable salt or ester thereof, or a composition according to clause 33, for use in the treatment of cancer.

36. A method of treating cancer in a patient in need thereof, comprising administering to said patient a therapeutically effective amount of compound according to any one of clauses 1 to 32, or a pharmaceutically acceptable salt or ester thereof, or a composition according to clause 33.

37. The compound according to clause 35 or the method according to clause 36, wherein the cancer is selected from lung cancer including non-small cell lung cancer and small cell lung cancer, colon cancer, breast cancer, pancreas cancer, sarcoma, ovarian cancer, and gastric cancer.

38. The compound or method according to clause 37, wherein the cancer is selected from lung cancer including non-small cell lung cancer and small cell lung cancer, breast cancer, pancreas carcinoma and colorectal cancer.

39. A process for obtaining a compound of formula I as defined in clause 1 or a pharmaceutically acceptable salt or ester thereof, a compound of formula IA as defined in clause 2 or a pharmaceutically acceptable salt or ester thereof, or a compound of formula IB as defined in clause 3 or a pharmaceutically acceptable salt or ester thereof:

comprising the step of reacting a compound of formula II with a compound of formula III to give a compound of formula IV:

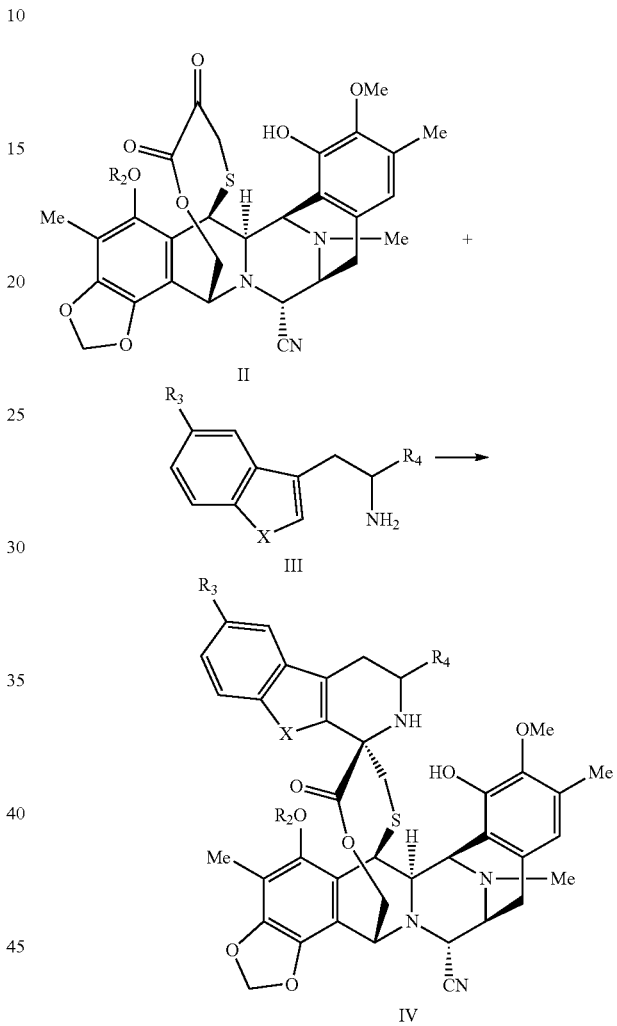

wherein:
X is —NH— or —O—;
$R_2$ is a —C(=O)$R^a$ group;
$R_3$ is hydrogen or a —O$R^b$ group;
$R_4$ is selected from hydrogen, —CH$_2$OH, —CH$_2$OC(=O)$R^c$ and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

40. The process according to clause 39, comprising the further step of replacing the cyano group in the compound of formula IV with a hydroxy group to give a compound of formula I, or IA or IB where $R_1$ is OH.

41. A kit comprising a therapeutically effective amount of a compound according to any one of clauses 1 to 32 and a pharmaceutically acceptable carrier.

42. The kit according to clause 41 further comprising instructions for use of the compound in the treatment of cancer, and more preferably a cancer selected from lung cancer, including non-small cell lung cancer and small cell lung cancer, colon cancer, breast cancer, pancreas cancer, sarcoma, ovarian cancer, and gastric cancer.

43. A compound of formula I, or a pharmaceutically acceptable salt or ester thereof:

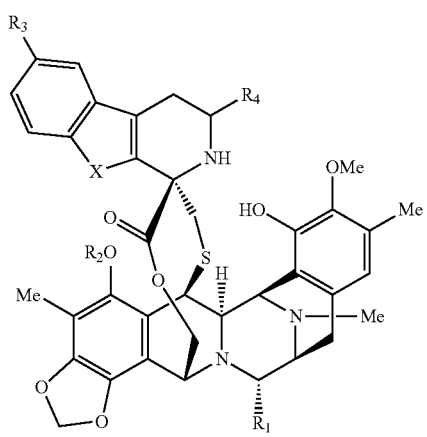

I wherein:
X is —NH— or —O—;
$R_1$ is —OH or —CN;
$R_2$ is a —C(=O)$R^a$ group;
$R_3$ is hydrogen or a —O$R^b$ group;
$R_4$ is selected from hydrogen, —CH$_2$OH, —CH$_2$O—(C=O)$R^c$, —CH$_2$NH$_2$ and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino;
with the proviso that when $R_4$ is hydrogen then X is —O—.

44. The compound according to clause 43 selected from formula Ia or Ib, or a pharmaceutically acceptable salt or ester thereof:

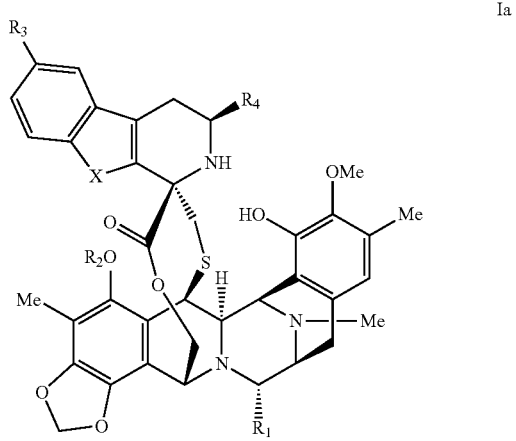

Ia

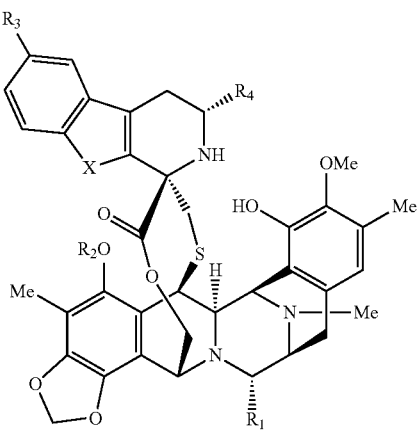

Ib wherein:
X is —NH— or —O—;
$R_1$ is —OH or —CN;
$R_2$ is a —C(=O)$R^a$ group;
$R_3$ is hydrogen or a —O$R^b$ group;
$R_4$ is selected from —CH$_2$OH, —CH$_2$OC(=O)$R^c$, —CH$_2$NH$_2$, and —CH$_2$NHProt$^{NH}$;
$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;
$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and
Prot$^{NH}$ is a protecting group for amino.

45. The compound according to clause 43 or clause 44 wherein X is —NH—.

46. The compound according to clause 43 or clause 44 wherein X is —O—.

47. The compound according to any one of clauses 43 to 46 wherein $R_4$ is selected from —CH$_2$OH, —CH$_2$O(C=O)$R^c$, —CH$_2$NH$_2$, and —CH$_2$NHProt$^{NH}$ wherein $R^c$ is substituted or unsubstituted $C_1$-$C_6$ alkyl, preferably methyl; particularly preferably wherein $R_4$ is —CH$_2$OH or —CH$_2$NH$_2$.

48. The compound according to clause 43 of formula Ic or a pharmaceutically acceptable salt or ester thereof

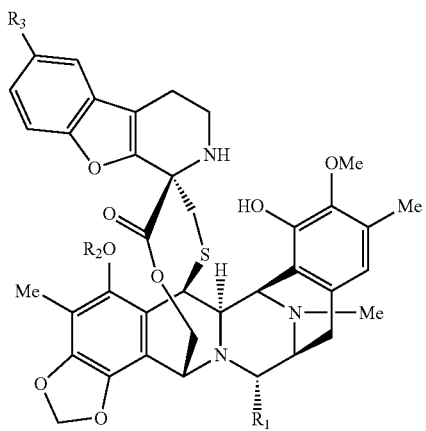

Ic wherein:

$R_1$ is —OH or —CN;

$R_2$ is a —C(=O)$R^a$ group;

$R_3$ is hydrogen or a —O$R^b$ group;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

49. The compound according to any one of clauses 43 to 48 wherein $R_1$ is —OH; and/or wherein $R_2$ is a —C(=O)$R^a$ group where $R^a$ is substituted or unsubstituted $C_1$-$C_6$ alkyl, preferably acetyl.

50. The compound according to any one of clauses 43 to 49, wherein $R_3$ is hydrogen.

51. The compound according to any one of clauses 43 to 49, wherein $R_3$ is —O$R^b$; preferably wherein $R^b$ is substituted or unsubstituted $C_1$-$C_6$ alkyl, more preferably wherein $R^b$ is methoxy.

52. The compound according to clause 43 of formula:

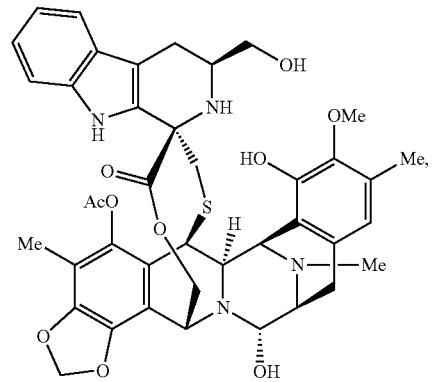

-continued

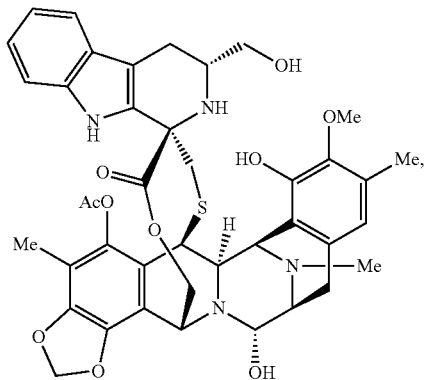

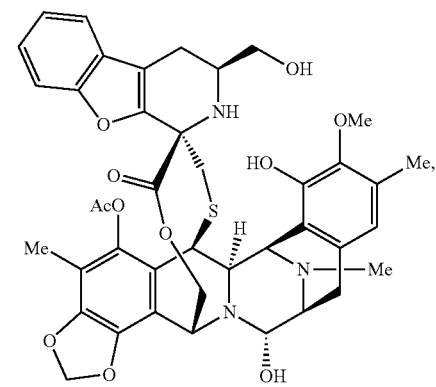

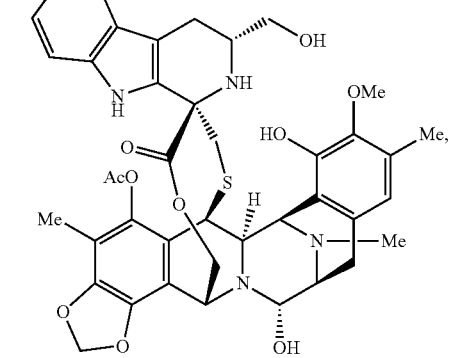

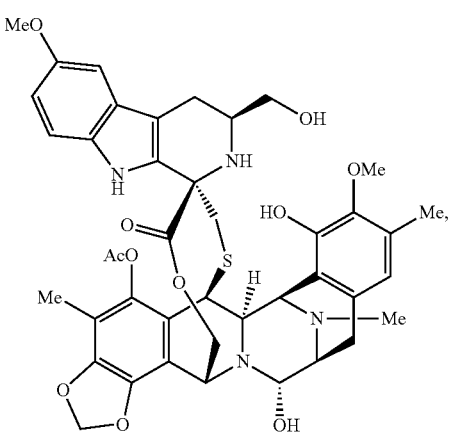

227
-continued
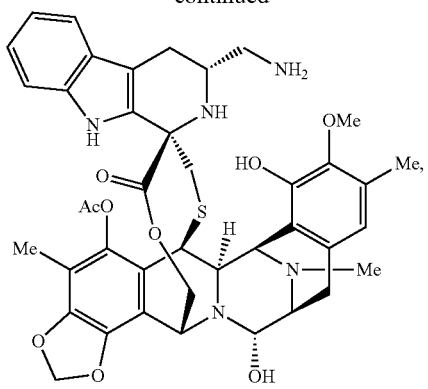
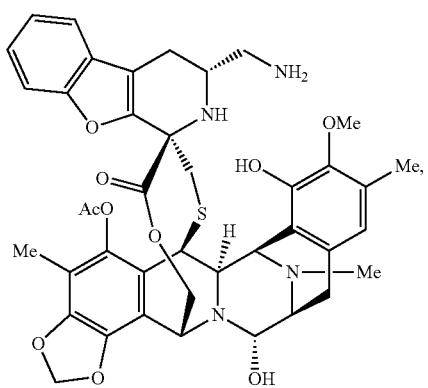
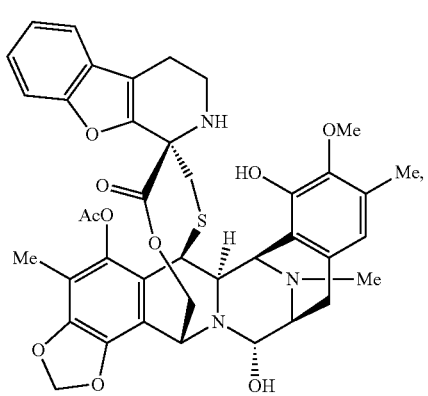
228
-continued
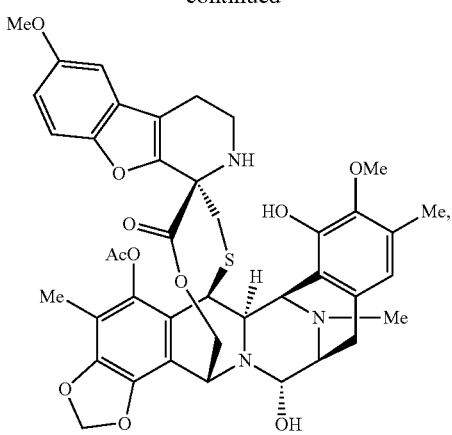
or a pharmaceutically acceptable salt or ester thereof; preferably of formula:
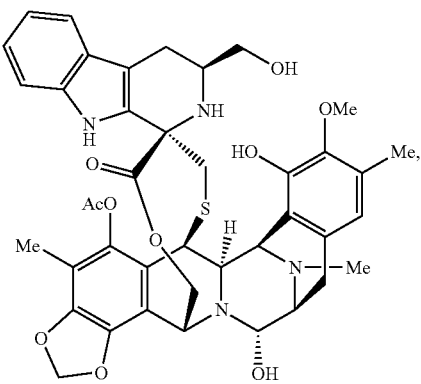
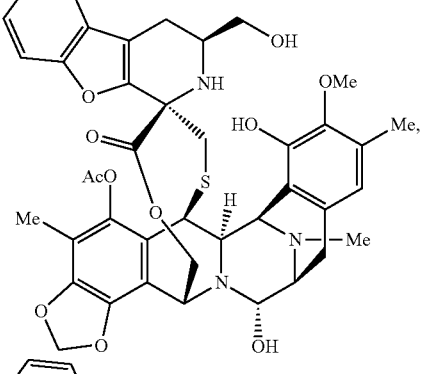
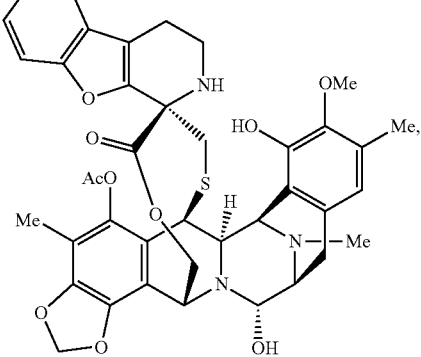

229
-continued
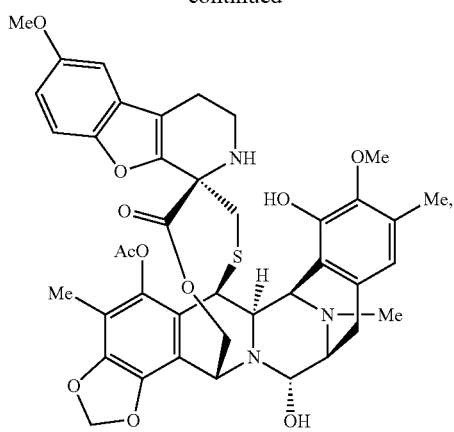
or a pharmaceutically acceptable salt or ester thereof.
53. The compound according to clause 43 of formula:
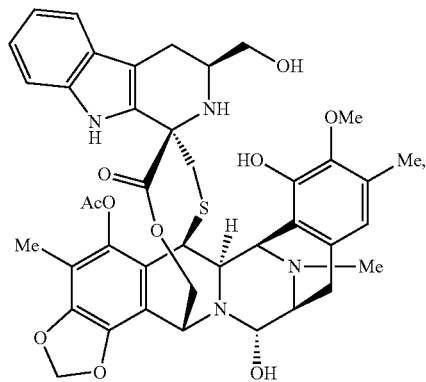
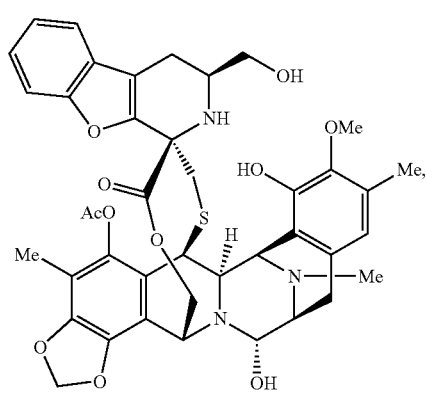
230
-continued
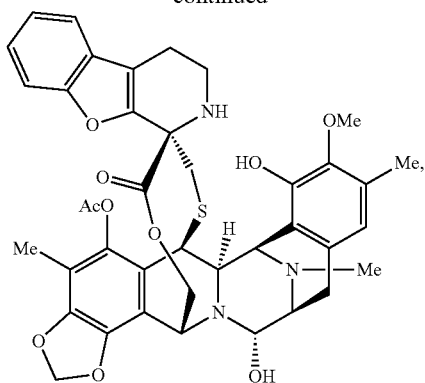
or a pharmaceutically acceptable salt or ester thereof.
54. The compound according to clause 45 of formula:
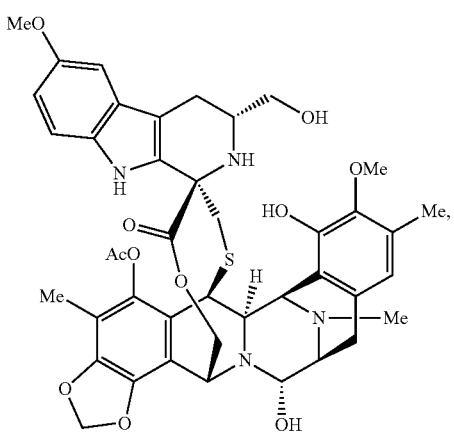
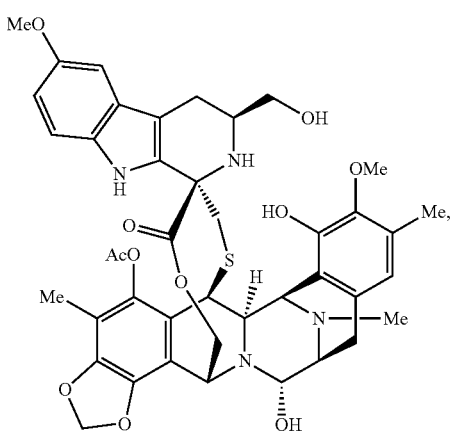

-continued

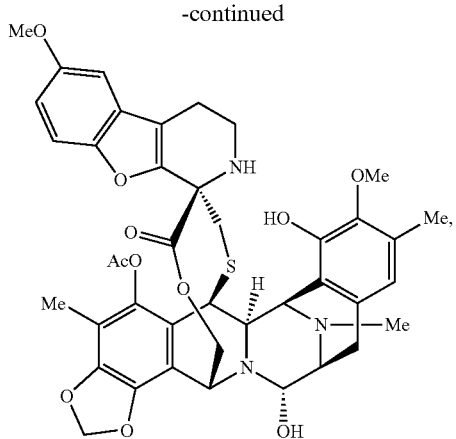

or a pharmaceutically acceptable salt or ester thereof; preferably of formula:

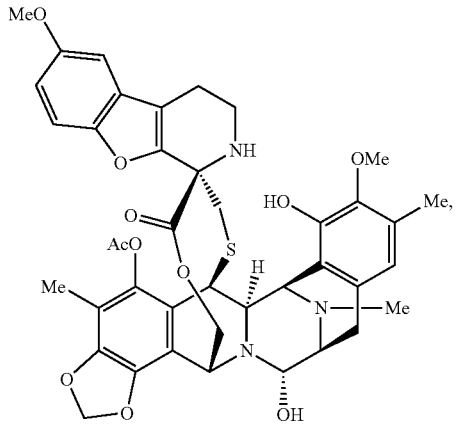

or a pharmaceutically acceptable salt or ester thereof.

55. A pharmaceutical composition comprising a compound according to any one of clauses 43 to 53 or a pharmaceutically acceptable salt or ester thereof and a pharmaceutically acceptable carrier.

56. A compound according to any one of clauses 43 to 54, or a pharmaceutically acceptable salt or ester thereof, or a composition according to clause 55, for use as a medicament; or a compound according to any one of clauses 43 to 54, or a pharmaceutically acceptable salt or ester thereof, or a composition according to clause 55, for use in the treatment of cancer; preferably wherein the cancer is selected from lung cancer including non-small cell lung cancer and small cell lung cancer, colon cancer, breast cancer, pancreas cancer, sarcoma, ovarian cancer, and gastric cancer; even more preferably wherein the cancer is selected from lung cancer including non-small cell lung cancer and small cell lung cancer, breast cancer, pancreas carcinoma and colorectal cancer.

57. A process for obtaining a compound of formula I as defined in clause 43 or a pharmaceutically acceptable salt or ester thereof:
comprising the step of reacting a compound of formula II with a compound of formula III to give a compound of formula IV:

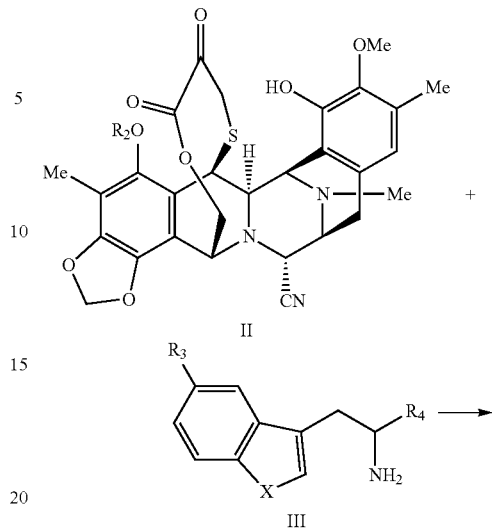

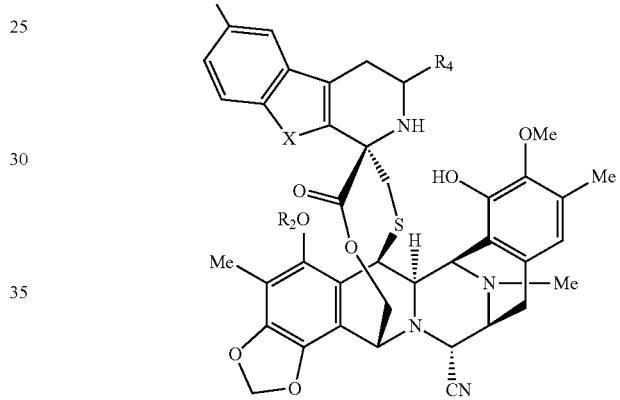

wherein:

X is —NH— or —O—;

$R_2$ is a —C(=O)$R^a$ group;

$R_3$ is hydrogen or a —O$R^b$ group;

$R_4$ is selected from hydrogen, —CH$_2$OH, —CH$_2$OC(=O)$R^c$ and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino;

with the proviso that when $R_4$ is hydrogen then X is —O—;

the process optionally comprising the further step of replacing the cyano group in the compound of formula IV with a hydroxy group to give a compound of formula I, or IA or IB where $R_1$ is OH.

The invention claimed is:

1. A compound of formula I, or a pharmaceutically acceptable salt thereof:

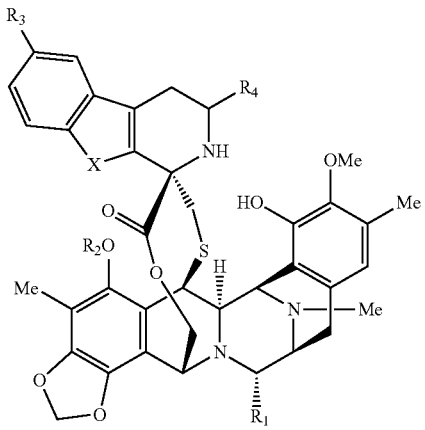

wherein:

X is —NH— or —O—;

$R_1$ is —OH or —CN;

$R_2$ is a —C(=O)$R^a$ group;

$R_3$ is hydrogen or a —O$R^b$ group;

$R_4$ is selected from hydrogen, —CH$_2$OH, —CH$_2$O—(C=O)$R^c$, —CH$_2$NH$_2$ and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino;

with the proviso that when $R_4$ is hydrogen then X is —O—;

where substituted groups are substituted at one or more available positions by one or more substituents selected from OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, protected amino, protected SH, $C_1$-$C_{12}$ alkyl, $C_2$-$C_{12}$ alkenyl, $C_2$-$C_{12}$ alkynyl, aryl, and heterocyclic group; where each of the R' groups is independently selected from the group consisting of hydrogen, OH, NO$_2$, NH$_2$, SH, CN, halogen, COH, COalkyl, CO$_2$H, $C_1$-$C_{12}$ alkyl, $C_2$-$C_{12}$ alkenyl, $C_2$-$C_{12}$ alkynyl, aryl, and heterocyclic group.

2. The compound according to claim 1 selected from formula Ia or Ib, or a pharmaceutically acceptable salt thereof:

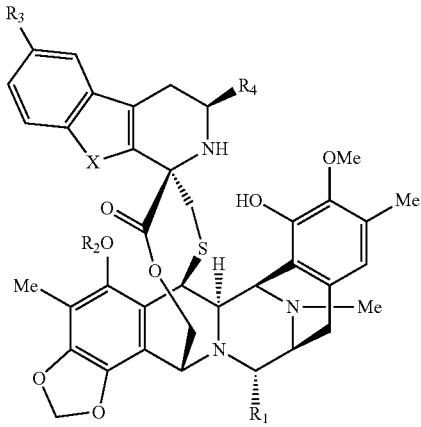

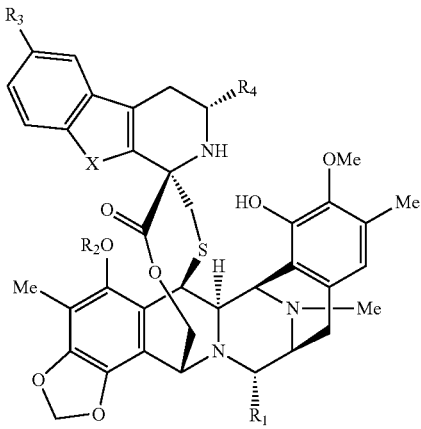

wherein:

$R_4$ is selected from —CH$_2$OH, —CH$_2$OC(=O)$R^c$, —CH$_2$NH$_2$, and —CH$_2$NHProt$^{NH}$.

3. The compound according to claim 1, wherein X is —NH—.

4. The compound according to claim 1, wherein X is —O—.

5. The compound according to claim 1, wherein $R_4$ is selected from —CH$_2$OH, —CH$_2$O(C=O)$R^c$, —CH$_2$NH$_2$, and —CH$_2$NHProt$^{NH}$ wherein $R^c$ is substituted or unsubstituted $C_1$-$C_6$ alkyl.

6. The compound according to claim 5, wherein $R^c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl.

7. The compound according to claim 1, wherein $R_4$ is H, —CH$_2$OH or —CH$_2$NH$_2$.

8. The compound according to claim 1, wherein $R_4$ is —CH$_2$OH.

9. The compound according to claim 1, wherein $R_4$ is —CH$_2$NH$_2$.

10. The compound according to claim 1, of formula Ic or a pharmaceutically acceptable salt thereof

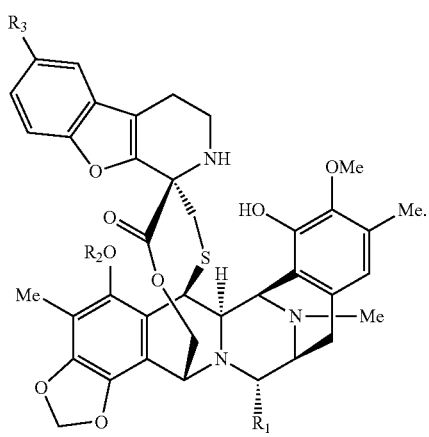

Ic

11. The compound according to claim 1, wherein $R^1$ is —OH.
12. The compound according to claim 1, wherein $R^a$ is substituted or unsubstituted $C_1$-$C_6$ alkyl.
13. The compound according to claim 12 wherein $R_2$ is acetyl.
14. The compound according to claim 1, wherein $R_3$ is —$OR^b$ wherein $R^b$ is substituted or unsubstituted $C_1$-$C_6$ alkyl.
15. The compound according to claim 1 wherein $R_3$ is hydrogen.
16. The compound according to claim 14 wherein $R_3$ is methoxy.
17. The compound according to claim 1 of formula:

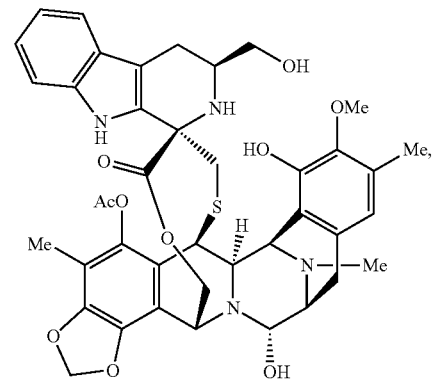

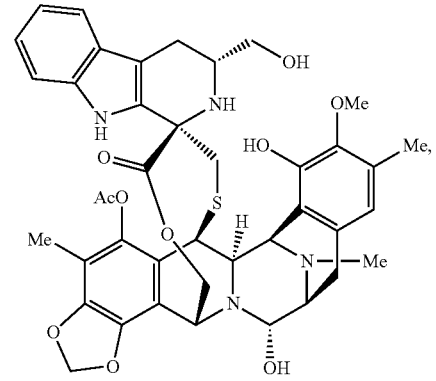

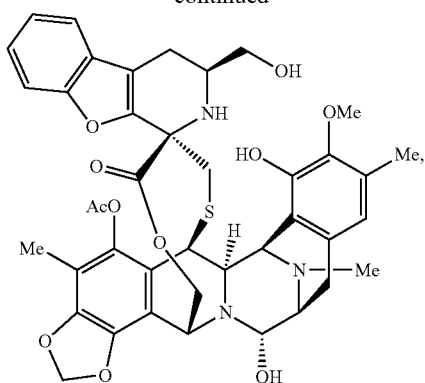

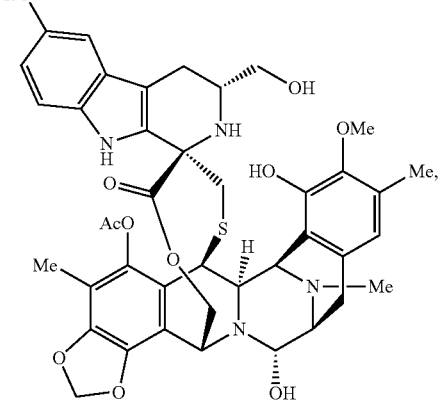

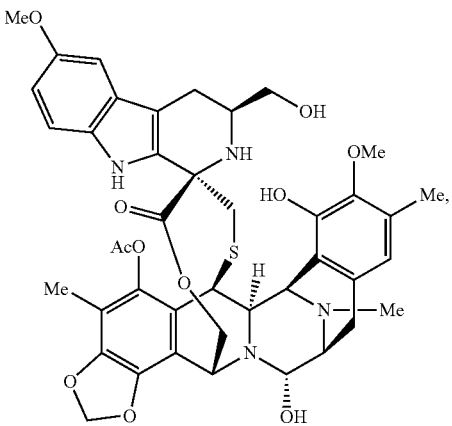

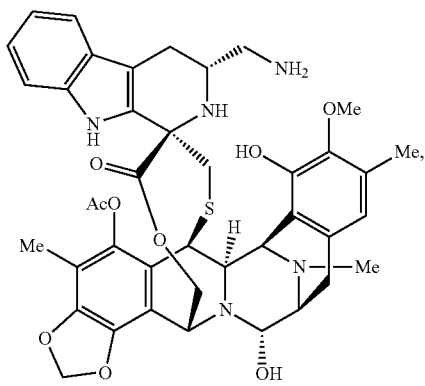

-continued
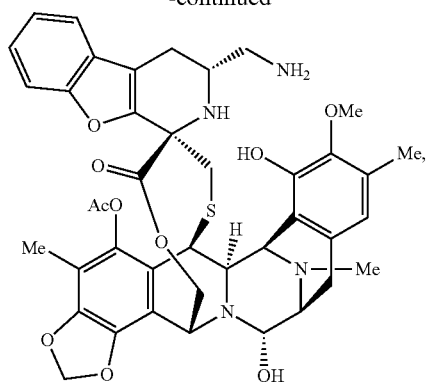
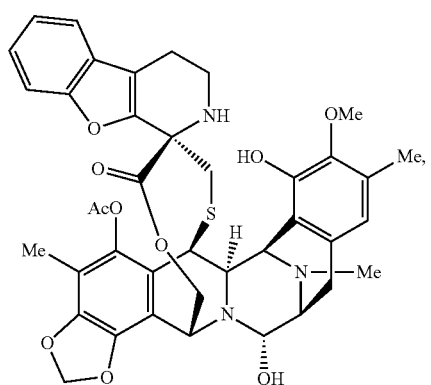
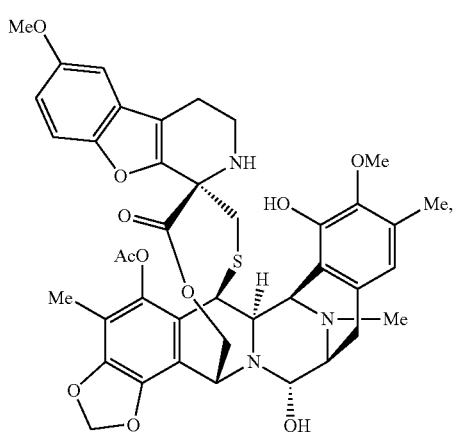
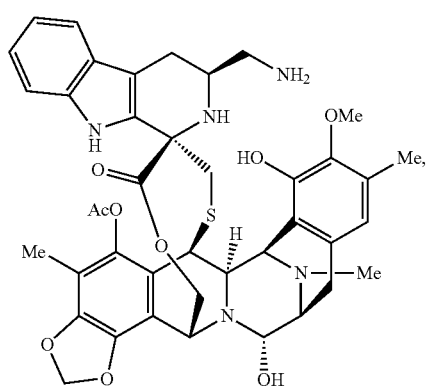 [SMILES: COc1c(C)cc2c(c1O)[C@@H]1[C@@H]3[C@@H]4SC[C@]5(N[C@H](CO)Cc6c5oc5ccccc65)C(=O)OC[C@@H](c5c6c(c(C)c(OC(C)=O)c54)OCO6)N3[C@@H](C#N)[C@H](C2)N1C]
-continued
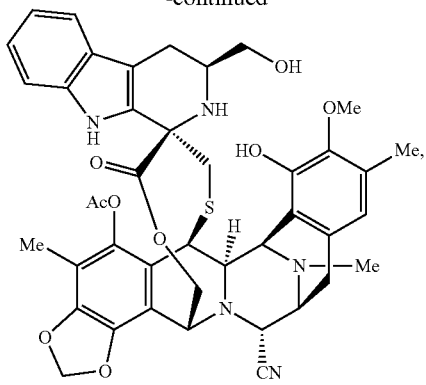
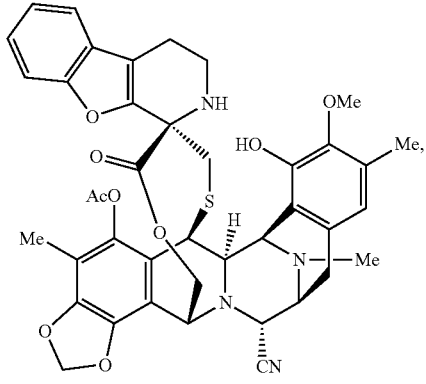
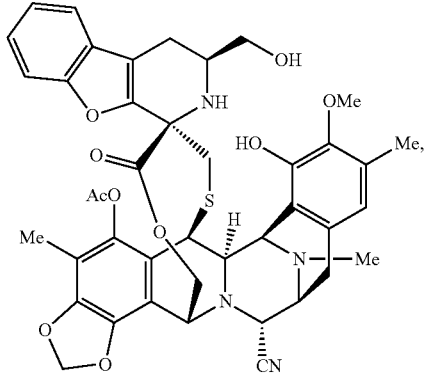
or a pharmaceutically acceptable salt thereof.
18. The compound according to claim 1 of formula:
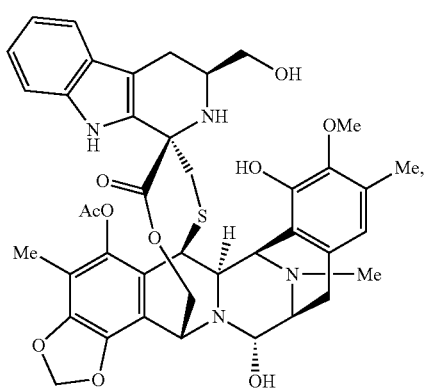 [SMILES: COc1c(C)cc2c(c1O)[C@@H]1[C@@H]3[C@@H]4SC[C@]5(N[C@H](CO)Cc6c5[nH]c5ccccc65)C(=O)OC[C@@H](c5c6c(c(C)c(OC(C)=O)c54)OCO6)N3[C@@H](O)[C@H](C2)N1C]
or a pharmaceutically acceptable salt thereof.

19. The compound according to claim 1 of formula:

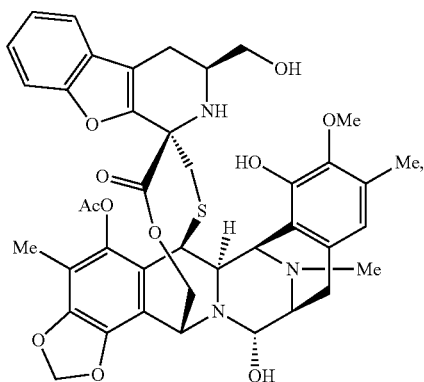 [SMILES: COc1c(C)cc2c(c1O)[C@@H]1[C@@H]3[C@@H]4SC[C@]5(N[C@H](CO)Cc6c5oc5ccccc65)C(=O)OC[C@@H](c5c6c(c(C)c(OC(C)=O)c54)OCO6)N3[C@@H](O)[C@H](C2)N1C]

or a pharmaceutically acceptable salt thereof.

20. The compound according to claim 1 of formula:

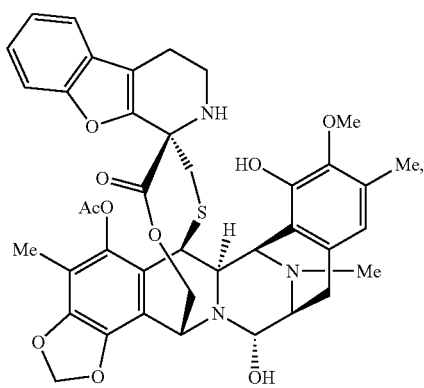 [SMILES: COc1c(C)cc2c(c1O)[C@@H]1[C@@H]3[C@@H]4SC[C@]5(NCCc6c5oc5ccccc65)C(=O)OC[C@@H](c5c6c(c(C)c(OC(C)=O)c54)OCO6)N3[C@@H](O)[C@H](C2)N1C]

or a pharmaceutically acceptable salt thereof.

21. The compound according to claim 1 of formula:

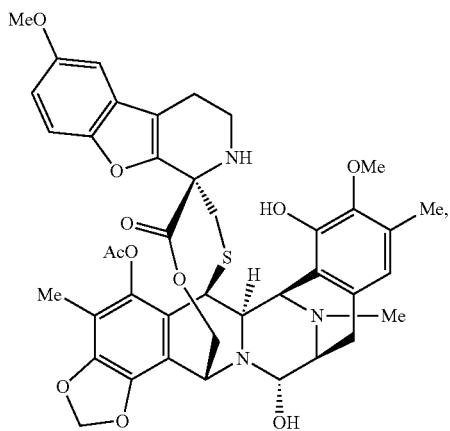 [SMILES: COc1ccc2oc3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

or a pharmaceutically acceptable salt thereof.

22. The compound according to claim 1, wherein the salt is selected from hydrochloride, hydrobromide, hydroiodide, sulfate, nitrate, phosphate, acetate, trifluoroacetate, maleate, fumarate, citrate, oxalate, succinate, tartrate, malate, mandelate, methanesulfonate, p-toluenesulfonate, sodium, potassium, calcium, ammonium, ethylenediamine, ethanolamine, N,N-dialkylenethanolamine, triethanolamine and basic amino acids.

23. The compound according to claim 1, of formula IC, or a pharmaceutically acceptable salt thereof:

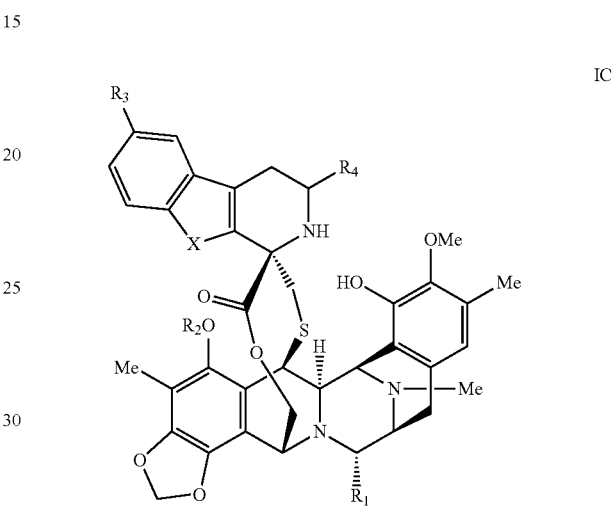

wherein:
X is —NH—; and
$R_4$ is selected from —$CH_2OH$, —$CH_2O$—(C=O)$R^c$, —$CH_2NH_2$ and —$CH_2NHProt^{NH}$.

24. The compound according to claim 23 selected from formula ICa or ICb, or a pharmaceutically acceptable salt thereof:

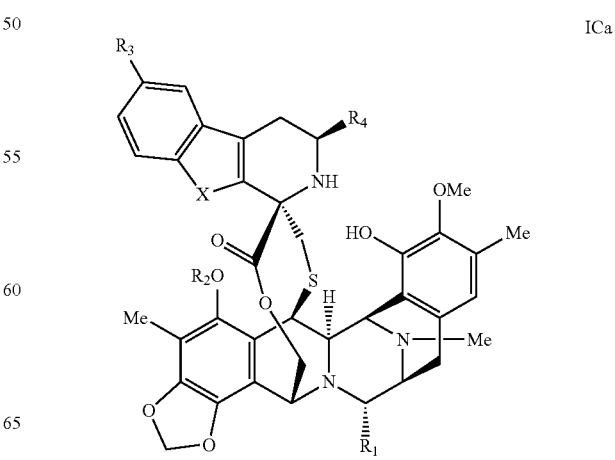

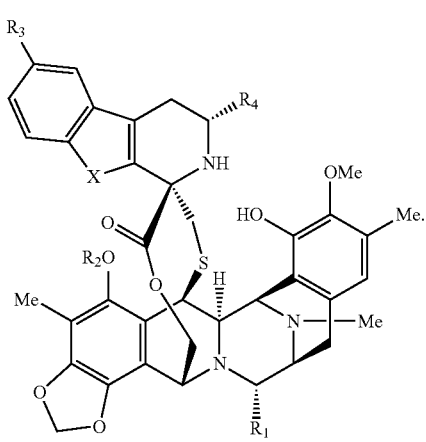

ICb

25. The compound according to claim 23, wherein $R_4$ is —CH$_2$OH or —CH$_2$NH$_2$.

26. The compound according to claim 1 of formula ID, or a pharmaceutically acceptable salt thereof:

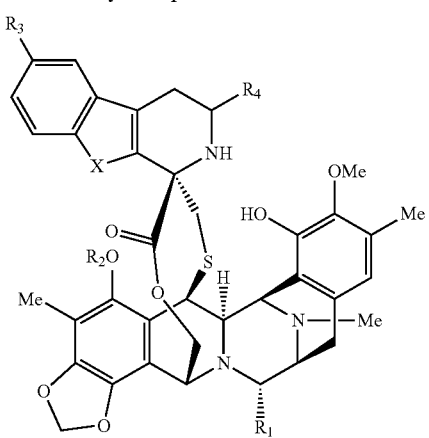

ID wherein:
X is —O—.

27. The compound according to claim 26 selected from formula IDa or IDb, or a pharmaceutically acceptable salt thereof:

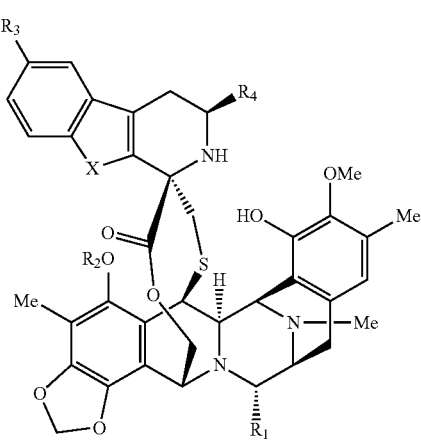

IDa

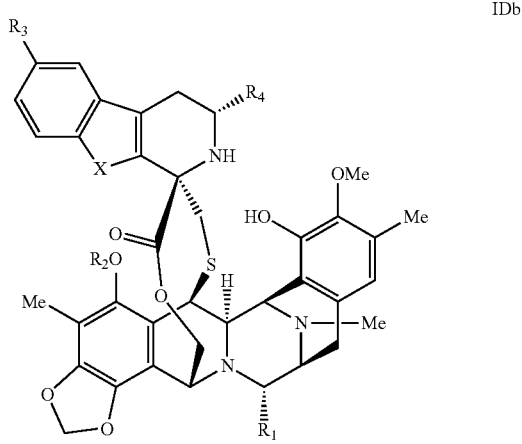

IDb wherein:
$R_4$ is selected from —CH$_2$OH, —CH$_2$OC(=O)R$^c$, —CH$_2$NH$_2$, and —CH$_2$NHProt$^{NH}$.

28. The compound according to claim 26, wherein $R_4$ is H, —CH$_2$OH or —CH$_2$NH$_2$.

29. The compound according to claim 1 of formula IE, or a pharmaceutically acceptable salt thereof:

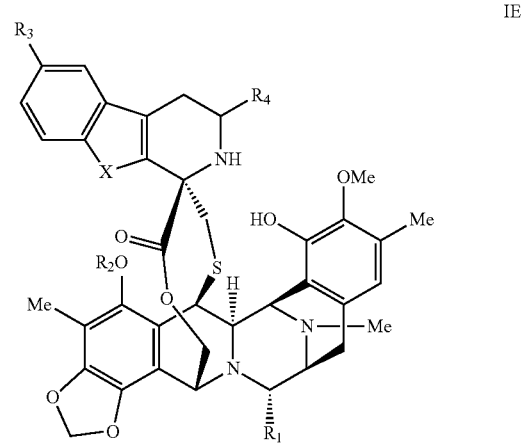

IE wherein:
$R_4$ is selected from —CH$_2$NH$_2$ and —CH$_2$NHProt$^{NH}$.

30. The compound according to claim 29 wherein X is —NH—.

31. The compound according to claim 29 wherein X is —O—.

32. The compound according to claim 29, wherein $R_4$ is —CH$_2$NH$_2$.

33. The compound according to claim 1 of formula IA or a pharmaceutically acceptable salt thereof:

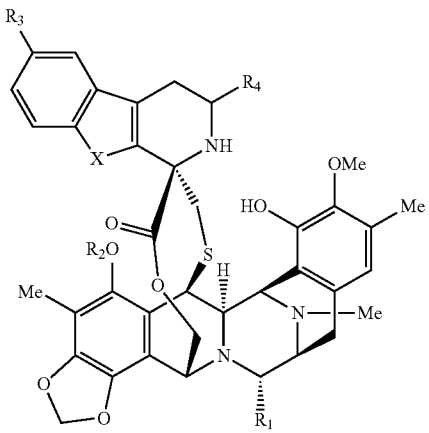

IA wherein:
R$_3$ is hydrogen; and
with the proviso that when R$_4$ is hydrogen then X is —O—.

34. The compound according to claim 33, wherein X is —NH—.

35. The compound according to claim 33, wherein X is —O—.

36. The compound according to claim 33, wherein R$_4$ is H, —CH$_2$OH or —CH$_2$NH$_2$.

37. The compound according to claim 1 of formula IB or a pharmaceutically acceptable salt thereof:

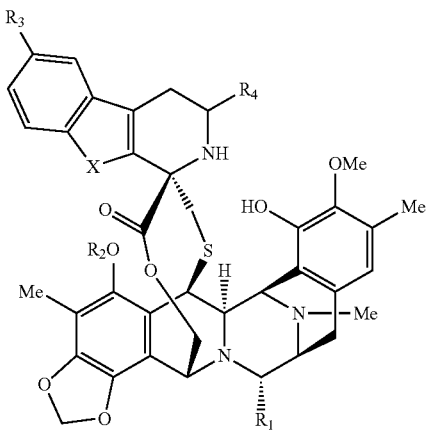

IB wherein:
R$_3$ is a —OR$^b$ group; and
with the proviso that when R$_4$ is hydrogen then X is —O—.

38. The compound according to claim 37, wherein X is —NH—.

39. The compound according to claim 37, wherein X is —O—.

40. The compound according to claim 37, wherein R$_4$ is H, —CH$_2$OH or —CH$_2$NH$_2$.

41. The compound according to claim 6, wherein R$^c$ is methyl.

42. The compound according to claim 12, wherein R$^a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl.

43. The compound according to claim 14, wherein R$^b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl.

44. A pharmaceutical composition comprising an effective amount of the compound according to any one of claims 1 to 15, 16 to 24, 25, 26, 27, 28, 29, 30 to 32, 33, 34, 35, 36, 37, 38, 39, 40 and 41-43 or a pharmaceutically acceptable salt thereof and a pharmaceutically acceptable carrier.

45. The pharmaceutical composition according to claim 44 in dosage form.

46. A method of treating cancer in a patient in need thereof, comprising administering to said patient a therapeutically effective amount of compound according to any one of claims 1 to 15, 16 to 24, 25, 26, 27, 28, 29, 30 to 32, 33, 34, 35, 36, 37, 38, 39, 40 and 41-43, or a pharmaceutically acceptable salt thereof, wherein the cancer is selected from lung cancer, non-small cell lung cancer, small cell lung cancer, colon cancer, colorectal cancer, breast cancer, pancreas cancer, sarcoma, ovarian cancer, prostate cancer and gastric cancer.

47. The method according to claim 46, wherein the cancer is selected from lung cancer, non-small cell lung cancer, small cell lung cancer, breast cancer, pancreas cancer and colorectal cancer.

48. A process for obtaining a compound as defined in any one of claims 1 to 15, 16 to 24, 25, 26, 27, 28, 29, 30 to 32, 33, 34, 35, 36, 37, 38, 39, 40 and 41-43 or a pharmaceutically acceptable salt thereof:

comprising the step of reacting a compound of formula II with a compound of formula III to give a compound of formula IV:

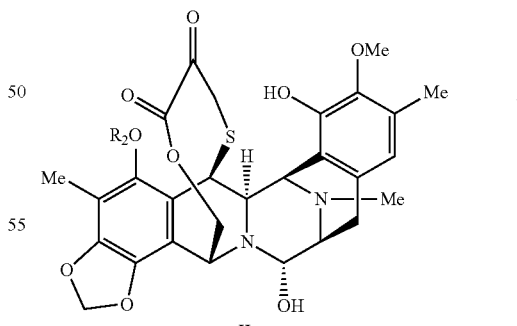

II

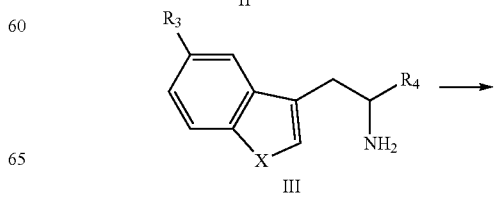

III

-continued

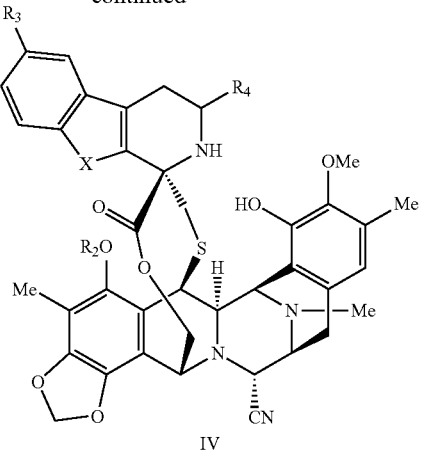

IV wherein (where allowed by possible substituent groups):

X is —NH— or —O—;

$R_2$ is a —C(=O)$R^a$ group;

$R_3$ is hydrogen or a —O$R^b$ group;

$R_4$ is selected from hydrogen, —CH$_2$OH, —CH$_2$OC(=O)$R^c$ and —CH$_2$NHProt$^{NH}$;

$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl;

$R^b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R^c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and Prot$^{NH}$ is a protecting group for amino;

with the proviso that when $R_4$ is hydrogen then X is —O—;

where substituted groups are substituted at one or more available positions by one or more substituents selected from OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, protected amino, protected SH, $C_1$-$C_{12}$ alkyl, $C_2$-$C_{12}$ alkenyl, $C_2$-$C_{12}$ alkynyl, aryl, and heterocyclic group; where each of the R' groups is independently selected from the group consisting of hydrogen, OH, NO$_2$, NH$_2$, SH, CN, halogen, COH, COalkyl, CO$_2$H, $C_1$-$C_{12}$ alkyl, $C_2$-$C_{12}$ alkenyl, $C_2$-$C_{12}$ alkynyl, aryl, and heterocyclic group.

49. The process according to claim 48, comprising the further step of replacing the cyano group in the compound of formula IV with a hydroxy group to give a compound of formula I, where $R_1$ is OH.

50. A kit comprising a therapeutically effective amount of a compound according to any one of claims 1 to 15, 16 to 24, 25, 26, 27, 28, 29, 30 to 32, 33, 34, 35, 36, 37, 38, 39, 40 and 41 to 43 and a pharmaceutically acceptable carrier.

51. The kit according to claim 50 further comprising instructions for use of the compound in the treatment of a cancer selected from lung cancer, non-small cell lung cancer, small cell lung cancer, colon cancer, colorectal cancer, breast cancer, pancreas cancer, sarcoma, ovarian cancer, prostate cancer and gastric cancer.

* * * * *

UNITED STATES PATENT AND TRADEMARK OFFICE
CERTIFICATE OF CORRECTION

PATENT NO. : 10,538,535 B2
APPLICATION NO. : 15/964381
DATED : January 21, 2020
INVENTOR(S) : María del Carmen Cuevas Marchante et al.

Page 1 of 3

It is certified that error appears in the above-identified patent and that said Letters Patent is hereby corrected as shown below:

In the Specification

Column 106, Lines 20-40, the formula reading:

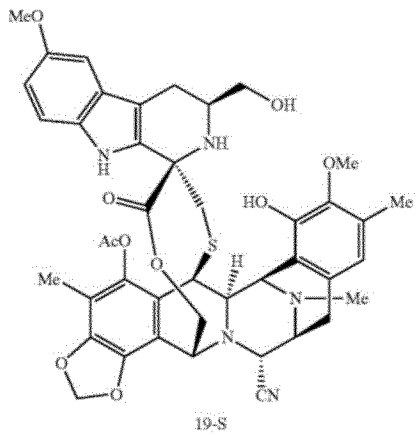

Should read:

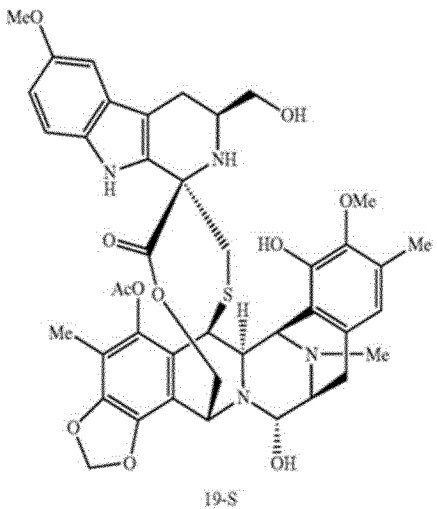

Signed and Sealed this
Twenty-fifth Day of July, 2023

Katherine Kelly Vidal
*Director of the United States Patent and Trademark Office*

Column 108, Lines 20-39, the formula reading:
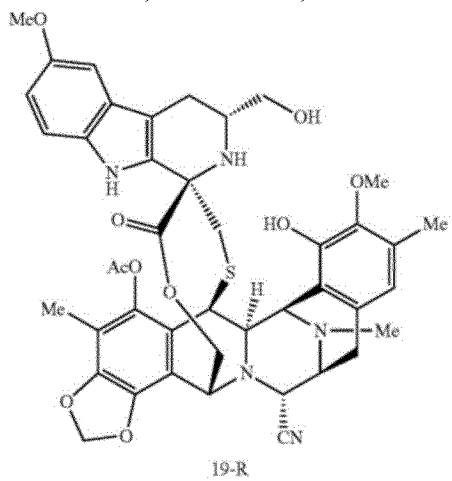
Should read:
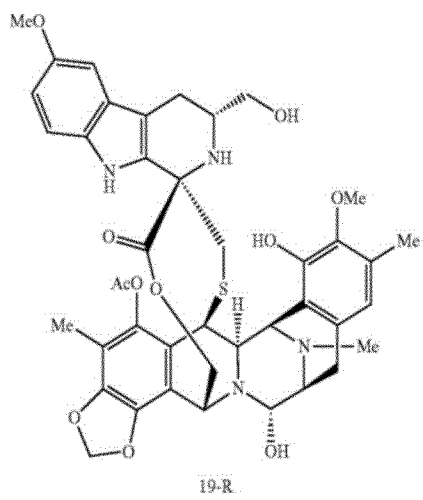
Column 149, Lines 20-40, the formula reading:
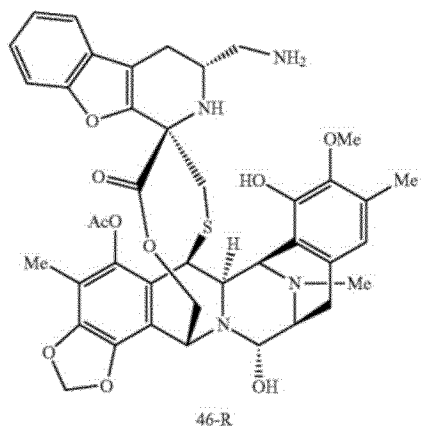

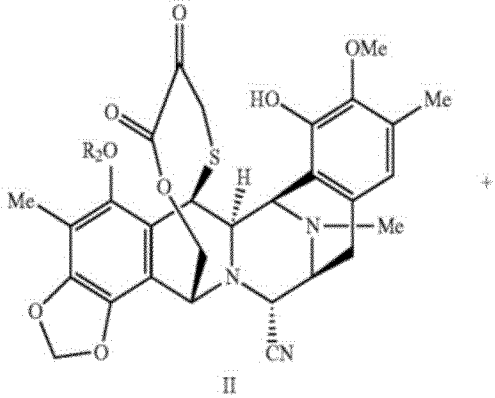

Should read:
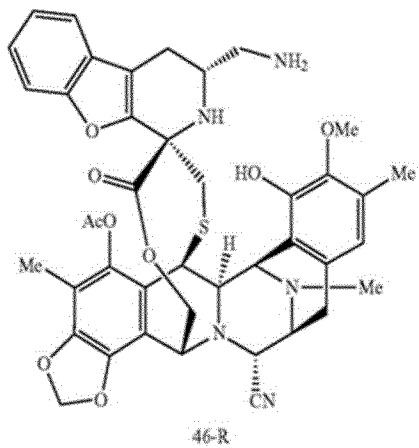
Column 212, Line 62, the term:
"–C(=O)R'''"
Should read:
–C(=O)R$^a$
In the Claims
Column 244, Lines 45-59, the formula reading:
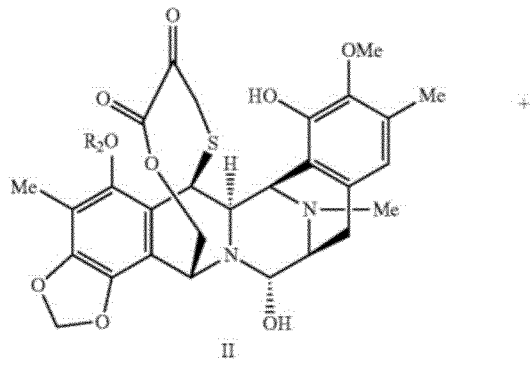
Should read: